US012649031B2

(12) United States Patent
Miller et al.

(10) Patent No.: US 12,649,031 B2
(45) Date of Patent: Jun. 9, 2026

(54) METHODS FOR DELIVERING AGENTS WITH PRE-FILLED SYRINGES TO MINIMIZE INTRAOCULAR INFLAMMATION

(71) Applicant: Regeneron Pharmaceuticals, Inc., Tarrytown, NY (US)

(72) Inventors: Nilsen Miller, East Greenbush, NY (US); Trevor Langley, Rensselaer, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

(21) Appl. No.: 17/930,373

(22) Filed: Sep. 7, 2022

(65) Prior Publication Data

US 2023/0080971 A1 Mar. 16, 2023

Related U.S. Application Data

(60) Provisional application No. 63/324,762, filed on Mar. 29, 2022, provisional application No. 63/263,006, filed on Oct. 25, 2021, provisional application No. 63/241,656, filed on Sep. 8, 2021.

(51) Int. Cl.
| *A61M 5/31* | (2006.01) |
| *A61M 5/34* | (2006.01) |
| *A61P 27/02* | (2006.01) |
| *A61M 5/50* | (2006.01) |

(52) U.S. Cl.
CPC .............. *A61M 5/31* (2013.01); *A61M 5/344* (2013.01); *A61P 27/02* (2018.01); *A61M 2005/5033* (2013.01)

(58) Field of Classification Search
CPC .......... A61M 2005/5033; A61M 5/344; A61M 5/31; A61P 27/02
See application file for complete search history.

(56) References Cited

U.S. PATENT DOCUMENTS

| | | | |
|---|---|---|---|
| 2,129,675 | A | 9/1938 | Cole |
| 2,375,711 | A | 5/1945 | Joseph |
| 2,739,590 | A | 3/1956 | Yochem |
| 2,792,834 | A | 5/1957 | Leon |
| 3,122,280 | A | 2/1964 | Goda |
| 3,128,765 | A | 4/1964 | Tint |
| 3,236,423 | A | 2/1966 | Marbach et al. |
| 3,236,434 | A | 2/1966 | Taddeau |
| 3,337,095 | A | 8/1967 | Marbach et al. |
| 3,608,550 | A | 9/1971 | Stawski |
| 3,610,241 | A | 10/1971 | Lemarie |
| 3,797,487 | A | 3/1974 | Schmidt |
| 3,934,586 | A | 1/1976 | Easton et al. |
| 4,117,728 | A | 10/1978 | Johnson |
| 4,152,939 | A | 5/1979 | Renshaw |
| 4,169,123 | A | 9/1979 | Moore et al. |

| | | | |
|---|---|---|---|
| 4,357,971 | A | 11/1982 | Friedman |
| 4,391,272 | A | 7/1983 | Staempfli |
| 4,444,335 | A | 4/1984 | Wood et al. |
| 4,475,905 | A | 10/1984 | Himmelstrup |
| 4,512,951 | A | 4/1985 | Koubek |
| 4,654,035 | A | 3/1987 | Ando |
| 4,840,616 | A | 6/1989 | Banks |
| 4,852,768 | A | 8/1989 | Bartsch |
| 4,871,094 | A | 10/1989 | Gall et al. |
| 4,915,692 | A | 4/1990 | Verlier |
| 4,915,695 | A | 4/1990 | Koobs |
| 5,009,645 | A | 4/1991 | Silver et al. |
| 5,080,649 | A | 1/1992 | Vetter |
| 5,084,017 | A | 1/1992 | Maffetone |
| RE33,821 | E | 2/1992 | Banks |
| 5,092,842 | A | 3/1992 | Bechtold et al. |
| 5,114,406 | A | 5/1992 | Gabriel et al. |
| 5,173,258 | A | 12/1992 | Childers |
| 5,284,132 | A | 2/1994 | Geier |
| 5,295,976 | A | 3/1994 | Harris |
| 5,318,544 | A | 6/1994 | Drypen et al. |
| 5,358,497 | A | 10/1994 | Dorsey et al. |
| 5,364,374 | A | 11/1994 | Morrison et al. |
| 5,364,590 | A | 11/1994 | Hillebrenner |
| 5,370,620 | A | 12/1994 | Shonfeld |
| 5,380,295 | A | 1/1995 | Vacca |
| 5,439,643 | A | 8/1995 | Liebert |

(Continued)

FOREIGN PATENT DOCUMENTS

| | | |
|---|---|---|
| AU | 54957/69 | 11/1970 |
| AU | 40517/85 A | 10/1985 |

(Continued)

OTHER PUBLICATIONS

Daniela P. Reyes-Capo, MD et al., "Trends in Endophthalmitis Associated With Intravitreal Injection of Anti-VEGF Agents at a Tertiary Referral Center", Clinical Science, Jun. 2021, vol. 52, No. 6, pp. 319-326.

Florian Baudin, MD et al., "Association of Acute Endophthalmitis With Intravitreal Injections of Corticosteroids or Anti-Vascular Growth Factor Agents in a Nationwide Study in France", JAMA Ophthalmology, Dec. 2018, vol. 136, No. 12, pp. 1352-1358.

Philip P. Storey et al., "The Impact of Prefilled Syringes on Endophthalmitis Following Intravitreal Injection of Ranibizumab", vol. 199, Mar. 2019, pp. 200-208.

U.S. Department of Health and Human Services, Food and Drug Administration, Center for Drug Evaluation and Research (CDER), Center for Biologics Evaluation and Research (CBER), "Guidance for Industry Container Closure Systems for Packaging Human Drugs and Biologics" Chemistry, Manufacturing, and Controls Documentation, May 1999 (56 pages).

(Continued)

*Primary Examiner* — Sean M Basquill

(74) *Attorney, Agent, or Firm* — Bookoff McAndrews, PLLC

(57) ABSTRACT

A method of treating an eye disorder in a patient that may include administering a medicament to the patient with a prefilled syringe, wherein the administration of the medicament with the prefilled syringe is configured to treat the eye disorder and decrease a rate of likelihood of an ocular infection to the patient's eye.

32 Claims, 95 Drawing Sheets

(56)                References Cited

U.S. PATENT DOCUMENTS

| | | | |
|---|---|---|---|
| 5,472,667 A | 12/1995 | Karthaus et al. |
| 5,485,853 A | 1/1996 | Stubbs |
| 5,507,727 A | 4/1996 | Crainich |
| 5,533,970 A | 7/1996 | Berger et al. |
| 5,545,147 A | 8/1996 | Harris |
| 5,554,122 A | 9/1996 | Emanuel |
| 5,593,391 A | 1/1997 | Stanners |
| 5,688,251 A | 11/1997 | Chanoch |
| 5,700,247 A | 12/1997 | Grimard et al. |
| 5,749,203 A | 5/1998 | McGowan, Jr. |
| 5,779,973 A | 7/1998 | Edwards et al. |
| 5,792,422 A | 8/1998 | Lin et al. |
| 5,792,435 A | 8/1998 | Mueller et al. |
| 5,795,337 A | 8/1998 | Grimard |
| 5,801,156 A | 9/1998 | Robinson et al. |
| 5,807,343 A | 9/1998 | Tucker et al. |
| 5,807,345 A | 9/1998 | Grabenkort |
| 5,820,603 A | 10/1998 | Tucker et al. |
| 5,827,233 A | 10/1998 | Futagawa et al. |
| 5,833,669 A | 11/1998 | Wyrick |
| 5,834,313 A | 11/1998 | Lin |
| 5,843,034 A | 12/1998 | Redfern et al. |
| 5,904,897 A | 5/1999 | Kendall et al. |
| 5,911,950 A | 6/1999 | Chen et al. |
| 5,919,418 A | 7/1999 | Kendall et al. |
| 5,925,316 A | 7/1999 | Kendall et al. |
| 5,951,526 A | 9/1999 | Korisch et al. |
| 5,961,495 A | 10/1999 | Walters et al. |
| 5,961,921 A | 10/1999 | Addy et al. |
| 5,971,956 A | 10/1999 | Epstein |
| 5,976,113 A | 11/1999 | Morigi et al. |
| 5,980,487 A | 11/1999 | Jones et al. |
| 5,980,825 A | 11/1999 | Addy et al. |
| 5,988,452 A | 11/1999 | Dent et al. |
| 6,030,579 A | 2/2000 | Addy et al. |
| 6,042,571 A | 3/2000 | Hjertman et al. |
| 6,066,294 A | 5/2000 | Lin et al. |
| 6,068,817 A | 5/2000 | Addy et al. |
| 6,077,480 A | 6/2000 | Edwards et al. |
| 6,096,010 A | 8/2000 | Walters et al. |
| 6,096,266 A | 8/2000 | Duroselle |
| 6,120,730 A | 9/2000 | Palaniappan et al. |
| 6,126,640 A | 10/2000 | Tucker et al. |
| 6,132,679 A | 10/2000 | Conviser |
| 6,132,680 A | 10/2000 | Addy et al. |
| 6,142,976 A | 11/2000 | Kubo |
| 6,142,977 A | 11/2000 | Kolberg et al. |
| 6,164,044 A | 12/2000 | Porfano et al. |
| 6,174,502 B1 | 1/2001 | Addy et al. |
| 6,187,265 B1 | 2/2001 | Wu et al. |
| 6,189,195 B1 | 2/2001 | Reilly et al. |
| 6,189,292 B1 | 2/2001 | Odell et al. |
| 6,193,931 B1 | 2/2001 | Lin et al. |
| 6,203,756 B1 | 3/2001 | Lin et al. |
| 6,224,828 B1 | 5/2001 | Lin et al. |
| 6,228,324 B1 | 5/2001 | Hasegawa et al. |
| 6,250,052 B1 | 6/2001 | Porfano et al. |
| 6,263,641 B1 | 7/2001 | Odell et al. |
| 6,264,629 B1 | 7/2001 | Landau |
| 6,273,152 B1 | 8/2001 | Buehler et al. |
| 6,279,622 B1 | 8/2001 | Nguyen et al. |
| 6,319,235 B1 | 11/2001 | Yoshino |
| 6,319,480 B1 | 11/2001 | Addy et al. |
| 6,325,972 B1 | 12/2001 | Jacobs et al. |
| 6,349,850 B1 | 2/2002 | Cheikh |
| 6,378,526 B1 | 4/2002 | Bowman et al. |
| 6,390,155 B1 | 5/2002 | Nguyen |
| 6,391,008 B1 | 5/2002 | Tsai |
| 6,394,111 B1 | 5/2002 | Jacobs et al. |
| 6,397,849 B1 | 6/2002 | Bowman et al. |
| 6,398,762 B1 | 6/2002 | Vetter et al. |
| 6,406,666 B1 | 6/2002 | Cicha et al. |
| 6,419,656 B1 | 7/2002 | Vetter et al. |
| 6,450,993 B1 | 9/2002 | Lin |
| 6,451,254 B1 | 9/2002 | Wang et al. |
| 6,451,255 B1 | 9/2002 | Williams et al. |
| 6,451,272 B1 | 9/2002 | Fryer et al. |
| 6,454,874 B1 | 9/2002 | Jacobs et al. |
| 6,491,881 B2 | 12/2002 | Fryer et al. |
| 6,494,964 B1 | 12/2002 | Jacobs et al. |
| 6,495,100 B1 | 12/2002 | Lin et al. |
| 6,511,457 B2 | 1/2003 | Thompson |
| D470,234 S | 2/2003 | Mahurkar |
| 6,516,817 B2 | 2/2003 | Jacobs et al. |
| 6,516,818 B2 | 2/2003 | Jacobs et al. |
| 6,528,015 B1 | 3/2003 | Lin et al. |
| 6,528,016 B1 | 3/2003 | Kohler et al. |
| 6,528,017 B2 | 3/2003 | Jacobs et al. |
| 6,530,399 B2 | 3/2003 | Nguyen et al. |
| 6,530,906 B2 | 3/2003 | Hu |
| 6,562,006 B1 | 5/2003 | Hjertman et al. |
| 6,589,481 B1 | 7/2003 | Lin et al. |
| 6,627,150 B1 | 9/2003 | Wang et al. |
| 6,645,429 B1 | 11/2003 | Raniwala |
| 6,656,426 B1 | 12/2003 | Wang et al. |
| 6,656,427 B2 | 12/2003 | Lin et al. |
| 6,673,313 B2 | 1/2004 | Wang et al. |
| 6,682,696 B1 | 1/2004 | Bjerborn |
| D489,819 S | 5/2004 | Ford |
| 6,734,405 B2 | 5/2004 | Centanni et al. |
| 6,746,647 B2 | 6/2004 | Kohler et al. |
| 6,746,652 B2 | 6/2004 | Khorzad et al. |
| 6,790,410 B2 | 9/2004 | Metzner et al. |
| 6,792,743 B2 | 9/2004 | Odell et al. |
| 6,807,797 B2 | 10/2004 | Forsberg et al. |
| 6,808,681 B2 | 10/2004 | Bjerborn |
| 6,815,206 B2 | 11/2004 | Lin et al. |
| 6,852,279 B2 | 2/2005 | Williams et al. |
| 6,906,296 B2 | 6/2005 | Centanni et al. |
| 6,942,638 B1 | 9/2005 | Quinn |
| 6,945,962 B2 | 9/2005 | Koenig et al. |
| 6,967,315 B2 | 11/2005 | Centanni et al. |
| 6,977,061 B2 | 12/2005 | Lin et al. |
| 6,996,952 B2 | 2/2006 | Gupta et al. |
| 7,014,813 B1 | 3/2006 | Watling et al. |
| 7,040,485 B2 | 5/2006 | Gupta et al. |
| 7,048,887 B2 | 5/2006 | Frost et al. |
| 7,108,832 B2 | 9/2006 | Christensen et al. |
| 7,146,746 B2 | 12/2006 | Kawasaki |
| 7,169,133 B2 | 1/2007 | Broennimann et al. |
| 7,179,419 B2 | 2/2007 | Lin et al. |
| 7,186,373 B2 | 3/2007 | Centanni |
| 7,201,869 B2 | 4/2007 | Williams et al. |
| D543,625 S | 5/2007 | Numata et al. |
| 7,229,590 B2 | 6/2007 | Awakowicz et al. |
| 7,229,591 B2 | 6/2007 | Wu et al. |
| 7,238,330 B2 | 7/2007 | Hill et al. |
| 7,246,627 B2 | 7/2007 | Jacobs et al. |
| 7,252,800 B2 | 8/2007 | Jacobs et al. |
| 7,267,806 B2 | 9/2007 | Kendall et al. |
| 7,273,594 B2 | 9/2007 | Lin et al. |
| 7,285,254 B2 | 10/2007 | Lin et al. |
| 7,294,305 B2 | 11/2007 | Lin et al. |
| 7,296,678 B2 | 11/2007 | Raynal-Olive et al. |
| 7,300,638 B2 | 11/2007 | Williams et al. |
| 7,303,073 B2 | 12/2007 | Raynal-Olive et al. |
| 7,303,748 B2 | 12/2007 | Wiegand et al. |
| 7,329,241 B2 | 2/2008 | Horvath et al. |
| 7,354,581 B2 | 4/2008 | Cedarbaum et al. |
| 7,371,345 B2 | 5/2008 | Stewart et al. |
| 7,396,347 B2 | 7/2008 | Hjertman et al. |
| 7,407,494 B2 | 8/2008 | Bostrom et al. |
| 7,431,900 B2 | 10/2008 | Hill et al. |
| 7,452,504 B2 | 11/2008 | Wu et al. |
| 7,459,028 B2 | 12/2008 | Kral et al. |
| 7,459,133 B2 | 12/2008 | Swank |
| 7,468,159 B2 | 12/2008 | Lin et al. |
| 7,481,974 B2 | 1/2009 | Sizer |
| 7,491,371 B2 | 2/2009 | Moller et al. |
| 7,517,334 B2 | 4/2009 | Jacobs et al. |
| 7,531,172 B2 | 5/2009 | Stahl et al. |
| 7,531,173 B2 | 5/2009 | Wiegand et al. |
| 7,534,233 B2 | 5/2009 | Schiller et al. |
| 7,550,122 B2 | 6/2009 | Buczynski et al. |

(56) References Cited

U.S. PATENT DOCUMENTS

| | | |
|---|---|---|
| 7,553,486 B2 | 6/2009 | Finger |
| 7,556,767 B2 | 7/2009 | Lin et al. |
| 7,564,983 B2 | 7/2009 | Ibuka et al. |
| 7,569,180 B2 | 8/2009 | Kohler et al. |
| 7,575,716 B2 | 8/2009 | Wu et al. |
| 7,578,969 B2 | 8/2009 | Mielnik et al. |
| 7,582,257 B2 | 9/2009 | Bedard et al. |
| 7,604,773 B2 | 10/2009 | Ekstrom et al. |
| 7,608,218 B2 | 10/2009 | Fryer et al. |
| 7,608,228 B2 | 10/2009 | Horacek et al. |
| 7,611,495 B1 | 11/2009 | Gianturco |
| 7,625,534 B2 | 12/2009 | Horacek et al. |
| 7,638,090 B2 | 12/2009 | Hyde et al. |
| 7,640,782 B2 | 1/2010 | Hill |
| 7,645,267 B2 | 1/2010 | Vetter et al. |
| 7,666,369 B2 | 2/2010 | Bondar |
| 7,670,550 B2 | 3/2010 | Lin et al. |
| 7,704,237 B2 | 4/2010 | Fisher et al. |
| 7,704,238 B2 | 4/2010 | Diller et al. |
| 7,704,426 B2 | 4/2010 | Earhart et al. |
| 7,713,473 B2 | 5/2010 | Kendall et al. |
| 7,727,195 B2 | 6/2010 | Norton |
| 7,727,201 B2 | 6/2010 | Kirchhofer |
| 7,727,464 B2 | 6/2010 | Frost |
| 7,749,200 B2 | 7/2010 | Graf et al. |
| 7,754,156 B2 | 7/2010 | Hyde et al. |
| 7,758,825 B2 | 7/2010 | Kabrick |
| 7,803,315 B2 | 9/2010 | McDonnell et al. |
| 7,803,316 B2 | 9/2010 | Lin et al. |
| 7,807,100 B2 | 10/2010 | Choperena et al. |
| 7,807,164 B2 | 10/2010 | Furfine et al. |
| 7,811,263 B2 | 10/2010 | Burren et al. |
| 7,824,610 B2 | 11/2010 | Ko |
| 7,850,906 B2 | 12/2010 | Watling et al. |
| D631,153 S | 1/2011 | McGlothlin et al. |
| 7,870,959 B2 | 1/2011 | Kuo et al. |
| 7,871,565 B2 | 1/2011 | Jethrow et al. |
| 7,880,887 B2 | 2/2011 | Olson et al. |
| 7,892,486 B2 | 2/2011 | Mizuno et al. |
| 7,910,055 B2 | 3/2011 | Bondar |
| 7,918,824 B2 | 4/2011 | Bishop et al. |
| 7,919,059 B2 | 4/2011 | Hill |
| 7,954,521 B2 | 6/2011 | Py et al. |
| 7,954,672 B2 | 6/2011 | Keller |
| 7,976,506 B2 | 7/2011 | Vitullo et al. |
| 7,981,361 B2 | 7/2011 | Bacik |
| 8,007,717 B2 | 8/2011 | Hill |
| 8,017,074 B2 | 9/2011 | Arnold et al. |
| 8,025,848 B2 | 9/2011 | McVey et al. |
| 8,029,725 B2 | 10/2011 | Olsson et al. |
| 8,034,288 B2 | 10/2011 | Burns et al. |
| 8,039,022 B2 | 10/2011 | Minamikawa et al. |
| 8,062,590 B1 | 11/2011 | Ricciardi et al. |
| 8,071,021 B2 | 12/2011 | Hill |
| 8,075,533 B2 | 12/2011 | Lee |
| 8,075,547 B2 | 12/2011 | Lee |
| 8,083,999 B2 | 12/2011 | Busujima |
| 8,105,293 B2 | 1/2012 | Pickhard |
| 8,110,156 B2 | 2/2012 | Ricciardi et al. |
| 8,114,342 B2 | 2/2012 | Jung et al. |
| 8,118,788 B2 | 2/2012 | Frezza |
| 8,124,127 B2 | 2/2012 | Faucher et al. |
| 8,129,579 B2 | 3/2012 | McVey et al. |
| 8,132,600 B2 | 3/2012 | Py et al. |
| 8,147,752 B2 | 4/2012 | Iwashita et al. |
| 8,147,771 B2 | 4/2012 | Yokoi et al. |
| 8,163,234 B2 | 4/2012 | Fedegari |
| 8,178,042 B2 | 5/2012 | Jung et al. |
| 8,187,597 B2 | 5/2012 | Shima et al. |
| 8,196,741 B2 | 6/2012 | Finke et al. |
| 8,205,416 B2 | 6/2012 | Hansen |
| 8,216,575 B2 | 7/2012 | Yu |
| 8,221,679 B2 | 7/2012 | Golkowski |
| 8,230,616 B2 | 7/2012 | McLaren et al. |
| 8,246,577 B2 | 8/2012 | Schrul et al. |
| 8,246,949 B2 | 8/2012 | Higuchi et al. |
| 8,252,229 B2 | 8/2012 | Thomas et al. |
| 8,263,016 B2 | 9/2012 | Kanner |
| 8,263,102 B2 | 9/2012 | Labrecque et al. |
| 8,268,238 B2 | 9/2012 | Bondar et al. |
| 8,268,257 B2 | 9/2012 | Frost |
| 8,276,583 B2 | 10/2012 | Farieta et al. |
| 8,277,724 B2 | 10/2012 | Jung et al. |
| 8,277,728 B2 | 10/2012 | Lambert et al. |
| 8,293,174 B2 | 10/2012 | Kaiser et al. |
| 8,312,836 B2 | 11/2012 | Corbeil et al. |
| 8,323,582 B2 | 12/2012 | Ko |
| 8,329,098 B2 | 12/2012 | Kanner |
| 8,329,113 B2 | 12/2012 | Kanner |
| 8,329,119 B2 | 12/2012 | Pearcy et al. |
| 8,333,931 B2 | 12/2012 | Kanner |
| 8,337,772 B2 | 12/2012 | Laumer et al. |
| 8,343,435 B2 | 1/2013 | Kanner |
| 8,348,905 B2 | 1/2013 | Radmer et al. |
| 8,349,272 B2 | 1/2013 | Hill |
| 8,357,331 B2 | 1/2013 | McVey et al. |
| 8,366,680 B2 | 2/2013 | Raab |
| 8,366,995 B2 | 2/2013 | McLaren et al. |
| 8,367,099 B2 | 2/2013 | Herweck et al. |
| 8,388,761 B2 | 3/2013 | Iwashita et al. |
| 8,394,068 B2 | 3/2013 | Kosinski et al. |
| 8,399,006 B2 | 3/2013 | De Juan, Jr. et al. |
| 8,414,912 B2 | 4/2013 | Ciolino et al. |
| 8,425,837 B2 | 4/2013 | Carbone et al. |
| 8,425,852 B2 | 4/2013 | Matsuuchi et al. |
| 8,428,447 B2 | 4/2013 | Von Stenglin |
| 8,431,076 B2 | 4/2013 | Fraundorfer |
| 8,431,077 B2 | 4/2013 | Goncalves |
| 8,435,459 B2 | 5/2013 | Reddy et al. |
| 8,435,460 B2 | 5/2013 | Hirosawa et al. |
| 8,444,919 B2 | 5/2013 | Erickson |
| 8,486,332 B1 | 7/2013 | Ricciardi et al. |
| 8,497,004 B2 | 7/2013 | Davis et al. |
| 8,501,291 B2 | 8/2013 | Davis et al. |
| 8,506,900 B1 | 8/2013 | Ricciardi et al. |
| 8,512,633 B2 | 8/2013 | Cregger et al. |
| 8,521,273 B2 | 8/2013 | Kliman |
| 8,529,832 B2 | 9/2013 | Lee |
| 8,557,365 B2 | 10/2013 | Maguire, Jr. et al. |
| 8,574,618 B2 | 11/2013 | Herweck et al. |
| 8,574,627 B2 | 11/2013 | Martakos et al. |
| 8,580,086 B2 | 11/2013 | Matsuuchi et al. |
| 8,585,832 B2 | 11/2013 | Lin et al. |
| 8,591,807 B2 | 11/2013 | Berentsveig et al. |
| 8,591,808 B2 | 11/2013 | Berentsveig et al. |
| 8,597,680 B2 | 12/2013 | Coppeta et al. |
| 8,617,109 B2 | 12/2013 | Kronestedt et al. |
| 8,621,824 B2 | 1/2014 | Mielnik et al. |
| 8,623,395 B2 | 1/2014 | De Juan, Jr. et al. |
| 8,628,501 B2 | 1/2014 | Hadden |
| 8,636,713 B2 | 1/2014 | Prausnitz et al. |
| 8,641,982 B2 | 2/2014 | Burgmeier et al. |
| 8,652,403 B2 | 2/2014 | Reddy et al. |
| 8,657,804 B2 | 2/2014 | Horne et al. |
| 8,658,089 B2 | 2/2014 | Berentsveig et al. |
| 8,658,092 B2 | 2/2014 | Kohler et al. |
| 8,663,555 B2 | 3/2014 | Shiosawa |
| 8,663,639 B2 | 3/2014 | Dor et al. |
| 8,668,881 B2 | 3/2014 | Hill et al. |
| 8,685,336 B2 | 4/2014 | Bondar |
| 8,685,337 B2 | 4/2014 | Beckmann et al. |
| 8,696,986 B2 | 4/2014 | Rovison, Jr. et al. |
| 8,703,066 B2 | 4/2014 | Vaughn et al. |
| 8,715,570 B2 | 5/2014 | Lindblad et al. |
| 8,721,601 B2 | 5/2014 | Burren et al. |
| 8,721,983 B2 | 5/2014 | Yokoi et al. |
| 8,721,984 B2 | 5/2014 | Carbone et al. |
| 8,722,077 B2 | 5/2014 | Labrecque et al. |
| 8,722,132 B2 | 5/2014 | Labrecque et al. |
| 8,727,117 B2 | 5/2014 | Maasarani |
| 8,733,551 B2 | 5/2014 | Parker et al. |
| 8,741,227 B2 | 6/2014 | Yokoi et al. |
| 8,747,739 B2 | 6/2014 | Parker et al. |
| 8,758,679 B2 | 6/2014 | Hyde et al. |

(56)      References Cited

U.S. PATENT DOCUMENTS

| | | |
|---|---|---|
| 8,758,681 B2 | 6/2014 | Golkowski |
| 8,765,064 B2 | 7/2014 | Yokoi et al. |
| 8,771,595 B2 | 7/2014 | Paskalov |
| 8,790,576 B2 | 7/2014 | Bauer et al. |
| 8,802,006 B2 | 8/2014 | Thomas et al. |
| 8,808,225 B2 | 8/2014 | Prausnitz et al. |
| 8,808,622 B2 | 8/2014 | Arnold et al. |
| 8,808,631 B2 | 8/2014 | Hill et al. |
| 8,821,807 B2 | 9/2014 | Schwartz et al. |
| 8,821,943 B2 | 9/2014 | Kompella et al. |
| 8,834,790 B2 | 9/2014 | Boschi et al. |
| 8,834,808 B2 | 9/2014 | Drenguis |
| 8,834,884 B2 | 9/2014 | Trogden et al. |
| 8,840,836 B2 | 9/2014 | Olson |
| 8,858,611 B2 | 10/2014 | Ramzipoor et al. |
| 8,858,978 B2 | 10/2014 | Labrecque et al. |
| 8,865,066 B2 | 10/2014 | Rovison et al. |
| 8,871,145 B2 | 10/2014 | Paskalov |
| 8,894,926 B2 | 11/2014 | Hanada et al. |
| 8,895,239 B2 | 11/2014 | Franciskovich et al. |
| 8,900,201 B2 | 12/2014 | Edhouse et al. |
| 8,911,402 B2 | 12/2014 | Veasey et al. |
| 8,911,426 B2 | 12/2014 | Coppeta et al. |
| 8,911,768 B2 | 12/2014 | Whitcup et al. |
| 8,915,404 B2 | 12/2014 | Farne' et al. |
| 8,919,359 B2 | 12/2014 | Iwashita et al. |
| 8,932,535 B2 | 1/2015 | Hyde et al. |
| 8,936,577 B2 | 1/2015 | Lee et al. |
| 8,940,245 B2 | 1/2015 | Reddy et al. |
| 8,945,048 B2 | 2/2015 | Thorley et al. |
| 8,945,468 B2 | 2/2015 | Reddy et al. |
| 8,948,863 B2 | 2/2015 | Kraft et al. |
| 8,956,655 B2 | 2/2015 | Lyons et al. |
| 8,956,830 B2 | 2/2015 | Prentice et al. |
| 8,961,872 B2 | 2/2015 | Fehr et al. |
| 8,962,023 B2 | 2/2015 | Labrecque et al. |
| 8,968,651 B2 | 3/2015 | Hayashi et al. |
| 8,974,730 B2 | 3/2015 | Burns et al. |
| 8,974,737 B2 | 3/2015 | Erickson |
| 8,979,807 B2 | 3/2015 | Grunhut et al. |
| 8,992,484 B2 | 3/2015 | Radmer et al. |
| 8,992,837 B2 | 3/2015 | Jung et al. |
| 8,992,853 B2 | 3/2015 | Stratman et al. |
| 9,011,767 B2 | 4/2015 | Wiget |
| D729,931 S | 5/2015 | Takeuchi et al. |
| 9,022,001 B2 | 5/2015 | Shafto |
| 9,022,079 B2 | 5/2015 | Py et al. |
| 9,023,350 B2 | 5/2015 | Gallo Barraco |
| 9,028,749 B2 | 5/2015 | Ryu et al. |
| 9,033,934 B2 | 5/2015 | Karlsson et al. |
| 9,034,249 B2 | 5/2015 | Foreman et al. |
| 9,044,548 B2 | 6/2015 | Miller et al. |
| 9,050,385 B2 | 6/2015 | Weinberger et al. |
| 9,078,435 B2 | 7/2015 | Dunn |
| 9,078,943 B2 | 7/2015 | Herold et al. |
| 9,101,679 B2 | 8/2015 | Robitaille et al. |
| 9,108,835 B2 | 8/2015 | Hayakawa et al. |
| 9,114,212 B2 | 8/2015 | Enggaard et al. |
| 9,120,660 B2 | 9/2015 | Sangi et al. |
| 9,120,661 B2 | 9/2015 | Sangi et al. |
| 9,125,960 B2 | 9/2015 | Stratman et al. |
| 9,125,988 B2 | 9/2015 | Karlsson |
| 9,138,005 B2 | 9/2015 | Berentsveig et al. |
| 9,144,648 B2 | 9/2015 | Lesch, Jr. et al. |
| D741,476 S | 10/2015 | Hiraoka et al. |
| 9,156,576 B2 | 10/2015 | Pjanic et al. |
| 9,173,968 B2 | 11/2015 | Hanada |
| 9,180,047 B2 | 11/2015 | Andino et al. |
| 9,180,217 B2 | 11/2015 | Arnold et al. |
| 9,186,460 B2 | 11/2015 | MacDonald et al. |
| 9,192,164 B2 | 11/2015 | Berentsveig et al. |
| 9,192,567 B2 | 11/2015 | Rabinovich-Guilatt et al. |
| 9,192,725 B2 | 11/2015 | Kawamura |
| 9,213,341 B2 | 12/2015 | Hill |
| 9,217,168 B2 | 12/2015 | Prentice |
| 9,220,631 B2 | 12/2015 | Sigg et al. |
| 9,220,820 B2 | 12/2015 | Faucher et al. |
| D747,796 S | 1/2016 | Romao |
| 9,226,495 B2 | 1/2016 | Berentsveig et al. |
| 9,238,106 B2 | 1/2016 | Jones |
| 9,241,491 B2 | 1/2016 | Berentsveig et al. |
| 9,242,053 B2 | 1/2016 | Wozencroft |
| 9,242,753 B2 | 1/2016 | Gay et al. |
| 9,248,229 B2 | 2/2016 | Devouassoux et al. |
| 9,254,338 B2 | 2/2016 | Yancopoulos |
| 9,254,343 B2 | 2/2016 | Herold et al. |
| 9,265,604 B2 | 2/2016 | Woods |
| 9,265,814 B2 | 2/2016 | Kauper et al. |
| 9,265,827 B2 | 2/2016 | Wiegand et al. |
| 9,271,866 B2 | 3/2016 | Humayun et al. |
| 9,284,369 B2 | 3/2016 | Ferrara et al. |
| 9,289,560 B2 | 3/2016 | Raab et al. |
| 9,295,744 B2 | 3/2016 | Rovison et al. |
| 9,302,021 B2 | 4/2016 | Klobusnik |
| 9,308,124 B2 | 4/2016 | Humayun et al. |
| 9,320,647 B2 | 4/2016 | Lerner et al. |
| 9,320,819 B2 | 4/2016 | Koyama |
| 9,320,820 B2 | 4/2016 | Rovison, Jr. et al. |
| 9,339,573 B2 | 5/2016 | Seidenberg et al. |
| 9,339,575 B2 | 5/2016 | Crawford et al. |
| 9,340,594 B2 | 5/2016 | Furfine et al. |
| 9,345,838 B2 | 5/2016 | Plumptre |
| 9,345,866 B2 | 5/2016 | Kubo et al. |
| 9,352,104 B2 | 5/2016 | Thorley et al. |
| 9,358,301 B2 | 6/2016 | Friberg et al. |
| 9,364,571 B2 | 6/2016 | Ahiska |
| 9,388,239 B2 | 7/2016 | Baldi et al. |
| D765,241 S | 8/2016 | Holland |
| 9,402,928 B2 | 8/2016 | Tremblay et al. |
| 9,403,330 B2 | 8/2016 | Laumer et al. |
| 9,408,746 B2 | 8/2016 | Lerner et al. |
| 9,408,931 B1 | 8/2016 | Ricciardi et al. |
| 9,408,965 B2 | 8/2016 | Christensen |
| 9,410,191 B2 | 8/2016 | Alvarez, Jr. et al. |
| 9,414,960 B2 | 8/2016 | Woods |
| 9,421,129 B2 | 8/2016 | Lerner |
| 9,427,485 B2 | 8/2016 | Tremblay et al. |
| 9,439,991 B2 | 9/2016 | Schwartz et al. |
| 9,452,138 B2 | 9/2016 | Trollsas et al. |
| 9,452,231 B2 | 9/2016 | Nonnenmacher |
| 9,457,114 B2 | 10/2016 | Loy |
| 9,463,259 B2 | 10/2016 | Hanada |
| 9,474,688 B2 | 10/2016 | Weeks et al. |
| 9,474,815 B2 | 10/2016 | Dufresne et al. |
| 9,475,225 B2 | 10/2016 | Giraud et al. |
| D770,612 S | 11/2016 | Green et al. |
| 9,480,763 B2 | 11/2016 | Dufresne et al. |
| 9,480,764 B2 | 11/2016 | Tremblay et al. |
| 9,480,765 B2 | 11/2016 | Tremblay et al. |
| 9,487,810 B2 | 11/2016 | Prentice et al. |
| 9,498,549 B2 | 11/2016 | Kanno et al. |
| 9,504,603 B2 | 11/2016 | Lerner |
| 9,505,598 B2 | 11/2016 | Niehr et al. |
| 9,505,830 B2 | 11/2016 | Ordas et al. |
| 9,522,202 B1 | 12/2016 | Ahiska et al. |
| 9,522,205 B2 | 12/2016 | Ahiska |
| 9,526,837 B2 | 12/2016 | Carrel et al. |
| 9,526,841 B2 | 12/2016 | Kubo et al. |
| 9,533,065 B2 | 1/2017 | Foreman et al. |
| 9,533,100 B2 | 1/2017 | Jones |
| 9,539,352 B2 | 1/2017 | Keener et al. |
| 9,539,391 B2 | 1/2017 | Lee et al. |
| 9,541,487 B2 | 1/2017 | Saito et al. |
| 9,545,473 B2 | 1/2017 | Devouassoux et al. |
| 9,545,481 B1 | 1/2017 | Rafaat |
| 9,554,968 B2 | 1/2017 | Weikart et al. |
| 9,555,146 B2 | 1/2017 | Fehr et al. |
| D778,174 S | 2/2017 | Zhang et al. |
| 9,561,297 B2 | 2/2017 | Kreber |
| 9,566,360 B2 | 2/2017 | Morikawa et al. |
| 9,566,361 B2 | 2/2017 | Morikawa et al. |
| 9,572,800 B2 | 2/2017 | Zarnitsyn et al. |
| 9,572,932 B2 | 2/2017 | Eggert et al. |
| 9,572,940 B2 | 2/2017 | Horlock |

(56) References Cited

U.S. PATENT DOCUMENTS

| | | | |
|---|---|---|---|
| 9,592,324 | B2 | 3/2017 | Herweck et al. |
| 9,593,004 | B2 | 3/2017 | Hayakawa et al. |
| 9,597,377 | B2 | 3/2017 | Fan |
| 9,603,739 | B2 | 3/2017 | Lerner |
| 9,604,015 | B2 | 3/2017 | Gramage Pina |
| 9,604,740 | B2 | 3/2017 | Py |
| 9,610,559 | B2 | 4/2017 | Riskin et al. |
| 9,616,148 | B2 | 4/2017 | Klaassen et al. |
| 9,616,368 | B2 | 4/2017 | Turbett et al. |
| 9,617,135 | B2 | 4/2017 | Hayakawa et al. |
| 9,617,136 | B2 | 4/2017 | Hayakawa et al. |
| 9,629,936 | B2 | 4/2017 | Salmisuo |
| 9,636,253 | B1 | 5/2017 | Andino et al. |
| 9,636,332 | B2 | 5/2017 | Zarnitsyn et al. |
| 9,637,604 | B2 | 5/2017 | Ito et al. |
| 9,650,444 | B2 | 5/2017 | Wiegand et al. |
| 9,655,987 | B2 | 5/2017 | Hayashi et al. |
| 9,662,244 | B2 | 5/2017 | Hatta et al. |
| 9,662,412 | B2 | 5/2017 | Ferrell et al. |
| 9,662,450 | B2 | 5/2017 | Jones et al. |
| 9,663,810 | B2 | 5/2017 | Prentice |
| D790,691 | S | 6/2017 | Davis et al. |
| 9,668,915 | B2 | 6/2017 | Haffner et al. |
| 9,669,069 | B2 | 6/2017 | Yancopoulos |
| 9,669,988 | B2 | 6/2017 | Kojima et al. |
| 9,675,763 | B2 | 6/2017 | Huet |
| 9,677,105 | B2 | 6/2017 | Collins et al. |
| 9,682,154 | B2 | 6/2017 | Leubitz et al. |
| 9,682,163 | B2 | 6/2017 | Loy et al. |
| 9,682,175 | B2 | 6/2017 | Labrecque et al. |
| 9,694,095 | B2 | 7/2017 | Paskalov |
| 9,708,390 | B2 | 7/2017 | Sivakumar et al. |
| RE46,510 | E | 8/2017 | Odell et al. |
| D794,185 | S | 8/2017 | Dolk et al. |
| D794,187 | S | 8/2017 | Dolk et al. |
| 9,717,854 | B2 | 8/2017 | Evans et al. |
| 9,724,438 | B2 | 8/2017 | Turbett |
| 9,731,041 | B2 | 8/2017 | Akutsu |
| 9,737,667 | B2 | 8/2017 | Holmqvist et al. |
| 9,750,832 | B2 | 9/2017 | Paver, Jr. |
| 9,750,887 | B2 | 9/2017 | Hirschel et al. |
| 9,750,888 | B2 | 9/2017 | Raab et al. |
| 9,757,452 | B2 | 9/2017 | Pham |
| 9,766,012 | B2 | 9/2017 | McLaren et al. |
| 9,770,361 | B2 | 9/2017 | Andino et al. |
| 9,770,559 | B2 | 9/2017 | Armstrong |
| D800,900 | S | 10/2017 | Darras et al. |
| 9,775,924 | B2 | 10/2017 | Tanimoto et al. |
| 9,776,161 | B2 | 10/2017 | Igney et al. |
| 9,788,995 | B2 | 10/2017 | Prausnitz et al. |
| 9,801,967 | B2 | 10/2017 | Wiget et al. |
| 9,802,726 | B2 | 10/2017 | Mielnik et al. |
| 9,808,548 | B2 | 11/2017 | Toreki et al. |
| 9,814,795 | B2 | 11/2017 | Dufresne et al. |
| 9,814,796 | B2 | 11/2017 | Dunn |
| 9,814,840 | B2 | 11/2017 | Cowe et al. |
| 9,827,341 | B2 | 11/2017 | Fehr et al. |
| 9,833,523 | B2 | 12/2017 | Christoforidis et al. |
| 9,849,203 | B2 | 12/2017 | Rovison, Jr. et al. |
| 9,849,244 | B2 | 12/2017 | Plumptre et al. |
| 9,849,323 | B2 | 12/2017 | Park et al. |
| 9,855,354 | B2 | 1/2018 | Lho et al. |
| 9,861,715 | B2 | 1/2018 | Charlez et al. |
| 9,867,948 | B2 | 1/2018 | Selz et al. |
| 9,872,961 | B2 | 1/2018 | Fourt et al. |
| D810,282 | S | 2/2018 | Ratjen |
| 9,895,259 | B2 | 2/2018 | Lerner |
| 9,896,480 | B2 | 2/2018 | Mackel et al. |
| D812,223 | S | 3/2018 | Evans et al. |
| D814,026 | S | 3/2018 | Darras et al. |
| 9,907,913 | B2 | 3/2018 | Kosinski et al. |
| 9,913,750 | B2 | 3/2018 | Lerner |
| 9,919,057 | B2 | 3/2018 | Kim et al. |
| 9,925,340 | B2 | 3/2018 | Glocker |
| D815,279 | S | 4/2018 | Darras et al. |
| 9,931,330 | B2 | 4/2018 | Zarnitsyn et al. |
| 9,932,630 | B2 | 4/2018 | Alvarez, Jr. et al. |
| 9,937,099 | B2 | 4/2018 | Weikart et al. |
| 9,937,335 | B2 | 4/2018 | Moss et al. |
| 9,943,573 | B2 | 4/2018 | Constable et al. |
| 9,950,116 | B2 | 4/2018 | Plumptre et al. |
| 9,956,114 | B2 | 5/2018 | Andino et al. |
| 9,957,324 | B2 | 5/2018 | Josiah et al. |
| 9,962,333 | B2 | 5/2018 | Gaillard et al. |
| 9,962,493 | B2 | 5/2018 | Guthart |
| 9,968,603 | B2 | 5/2018 | Astafieva et al. |
| 9,968,743 | B2 | 5/2018 | Kuwahara et al. |
| 9,982,032 | B2 | 5/2018 | Park et al. |
| D819,805 | S | 6/2018 | Knight et al. |
| 9,993,568 | B2 | 6/2018 | Kim et al. |
| 9,995,706 | B2 | 6/2018 | Schenk et al. |
| 9,999,595 | B2 | 6/2018 | Rakic et al. |
| 10,004,788 | B2 | 6/2018 | Constable et al. |
| 10,010,447 | B2 | 7/2018 | Kashani et al. |
| 10,016,338 | B2 | 7/2018 | Weikart et al. |
| 10,022,502 | B2 | 7/2018 | Wong et al. |
| 10,034,922 | B2 | 7/2018 | Kim |
| 10,035,850 | B2 | 7/2018 | Gekkieva et al. |
| 10,039,850 | B2 | 8/2018 | Taggart et al. |
| 10,046,027 | B2 | 8/2018 | Jensen et al. |
| 10,058,106 | B2 | 8/2018 | Itarashiki et al. |
| 10,064,997 | B2 | 9/2018 | Evans et al. |
| 10,065,784 | B2 | 9/2018 | Tanoguchi |
| 10,073,949 | B2 | 9/2018 | Ballou, Jr. et al. |
| 10,080,682 | B2 | 9/2018 | Horvath et al. |
| D830,540 | S | 10/2018 | Rolfs et al. |
| D830,543 | S | 10/2018 | Walker et al. |
| 10,092,708 | B2 | 10/2018 | Thorley et al. |
| 10,106,605 | B2 | 10/2018 | Ghosh et al. |
| 10,111,975 | B2 | 10/2018 | Laflamme et al. |
| 10,117,774 | B2 | 11/2018 | Humayun et al. |
| 10,130,681 | B2 | 11/2018 | Yancopoulos |
| 10,137,249 | B2 | 11/2018 | Oakley et al. |
| D838,363 | S | 1/2019 | Katagiri et al. |
| 10,166,142 | B2 | 1/2019 | De Juan, Jr. et al. |
| 10,172,682 | B2 | 1/2019 | Van Der Raad-Meijer et al. |
| 10,179,206 | B2 | 1/2019 | Bendek et al. |
| 10,182,969 | B2 | 1/2019 | Arnott et al. |
| 10,195,348 | B2 | 2/2019 | Komann |
| 10,196,685 | B2 | 2/2019 | Alvarez, Jr. et al. |
| 10,206,813 | B2 | 2/2019 | Haffner et al. |
| 10,213,556 | B2 | 2/2019 | Young et al. |
| 10,213,557 | B2 | 2/2019 | Eggert et al. |
| 10,213,558 | B2 | 2/2019 | Raghuveer et al. |
| 10,214,338 | B2 | 2/2019 | Devouassoux et al. |
| 10,214,827 | B2 | 2/2019 | Cabot et al. |
| 10,226,728 | B2 | 3/2019 | Turbett et al. |
| 10,232,119 | B2 | 3/2019 | Raab et al. |
| D845,476 | S | 4/2019 | Evans et al. |
| 10,245,178 | B1 | 4/2019 | Heitzmann et al. |
| 10,245,335 | B2 | 4/2019 | Turbett et al. |
| D849,935 | S | 5/2019 | Rolfs et al. |
| 10,279,060 | B2 | 5/2019 | Deprey et al. |
| 10,293,068 | B2 | 5/2019 | Ruley et al. |
| 10,293,965 | B2 | 5/2019 | Lu et al. |
| D851,753 | S | 6/2019 | Green |
| 10,314,929 | B2 | 6/2019 | Nowruzi et al. |
| 10,329,073 | B2 | 6/2019 | Tanoguchi |
| 10,350,306 | B2 | 7/2019 | Sieving et al. |
| 10,350,318 | B2 | 7/2019 | Sharma |
| 10,350,346 | B2 | 7/2019 | Kerschbaumer et al. |
| 10,363,214 | B2 | 7/2019 | Whitcup et al. |
| 10,369,107 | B2 | 8/2019 | McDonnell et al. |
| 10,369,241 | B2 | 8/2019 | Min et al. |
| 10,370,442 | B2 | 8/2019 | Portugal et al. |
| 10,376,582 | B2 | 8/2019 | Cini et al. |
| 10,383,954 | B2 | 8/2019 | Leubitz et al. |
| 10,383,966 | B2 | 8/2019 | Dufresne et al. |
| 10,385,842 | B2 | 8/2019 | Kuczek et al. |
| 10,391,259 | B2 | 8/2019 | Tran et al. |
| 10,398,796 | B2 | 9/2019 | Shomali et al. |
| 10,420,724 | B2 | 9/2019 | Jarrett et al. |
| 10,426,659 | B2 | 10/2019 | Myung et al. |
| 10,426,817 | B2 | 10/2019 | Rudolf et al. |

(56)        References Cited

U.S. PATENT DOCUMENTS

| | | | |
|---|---|---|---|
| D865,946 | S | 11/2019 | Horlock |
| 10,471,212 | B2 | 11/2019 | Ashmead et al. |
| 10,478,335 | B2 | 11/2019 | Lerner |
| 10,517,756 | B2 | 12/2019 | Andino et al. |
| 10,519,226 | B2 | 12/2019 | Rau et al. |
| 10,524,957 | B2 | 1/2020 | Lerner |
| 10,537,494 | B2 | 1/2020 | Weikart et al. |
| 10,537,563 | B2 | 1/2020 | Adams et al. |
| 10,556,008 | B2 | 2/2020 | Pham |
| 10,568,934 | B2 | 2/2020 | Hohman |
| 10,568,951 | B2 | 2/2020 | Sigl |
| D878,569 | S | 3/2020 | Reynolds et al. |
| D878,576 | S | 3/2020 | Johnson |
| 10,576,128 | B2 | 3/2020 | Sigl |
| 10,576,178 | B2 | 3/2020 | Goncalves |
| 10,588,855 | B2 | 3/2020 | Ambati et al. |
| 10,603,427 | B2 | 3/2020 | Hasumi |
| 10,617,557 | B2 | 4/2020 | De Juan et al. |
| 10,617,778 | B2 | 4/2020 | Roberts et al. |
| 10,632,013 | B2 | 4/2020 | Prausnitz et al. |
| 10,647,461 | B2 | 5/2020 | Altmann et al. |
| 10,653,621 | B2 | 5/2020 | Wu et al. |
| 10,656,152 | B2 | 5/2020 | De Juan, Jr. et al. |
| 10,683,345 | B2 | 6/2020 | Duerr et al. |
| D889,639 | S | 7/2020 | Johnson et al. |
| D891,611 | S | 7/2020 | Valentin et al. |
| 10,709,313 | B2 | 7/2020 | Stephenson |
| 10,709,803 | B2 | 7/2020 | Laflamme et al. |
| 10,710,759 | B2 | 7/2020 | Lu et al. |
| 10,722,396 | B2 | 7/2020 | Andino et al. |
| D892,313 | S | 8/2020 | Lin |
| D892,321 | S | 8/2020 | Newton |
| 10,729,799 | B2 | 8/2020 | Zydowicz et al. |
| 10,730,825 | B2 | 8/2020 | Bavik et al. |
| 10,730,944 | B2 | 8/2020 | Giurleo et al. |
| 10,751,417 | B2 | 8/2020 | Adams et al. |
| 10,752,901 | B2 | 8/2020 | Corson et al. |
| D895,110 | S | 9/2020 | Takada et al. |
| 10,765,759 | B2 | 9/2020 | Healy et al. |
| 10,773,014 | B2 | 9/2020 | Maasarani |
| 10,781,027 | B2 | 9/2020 | Devouassoux et al. |
| 10,786,462 | B2 | 9/2020 | Jarrett et al. |
| 10,792,312 | B2 | 10/2020 | Ferraro et al. |
| 10,793,307 | B2 | 10/2020 | Nohara et al. |
| 10,799,639 | B2 | 10/2020 | Wei |
| 10,799,642 | B2 | 10/2020 | Wong et al. |
| 10,806,630 | B2 | 10/2020 | Price et al. |
| 10,806,850 | B2 | 10/2020 | Patel et al. |
| 10,813,788 | B2 | 10/2020 | De Juan, Jr. et al. |
| 10,813,789 | B2 | 10/2020 | Haffner et al. |
| 10,821,221 | B2 | 11/2020 | Takahashi et al. |
| 10,823,715 | B2 | 11/2020 | Cregger et al. |
| 10,828,122 | B2 | 11/2020 | Takken et al. |
| 10,828,345 | B2 | 11/2020 | Yancopoulos |
| 10,828,392 | B2 | 11/2020 | Baer |
| 10,839,960 | B2 | 11/2020 | Ballou, Jr. et al. |
| 10,851,165 | B2 | 12/2020 | Freeman et al. |
| 10,857,205 | B2 | 12/2020 | Yancopoulos |
| 10,864,291 | B2 | 12/2020 | Fox, III |
| 10,876,144 | B2 | 12/2020 | Centanni et al. |
| 10,888,601 | B2 | 1/2021 | Yancopoulos |
| 10,889,848 | B2 | 1/2021 | Franciskovich et al. |
| 10,900,062 | B2 | 1/2021 | Franciskovich et al. |
| 10,905,586 | B2 | 2/2021 | Prausnitz et al. |
| 10,905,587 | B2 | 2/2021 | Lerner |
| 10,905,784 | B2 | 2/2021 | Kelly et al. |
| 10,905,786 | B2 | 2/2021 | Shodder |
| 10,906,969 | B2 | 2/2021 | Lee et al. |
| 10,912,623 | B2 | 2/2021 | Takken et al. |
| 10,912,714 | B2 | 2/2021 | Weikart et al. |
| 10,918,754 | B2 | 2/2021 | Shodder |
| 10,925,927 | B2 | 2/2021 | Brockmeyer et al. |
| 10,961,304 | B2 | 3/2021 | Eriksson et al. |
| 10,961,350 | B2 | 3/2021 | Momtaz et al. |
| 10,973,681 | B2 | 4/2021 | Andino et al. |
| 10,973,879 | B2 | 4/2021 | Vitti et al. |
| 10,980,766 | B2 | 4/2021 | Huang et al. |
| 10,980,890 | B2 | 4/2021 | Kim et al. |
| 10,993,834 | B2 | 5/2021 | Kahook |
| 10,994,914 | B2 | 5/2021 | Erickson |
| 11,000,607 | B2 | 5/2021 | Sharma |
| 11,007,259 | B2 | 5/2021 | Murakami et al. |
| 11,020,530 | B2 | 6/2021 | Takeuchi et al. |
| 11,020,531 | B2 | 6/2021 | Ashmead et al. |
| 11,026,885 | B2 | 6/2021 | Ashton et al. |
| 11,028,448 | B2 | 6/2021 | Innocenti et al. |
| 11,052,094 | B2 | 7/2021 | Ostrow et al. |
| 11,052,095 | B2 | 7/2021 | Ostrow et al. |
| 11,052,130 | B2 | 7/2021 | Kim et al. |
| 11,065,151 | B2 | 7/2021 | De Juan, Jr. et al. |
| 11,077,188 | B2 | 8/2021 | Kauvar et al. |
| 11,077,219 | B2 | 8/2021 | Lim et al. |
| 11,078,262 | B2 | 8/2021 | Hughes et al. |
| 11,090,445 | B2 | 8/2021 | Diaz et al. |
| 11,096,822 | B2 | 8/2021 | Yamamoto et al. |
| 11,097,029 | B2 | 8/2021 | Dufresne et al. |
| 11,098,110 | B2 | 8/2021 | Gekkieva et al. |
| 11,103,552 | B2 | 8/2021 | Graham et al. |
| 11,103,644 | B2 | 8/2021 | Bryant et al. |
| 11,110,001 | B2 | 9/2021 | Bachelder et al. |
| 11,110,226 | B2 | 9/2021 | Bryant et al. |
| 11,111,291 | B2 | 9/2021 | Famili et al. |
| 11,116,695 | B2 | 9/2021 | Weikart et al. |
| 11,124,324 | B2 | 9/2021 | Meoni |
| 11,135,266 | B2 | 10/2021 | Kerwin et al. |
| 11,147,925 | B2 | 10/2021 | Bryant et al. |
| 11,154,420 | B2 | 10/2021 | Yamamoto et al. |
| 11,160,918 | B2 | 11/2021 | Cook et al. |
| 11,160,951 | B2 | 11/2021 | Mottola et al. |
| 11,161,916 | B2 | 11/2021 | Gschwind et al. |
| 11,179,521 | B2 | 11/2021 | Bryant et al. |
| 11,185,383 | B2 | 11/2021 | Turbett |
| 11,185,499 | B2 | 11/2021 | Desai et al. |
| 11,185,635 | B2 | 11/2021 | Bryant et al. |
| 11,191,860 | B2 | 12/2021 | Lim et al. |
| 11,202,762 | B2 | 12/2021 | Mihov et al. |
| 11,209,444 | B2 | 12/2021 | Baldwin et al. |
| D940,302 | S | 1/2022 | Wu |
| D940,306 | S | 1/2022 | Osypka et al. |
| 11,214,426 | B2 | 1/2022 | Devouassoux et al. |
| 11,219,552 | B2 | 1/2022 | Olson |
| 11,224,555 | B2 | 1/2022 | Chudek et al. |
| 11,241,380 | B2 | 2/2022 | Freeman et al. |
| 11,253,572 | B2 | 2/2022 | Yancopoulos |
| 11,253,620 | B2 | 2/2022 | Golkowski et al. |
| 11,253,622 | B2 | 2/2022 | Lim |
| 11,266,608 | B2 | 3/2022 | Kang-Mieler et al. |
| 11,266,743 | B2 | 3/2022 | Wimley et al. |
| 11,273,230 | B1 | 3/2022 | Baumgartner et al. |
| 11,279,075 | B2 | 3/2022 | Hannafin et al. |
| 11,291,636 | B2 | 4/2022 | Chen et al. |
| 11,298,405 | B2 | 4/2022 | Brockmeyer et al. |
| 11,298,437 | B2 | 4/2022 | Conseil et al. |
| 11,298,463 | B2 | 4/2022 | Tan-Malecki et al. |
| D950,721 | S | 5/2022 | Howes et al. |
| D953,089 | S | 5/2022 | Scheinert |
| 11,324,845 | B1 | 5/2022 | Ricciardi et al. |
| 11,331,430 | B2 | 5/2022 | Dobson |
| 11,344,643 | B2 | 5/2022 | Golkowski et al. |
| D954,258 | S | 6/2022 | Hang et al. |
| D954,942 | S | 6/2022 | Lee |
| D956,205 | S | 6/2022 | Nimkar et al. |
| 11,351,282 | B2 | 6/2022 | Lim et al. |
| 11,351,347 | B2 | 6/2022 | Myung et al. |
| 11,357,877 | B2 | 6/2022 | Henniges et al. |
| 11,369,591 | B2 | 6/2022 | Jarrett et al. |
| 11,369,708 | B2 | 6/2022 | Spallek et al. |
| D957,630 | S | 7/2022 | Punim |
| 11,382,955 | B2 | 7/2022 | Ferrara |
| 11,383,006 | B2 | 7/2022 | Hughes et al. |
| 11,389,556 | B2 | 7/2022 | Henniges et al. |
| 11,389,594 | B2 | 7/2022 | Smith et al. |
| D961,067 | S | 8/2022 | Schootstra et al. |
| 11,400,080 | B2 | 8/2022 | Maturi |

(56) References Cited

U.S. PATENT DOCUMENTS

| | | | |
|---|---|---|---|
| 11,406,592 | B2 | 8/2022 | De Juan, Jr. et al. |
| 11,419,985 | B2 | 8/2022 | Wei |
| 11,426,306 | B2 | 8/2022 | Haffner et al. |
| D965,141 | S | 9/2022 | Oldfield et al. |
| 11,433,118 | B2 | 9/2022 | Ferrara |
| 11,452,811 | B2 | 9/2022 | Kerschbaumer et al. |
| D967,414 | S | 10/2022 | Cebadera Miranda |
| 11,458,199 | B2 | 10/2022 | Santos et al. |
| 11,459,374 | B2 | 10/2022 | Tustian et al. |
| 11,478,465 | B2 | 10/2022 | Eriksson et al. |
| D969,992 | S | 11/2022 | Espinoza |
| 11,504,431 | B2 | 11/2022 | Prausnitz et al. |
| 11,505,593 | B2 | 11/2022 | Wang et al. |
| 11,510,869 | B2 | 11/2022 | Doshi |
| D973,203 | S | 12/2022 | Tyrsing et al. |
| D973,873 | S | 12/2022 | Tyrsing et al. |
| 11,518,984 | B2 | 12/2022 | Her et al. |
| 11,524,998 | B2 | 12/2022 | Bigelow et al. |
| 11,525,001 | B2 | 12/2022 | Giurleo et al. |
| 11,534,396 | B2 | 12/2022 | Blizzard et al. |
| 11,534,517 | B2 | 12/2022 | Herrig et al. |
| 11,541,139 | B2 | 1/2023 | Eveland |
| 11,542,317 | B1 | 1/2023 | Wang et al. |
| 11,554,215 | B2 | 1/2023 | Hawson et al. |
| 11,554,886 | B2 | 1/2023 | Procyshyn et al. |
| 11,559,428 | B2 | 1/2023 | Andino et al. |
| 11,559,520 | B2 | 1/2023 | Surber |
| 11,559,564 | B2 | 1/2023 | Yancopoulos |
| 11,564,834 | B2 | 1/2023 | Bley et al. |
| 11,564,907 | B2 | 1/2023 | Muller et al. |
| D979,054 | S | 2/2023 | Lee-Sepsick et al. |
| D979,750 | S | 2/2023 | Dyk |
| 11,576,948 | B2 | 2/2023 | Ferrara |
| 11,584,774 | B2 | 2/2023 | Iyer et al. |
| RE49,474 | E | 3/2023 | Golkowski |
| 11,596,545 | B2 | 3/2023 | Andino et al. |
| 11,596,667 | B2 | 3/2023 | Rezaei |
| 11,607,468 | B2 | 3/2023 | Kleinmann et al. |
| D983,965 | S | 4/2023 | Siddiqui |
| 11,618,782 | B2 | 4/2023 | Ziegelaar et al. |
| 11,622,884 | B2 | 4/2023 | Bley et al. |
| 11,633,300 | B2 | 4/2023 | Lazar |
| 11,633,545 | B2 | 4/2023 | Vedrine et al. |
| D986,413 | S | 5/2023 | Atterbury et al. |
| D987,820 | S | 5/2023 | Yabe |
| 11,638,631 | B2 | 5/2023 | Berner |
| 11,642,214 | B2 | 5/2023 | Loria |
| 11,642,310 | B2 | 5/2023 | De Juan, Jr. et al. |
| 11,642,487 | B2 | 5/2023 | Heimbuch et al. |
| 11,654,046 | B2 | 5/2023 | Weikart et al. |
| 11,660,266 | B2 | 5/2023 | Jiang et al. |
| D989,302 | S | 6/2023 | Hang et al. |
| D989,951 | S | 6/2023 | Renou et al. |
| 11,666,632 | B2 | 6/2023 | Brockmeyer et al. |
| 11,672,800 | B2 | 6/2023 | Campbell et al. |
| 11,672,880 | B2 | 6/2023 | Bohnert et al. |
| 11,679,027 | B2 | 6/2023 | De Juan, Jr. et al. |
| 11,680,266 | B2 | 6/2023 | D'Amore et al. |
| 11,692,027 | B2 | 7/2023 | Kraft et al. |
| 11,696,967 | B2 | 7/2023 | Nowruzi et al. |
| 11,707,506 | B2 | 7/2023 | Yancopoulos |
| 11,707,531 | B2 | 7/2023 | Iyer |
| 11,707,577 | B2 | 7/2023 | Shetty et al. |
| 11,712,490 | B2 | 8/2023 | Lim et al. |
| 11,712,491 | B2 | 8/2023 | Truong et al. |
| 11,723,982 | B2 | 8/2023 | Healy et al. |
| 11,725,246 | B2 | 8/2023 | Ghosh et al. |
| 11,730,794 | B2 | 8/2023 | Yancopoulos |
| 11,738,007 | B2 | 8/2023 | Gurkan et al. |
| 11,738,064 | B2 | 8/2023 | Kim et al. |
| 11,739,294 | B2 | 8/2023 | Klassen et al. |
| D998,146 | S | 9/2023 | Kelleher et al. |
| 11,752,101 | B2 | 9/2023 | Yamamoto et al. |
| 11,752,225 | B2 | 9/2023 | Shieu et al. |
| 11,759,537 | B2 | 9/2023 | Matsuo et al. |
| 11,759,577 | B2 | 9/2023 | Shanley et al. |
| 11,766,489 | B2 | 9/2023 | Kirn et al. |
| 11,766,494 | B2 | 9/2023 | Takahashi et al. |
| 11,766,497 | B2 | 9/2023 | Takahashi et al. |
| 11,786,396 | B2 | 10/2023 | De Juan, Jr. et al. |
| 11,793,926 | B2 | 10/2023 | Cook et al. |
| 11,795,136 | B2 | 10/2023 | Bavik et al. |
| 11,806,513 | B2 | 11/2023 | Bowman et al. |
| 11,813,196 | B2 | 11/2023 | Erickson et al. |
| 11,819,454 | B2 | 11/2023 | Nazzaro |
| 11,826,431 | B2 | 11/2023 | Wei et al. |
| D1,025,354 | S | 4/2024 | Ullsten et al. |
| D1,028,225 | S | 5/2024 | Kubo et al. |
| D1,037,440 | S | 7/2024 | Suzuki et al. |
| 12,048,837 | B2 | 7/2024 | Bryant et al. |
| 12,059,555 | B2 | 8/2024 | Mismar et al. |
| D1,048,392 | S | 10/2024 | Hang et al. |
| 2001/0021382 | A1 | 9/2001 | Ferrara et al. |
| 2001/0031221 | A1 | 10/2001 | Wu et al. |
| 2002/0081228 | A1 | 6/2002 | Hui et al. |
| 2002/0098111 | A1 | 7/2002 | Nguyen et al. |
| 2002/0098187 | A1 | 7/2002 | Ferrara et al. |
| 2002/0119075 | A1 | 8/2002 | Jacobs et al. |
| 2002/0122744 | A1 | 9/2002 | Hui et al. |
| 2002/0161334 | A1 | 10/2002 | Castellano et al. |
| 2002/0177819 | A1 | 11/2002 | Barker et al. |
| 2002/0194630 | A1 | 12/2002 | Manning et al. |
| 2003/0004467 | A1 | 1/2003 | Musick et al. |
| 2003/0032928 | A1 | 2/2003 | Sudo et al. |
| 2003/0049165 | A1 | 3/2003 | Yamamoto et al. |
| 2003/0063997 | A1 | 4/2003 | Fryer et al. |
| 2003/0138347 | A1 | 7/2003 | Lin |
| 2003/0139707 | A1 | 7/2003 | Hommann et al. |
| 2003/0236503 | A1 | 12/2003 | Koenig et al. |
| 2004/0028556 | A1 | 2/2004 | Frost et al. |
| 2004/0064105 | A1 | 4/2004 | Capes et al. |
| 2004/0097883 | A1 | 5/2004 | Roe |
| 2004/0162528 | A1 | 8/2004 | Horvath et al. |
| 2004/0170527 | A1 | 9/2004 | Jacobs et al. |
| 2004/0191114 | A1 | 9/2004 | Frost et al. |
| 2004/0199113 | A1 | 10/2004 | Capes et al. |
| 2004/0220524 | A1 | 11/2004 | Sadowski et al. |
| 2004/0236285 | A1 | 11/2004 | Fisher et al. |
| 2005/0004530 | A1 | 1/2005 | Grabenkort et al. |
| 2005/0027255 | A1 | 2/2005 | Lavi et al. |
| 2005/0042130 | A1 | 2/2005 | Lin et al. |
| 2005/0090782 | A1 | 4/2005 | Marshall et al. |
| 2005/0131354 | A1 | 6/2005 | Tachikawa et al. |
| 2005/0163655 | A1 | 7/2005 | Lin et al. |
| 2005/0182370 | A1 | 8/2005 | Hato |
| 2005/0215957 | A1 | 9/2005 | Hynes |
| 2006/0008378 | A1 | 1/2006 | Imai et al. |
| 2006/0067856 | A1 | 3/2006 | Martensson et al. |
| 2006/0067976 | A1 | 3/2006 | Ferraro et al. |
| 2006/0088596 | A1 | 4/2006 | Labrecque et al. |
| 2006/0153693 | A1 | 7/2006 | Fiechter et al. |
| 2006/0193862 | A1 | 8/2006 | Ferrara et al. |
| 2006/0223027 | A1 | 10/2006 | Smith et al. |
| 2006/0258988 | A1 | 11/2006 | Keitel et al. |
| 2006/0264815 | A1 | 11/2006 | Hommann et al. |
| 2006/0270984 | A1 | 11/2006 | Hommann |
| 2006/0270985 | A1 | 11/2006 | Hommann et al. |
| 2006/0280646 | A1 | 12/2006 | Shiosawa |
| 2007/0003432 | A1 | 1/2007 | Christensen et al. |
| 2007/0006551 | A1 | 1/2007 | Sizer |
| 2007/0014691 | A1 | 1/2007 | Lin et al. |
| 2007/0016142 | A1 | 1/2007 | Burren et al. |
| 2007/0027101 | A1 | 2/2007 | Guyer et al. |
| 2007/0048177 | A1 | 3/2007 | Lin et al. |
| 2007/0059302 | A1 | 3/2007 | Baca et al. |
| 2007/0084144 | A1 | 4/2007 | Labrecque et al. |
| 2007/0088268 | A1 | 4/2007 | Edwards et al. |
| 2007/0092398 | A1 | 4/2007 | McDonald |
| 2007/0098591 | A1 | 5/2007 | Frinke et al. |
| 2007/0098592 | A1 | 5/2007 | Buczynski et al. |
| 2007/0154570 | A1 | 7/2007 | Miller et al. |
| 2007/0172383 | A1 | 7/2007 | Williams et al. |
| 2007/0190058 | A1 | 8/2007 | Shams |
| 2007/0203144 | A1 | 8/2007 | Kusari et al. |

(56)     References Cited

U.S. PATENT DOCUMENTS

| 2007/0231188 A1 | 10/2007 | Jung et al. |
| 2007/0231192 A1 | 10/2007 | Jung et al. |
| 2007/0231193 A1 | 10/2007 | Jung et al. |
| 2007/0231194 A1 | 10/2007 | Jung et al. |
| 2007/0231201 A1 | 10/2007 | Roberts et al. |
| 2007/0231202 A1 | 10/2007 | Roberts et al. |
| 2007/0233001 A1 | 10/2007 | Burroughs et al. |
| 2007/0233009 A1 | 10/2007 | Kirchhofer |
| 2007/0253959 A1 | 11/2007 | Ferrara et al. |
| 2007/0258873 A1 | 11/2007 | Wu et al. |
| 2007/0265580 A1 | 11/2007 | Tachikawa et al. |
| 2007/0280902 A1 | 12/2007 | Rabinovich-Guilatt et al. |
| 2007/0281913 A1 | 12/2007 | Rabinovich-Guilatt et al. |
| 2007/0281914 A1 | 12/2007 | Rabinovich-Guilatt et al. |
| 2007/0292305 A1 | 12/2007 | Dempsey et al. |
| 2008/0019977 A1 | 1/2008 | Adamis |
| 2008/0025869 A1 | 1/2008 | Kendall et al. |
| 2008/0065027 A1 | 3/2008 | Sharp |
| 2008/0071227 A1 | 3/2008 | Moser et al. |
| 2008/0082044 A1 | 4/2008 | Sharon et al. |
| 2008/0085223 A1 | 4/2008 | Jung et al. |
| 2008/0131342 A1 | 6/2008 | Wu et al. |
| 2008/0135130 A1 | 6/2008 | Py et al. |
| 2008/0160019 A1 | 7/2008 | Wood et al. |
| 2008/0181900 A1 | 7/2008 | Ferrara et al. |
| 2008/0183138 A1 | 7/2008 | Moser et al. |
| 2008/0202961 A1 | 8/2008 | Sharp |
| 2008/0208123 A1 | 8/2008 | Hommann |
| 2008/0226496 A1 | 9/2008 | Rivkine et al. |
| 2008/0233251 A1 | 9/2008 | Sizer |
| 2008/0269692 A1 | 10/2008 | James et al. |
| 2008/0279736 A1 | 11/2008 | Frinke et al. |
| 2009/0005735 A1 | 1/2009 | Wikner et al. |
| 2009/0062746 A1 | 3/2009 | Heffernan et al. |
| 2009/0071104 A1 | 3/2009 | Fischer |
| 2009/0074786 A1 | 3/2009 | Dor et al. |
| 2009/0087424 A1 | 4/2009 | Miyamoto et al. |
| 2009/0087921 A1 | 4/2009 | Hill |
| 2009/0098139 A1 | 4/2009 | Katz et al. |
| 2009/0110596 A1 | 4/2009 | Christensen et al. |
| 2009/0123330 A1 | 5/2009 | Moller et al. |
| 2009/0149743 A1 | 6/2009 | Barron et al. |
| 2009/0169556 A1 | 7/2009 | Ferrara et al. |
| 2009/0196903 A1 | 8/2009 | Kliman |
| 2009/0208378 A1 | 8/2009 | Jung et al. |
| 2009/0232697 A1 | 9/2009 | Martensson et al. |
| 2009/0232703 A1 | 9/2009 | Jung et al. |
| 2009/0254036 A1 | 10/2009 | Asmussen et al. |
| 2009/0275914 A1 | 11/2009 | Harms et al. |
| 2009/0299278 A1 | 12/2009 | Lesch, Jr. et al. |
| 2009/0324445 A1 | 12/2009 | Kohler et al. |
| 2010/0016807 A1 | 1/2010 | Thilly |
| 2010/0034697 A1 | 2/2010 | Weinberger et al. |
| 2010/0036320 A1 | 2/2010 | Cox et al. |
| 2010/0086447 A1 | 4/2010 | Jung et al. |
| 2010/0090837 A1 | 4/2010 | Jung et al. |
| 2010/0111963 A1 | 5/2010 | Shams |
| 2010/0119523 A1 | 5/2010 | Ferrara et al. |
| 2010/0152671 A1 | 6/2010 | Raab et al. |
| 2010/0160894 A1 | 6/2010 | Julian et al. |
| 2010/0166603 A1 | 7/2010 | Opie |
| 2010/0172795 A1 | 7/2010 | Lothar |
| 2010/0175779 A1 | 7/2010 | Ogawa et al. |
| 2010/0185205 A1 | 7/2010 | Novakovic et al. |
| 2010/0186739 A1 | 7/2010 | Kronestedt et al. |
| 2010/0292672 A1 | 11/2010 | Lee |
| 2010/0298779 A1 | 11/2010 | Hetzler et al. |
| 2010/0305514 A1 | 12/2010 | Valenti et al. |
| 2010/0316652 A1 | 12/2010 | Ferrara et al. |
| 2010/0318063 A1 | 12/2010 | Soll |
| 2011/0009829 A1 | 1/2011 | Kosinski et al. |
| 2011/0009830 A1 | 1/2011 | Kosinski et al. |
| 2011/0076192 A1 | 3/2011 | Robitaille et al. |
| 2011/0092915 A1 | 4/2011 | Olson et al. |
| 2011/0098640 A1 | 4/2011 | Horne et al. |
| 2011/0110932 A1 | 5/2011 | Patel |
| 2011/0176959 A1 | 7/2011 | Ko |
| 2011/0190709 A1 | 8/2011 | Mitsuno et al. |
| 2011/0217204 A1 | 9/2011 | Franciskovich et al. |
| 2011/0276026 A1 | 11/2011 | Dowds |
| 2011/0280765 A1 | 11/2011 | Hirose et al. |
| 2011/0287024 A1 | 11/2011 | Ferrara et al. |
| 2012/0009085 A1 | 1/2012 | Burger |
| 2012/0009185 A1 | 1/2012 | Shams |
| 2012/0035528 A1 | 2/2012 | Coppeta et al. |
| 2012/0070428 A1 | 3/2012 | Chan et al. |
| 2012/0104045 A1 | 5/2012 | Chang |
| 2012/0114524 A1 | 5/2012 | Sigg |
| 2012/0128670 A1 | 5/2012 | Barr et al. |
| 2012/0143146 A1 | 6/2012 | Strehl et al. |
| 2012/0189495 A1 | 7/2012 | Franciskovich et al. |
| 2012/0197211 A1 | 8/2012 | Brister et al. |
| 2012/0203184 A1 | 8/2012 | Selz et al. |
| 2012/0213672 A1 | 8/2012 | Adams et al. |
| 2012/0226240 A1 | 9/2012 | Bedford et al. |
| 2012/0230870 A1 | 9/2012 | Franciskovich et al. |
| 2012/0232492 A1 | 9/2012 | Hato |
| 2012/0283654 A1 | 11/2012 | Macdonald et al. |
| 2013/0004380 A1 | 1/2013 | Yoo |
| 2013/0004384 A1 | 1/2013 | Yoo |
| 2013/0004486 A1 | 1/2013 | Chan et al. |
| 2013/0006192 A1 | 1/2013 | Teucher et al. |
| 2013/0028794 A1 | 1/2013 | Silvestri et al. |
| 2013/0028911 A1 | 1/2013 | Ferrara et al. |
| 2013/0060232 A1 | 3/2013 | Adlon et al. |
| 2013/0082057 A1 | 4/2013 | Schiff et al. |
| 2013/0084215 A1 | 4/2013 | Fukui et al. |
| 2013/0085452 A1 | 4/2013 | Schiff et al. |
| 2013/0085455 A1 | 4/2013 | Manke et al. |
| 2013/0085458 A1 | 4/2013 | Manke et al. |
| 2013/0105025 A1 | 5/2013 | Fehr et al. |
| 2013/0110054 A1 | 5/2013 | Raab et al. |
| 2013/0136697 A1 | 5/2013 | Kannan et al. |
| 2013/0150803 A1 | 6/2013 | Shetty et al. |
| 2013/0156641 A1 | 6/2013 | Paskalov |
| 2013/0195806 A1 | 8/2013 | Gay et al. |
| 2013/0197016 A1 | 8/2013 | Brigell et al. |
| 2013/0218081 A1 | 8/2013 | Roth |
| 2013/0218130 A1 | 8/2013 | Plumptre et al. |
| 2013/0224110 A1 | 8/2013 | Bynoe |
| 2013/0236359 A1 | 9/2013 | Burger |
| 2013/0289491 A1 | 10/2013 | Kramer et al. |
| 2013/0296779 A1 | 11/2013 | Kuehne et al. |
| 2013/0303985 A1 | 11/2013 | Wotton et al. |
| 2013/0310744 A1 | 11/2013 | Brereton |
| 2013/0317431 A1 | 11/2013 | Kramer et al. |
| 2013/0317477 A1 | 11/2013 | Edwards et al. |
| 2013/0323242 A1 | 12/2013 | Everett et al. |
| 2013/0324924 A1 | 12/2013 | Brereton et al. |
| 2014/0005610 A1 | 1/2014 | Kakiuchi et al. |
| 2014/0012227 A1 | 1/2014 | Sigg et al. |
| 2014/0020331 A1 | 1/2014 | Chin et al. |
| 2014/0058335 A1 | 2/2014 | Mudd |
| 2014/0086934 A1 | 3/2014 | Shams |
| 2014/0093499 A1 | 4/2014 | Gschwind et al. |
| 2014/0109519 A1 | 4/2014 | Hayakawa et al. |
| 2014/0109529 A1 | 4/2014 | Hayakawa et al. |
| 2014/0114208 A1 | 4/2014 | Smith et al. |
| 2014/0135712 A1 | 5/2014 | Horne et al. |
| 2014/0148792 A1 | 5/2014 | Coppeta et al. |
| 2014/0154132 A1 | 6/2014 | Frieze et al. |
| 2014/0170020 A1 | 6/2014 | Hiruta |
| 2014/0179621 A1 | 6/2014 | Patel et al. |
| 2014/0180217 A1 | 6/2014 | Kuczek et al. |
| 2014/0193299 A1 | 7/2014 | Leamy et al. |
| 2014/0205507 A1 | 7/2014 | Yokoi et al. |
| 2014/0221934 A1 | 8/2014 | Janvier et al. |
| 2014/0223862 A1 | 8/2014 | Nicoletti et al. |
| 2014/0241953 A1 | 8/2014 | Lho et al. |
| 2014/0271622 A1 | 9/2014 | Prentice |
| 2014/0288507 A1 | 9/2014 | Samuel |
| 2014/0288511 A1 | 9/2014 | Tan-Malecki et al. |
| 2014/0294816 A1 | 10/2014 | Shima et al. |
| 2014/0301895 A1 | 10/2014 | Opie et al. |

(56) References Cited

U.S. PATENT DOCUMENTS

| | | |
|---|---|---|
| 2014/0303556 A1 | 10/2014 | Travanty |
| 2014/0336589 A1 | 11/2014 | Sund et al. |
| 2014/0348703 A1 | 11/2014 | Thomas et al. |
| 2014/0350516 A1 | 11/2014 | Schwab et al. |
| 2014/0377276 A1 | 12/2014 | Ferrara et al. |
| 2015/0010432 A1 | 1/2015 | Olson |
| 2015/0017163 A1 | 1/2015 | Patel et al. |
| 2015/0018771 A1 | 1/2015 | Schenker et al. |
| 2015/0037204 A1 | 2/2015 | Geiger et al. |
| 2015/0037205 A1 | 2/2015 | Miyahara et al. |
| 2015/0037422 A1 | 2/2015 | Kaplan et al. |
| 2015/0044094 A1 | 2/2015 | Cadieux et al. |
| 2015/0051551 A1 | 2/2015 | Hirschel et al. |
| 2015/0073355 A1 | 3/2015 | Hirschel et al. |
| 2015/0078961 A1 | 3/2015 | Opie |
| 2015/0105734 A1 | 4/2015 | Bryant et al. |
| 2015/0110670 A1 | 4/2015 | Opie et al. |
| 2015/0119810 A1 | 4/2015 | Jakob et al. |
| 2015/0126458 A1 | 5/2015 | Hohman et al. |
| 2015/0152503 A1 | 6/2015 | Boisen et al. |
| 2015/0157709 A1 | 6/2015 | Everett et al. |
| 2015/0157801 A1 | 6/2015 | Tran et al. |
| 2015/0182623 A1 | 7/2015 | Everett et al. |
| 2015/0182651 A1 | 7/2015 | Tanimoto et al. |
| 2015/0183540 A1 | 7/2015 | Lothar |
| 2015/0190566 A1 | 7/2015 | Okihara |
| 2015/0197359 A1 | 7/2015 | Nohara et al. |
| 2015/0202289 A1 | 7/2015 | Shima et al. |
| 2015/0205985 A1 | 7/2015 | Jinadatha |
| 2015/0208648 A1 | 7/2015 | Iwashita et al. |
| 2015/0209455 A1 | 7/2015 | Turbett et al. |
| 2015/0224266 A1 | 8/2015 | Plumptre et al. |
| 2015/0239594 A1 | 8/2015 | Batema |
| 2015/0273097 A1 | 10/2015 | Murayama et al. |
| 2015/0274397 A1 | 10/2015 | Dunn |
| 2015/0297453 A1 | 10/2015 | Kim et al. |
| 2015/0297454 A1 | 10/2015 | Sanders et al. |
| 2015/0297675 A1 | 10/2015 | Osborne |
| 2015/0297839 A1 | 10/2015 | Sanders et al. |
| 2015/0305342 A1 | 10/2015 | Burke et al. |
| 2015/0305343 A1 | 10/2015 | Burke et al. |
| 2015/0305344 A1 | 10/2015 | Burke et al. |
| 2015/0306259 A1 | 10/2015 | Deutschle et al. |
| 2015/0306266 A1 | 10/2015 | Burke et al. |
| 2015/0313250 A1 | 11/2015 | Itarashiki et al. |
| 2015/0320503 A1 | 11/2015 | Bezdikian |
| 2015/0320782 A1 | 11/2015 | Panjwani et al. |
| 2015/0328151 A1 | 11/2015 | Ballou, Jr. et al. |
| 2015/0335826 A1 | 11/2015 | Huet |
| 2015/0352238 A1 | 12/2015 | Dufresne et al. |
| 2015/0352298 A1 | 12/2015 | Egerström et al. |
| 2015/0373986 A1 | 12/2015 | Burke et al. |
| 2015/0374924 A1 | 12/2015 | Keitel et al. |
| 2016/0008540 A1 | 1/2016 | Fourt et al. |
| 2016/0009433 A1 | 1/2016 | Tanaka et al. |
| 2016/0022919 A1 | 1/2016 | Cammish et al. |
| 2016/0038589 A1 | 2/2016 | Patel |
| 2016/0090205 A1 | 3/2016 | Py et al. |
| 2016/0106928 A1 | 4/2016 | Davis et al. |
| 2016/0114065 A1 | 4/2016 | Thomas et al. |
| 2016/0121010 A1 | 5/2016 | Harada et al. |
| 2016/0129080 A1 | 5/2016 | Osborne |
| 2016/0130321 A1 | 5/2016 | Burian |
| 2016/0137717 A1 | 5/2016 | Burian |
| 2016/0144122 A1 | 5/2016 | Locati et al. |
| 2016/0144128 A1 | 5/2016 | Oakley et al. |
| 2016/0151578 A1 | 6/2016 | Oakley et al. |
| 2016/0159893 A1 | 6/2016 | Burian et al. |
| 2016/0166765 A1 | 6/2016 | Tan-Malecki et al. |
| 2016/0168240 A1 | 6/2016 | Burian et al. |
| 2016/0183522 A1 | 6/2016 | Rovison et al. |
| 2016/0185474 A1 | 6/2016 | Bronner et al. |
| 2016/0193375 A1 | 7/2016 | Laflamme et al. |
| 2016/0193421 A1 | 7/2016 | Bayer et al. |
| 2016/0199578 A1 | 7/2016 | Tan-Malecki et al. |
| 2016/0199582 A1 | 7/2016 | Tan-Malecki et al. |
| 2016/0199583 A1 | 7/2016 | Tan-Malecki et al. |
| 2016/0200461 A1 | 7/2016 | Broadbent et al. |
| 2016/0206767 A1 | 7/2016 | Park et al. |
| 2016/0213852 A1 | 7/2016 | Harms et al. |
| 2016/0220540 A1 | 8/2016 | Peters et al. |
| 2016/0220759 A1 | 8/2016 | Enggaard et al. |
| 2016/0220761 A1 | 8/2016 | Shetty et al. |
| 2016/0220762 A1 | 8/2016 | Goral et al. |
| 2016/0228642 A1 | 8/2016 | Cowe |
| 2016/0235873 A1 | 8/2016 | Rovison, Jr. et al. |
| 2016/0235877 A1 | 8/2016 | Ruley et al. |
| 2016/0250367 A1 | 9/2016 | Hijikata et al. |
| 2016/0257054 A1 | 9/2016 | Hayakawa et al. |
| 2016/0257055 A1 | 9/2016 | Hayakawa et al. |
| 2016/0263269 A1 | 9/2016 | Hayakawa et al. |
| 2016/0264969 A1 | 9/2016 | Patel et al. |
| 2016/0272347 A1 | 9/2016 | Procyshyn et al. |
| 2016/0279339 A1 | 9/2016 | Schenker et al. |
| 2016/0296550 A1 | 10/2016 | Patel et al. |
| 2016/0296652 A1 | 10/2016 | Leamy et al. |
| 2016/0303791 A1 | 10/2016 | Hannafin et al. |
| 2016/0310417 A1 | 10/2016 | Prausnitz et al. |
| 2016/0317688 A1 | 11/2016 | Deprey et al. |
| 2016/0317752 A1 | 11/2016 | Cowe |
| 2016/0324998 A1 | 11/2016 | Reed et al. |
| 2016/0325047 A1 | 11/2016 | Vedrine et al. |
| 2016/0325482 A1 | 11/2016 | Hayakawa et al. |
| 2016/0347492 A1 | 12/2016 | Lu et al. |
| 2016/0348160 A1 | 12/2016 | Alvarez, Jr. et al. |
| 2016/0361450 A1 | 12/2016 | Dufresne et al. |
| 2016/0375160 A1 | 12/2016 | Hayakawa |
| 2016/0375167 A1 | 12/2016 | Min et al. |
| 2017/0001744 A1 | 1/2017 | Konze et al. |
| 2017/0007729 A1 | 1/2017 | Bertomeu Asategui |
| 2017/0014539 A1 | 1/2017 | Min et al. |
| 2017/0027175 A1 | 2/2017 | Dunn |
| 2017/0035922 A1 | 2/2017 | Stratman et al. |
| 2017/0035958 A1 | 2/2017 | Thomas et al. |
| 2017/0042816 A1 | 2/2017 | Trollsas et al. |
| 2017/0049916 A1 | 2/2017 | Ikeda |
| 2017/0056469 A1 | 3/2017 | Iezzi |
| 2017/0056541 A1 | 3/2017 | Sveningsson |
| 2017/0056923 A1 | 3/2017 | Hioki et al. |
| 2017/0057635 A1 | 3/2017 | Strayer |
| 2017/0072081 A1 | 3/2017 | Alvarez, Jr. et al. |
| 2017/0080086 A1 | 3/2017 | Vitti et al. |
| 2017/0080159 A1 | 3/2017 | Wei |
| 2017/0100284 A1 | 4/2017 | Lerner |
| 2017/0100306 A1 | 4/2017 | Weikart et al. |
| 2017/0100542 A1 | 4/2017 | Norton et al. |
| 2017/0100543 A1 | 4/2017 | Cabiri et al. |
| 2017/0106109 A1 | 4/2017 | Morikawa et al. |
| 2017/0107008 A1 | 4/2017 | Ichikawa |
| 2017/0129635 A1 | 5/2017 | Hijikata et al. |
| 2017/0157207 A1 | 6/2017 | Hohman et al. |
| 2017/0157316 A1 | 6/2017 | Browne |
| 2017/0158365 A1 | 6/2017 | Py |
| 2017/0166341 A1 | 6/2017 | Hayakawa et al. |
| 2017/0166342 A1 | 6/2017 | Hayakawa et al. |
| 2017/0173161 A1 | 6/2017 | Kaplan et al. |
| 2017/0173267 A1 | 6/2017 | Ashmead et al. |
| 2017/0175069 A1 | 6/2017 | Baker, Jr. et al. |
| 2017/0182253 A1 | 6/2017 | Folk et al. |
| 2017/0182259 A1 | 6/2017 | Fukushi et al. |
| 2017/0189619 A1 | 7/2017 | Constantineau et al. |
| 2017/0189843 A1 | 7/2017 | Turbett et al. |
| 2017/0197003 A1 | 7/2017 | Taggart |
| 2017/0197024 A1 | 7/2017 | Kiminami et al. |
| 2017/0203043 A1 | 7/2017 | Rusch et al. |
| 2017/0203052 A1 | 7/2017 | Abe et al. |
| 2017/0203869 A1 | 7/2017 | Lucani et al. |
| 2017/0208802 A1 | 7/2017 | Franciskovich et al. |
| 2017/0217617 A1 | 8/2017 | Sato et al. |
| 2017/0217661 A1 | 8/2017 | Erickson |
| 2017/0224435 A1 | 8/2017 | Godfrey et al. |
| 2017/0224858 A1 | 8/2017 | Stibich |
| 2017/0232199 A1 | 8/2017 | Fiedler |
| 2017/0233782 A1 | 8/2017 | Collins et al. |

(56) References Cited

U.S. PATENT DOCUMENTS

| 2017/0246401 | A1 | 8/2017 | Keenan |
| 2017/0258633 | A1 | 9/2017 | Vure et al. |
| 2017/0274147 | A1 | 9/2017 | Raghuveer et al. |
| 2017/0275581 | A1 | 9/2017 | Nishimura et al. |
| 2017/0281872 | A1 | 10/2017 | Guthart |
| 2017/0281876 | A1 | 10/2017 | Odell et al. |
| 2017/0290987 | A1 | 10/2017 | Mandaroux et al. |
| 2017/0296756 | A1 | 10/2017 | Giraud et al. |
| 2017/0304476 | A1 | 10/2017 | Taggart et al. |
| 2017/0312378 | A1 | 11/2017 | Goncalves |
| 2017/0326262 | A1 | 11/2017 | Paver, Jr. |
| 2017/0340830 | A1 | 11/2017 | Wieselblad et al. |
| 2017/0348450 | A1 | 12/2017 | Akutsu |
| 2018/0036488 | A1 | 2/2018 | Wei |
| 2018/0042765 | A1 | 2/2018 | Noronha et al. |
| 2018/0057602 | A1 | 3/2018 | Theuer et al. |
| 2018/0126085 | A1 | 5/2018 | Bowman et al. |
| 2018/0126086 | A1 | 5/2018 | Kosinski et al. |
| 2018/0133288 | A1 | 5/2018 | Kim et al. |
| 2018/0147214 | A1 | 5/2018 | Ostrow et al. |
| 2018/0171004 | A1 | 6/2018 | Gokarn et al. |
| 2018/0177948 | A1 | 6/2018 | Raab et al. |
| 2018/0177949 | A1 | 6/2018 | De Waal Malefijt et al. |
| 2018/0194835 | A1 | 7/2018 | Burian et al. |
| 2018/0207091 | A1 | 7/2018 | Brown |
| 2018/0221483 | A1 | 8/2018 | Gaillard et al. |
| 2018/0221584 | A1 | 8/2018 | Grimoldby et al. |
| 2018/0228649 | A1 | 8/2018 | Lerner |
| 2018/0237430 | A1 | 8/2018 | Peters et al. |
| 2018/0243513 | A1 | 8/2018 | Rolfs et al. |
| 2018/0250474 | A1 | 9/2018 | Wei |
| 2018/0251457 | A1 | 9/2018 | Peters et al. |
| 2018/0256747 | A1 | 9/2018 | Hawthorne et al. |
| 2018/0263816 | A1 | 9/2018 | Lerner |
| 2018/0264111 | A1 | 9/2018 | Pedrussio et al. |
| 2018/0280622 | A1 | 10/2018 | Li et al. |
| 2018/0280623 | A1* | 10/2018 | Pilkington ........ A61M 5/31515 |
| 2018/0311319 | A1 | 11/2018 | Constable et al. |
| 2018/0326126 | A1 | 11/2018 | Fiedler |
| 2018/0333296 | A1 | 11/2018 | Heitzmann et al. |
| 2018/0333300 | A1 | 11/2018 | Lerner |
| 2018/0361080 | A1 | 12/2018 | Diaz et al. |
| 2019/0001065 | A1 | 1/2019 | Daniel |
| 2019/0015597 | A1 | 1/2019 | Holmqvist et al. |
| 2019/0016817 | A1 | 1/2019 | Taddei et al. |
| 2019/0030253 | A1 | 1/2019 | Barbour |
| 2019/0076603 | A1 | 3/2019 | Thorley et al. |
| 2019/0105230 | A1 | 4/2019 | Arnott et al. |
| 2019/0106725 | A1 | 4/2019 | Cregger et al. |
| 2019/0106726 | A1 | 4/2019 | Cregger et al. |
| 2019/0111212 | A1 | 4/2019 | Schiff et al. |
| 2019/0143049 | A1 | 5/2019 | Bilgic |
| 2019/0183842 | A1 | 6/2019 | Huang et al. |
| 2019/0201430 | A1 | 7/2019 | Vavvas et al. |
| 2019/0224356 | A1 | 7/2019 | Nowruzi et al. |
| 2019/0231913 | A1 | 8/2019 | Ruley et al. |
| 2019/0231986 | A1 | 8/2019 | Devaraneni et al. |
| 2019/0290485 | A1 | 9/2019 | Andino et al. |
| 2019/0343918 | A1 | 11/2019 | Graham et al. |
| 2019/0358123 | A1 | 11/2019 | Weikart et al. |
| 2019/0365565 | A1 | 12/2019 | Bryant et al. |
| 2019/0381008 | A1 | 12/2019 | Zeitz et al. |
| 2019/0381087 | A1 | 12/2019 | Patel et al. |
| 2019/0388522 | A1 | 12/2019 | Burian et al. |
| 2020/0000635 | A1 | 1/2020 | Lerner |
| 2020/0001062 | A1 | 1/2020 | Moss et al. |
| 2020/0002411 | A1 | 1/2020 | Famili et al. |
| 2020/0023076 | A1 | 1/2020 | Fotin-Mleczek et al. |
| 2020/0031917 | A1 | 1/2020 | Kraft et al. |
| 2020/0048341 | A1 | 2/2020 | Ghosh et al. |
| 2020/0054635 | A1 | 2/2020 | Campbell et al. |
| 2020/0069770 | A1 | 3/2020 | Rudolf et al. |
| 2020/0069814 | A1 | 3/2020 | Zhao et al. |
| 2020/0069816 | A1 | 3/2020 | Kim et al. |
| 2020/0085735 | A1 | 3/2020 | Brown |
| 2020/0093852 | A1 | 3/2020 | Nelms et al. |
| 2020/0101186 | A1 | 4/2020 | Shodder |
| 2020/0114029 | A1 | 4/2020 | Zhang et al. |
| 2020/0121817 | A1 | 4/2020 | Anraku et al. |
| 2020/0129435 | A1 | 4/2020 | Akbari et al. |
| 2020/0147056 | A1 | 5/2020 | Maturi |
| 2020/0155764 | A1 | 5/2020 | Kakiuchi et al. |
| 2020/0163877 | A1 | 5/2020 | Santos et al. |
| 2020/0171244 | A1 | 6/2020 | Weikart et al. |
| 2020/0179167 | A1 | 6/2020 | Bryant et al. |
| 2020/0188405 | A1 | 6/2020 | Kaushal |
| 2020/0188589 | A1 | 6/2020 | Hawson et al. |
| 2020/0188590 | A1 | 6/2020 | Hamlin |
| 2020/0188593 | A1* | 6/2020 | Carrel ................. A61M 5/3156 |
| 2020/0190179 | A1 | 6/2020 | Sigg et al. |
| 2020/0206025 | A1 | 7/2020 | Chalberg, Jr. et al. |
| 2020/0214888 | A1 | 7/2020 | Bryant et al. |
| 2020/0214889 | A1 | 7/2020 | Lerner |
| 2020/0215079 | A1 | 7/2020 | Yang et al. |
| 2020/0222233 | A1 | 7/2020 | Rotenstreich |
| 2020/0222547 | A1 | 7/2020 | Stark et al. |
| 2020/0230237 | A1 | 7/2020 | Kauvar et al. |
| 2020/0230279 | A1 | 7/2020 | Nowruzi et al. |
| 2020/0237862 | A1 | 7/2020 | Sigl |
| 2020/0237997 | A1 | 7/2020 | Brockmeyer et al. |
| 2020/0246510 | A1 | 8/2020 | Kobayashi et al. |
| 2020/0246533 | A1 | 8/2020 | Patel et al. |
| 2020/0261266 | A1 | 8/2020 | Bley et al. |
| 2020/0268899 | A1 | 8/2020 | Iyer |
| 2020/0270299 | A1 | 8/2020 | Iyer et al. |
| 2020/0276261 | A1 | 9/2020 | Zhao et al. |
| 2020/0276322 | A1 | 9/2020 | Wimley et al. |
| 2020/0277364 | A1 | 9/2020 | Yoo et al. |
| 2020/0297869 | A1 | 9/2020 | Cepeda et al. |
| 2020/0297919 | A1 | 9/2020 | Hemminger et al. |
| 2020/0306401 | A1 | 10/2020 | Cookson et al. |
| 2020/0330634 | A1 | 10/2020 | Herrig et al. |
| 2020/0368331 | A1 | 11/2020 | Borodic |
| 2020/0368445 | A1 | 11/2020 | Weber et al. |
| 2020/0375889 | A1 | 12/2020 | Hughes et al. |
| 2020/0384203 | A1 | 12/2020 | Wong et al. |
| 2020/0390724 | A1 | 12/2020 | Arkin et al. |
| 2020/0390725 | A1 | 12/2020 | Arkin et al. |
| 2020/0390907 | A1 | 12/2020 | Sieving et al. |
| 2020/0399656 | A1 | 12/2020 | Neitz et al. |
| 2020/0405808 | A1 | 12/2020 | Hohman |
| 2020/0405898 | A1 | 12/2020 | Laflamme et al. |
| 2021/0000758 | A1 | 1/2021 | Arkin et al. |
| 2021/0008158 | A1 | 1/2021 | Hohman et al. |
| 2021/0008284 | A1 | 1/2021 | Fiedler |
| 2021/0015662 | A1 | 1/2021 | Haffner et al. |
| 2021/0017266 | A1 | 1/2021 | Racine et al. |
| 2021/0022918 | A1 | 1/2021 | Prausnitz et al. |
| 2021/0023173 | A1 | 1/2021 | Yancopoulos |
| 2021/0030945 | A1 | 2/2021 | Cook et al. |
| 2021/0030946 | A1 | 2/2021 | Patel et al. |
| 2021/0047692 | A1 | 2/2021 | Ghosh et al. |
| 2021/0053165 | A1 | 2/2021 | Suzuki et al. |
| 2021/0060258 | A1 | 3/2021 | Mismar et al. |
| 2021/0077645 | A1 | 3/2021 | Mismar et al. |
| 2021/0085745 | A1 | 3/2021 | Innocenti et al. |
| 2021/0100856 | A1 | 4/2021 | Gasmi et al. |
| 2021/0106707 | A1 | 4/2021 | Shodder |
| 2021/0107999 | A1 | 4/2021 | Ehrlich et al. |
| 2021/0113660 | A1 | 4/2021 | Park et al. |
| 2021/0115124 | A1 | 4/2021 | Koenig et al. |
| 2021/0121524 | A1 | 4/2021 | Yancopoulos |
| 2021/0128840 | A1 | 5/2021 | Lilly et al. |
| 2021/0138034 | A1 | 5/2021 | Rudolf et al. |
| 2021/0139576 | A1 | 5/2021 | Osborne et al. |
| 2021/0147542 | A1 | 5/2021 | Giurleo et al. |
| 2021/0161706 | A1 | 6/2021 | Bryant et al. |
| 2021/0161971 | A1 | 6/2021 | Nagy et al. |
| 2021/0169689 | A1 | 6/2021 | Bley et al. |
| 2021/0169896 | A1 | 6/2021 | Zhao et al. |
| 2021/0169975 | A1 | 6/2021 | Rezaei |
| 2021/0170029 | A1 | 6/2021 | Gillespie et al. |
| 2021/0177951 | A1 | 6/2021 | Clube |
| 2021/0178080 | A1 | 6/2021 | Shetty et al. |

(56) References Cited

U.S. PATENT DOCUMENTS

| | | |
|---|---|---|
| 2021/0196510 A1 | 7/2021 | De Juan, Jr. et al. |
| 2021/0205410 A1 | 7/2021 | Vitti et al. |
| 2021/0207166 A1 | 7/2021 | Layton et al. |
| 2021/0212940 A1 | 7/2021 | Yamamoto et al. |
| 2021/0220173 A1 | 7/2021 | Andino et al. |
| 2021/0220435 A1 | 7/2021 | Brockmeyer et al. |
| 2021/0220436 A1 | 7/2021 | Kim et al. |
| 2021/0228539 A1 | 7/2021 | Corson et al. |
| 2021/0228574 A1 | 7/2021 | Whitcup et al. |
| 2021/0230261 A1 | 7/2021 | Yonan et al. |
| 2021/0236236 A1 | 8/2021 | Van Den Houdt et al. |
| 2021/0236649 A1 | 8/2021 | Burian et al. |
| 2021/0260047 A1 | 8/2021 | Zarnitsyn et al. |
| 2021/0260297 A1 | 8/2021 | Sawaguchi |
| 2021/0261297 A1 | 8/2021 | Bitong et al. |
| 2021/0268145 A1 | 9/2021 | Polo Martinez et al. |
| 2021/0275447 A1 | 9/2021 | Hong et al. |
| 2021/0283142 A1 | 9/2021 | Ostrow et al. |
| 2021/0283336 A1 | 9/2021 | Bryant et al. |
| 2021/0292402 A1 | 9/2021 | Sawaguchi |
| 2021/0315776 A1 | 10/2021 | Hang et al. |
| 2021/0322213 A1 | 10/2021 | Kahook |
| 2021/0322400 A1 | 10/2021 | Eriksson et al. |
| 2021/0324062 A1 | 10/2021 | Freichel et al. |
| 2021/0330826 A1 | 10/2021 | Nayar |
| 2021/0332142 A1 | 10/2021 | Yan et al. |
| 2021/0338678 A1 | 11/2021 | Zablow |
| 2021/0338871 A1 | 11/2021 | Wallace et al. |
| 2021/0340242 A1 | 11/2021 | Gekkieva et al. |
| 2021/0346552 A1 | 11/2021 | Eastep et al. |
| 2021/0347852 A1 | 11/2021 | Olson et al. |
| 2021/0353456 A1 | 11/2021 | Rotenstreich |
| 2021/0353714 A1 | 11/2021 | Graham et al. |
| 2021/0355206 A1 | 11/2021 | Ghosh et al. |
| 2021/0361769 A1 | 11/2021 | Kauvar et al. |
| 2021/0363231 A1 | 11/2021 | Famili et al. |
| 2021/0363270 A1 | 11/2021 | Park et al. |
| 2021/0369899 A1 | 12/2021 | Dufresne et al. |
| 2021/0379012 A1 | 12/2021 | Corson et al. |
| 2021/0379161 A1 | 12/2021 | Buice et al. |
| 2021/0393436 A1 | 12/2021 | Prausnitz et al. |
| 2021/0393649 A1 | 12/2021 | Ostrow et al. |
| 2021/0393738 A1 | 12/2021 | Ke |
| 2021/0393830 A1 | 12/2021 | Odim |
| 2021/0393883 A1 | 12/2021 | Shluzas |
| 2021/0395833 A1 | 12/2021 | Innocenti et al. |
| 2022/0001059 A1 | 1/2022 | Beringer et al. |
| 2022/0015945 A1 | 1/2022 | Lerner |
| 2022/0023245 A1 | 1/2022 | Snyder et al. |
| 2022/0023529 A1 | 1/2022 | Cook et al. |
| 2022/0025032 A1 | 1/2022 | Bigelow et al. |
| 2022/0031438 A1 | 2/2022 | Köhrer |
| 2022/0031952 A1 | 2/2022 | Bryant et al. |
| 2022/0054586 A1 | 2/2022 | Kim et al. |
| 2022/0071924 A1 | 3/2022 | Arkin et al. |
| 2022/0079876 A1 | 3/2022 | Blizzard et al. |
| 2022/0079889 A1 | 3/2022 | Panigrahi |
| 2022/0087863 A1 | 3/2022 | Bachelder et al. |
| 2022/0096596 A1 | 3/2022 | Hohman |
| 2022/0111015 A1 | 4/2022 | Constable et al. |
| 2022/0111093 A1 | 4/2022 | Storey et al. |
| 2022/0112278 A1 | 4/2022 | Li et al. |
| 2022/0117888 A1 | 4/2022 | Jiang et al. |
| 2022/0133866 A1 | 5/2022 | Schraermeyer |
| 2022/0133889 A1 | 5/2022 | Dranoff et al. |
| 2022/0133908 A1 | 5/2022 | Rejman et al. |
| 2022/0133981 A1 | 5/2022 | Dumont et al. |
| 2022/0142924 A1 | 5/2022 | McDonnell et al. |
| 2022/0143137 A1 | 5/2022 | Witt et al. |
| 2022/0162296 A1 | 5/2022 | Lin et al. |
| 2022/0168142 A1 | 6/2022 | Saim et al. |
| 2022/0175881 A1 | 6/2022 | Hohman et al. |
| 2022/0175883 A1 | 6/2022 | Brockmeyer et al. |
| 2022/0175979 A1 | 6/2022 | Ryan et al. |
| 2022/0220194 A1 | 7/2022 | Ziegelaar et al. |
| 2022/0226270 A1 | 7/2022 | Bazan et al. |
| 2022/0227855 A1 | 7/2022 | Tsiros et al. |
| 2022/0241623 A1 | 8/2022 | Ellison et al. |
| 2022/0249594 A1 | 8/2022 | Zhao et al. |
| 2022/0274976 A1 | 9/2022 | Peters et al. |
| 2022/0280341 A1 | 9/2022 | Prausnitz et al. |
| 2022/0280608 A1 | 9/2022 | Pakola et al. |
| 2022/0306732 A1 | 9/2022 | Bakhle et al. |
| 2022/0323681 A1 | 10/2022 | Fujiwara et al. |
| 2022/0331345 A1 | 10/2022 | Klier et al. |
| 2022/0331470 A1 | 10/2022 | Shodder et al. |
| 2022/0339108 A1 | 10/2022 | Jarrett et al. |
| 2022/0339148 A1 | 10/2022 | DeVries et al. |
| 2022/0339360 A1 | 10/2022 | Young et al. |
| 2022/0347094 A1 | 11/2022 | Blizzard et al. |
| 2022/0348646 A1 | 11/2022 | Bigelow et al. |
| 2022/0348678 A1 | 11/2022 | Kolesnick et al. |
| 2022/0354968 A1 | 11/2022 | Calias et al. |
| 2022/0355038 A1 | 11/2022 | Matsumoto |
| 2022/0356236 A1 | 11/2022 | Bigelow et al. |
| 2022/0362441 A1 | 11/2022 | Fiedler |
| 2022/0371760 A1 | 11/2022 | Redeker et al. |
| 2022/0378962 A1 | 12/2022 | Sias et al. |
| 2022/0379044 A1 | 12/2022 | Chitnis et al. |
| 2022/0380478 A1 | 12/2022 | Lederman |
| 2022/0387554 A1 | 12/2022 | Nelson |
| 2022/0395557 A1 | 12/2022 | McLaughlin et al. |
| 2022/0401390 A1 | 12/2022 | Feener et al. |
| 2023/0008104 A1 | 1/2023 | Kwan et al. |
| 2023/0010108 A1 | 1/2023 | Zhao et al. |
| 2023/0020295 A1 | 1/2023 | Fix |
| 2023/0026520 A1 | 1/2023 | Schutte et al. |
| 2023/0029307 A1 | 1/2023 | Ferrara |
| 2023/0047299 A1 | 2/2023 | Sawaguchi |
| 2023/0048205 A1 | 2/2023 | Lepschy et al. |
| 2023/0052782 A1 | 2/2023 | Hamlin et al. |
| 2023/0054032 A1 | 2/2023 | Pandey |
| 2023/0056171 A1 | 2/2023 | Krauss et al. |
| 2023/0056821 A1 | 2/2023 | Lu et al. |
| 2023/0063116 A1 | 3/2023 | Martin et al. |
| 2023/0066364 A1 | 3/2023 | Eriksson et al. |
| 2023/0078528 A1 | 3/2023 | Lerner |
| 2023/0080971 A1 | 3/2023 | Miller |
| 2023/0089914 A1 | 3/2023 | Kansara et al. |
| 2023/0090539 A1 | 3/2023 | Haffner et al. |
| 2023/0091723 A1 | 3/2023 | Weikart et al. |
| 2023/0097413 A1 | 3/2023 | Behar-Cohen et al. |
| 2023/0103552 A1 | 4/2023 | Goldberg et al. |
| 2023/0104800 A1 | 4/2023 | Li et al. |
| 2023/0113993 A1 | 4/2023 | Bryant et al. |
| 2023/0115871 A1 | 4/2023 | Zhao et al. |
| 2023/0115895 A1 | 4/2023 | Takahashi et al. |
| 2023/0118774 A1 | 4/2023 | Blizzard et al. |
| 2023/0123589 A1 | 4/2023 | Storey et al. |
| 2023/0126239 A1 | 4/2023 | Drenser et al. |
| 2023/0126447 A1 | 4/2023 | Huang et al. |
| 2023/0128124 A1 | 4/2023 | Yoshida |
| 2023/0130754 A1 | 4/2023 | Kim et al. |
| 2023/0134454 A1 | 5/2023 | Bush et al. |
| 2023/0135092 A1 | 5/2023 | Eaton et al. |
| 2023/0136536 A1 | 5/2023 | Cardinali et al. |
| 2023/0136844 A1 | 5/2023 | Lindblad et al. |
| 2023/0141766 A1 | 5/2023 | Takahashi et al. |
| 2023/0149629 A1 | 5/2023 | Hawson et al. |
| 2023/0157533 A1 | 5/2023 | Chang et al. |
| 2023/0157869 A1 | 5/2023 | Andino et al. |
| 2023/0165931 A1 | 6/2023 | Zhao et al. |
| 2023/0166092 A1 | 6/2023 | Unger et al. |
| 2023/0167170 A1 | 6/2023 | Pham et al. |
| 2023/0181357 A1 | 6/2023 | Pinchuk et al. |
| 2023/0181686 A1 | 6/2023 | Fu et al. |
| 2023/0201371 A1 | 6/2023 | Ciulla et al. |
| 2023/0201387 A1 | 6/2023 | Shieu et al. |
| 2023/0211026 A1 | 7/2023 | Kawasaki et al. |
| 2023/0226280 A1 | 7/2023 | Lerner |
| 2023/0233373 A1 | 7/2023 | Chang |
| 2023/0233375 A1 | 7/2023 | Patel et al. |
| 2023/0240643 A1 | 8/2023 | Cermak et al. |
| 2023/0248806 A1 | 8/2023 | Sigl |

(56) References Cited

U.S. PATENT DOCUMENTS

| | | |
|---|---|---|
| 2023/0248855 A1 | 8/2023 | Ludwig et al. |
| 2023/0248898 A1 | 8/2023 | Cook et al. |
| 2023/0256107 A1 | 8/2023 | Kelley, Jr. et al. |
| 2023/0263957 A1 | 8/2023 | Taha et al. |
| 2023/0265199 A1 | 8/2023 | Sapieha et al. |
| 2023/0270670 A1 | 8/2023 | Yoon et al. |
| 2023/0270903 A1 | 8/2023 | Bohnert et al. |
| 2023/0271871 A1 | 8/2023 | Chillon et al. |
| 2023/0271999 A1 | 8/2023 | Iyer et al. |
| 2023/0277375 A1 | 9/2023 | Egloff et al. |
| 2023/0279090 A1 | 9/2023 | Dengl et al. |
| 2023/0285282 A1 | 9/2023 | Blizzard et al. |
| 2023/0285678 A1 | 9/2023 | Sakhrani et al. |
| 2023/0293731 A1 | 9/2023 | Fotin-Mleczek et al. |
| 2023/0295266 A1 | 9/2023 | Vitti et al. |
| 2023/0302085 A1 | 9/2023 | Vitti et al. |
| 2023/0302156 A1 | 9/2023 | Jiang et al. |
| 2023/0303305 A1 | 9/2023 | Abrams et al. |
| 2023/0310734 A1 | 10/2023 | Tono et al. |
| 2023/0312697 A1 | 10/2023 | Sikorski et al. |
| 2023/0317288 A1 | 10/2023 | Li et al. |
| 2023/0322911 A1 | 10/2023 | Blumenkranz et al. |
| 2023/0330287 A1 | 10/2023 | Morrison |
| 2023/0330323 A1 | 10/2023 | Dominguez et al. |
| 2023/0338483 A1 | 10/2023 | Schraermeyer |
| 2023/0338599 A1 | 10/2023 | Olson et al. |
| 2023/0355544 A1 | 11/2023 | Gong et al. |
| 2023/0355818 A1 | 11/2023 | Golkowski et al. |
| 2023/0355885 A1 | 11/2023 | Shetty et al. |
| 2023/0363941 A1 | 11/2023 | Andino et al. |
| 2023/0364086 A1 | 11/2023 | Campbell et al. |
| 2023/0364289 A1 | 11/2023 | Nowruzi et al. |
| 2023/0364349 A1 | 11/2023 | Huang et al. |
| 2023/0372538 A1 | 11/2023 | Bee et al. |
| 2023/0381183 A1 | 11/2023 | Zhan et al. |
| 2023/0398233 A1 | 12/2023 | Ni et al. |
| 2023/0398251 A1 | 12/2023 | Nowruzi et al. |
| 2023/0414602 A1 | 12/2023 | Park |
| 2023/0414677 A1 | 12/2023 | Nagy et al. |
| 2023/0414770 A1 | 12/2023 | Stark et al. |
| 2023/0414788 A1 | 12/2023 | Bee et al. |
| 2023/0414800 A1 | 12/2023 | Shieu et al. |
| 2023/0414859 A1 | 12/2023 | Cook et al. |
| 2023/0416351 A1 | 12/2023 | Clemens et al. |
| 2023/0416353 A1 | 12/2023 | Osborne et al. |
| 2024/0000889 A1 | 1/2024 | Rezaei |
| 2024/0002489 A1 | 1/2024 | Ziegelaar et al. |
| 2024/0058461 A1 | 2/2024 | Iyer |

FOREIGN PATENT DOCUMENTS

| | | | |
|---|---|---|---|
| AU | 2006251769 | B2 | 7/2009 |
| AU | 2010320885 | A1 | 5/2012 |
| AU | 2010320885 | B2 | 3/2013 |
| AU | 201616239 | S | 12/2016 |
| BE | 853718 | A | 10/1977 |
| CA | 87137 | S | 7/1999 |
| CA | 2680335 | A1 | 9/2008 |
| CA | 2773015 | A1 | 4/2011 |
| CA | 2781483 | A1 | 5/2011 |
| CA | 167018 | S | 2/2017 |
| CA | 170630 | S | 2/2017 |
| CA | 175995 | S | 9/2018 |
| CA | 180221 | S | 4/2019 |
| CL | 199501972 | | 6/1995 |
| CL | 200003263 | | 11/2000 |
| CL | 20022008 | | 4/2002 |
| CL | 20022009 | | 4/2002 |
| CL | 20022010 | | 4/2002 |
| CL | 20022012 | | 4/2002 |
| CL | 20022013 | | 4/2002 |
| CL | 200400771 | | 4/2004 |
| CL | 200403345 | | 12/2004 |
| CL | 50273 | B1 | 1/2005 |
| CL | 47361 | B1 | 7/2005 |
| CL | 200703300 | | 6/2008 |
| CL | 200703301 | | 6/2008 |
| CL | 2010000322 | | 3/2011 |
| CL | 201102772 | | 2/2012 |
| CL | 201300288 | | 11/2013 |
| CL | 2013000289 | | 11/2013 |
| CL | 201800652 | | 3/2018 |
| CL | 202103018 | | 4/2020 |
| CL | 202002869 | | 5/2020 |
| CL | 202001590 | | 8/2020 |
| CL | 202002325 | | 8/2020 |
| CL | 202003174 | | 12/2020 |
| CL | 202103017 | | 11/2021 |
| CL | 202103019 | | 11/2021 |
| CL | 202401553 | | 11/2022 |
| CL | 202401555 | | 11/2022 |
| CL | 202103227 | | 5/2023 |
| CL | 202301422 | | 5/2023 |
| CL | 202302511 | | 2/2024 |
| CL | 202302512 | | 2/2024 |
| CL | 202302513 | | 2/2024 |
| CL | 202302514 | | 2/2024 |
| CL | 202302515 | | 2/2024 |
| CL | 202302516 | | 2/2024 |
| CL | 202302517 | | 2/2024 |
| CN | 1186699 | A | 7/1998 |
| CN | 1197398 | A | 10/1998 |
| CN | 1649638 | A | 8/2005 |
| CN | 2748094 | Y | 12/2005 |
| CN | 100540077 | C | 9/2009 |
| CN | 101616696 | A | 12/2009 |
| CN | 201356870 | Y | 12/2009 |
| CN | 101810870 | A | 8/2010 |
| CN | 202113444 | U | 1/2012 |
| CN | 102481418 | A | 5/2012 |
| CN | 102946930 | A | 2/2013 |
| CN | 103083698 | A | 5/2013 |
| CN | 203227124 | U | 10/2013 |
| CN | 103491985 | A | 1/2014 |
| CN | 104174058 | A | 12/2014 |
| CN | 204501944 | U | 7/2015 |
| CN | 204972542 | U | 1/2016 |
| CN | 105381520 | A | 3/2016 |
| CN | 105709308 | A | 6/2016 |
| CN | 205434581 | U | 8/2016 |
| CN | 205515660 | U | 8/2016 |
| CN | 106215286 | A | 12/2016 |
| CN | 106975125 | A | 7/2017 |
| CN | 107205843 | A | 9/2017 |
| CN | 108025137 | A | 5/2018 |
| CN | 304679488 | S | 6/2018 |
| CN | 109172952 | A | 1/2019 |
| CN | 109310821 | A | 2/2019 |
| CN | 109641107 | A | 4/2019 |
| CN | 110115657 | | 8/2019 |
| CN | 110913926 | A | 3/2020 |
| CN | 111249062 | | 6/2020 |
| CN | 111467539 | A | 7/2020 |
| CN | 213099452 | | 5/2021 |
| CN | 112972828 | | 6/2021 |
| CN | 306672665 | S | 7/2021 |
| CN | 306732751 | S | 8/2021 |
| CN | 306748066 | S | 8/2021 |
| CN | 215350708 | | 12/2021 |
| CN | 215350709 | | 12/2021 |
| CN | 215350710 | | 12/2021 |
| CN | 109310815 | | 6/2022 |
| CN | 110913926 | | 7/2022 |
| CN | 115054777 | | 9/2022 |
| CN | 109172952 | | 9/2023 |
| CN | 116710137 | | 9/2023 |
| CO | 11784-0001 | | 12/2020 |
| DE | 68509572 | | 9/1985 |
| DE | 19856167 | C1 | 5/2000 |
| DE | 10110126 | A1 | 9/2002 |
| DE | 20202005020468 | U1 | 2/2006 |
| DE | 102005008065 | A1 | 8/2006 |
| DK | 172984 | B1 | 11/1999 |
| DM | 212509 | | 4/2020 |

(56)  References Cited

FOREIGN PATENT DOCUMENTS

| | | | |
|----|---------------|----|---------|
| EP | 0208975 | A2 | 1/1987 |
| EP | 0901380 | A1 | 3/1999 |
| EP | 0904792 | A2 | 3/1999 |
| EP | 1019120 | A1 | 7/2000 |
| EP | 1061974 | A1 | 12/2000 |
| EP | 0846072 | B1 | 5/2001 |
| EP | 1283061 | A1 | 2/2003 |
| EP | 0774263 | B1 | 3/2003 |
| EP | 1368066 | A1 | 12/2003 |
| EP | 0880972 | B1 | 2/2004 |
| EP | 1061975 | B1 | 2/2004 |
| EP | 0971749 | B1 | 7/2004 |
| EP | 0937477 | B1 | 11/2004 |
| EP | 0002215510001 | | 11/2004 |
| EP | 1409046 | B1 | 3/2005 |
| EP | 0976415 | B1 | 5/2005 |
| EP | 1559443 | A1 | 8/2005 |
| EP | 1568389 | A1 | 8/2005 |
| EP | 0004943560001 | | 4/2006 |
| EP | 0004943560002 | | 4/2006 |
| EP | 0004943560003 | | 4/2006 |
| EP | 0005080490001 | | 5/2006 |
| EP | 1702636 | A1 | 9/2006 |
| EP | 1759715 | A1 | 3/2007 |
| EP | 1764115 | A1 | 3/2007 |
| EP | 1675632 | B1 | 9/2007 |
| EP | 1829577 | A2 | 9/2007 |
| EP | 1525015 | B1 | 10/2007 |
| EP | 1855742 | A1 | 11/2007 |
| EP | 1884250 | A1 | 2/2008 |
| EP | 1885414 | A1 | 2/2008 |
| EP | 1071487 | B1 | 3/2008 |
| EP | 1924309 | A1 | 5/2008 |
| EP | 1728529 | B1 | 7/2008 |
| EP | 1818069 | B1 | 9/2008 |
| EP | 1704887 | B1 | 10/2008 |
| EP | 1973592 | A2 | 10/2008 |
| EP | 1730999 | | 12/2008 |
| EP | 1855742 | B1 | 12/2008 |
| EP | 1605847 | B1 | 9/2009 |
| EP | 2121085 | A1 | 11/2009 |
| EP | 2134391 | A2 | 12/2009 |
| EP | 1488818 | B1 | 3/2010 |
| EP | 1735014 | B1 | 8/2010 |
| EP | 2094317 | B1 | 9/2010 |
| EP | 2253548 | A1 | 11/2010 |
| EP | 2253549 | A1 | 11/2010 |
| EP | 2292286 | A1 | 3/2011 |
| EP | 2139527 | B1 | 10/2011 |
| EP | 2371406 | | 10/2011 |
| EP | 2397174 | A2 | 12/2011 |
| EP | 1819368 | B1 | 3/2012 |
| EP | 1885414 | A4 | 4/2012 |
| EP | 2453928 | A1 | 5/2012 |
| EP | 1839679 | B1 | 8/2012 |
| EP | 1885414 | B1 | 11/2012 |
| EP | 2524693 | A1 | 11/2012 |
| EP | 2552349 | A1 | 2/2013 |
| EP | 1946075 | B1 | 3/2013 |
| EP | 2593369 | A1 | 5/2013 |
| EP | 2627377 | A1 | 8/2013 |
| EP | 2162652 | B1 | 9/2013 |
| EP | 1647285 | | 11/2013 |
| EP | 2125530 | B1 | 12/2013 |
| EP | 2214724 | B1 | 12/2013 |
| EP | 0024164870001 | | 3/2014 |
| EP | 2730512 | A1 | 5/2014 |
| EP | 2744523 | A2 | 6/2014 |
| EP | 2482890 | B1 | 12/2014 |
| EP | 2253549 | B1 | 3/2015 |
| EP | 2555820 | B1 | 3/2015 |
| EP | 2846754 | A1 | 3/2015 |
| EP | 2854762 | A1 | 4/2015 |
| EP | 2862587 | A1 | 4/2015 |
| EP | 1940476 | B1 | 5/2015 |
| EP | 2869813 | A1 | 5/2015 |
| EP | 2436407 | B1 | 6/2015 |
| EP | 2436408 | B1 | 6/2015 |
| EP | 1433705 | B1 | 7/2015 |
| EP | 2687478 | B1 | 8/2015 |
| EP | 2445552 | | 10/2015 |
| EP | 2939649 | A1 | 11/2015 |
| EP | 2604294 | B1 | 12/2015 |
| EP | 2488232 | B1 | 1/2016 |
| EP | 2198790 | B1 | 3/2016 |
| EP | 3009152 | A1 | 4/2016 |
| EP | 2601979 | | 5/2016 |
| EP | 3021900 | A1 | 5/2016 |
| EP | 2451489 | B1 | 6/2016 |
| EP | 3037379 | A1 | 6/2016 |
| EP | 1728529 | B2 | 7/2016 |
| EP | 1019120 | B1 | 8/2016 |
| EP | 3056223 | | 8/2016 |
| EP | 3057633 | A1 | 8/2016 |
| EP | 3070011 | A1 | 9/2016 |
| EP | 2387422 | B1 | 10/2016 |
| EP | 2949585 | B1 | 12/2016 |
| EP | 3108902 | A1 | 12/2016 |
| EP | 3116550 | A1 | 1/2017 |
| EP | 3130359 | A1 | 2/2017 |
| EP | 2394950 | B1 | 4/2017 |
| EP | 2925392 | B1 | 4/2017 |
| EP | 2407181 | B1 | 5/2017 |
| EP | 3160471 | A1 | 5/2017 |
| EP | 3162401 | A2 | 5/2017 |
| EP | 3170756 | A1 | 5/2017 |
| EP | 1973592 | B1 | 6/2017 |
| EP | 3192549 | A1 | 7/2017 |
| EP | 2944583 | B1 | 8/2017 |
| EP | 3017830 | B1 | 8/2017 |
| EP | 3199189 | A1 | 8/2017 |
| EP | 3202389 | A1 | 8/2017 |
| EP | 3202447 | A1 | 8/2017 |
| EP | 3202705 | A1 | 8/2017 |
| EP | 3213786 | A1 | 9/2017 |
| EP | 2550043 | B1 | 10/2017 |
| EP | 2666510 | B1 | 10/2017 |
| EP | 2134391 | B1 | 12/2017 |
| EP | 3108902 | | 7/2018 |
| EP | 2968729 | | 8/2018 |
| EP | 3170756 | B1 | 9/2018 |
| EP | 3377040 | | 9/2018 |
| EP | 2869813 | B1 | 11/2018 |
| EP | 3056224 | | 11/2018 |
| EP | 2451511 | B1 | 1/2019 |
| EP | 3424547 | | 1/2019 |
| EP | 2701773 | B1 | 2/2019 |
| EP | 3437678 | | 2/2019 |
| EP | 1919777 | B1 | 3/2019 |
| EP | 3452103 | A1 | 3/2019 |
| EP | 2858598 | B1 | 4/2019 |
| EP | 3470058 | | 4/2019 |
| EP | 2467084 | B1 | 7/2019 |
| EP | 2627377 | B1 | 8/2019 |
| EP | 3539597 | A1 | 9/2019 |
| EP | 3558088 | A2 | 10/2019 |
| EP | 3124005 | | 12/2019 |
| EP | 3581185 | A1 | 12/2019 |
| EP | 3065761 | B1 | 1/2020 |
| EP | 3395374 | B1 | 2/2020 |
| EP | 3600442 | A1 | 2/2020 |
| EP | 3630043 | | 4/2020 |
| EP | 3630062 | A2 | 4/2020 |
| EP | 3057633 | B1 | 5/2020 |
| EP | 3403622 | B1 | 5/2020 |
| EP | 3656373 | A1 | 5/2020 |
| EP | 2701778 | B1 | 7/2020 |
| EP | 3226895 | | 7/2020 |
| EP | 3685860 | A1 | 7/2020 |
| EP | 3687464 | A1 | 8/2020 |
| EP | 3687599 | | 8/2020 |
| EP | 3512775 | A4 | 9/2020 |
| EP | 3471780 | B1 | 10/2020 |
| EP | 3737426 | A1 | 11/2020 |

(56) References Cited

FOREIGN PATENT DOCUMENTS

| | | | |
|---|---|---|---|
| EP | 3738580 A1 | 11/2020 |
| EP | 3763384 | 1/2021 |
| EP | 3369437 B1 | 2/2021 |
| EP | 3452013 B1 | 2/2021 |
| EP | 3536310 | 4/2021 |
| EP | 3381444 | 5/2021 |
| EP | 2991706 B1 | 6/2021 |
| EP | 3363470 B1 | 6/2021 |
| EP | 3782807 | 6/2021 |
| EP | 3679922 | 7/2021 |
| EP | 3291812 B1 | 9/2021 |
| EP | 3484531 | 11/2021 |
| EP | 3685826 | 11/2021 |
| EP | 3193829 B1 | 12/2021 |
| EP | 3656373 | 2/2022 |
| EP | 3777834 | 2/2022 |
| EP | 3472317 B1 | 3/2022 |
| EP | 4025272 | 7/2022 |
| EP | 4028128 A1 | 7/2022 |
| EP | 4031208 | 7/2022 |
| EP | 3490732 B1 | 8/2022 |
| EP | 3875377 A4 | 8/2022 |
| EP | 2604295 | 9/2022 |
| EP | 3116553 | 9/2022 |
| EP | 4065150 A1 | 10/2022 |
| EP | 2887982 B1 | 11/2022 |
| EP | 3918105 B1 | 1/2023 |
| EP | 3934707 B1 | 1/2023 |
| EP | 2817033 B1 | 2/2023 |
| EP | 3897595 B1 | 3/2023 |
| EP | 4153494 | 3/2023 |
| EP | 2760509 | 4/2023 |
| EP | 3380040 B1 | 4/2023 |
| EP | 3685828 B1 | 4/2023 |
| EP | 3858405 | 4/2023 |
| EP | 4159220 A1 | 4/2023 |
| EP | 3600454 B1 | 6/2023 |
| EP | 4188467 A1 | 6/2023 |
| EP | 4201441 | 6/2023 |
| EP | 3384049 B1 | 8/2023 |
| EP | 4218862 | 8/2023 |
| EP | 4225235 A1 | 8/2023 |
| EP | 4245312 A1 | 9/2023 |
| EP | 4245336 A1 | 9/2023 |
| EP | 4249015 A1 | 9/2023 |
| EP | 4251204 A1 | 10/2023 |
| EP | 4255530 A1 | 10/2023 |
| EP | 4257509 | 10/2023 |
| EP | 4262894 | 10/2023 |
| EP | 3233056 B1 | 11/2023 |
| EP | 3681448 B1 | 11/2023 |
| EP | 4281123 A1 | 11/2023 |
| EP | 3746156 B1 | 12/2023 |
| EP | 3634543 | 6/2024 |
| FR | 711644 A | 9/1931 |
| FR | 1216753 A | 4/1960 |
| FR | 1412547 A | 10/1965 |
| FR | 2536285 A1 | 5/1984 |
| FR | 2561925 A3 | 10/1985 |
| FR | D053933-0001 | 10/2000 |
| GB | 1230522 A | 5/1971 |
| GB | 1550308 A | 8/1979 |
| IL | 70802 | 6/2023 |
| IN | 342357001 | 4/2021 |
| IN | 342359001 | 4/2021 |
| IN | 356804001 | 1/2022 |
| IN | 356808001 | 1/2022 |
| IN | 342358001 | 4/2022 |
| IT | MI20102322 A1 | 6/2012 |
| JP | S4824842 U | 3/1973 |
| JP | S54-117736 A | 9/1978 |
| JP | 55-107113 A | 8/1980 |
| JP | 60-175249 A | 9/1985 |
| JP | 1-121057 A | 5/1989 |
| JP | 4-503026 A | 6/1992 |
| JP | 74330 H | 1/1995 |
| JP | 7-7650 | 2/1995 |
| JP | H07244442 A | 9/1995 |
| JP | H11151301 A | 6/1999 |
| JP | 2000-197700 A | 7/2000 |
| JP | 2000202027 A | 7/2000 |
| JP | 2001-218843 A | 8/2001 |
| JP | 2001-526097 | 12/2001 |
| JP | 2003-199828 A | 7/2003 |
| JP | 2004-500201 A | 1/2004 |
| JP | 2004-49726 A | 2/2004 |
| JP | 2005-312699 A | 11/2005 |
| JP | 2006-26280 A | 2/2006 |
| JP | 4191409 B2 | 12/2008 |
| JP | 2008307237 A | 12/2008 |
| JP | 2009011481 A | 1/2009 |
| JP | 2009284951 A | 12/2009 |
| JP | 2010201055 A | 9/2010 |
| JP | 2010202448 A | 9/2010 |
| JP | 2011050601 A | 3/2011 |
| JP | 2012-85813 A | 5/2012 |
| JP | 2012179240 A | 9/2012 |
| JP | 2012528642 A | 11/2012 |
| JP | 2012-245180 A | 12/2012 |
| JP | 5163882 | 3/2013 |
| JP | 2013511309 A | 4/2013 |
| JP | 2014-4041 A | 1/2014 |
| JP | 2014515683 A | 7/2014 |
| JP | 5718157 B2 | 5/2015 |
| JP | 2015-123296 A | 7/2015 |
| JP | 5744927 | 7/2015 |
| JP | 2015-523867 A | 8/2015 |
| JP | 1531421 S | 8/2015 |
| JP | 2015-171514 | 10/2015 |
| JP | 5801314 B2 | 10/2015 |
| JP | 5907874 B2 | 4/2016 |
| JP | 1552403 S | 6/2016 |
| JP | 2016-120078 A | 7/2016 |
| JP | 2016124594 A | 7/2016 |
| JP | 5978742 B2 | 8/2016 |
| JP | 2016-538960 A | 12/2016 |
| JP | 2017-60837 | 3/2017 |
| JP | 6144264 | 6/2017 |
| JP | 6313038 | 4/2018 |
| JP | 1646523 S | 11/2019 |
| JP | 2020522351 A | 7/2020 |
| JP | 6781546 | 11/2020 |
| JP | 6920269 | 8/2021 |
| JP | D1700933 S | 11/2021 |
| JP | D1701001 S | 11/2021 |
| JP | 2023506180 | 2/2023 |
| JP | 7244442 | 3/2023 |
| JP | 2023071962 | 5/2023 |
| JP | 2023550458 | 12/2023 |
| KR | 20050004800 A | 1/2005 |
| KR | 100721549 B1 | 5/2007 |
| KR | 1020110022607 A | 2/2014 |
| KR | 10-1510680 B1 | 4/2015 |
| KR | 20150119092 A | 10/2015 |
| KR | 101774823 | 9/2017 |
| KR | 102232708 | 3/2021 |
| KR | 102288287 | 8/2021 |
| KR | 102299177 | 9/2021 |
| KR | 102341670 | 12/2021 |
| KR | 20220085906 | 6/2022 |
| MX | 03007940 A | 10/2004 |
| RU | 2488410 C2 | 7/2013 |
| RU | 2012125349 A | 12/2013 |
| SE | D060555-0002 | 1/2002 |
| SG | 30202008659 T | 12/2020 |
| SG | 30202008662 P | 12/2020 |
| SG | 30202008663 | 12/2020 |
| TW | M261222 U | 4/2005 |
| TW | 201215424 A | 4/2012 |
| TW | 201600133 A | 1/2016 |
| TW | D187080 S | 12/2017 |
| TW | 1632920 | 8/2018 |
| TW | 201831212 A | 9/2018 |
| TW | 201900234 A | 1/2019 |

(56)     References Cited

FOREIGN PATENT DOCUMENTS

| | | |
|---|---|---|
| TW | 1720632 | 3/2021 |
| TW | D215156 S | 11/2021 |
| TW | 202144033 A | 12/2021 |
| TW | D215855 S | 12/2021 |
| TW | D216479 S | 1/2022 |
| TW | D216480 S | 1/2022 |
| TW | 202237181 | 10/2022 |
| VN | 30028936000 | 12/2017 |
| VN | 30028632000 | 7/2018 |
| WO | WO-8601728 A2 | 3/1986 |
| WO | 9317726 A1 | 9/1993 |
| WO | WO-9320784 A1 | 10/1993 |
| WO | 9504563 A1 | 2/1995 |
| WO | 9512418 A1 | 5/1995 |
| WO | 9530444 | 11/1995 |
| WO | WO-9626754 A2 | 9/1996 |
| WO | WO-9630046 A1 | 10/1996 |
| WO | 9701362 A2 | 1/1997 |
| WO | 9708054 A1 | 3/1997 |
| WO | 9709080 A1 | 3/1997 |
| WO | 9744068 A1 | 11/1997 |
| WO | 9805366 | 2/1998 |
| WO | 9807453 A1 | 2/1998 |
| WO | 9819715 A1 | 5/1998 |
| WO | 9848856 A1 | 11/1998 |
| WO | 9856438 A1 | 12/1998 |
| WO | WO-9856439 A1 | 12/1998 |
| WO | 9915215 A1 | 4/1999 |
| WO | 9927971 A2 | 6/1999 |
| WO | 9945984 A1 | 9/1999 |
| WO | 9945985 A1 | 9/1999 |
| WO | 0154756 | 8/2001 |
| WO | WO-0178812 A1 | 10/2001 |
| WO | 0195959 A1 | 12/2001 |
| WO | WO-02072157 A1 | 9/2002 |
| WO | WO-03004080 A1 | 1/2003 |
| WO | 03057285 A2 | 7/2003 |
| WO | WO-03077976 A1 | 9/2003 |
| WO | WO-03080160 A1 | 10/2003 |
| WO | 03097133 A1 | 11/2003 |
| WO | 03057285 A3 | 12/2003 |
| WO | 2004032996 A2 | 4/2004 |
| WO | WO-2004035113 A2 | 4/2004 |
| WO | 2004032996 A3 | 7/2004 |
| WO | 2005032627 A1 | 4/2005 |
| WO | WO-2005067984 A1 | 7/2005 |
| WO | 2006047325 A1 | 5/2006 |
| WO | 2006089734 A1 | 8/2006 |
| WO | 2006130098 A1 | 12/2006 |
| WO | 2006130100 A1 | 12/2006 |
| WO | 2007002052 A2 | 1/2007 |
| WO | WO-2007011873 A2 | 1/2007 |
| WO | 2007024957 A1 | 3/2007 |
| WO | WO-2007035621 A1 * | 3/2007 .............. A61M 5/19 |
| WO | 2007083034 A2 | 7/2007 |
| WO | WO-2007084765 A2 | 7/2007 |
| WO | WO-2007087457 A2 | 8/2007 |
| WO | 2007103278 A2 | 9/2007 |
| WO | WO-2007112675 A1 | 10/2007 |
| WO | 2007130852 A2 | 11/2007 |
| WO | WO-2008051561 A2 | 5/2008 |
| WO | WO-2008058666 A1 | 5/2008 |
| WO | WO-2008058668 A1 | 5/2008 |
| WO | WO-2008063932 A2 | 5/2008 |
| WO | 2008083875 A1 | 7/2008 |
| WO | WO-2008101985 A2 | 8/2008 |
| WO | 2008110890 A1 | 9/2008 |
| WO | 2008111893 A1 | 9/2008 |
| WO | 2008112472 A2 | 9/2008 |
| WO | 2008112472 A3 | 11/2008 |
| WO | 2009007997 A2 | 1/2009 |
| WO | 2009092430 A1 | 7/2009 |
| WO | WO-2009086112 A2 | 7/2009 |
| WO | WO-2009089409 A2 | 7/2009 |
| WO | WO-2009155724 A2 | 12/2009 |
| WO | WO-2010081838 A2 | 7/2010 |
| WO | WO-2010085542 A2 | 7/2010 |
| WO | WO-2010088548 A1 | 8/2010 |
| WO | WO-2010127029 A1 | 11/2010 |
| WO | WO-2010127449 A1 | 11/2010 |
| WO | 2010149466 A2 | 12/2010 |
| WO | WO-2011006877 A1 * | 1/2011 .......... A61L 2/0094 |
| WO | 2011032513 A1 | 3/2011 |
| WO | 2011037437 A2 | 3/2011 |
| WO | WO-2011038487 A1 | 4/2011 |
| WO | WO-2011039211 A1 | 4/2011 |
| WO | 2011057335 | 5/2011 |
| WO | WO-2011061313 A1 | 5/2011 |
| WO | 2011069064 A1 | 6/2011 |
| WO | WO-2011073174 A1 | 6/2011 |
| WO | WO-2011073176 A1 | 6/2011 |
| WO | 2011081867 A2 | 7/2011 |
| WO | WO-2011085288 A2 | 7/2011 |
| WO | 2011117878 A1 | 9/2011 |
| WO | WO-2011115428 A2 | 9/2011 |
| WO | 2011125133 A1 | 10/2011 |
| WO | 2011133097 A1 | 10/2011 |
| WO | 2011137437 A2 | 11/2011 |
| WO | 2012007056 A1 | 1/2012 |
| WO | WO-2012003437 A1 | 1/2012 |
| WO | WO-2012019176 A2 | 2/2012 |
| WO | 2012049141 A1 | 4/2012 |
| WO | WO-2012055884 A1 | 5/2012 |
| WO | 2012074768 A1 | 6/2012 |
| WO | 2012075547 A1 | 6/2012 |
| WO | WO-2012097019 A1 | 7/2012 |
| WO | 2012118687 A1 | 9/2012 |
| WO | 2012125132 A1 | 9/2012 |
| WO | 2012158095 A1 | 11/2012 |
| WO | WO-2012148717 A1 | 11/2012 |
| WO | WO-2012149040 A2 | 11/2012 |
| WO | 2012/166287 A1 | 12/2012 |
| WO | 2012173562 A1 | 12/2012 |
| WO | 2013008426 A1 | 1/2013 |
| WO | WO-2013028537 A2 | 2/2013 |
| WO | 2013034986 A2 | 3/2013 |
| WO | WO-2012019139 A9 | 3/2013 |
| WO | WO-2013048310 A1 | 4/2013 |
| WO | 2013126260 A1 | 8/2013 |
| WO | WO-2013126799 A1 | 8/2013 |
| WO | WO-2013151904 A1 | 10/2013 |
| WO | 2013178771 A1 | 12/2013 |
| WO | 2013184270 A1 | 12/2013 |
| WO | 2013185776 A1 | 12/2013 |
| WO | 2014005728 A1 | 1/2014 |
| WO | 2014/033184 A1 | 3/2014 |
| WO | WO-2014036009 A1 | 3/2014 |
| WO | 2014049712 A1 | 4/2014 |
| WO | 2014049714 A1 | 4/2014 |
| WO | 2014068283 A2 | 5/2014 |
| WO | 2014073618 A1 | 5/2014 |
| WO | 2014079779 A1 | 5/2014 |
| WO | WO-2014074823 A1 | 5/2014 |
| WO | 2014102987 A1 | 7/2014 |
| WO | WO-2014105978 A1 | 7/2014 |
| WO | WO-2014162551 A1 | 10/2014 |
| WO | 2014187779 A1 | 11/2014 |
| WO | WO-2014179698 A2 | 11/2014 |
| WO | 2014/203181 A1 | 12/2014 |
| WO | WO-2014203182 A1 | 12/2014 |
| WO | WO-2014203183 A1 | 12/2014 |
| WO | 2015007808 A1 | 1/2015 |
| WO | WO-2015006734 A1 | 1/2015 |
| WO | WO-2015007811 A1 | 1/2015 |
| WO | 2015/032800 A2 | 3/2015 |
| WO | 2015031414 A2 | 3/2015 |
| WO | WO-2015033280 A1 | 3/2015 |
| WO | 2015047758 A2 | 4/2015 |
| WO | 2015055608 A1 | 4/2015 |
| WO | WO-2015045180 A1 | 4/2015 |
| WO | WO-2015069668 A1 | 5/2015 |
| WO | WO-2015073895 A1 | 5/2015 |
| WO | 2015047758 A3 | 7/2015 |
| WO | 2015135887 A1 | 9/2015 |

(56)           References Cited

FOREIGN PATENT DOCUMENTS

| | | | |
|---|---|---|---|
| WO | 2015157484 A1 | 10/2015 | |
| WO | 2015164413 A1 | 10/2015 | |
| WO | WO-2015164626 A2 | 10/2015 | |
| WO | WO-2015168619 A1 | 11/2015 | |
| WO | WO-2015195842 A1 | 12/2015 | |
| WO | WO-2015196085 A2 | 12/2015 | |
| WO | WO-2016033701 A1 | 3/2016 | |
| WO | WO-2016042162 A1 | 3/2016 | |
| WO | 2016052037 A1 | 4/2016 | |
| WO | 2016064288 A1 | 4/2016 | |
| WO | 2016068333 A1 | 5/2016 | |
| WO | WO-2016073918 A1 | 5/2016 | |
| WO | 2016094387 A2 | 6/2016 | |
| WO | 2016094658 A1 | 6/2016 | |
| WO | 2016140449 A1 | 9/2016 | |
| WO | 2016165976 A1 | 10/2016 | |
| WO | 2016168156 A1 | 10/2016 | |
| WO | 2016169718 A1 | 10/2016 | |
| WO | 2016180855 A1 | 11/2016 | |
| WO | 2016186502 A2 | 11/2016 | |
| WO | 2016187080 A1 | 11/2016 | |
| WO | 2016191535 A2 | 12/2016 | |
| WO | 2016193620 A1 | 12/2016 | |
| WO | 2016193624 A1 | 12/2016 | |
| WO | 2016199133 A1 | 12/2016 | |
| WO | 2017012789 A1 | 1/2017 | |
| WO | WO-2017014630 A1 | 1/2017 | |
| WO | 2017027876 A1 | 2/2017 | |
| WO | 2017030195 A1 | 2/2017 | |
| WO | WO-2017025928 A2 | 2/2017 | |
| WO | WO-2017046358 A1 | 3/2017 | |
| WO | 2017055462 A1 | 4/2017 | |
| WO | 2017057477 A1 | 4/2017 | |
| WO | 2017062407 A1 | 4/2017 | |
| WO | 2017062930 A1 | 4/2017 | |
| WO | 2017062931 A1 | 4/2017 | |
| WO | 2017062933 A1 | 4/2017 | |
| WO | WO-2017062304 A1 | 4/2017 | |
| WO | 2017087798 A1 | 5/2017 | |
| WO | WO-2017087871 A1 * | 5/2017 | ........... A61F 9/0017 |
| WO | 2017089197 A1 | 6/2017 | |
| WO | 2017103954 A1 | 6/2017 | |
| WO | 2017119582 A1 | 7/2017 | |
| WO | 2017126550 A1 | 7/2017 | |
| WO | WO-2017120601 A1 | 7/2017 | |
| WO | 2017129232 A1 | 8/2017 | |
| WO | 2017129685 A1 | 8/2017 | |
| WO | 2017137665 A1 | 8/2017 | |
| WO | 2017139375 A1 | 8/2017 | |
| WO | 2017139573 A1 | 8/2017 | |
| WO | 2017158805 A1 | 9/2017 | |
| WO | WO-2017158366 A2 | 9/2017 | |
| WO | WO-2017180480 A1 | 10/2017 | |
| WO | WO-2017191306 A1 | 11/2017 | |
| WO | WO-2017204787 A1 | 11/2017 | |
| WO | WO-2018031913 A1 | 2/2018 | |
| WO | WO-2018085759 A1 | 5/2018 | |
| WO | WO-2018085768 A2 | 5/2018 | |
| WO | WO-2018111862 A1 | 6/2018 | |
| WO | WO-2018141634 A1 | 8/2018 | |
| WO | 2018182929 A1 | 10/2018 | |
| WO | 2018218013 A2 | 11/2018 | |
| WO | WO-2018204140 A1 | 11/2018 | |
| WO | WO-2018215580 A1 | 11/2018 | |
| WO | WO-2018217995 A1 | 11/2018 | |
| WO | WO-2018224640 A1 | 12/2018 | |
| WO | WO-2018224644 A1 | 12/2018 | |
| WO | WO-2018232408 A1 | 12/2018 | |
| WO | WO-2019040397 A1 | 2/2019 | |
| WO | 2019063785 A1 | 4/2019 | |
| WO | 2019063786 A1 | 4/2019 | |
| WO | 2019084203 A1 | 5/2019 | |
| WO | WO-2019108770 A1 | 6/2019 | |
| WO | WO-2019175727 A1 | 9/2019 | |
| WO | WO-2019197361 A1 | 10/2019 | |
| WO | WO-2019217927 A1 | 11/2019 | |
| WO | WO-2020160256 A1 | 8/2020 | |
| WO | 2020183696 A1 | 9/2020 | |
| WO | WO-2020180951 A1 | 9/2020 | |
| WO | WO-2020247686 A1 * | 12/2020 | .......... A61M 5/3135 |
| WO | 2021021925 A1 | 2/2021 | |
| WO | 2021056020 A1 | 3/2021 | |
| WO | WO-2021046070 A1 | 3/2021 | |
| WO | WO-2021048779 A2 | 3/2021 | |
| WO | WO-2021050649 A1 | 3/2021 | |
| WO | WO-2021072265 A1 | 4/2021 | |
| WO | WO-2021108255 A1 | 6/2021 | |
| WO | WO-2021119544 A1 | 6/2021 | |
| WO | WO-2021168218 A1 | 8/2021 | |
| WO | WO-2021178899 A1 | 9/2021 | |
| WO | WO-2021183555 A1 | 9/2021 | |
| WO | WO-2021195163 A1 | 9/2021 | |
| WO | WO-2021240488 A1 | 12/2021 | |
| WO | WO-2021252647 A1 | 12/2021 | |
| WO | WO-2021252962 A1 | 12/2021 | |
| WO | WO-2022005100 A1 | 1/2022 | |
| WO | WO-2022011323 A1 | 1/2022 | |
| WO | WO-2022013172 A1 | 1/2022 | |
| WO | 2022034395 A1 | 2/2022 | |
| WO | WO-2022056326 A1 | 3/2022 | |
| WO | WO-2022066788 A1 | 3/2022 | |
| WO | WO-2022067330 A1 | 3/2022 | |
| WO | 2022081276 A1 | 4/2022 | |
| WO | WO-2022076549 A1 | 4/2022 | |
| WO | WO-2022076591 A1 | 4/2022 | |
| WO | WO-2022076938 A1 | 4/2022 | |
| WO | WO-2022093818 A1 | 5/2022 | |
| WO | WO-2022094340 A1 | 5/2022 | |
| WO | WO-2022111379 A1 | 6/2022 | |
| WO | WO-2022112957 A1 | 6/2022 | |
| WO | WO-2022131789 A1 | 6/2022 | |
| WO | WO-2022175601 A1 | 8/2022 | |
| WO | 2022195029 A1 | 9/2022 | |
| WO | 2022202382 A1 | 9/2022 | |
| WO | WO-2022183418 A1 | 9/2022 | |
| WO | WO-2022201084 A1 | 9/2022 | |
| WO | WO-2022204374 A1 | 9/2022 | |
| WO | 2022217192 A1 | 10/2022 | |
| WO | WO-2022212360 A1 | 10/2022 | |
| WO | WO-2022217110 A1 | 10/2022 | |
| WO | WO-2022220602 A1 | 10/2022 | |
| WO | WO-2022221315 A1 | 10/2022 | |
| WO | WO-2022221395 A1 | 10/2022 | |
| WO | WO-2022221537 A1 | 10/2022 | |
| WO | WO-2022223140 A1 | 10/2022 | |
| WO | WO-2022226347 A1 | 10/2022 | |
| WO | 2022229741 A1 | 11/2022 | |
| WO | 2022241048 A1 | 11/2022 | |
| WO | WO-2022229932 A1 | 11/2022 | |
| WO | WO-2022232790 A1 | 11/2022 | |
| WO | WO-2022246476 A1 | 11/2022 | |
| WO | 2022272257 | 12/2022 | |
| WO | WO-2022251710 A2 | 12/2022 | |
| WO | WO-2022268048 A1 | 12/2022 | |
| WO | WO-2023014892 A1 | 2/2023 | |
| WO | WO-2023039458 A1 | 3/2023 | |
| WO | WO-2023041697 A1 | 3/2023 | |
| WO | WO-2023047375 A2 | 3/2023 | |
| WO | WO-2023054503 A1 | 4/2023 | |
| WO | 2023073622 A1 | 5/2023 | |
| WO | WO-2023081528 A1 | 5/2023 | |
| WO | WO-2023091955 A1 | 5/2023 | |
| WO | 2023097258 A1 | 6/2023 | |
| WO | 2023114123 | 6/2023 | |
| WO | 2023117876 A1 | 6/2023 | |
| WO | 2023123799 A1 | 7/2023 | |
| WO | WO-2023130081 A1 | 7/2023 | |
| WO | WO-2023133058 A2 | 7/2023 | |
| WO | 2023148750 A1 | 8/2023 | |
| WO | 2023150685 A1 | 8/2023 | |
| WO | 2023157540 A1 | 8/2023 | |
| WO | WO-2023150566 A1 | 8/2023 | |
| WO | WO-2023153535 A1 | 8/2023 | |
| WO | WO-2023158990 A1 | 8/2023 | |

(56) References Cited

FOREIGN PATENT DOCUMENTS

| WO | 2023167982 A2 | 9/2023 |
| WO | WO-2023171360 A1 | 9/2023 |
| WO | WO-2023172585 A1 | 9/2023 |
| WO | WO-2023173055 A2 | 9/2023 |
| WO | WO-2023173088 A1 | 9/2023 |
| WO | WO-2023173093 A1 | 9/2023 |
| WO | WO-2023175549 A1 | 9/2023 |
| WO | WO-2023177691 A1 | 9/2023 |
| WO | WO-2023180450 A1 | 9/2023 |
| WO | WO-2022260939 A9 | 10/2023 |
| WO | 2023228073 A1 | 11/2023 |
| WO | WO-2023212273 A1 | 11/2023 |

OTHER PUBLICATIONS

Maitri Pancholy et al., "Endophthalmitis following Intravitreal Anti-Vascular Endothelial Growth Factor Therapy: Changes in Incidence and Outcomes over a 9-Year Period", Current Eye Research, 2021, vol. 46, No. 9, pp. 1370-1377.

Dilsher S. Dhoot, MD et al., "Rates of Suspected Endophthalmitis Following Intravitreal Injections in Clinical Practices In the United States", Clinical Science, © Ophthalmic Surgery, Lasers & Imaging Retina, Jun. 2021, vol. 52, No. 6, pp. 312-318.

Accura Xtreme White, Xtreme Class, 3D Systems, Manufacturing the future, 2015, 1 page.

Chilean Office Action issued on Jan. 26, 2022, in Chilean Patent Application No. 01590- 2020 (16 Pages, in Spanish).

Chinese Office Action issued on Jun. 24, 2022 in Chinese Patent Application No. 201880080564.7 (9 Pages, in Chinese).

Chinese Office Action issued on Nov. 26, 2021, in Chinese Patent Application No. 201880080564.7 (8 pages, in Chinese).

Columbian Office Action dated Apr. 13, 2022, in Columbian Patent Application No. NC2020/0007231 (30 pages, in Spanish with English translation).

Dilution Table 3Dose Unit Dose Injector, Instructions for Use, www.tsklab.com, 1 page.

Gattex (teduglutide) for Injection, Instructions for Use, 2019, 2 pages.

Indian Office Action issued on May 18, 2022, in Indian Patent Application No. 202047023695 (7 pages, in English).

International Preliminary Report on Patentability issued on May 6, 2021, in International Patent Application No. PCT/US2020/036200 {12 pages, in English).

International Search Report and Written Opinion dated Oct. 26, 2020, in International Patent Application No. PCT/US2020/036200 (19 pages, in English).

International Search Report and Written Opinion for Application No. PCT/US2018/065192, mailed on Jun. 4, 2019, 22 pages.

Japanese Notice of Allowance dated Oct. 25, 2021, in Japanese Patent Application No. 2020-026268 (4 pages, in Japanese with partial English translation).

Krader, Cheryl Guttman. "Pearls for Selecting a Syringe for Intravitreal Injection," Ophthamology Times, Jan. 2021, pp. 1 & 25, 52 p.

Lucentis Dosage, Generic name: Ranibizumab 10mg in 1mL, Dosage form: injection, solution, Lucentis Dosage Guide—Drugs. com , [retrieved on May 28, 2020]. Retrieved from the Internet: (URL: https://www.drugs.com/dosage/lucentis.html), 7 pages.

Lucentis Ranibizumab Injection, Prefilled Syringe Administration Preparation, Genentech, 2018, 30 pages.

New, Novel Prefillable Microfilter Injection Device for Intraocular Therapeutics, Congruence Medical Solutions INC, Gautam Shetty, phD , 2018, 19 Pages.

Proven and innovative injection systems delivering your product's potential, Vetter—Packaging systems and technologies for pharmaceutical products, Retrieved from Internet: (https://www.vetter-pharma.com/en/clinical-manufacturing/packaging/systems), 7 pages.

Taiwanese Search Report dated Sep. 8, 2021, in Taiwanese Patent Application No. 109306859 {1 Page, in English).

U.S. Appl. No. 62/467,065, inventor Wei; M., filed on Mar. 3, 2017.

Office Action in Colombian Application No. NC2020/0007231, dated Apr. 13, 2023, 38 pages (in Spanish with English translation).

Office Action in Colombian Application No. NC2023/0001752, dated Apr. 18, 2023, 33 pages (in Spanish with English translation).

Office Action in Colombian Application No. NC/2023/0001925, dated Apr. 18, 2023, 17 pages (in Spanish with English translation).

Office Action in Colombian Application No. NC2020/0001926, dated Jun. 23, 2023, 11 pages (in Spanish with English translation).

Decision of Patent Grant in Korean Application No. 10-2020-7019695, dated Aug. 11, 2023, 4 pages (in Korean with English translation).

International Search Report in International Patent Application No. PCT/USUS2022/076090, dated Dec. 6, 2022, 3 pages.

Sassalos et al., "Prefilled syringes for intravitreal drug delivery", Clinical Ophthalmology, vol. 13, pp. 701-706, doi: 10.2147/OPTH. S169044, Apr. 23, 2019.

Schargus et al., "Comparison of Syringes With Intravitreal Anti-VEGF Drugs: Particle Burden and Protein Aggregates in Brolucizumab, Aflibercept and Bevacizumab", Translational Vision Science Technoloy, vol. 10, No. 9, p. 21, doi: 10.1167/tvst.10.9.21, Aug. 18, 2021.

Subhi et al., "Prefilled syringes for intravitreal injection reduce preparation time", Danish Medical Journal, PMID: 27034182, Apr. 1, 2016.

Parenky et al., "Container Closure and Delivery Considerations for Intravitreal Drug Administration", AAPS PharmSciTech. Vol. 22, No. 3, doi: 10.1208/s12249-021-01949-4, Mar. 11, 2021.

"Regeneron 2019 Annual Report", regenron.com, 2019, Slides 14 and 14, XP002808067, retrieved from the Internet: URL:https://investor.regeneron.com/static-files/d2933d3d-f409-47e4-a637-c5ca52cf3b87, Published 2019, Retrieved Nov. 23, 2022.

Philip et al., "The Impact of Prefilled Syringes on Endophthalmitis Following Intravitreal Injection of Ranibizumab", American Journal of Ophthalmology United States, vol. 199, First Paragraph, DOI: 10.1016/J.AJO.2018.11.023, Feb. 28, 2019.

Search Report in Eurasian Patent Application No. 202391326, dated Sep. 15, 2023, 6 pages (in Russian with English translation).

Taiwanese Search Report for Application No. 112302459, mailed on Oct. 26, 2023, 4 pages.

Regeneron Pharmaceuticals, Inc.; Instructions, Date of Publication Oct. 2022; www.regeneron.com/downloads/dupixent_ifu-100-spanish. pdf (3 pages).

Bayer AG Jeringa Precargada dated Nov. 26, 2012; https://nomenclator. org/med/eylea-40-mg-ml-solucion (4 pages).

Colucciello, Michael, "Prefilled Syringe Delivery of Intravitreal Anti-VEGF Medications", 9th paragraph, XP002808066, retrieved from the Internet: URL: https://www.retinalphysician.com/issues/2019/march-2019/prefilled%20syringe-delivery-of-intravitreal-anti-veretinalphysician.com, Mar. 1, 2019, 06 pages.

Kocabora M.S., et al., "Intravitreal Silicone Oil Droplets Following Pegaptanib Injection," Acta Ophthalmologica, 88(2):e44-e45, Mar. 2010.

Kunjukunju N., et al., "Bilateral Avastin Injections," ARVO Annual Meeting Abstract, Investigative Ophthalmology & Visual Science Apr. 2009, vol. 50, 1876, 02 pages.

"Assessing the Impact on Drug Dose Delivery of Passive Safety Devices," Copyright © 2016 Frederick Furness Publishing Ltd., 4 pages.

"Special Feature—Injection Devices: Manufacturers Focus on 21st Century Technology While Still Tackling Traditional Challenges" (URL: https://drug-dev.com/special-feature-injection-devices-manufacturers-focus-on-21st-century-technology-while-still-tackling-traditional-challenges/); Contract Services, Drug Delivery, Featured Articles, Injection Devices, Sep. 2015, 24 pages.

Japanese Notice of Allowance issued in Japanese Patent Application No. 2023-084253 on Feb. 28, 2025 (3 pages; 3 pages English translation).

Regeneron prefilled syringe, posted on market-scope.com, posting date Dec. 13, 2019, retrieved Apr. 4, 2025, online, URL: https://www.market-scope.com/pages/news/4010/regeneron-s-eylea-injection-prefilled-syringe-now-available(Year: 2019).

English Translation of Matsuo et al. (Year: 2020).

(56)        References Cited

OTHER PUBLICATIONS

Fischer S.K., et al., "Specific Immune Response to Phospholipase B-Like 2 Protein, a Host Cell Impurity in Lebrikizumab Clinical Material," The AAPS Journal, Oct. 2016, vol. 19(1), pp. 254-263.
International search report and Written opinion for the application PCT/US2018/021013 dated May 11, 2018 (9 pages).
International Search Report in International Application No. PCT/US2022/071436, mailed Jul. 25, 2022 (7 pages).
Machine Translation of JP2009284951 (Year: 2009).

* cited by examiner

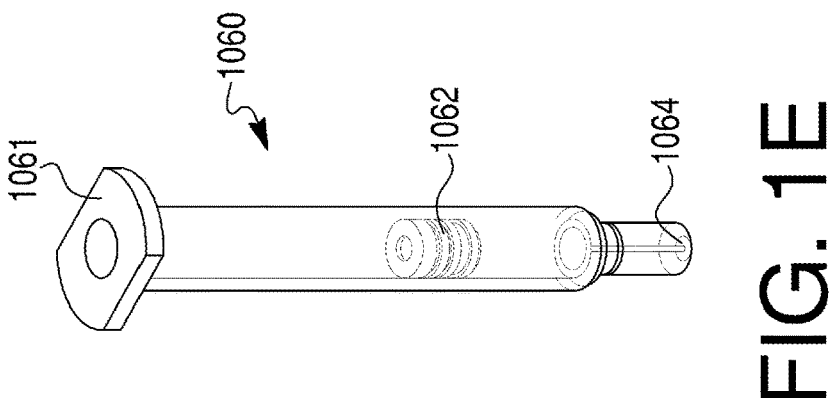
FIG. 1E
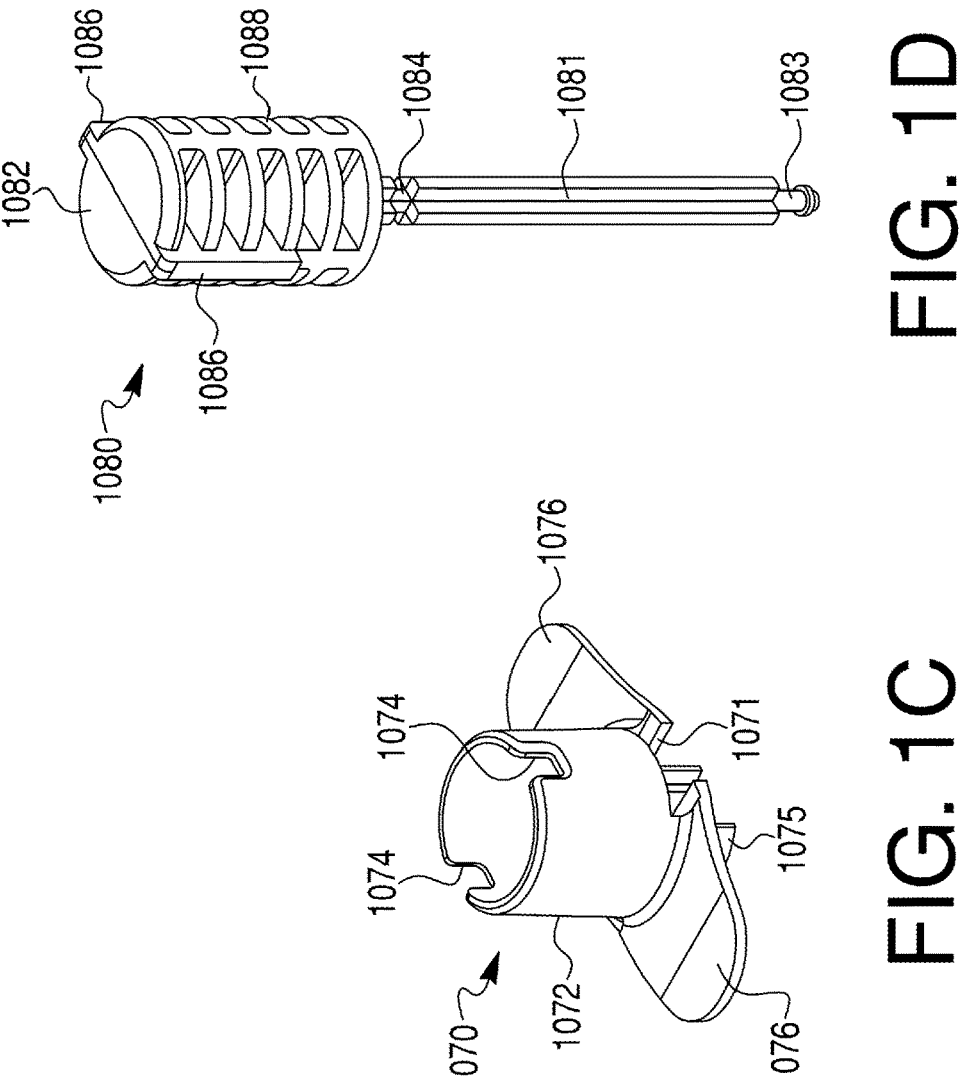
FIG. 1D
FIG. 1C

1080

1085

1081

1070

1092 1073

1070 1073

1092

1085

1081

1082

1086

1088 a b

1084 c

1081 d

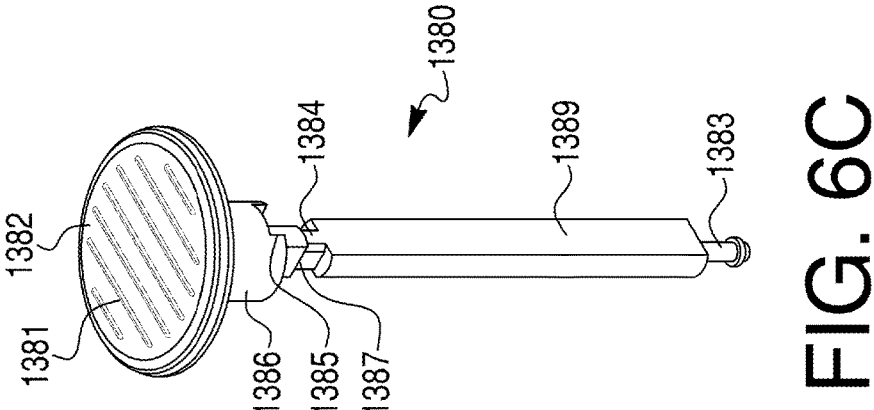
FIG. 6C
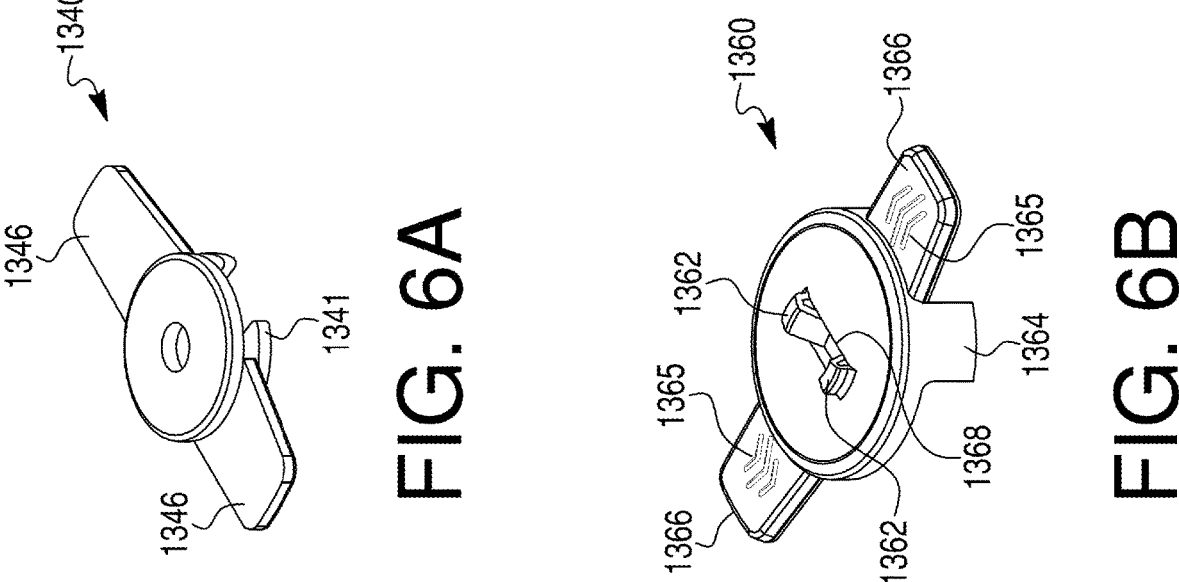
FIG. 6A
FIG. 6B

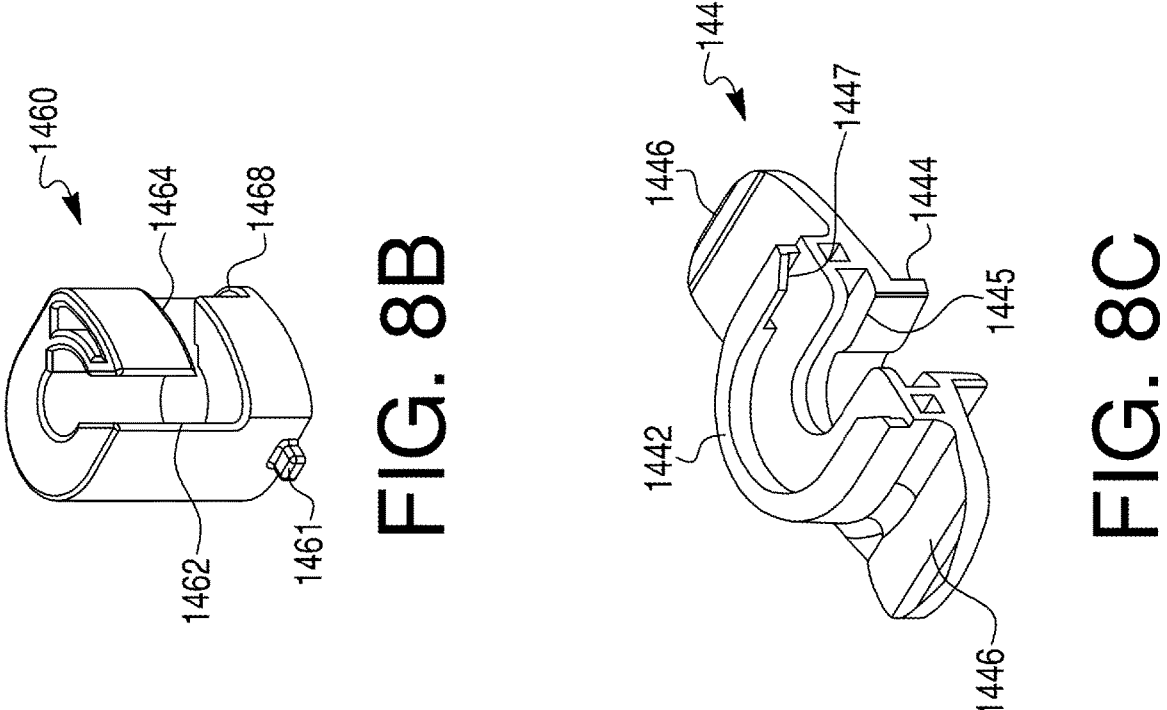
FIG. 8B
FIG. 8C
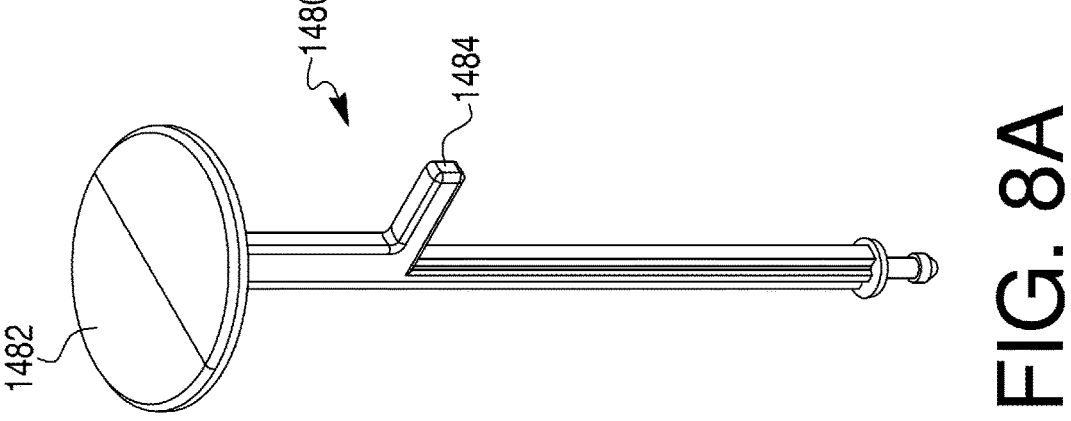
FIG. 8A 1910
1912
1960
1980
1920
1900
1990

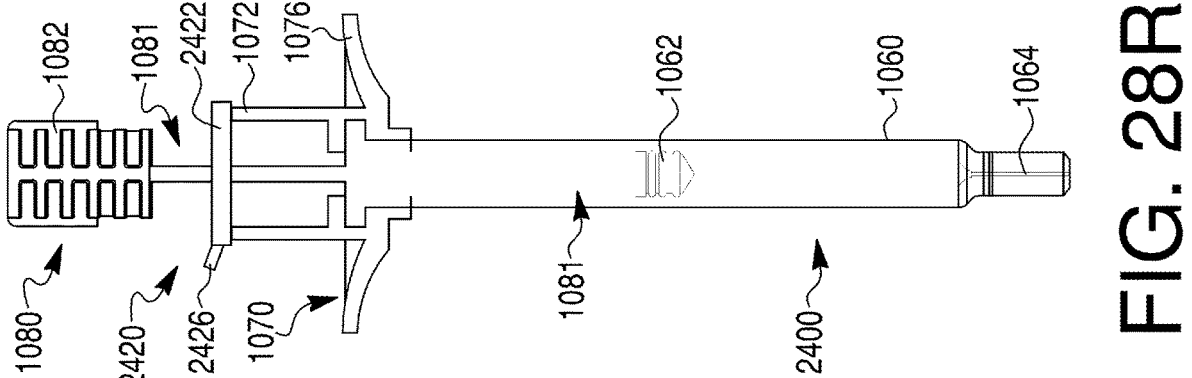
FIG. 28R
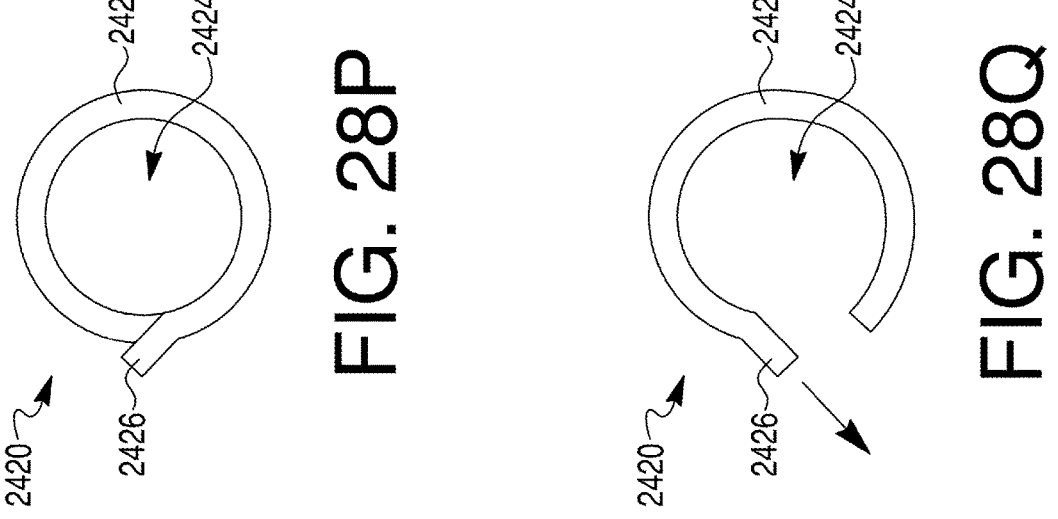
FIG. 28P
FIG. 28Q

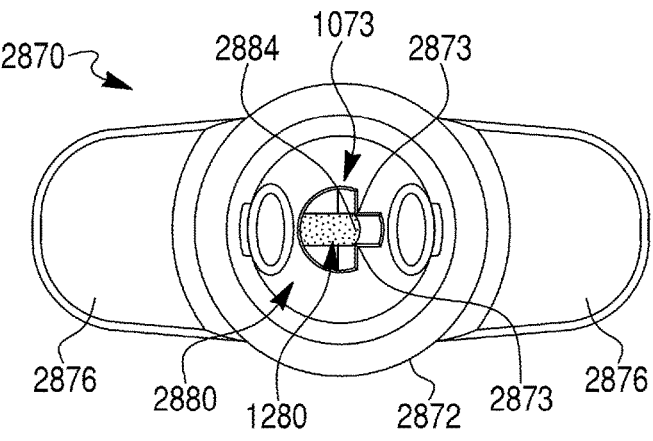
FIG. 40A
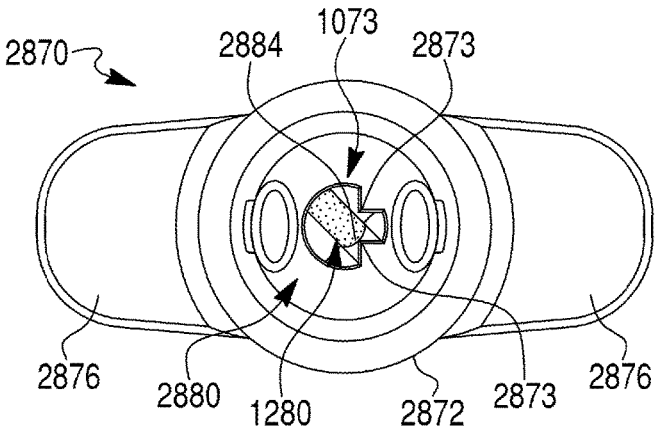
FIG. 40B
FIG. 40C

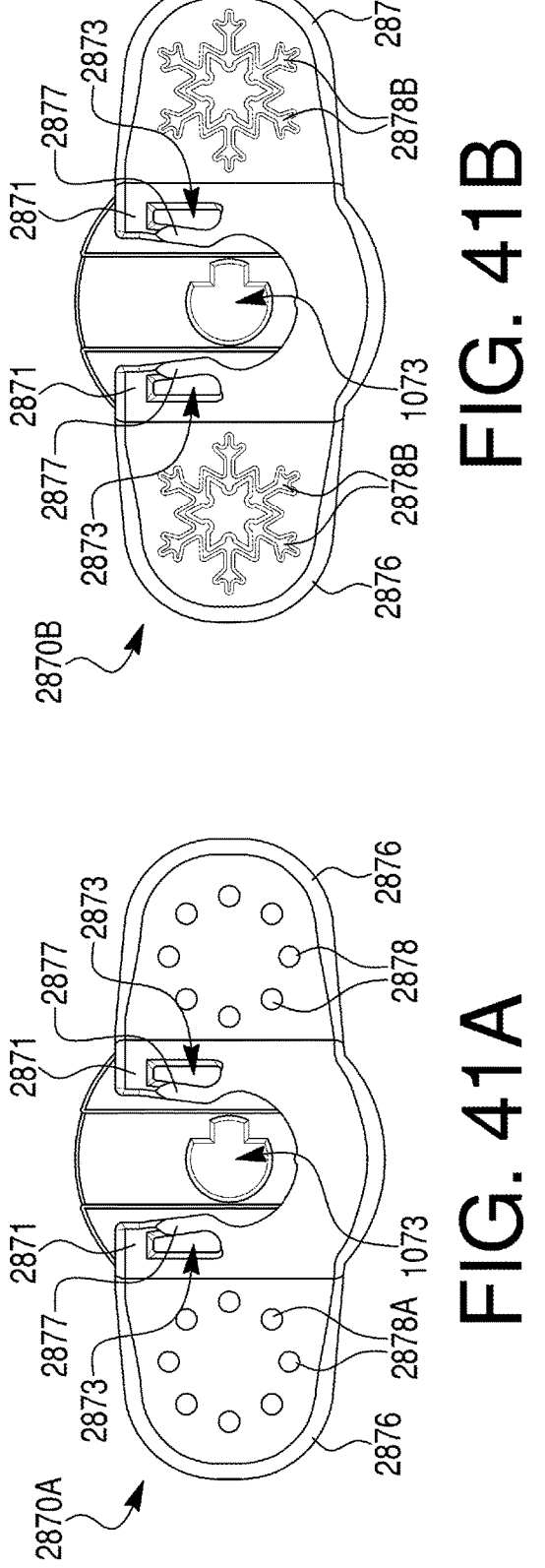
FIG. 41B
FIG. 41A
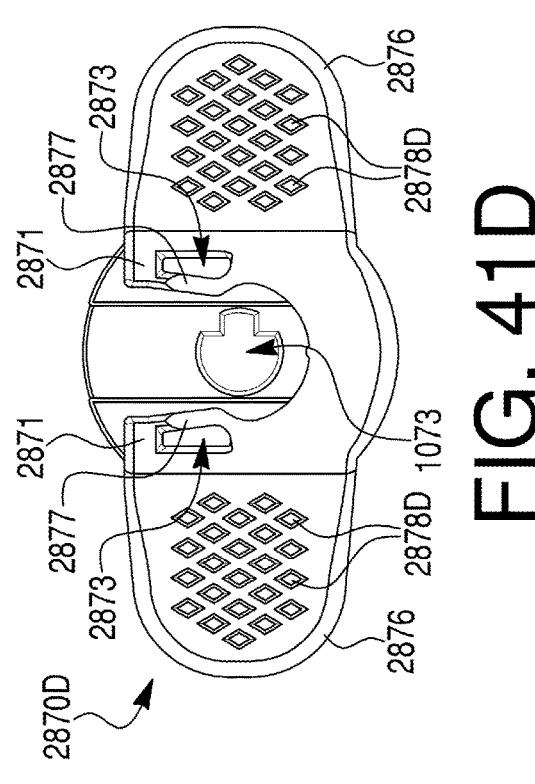
FIG. 41D
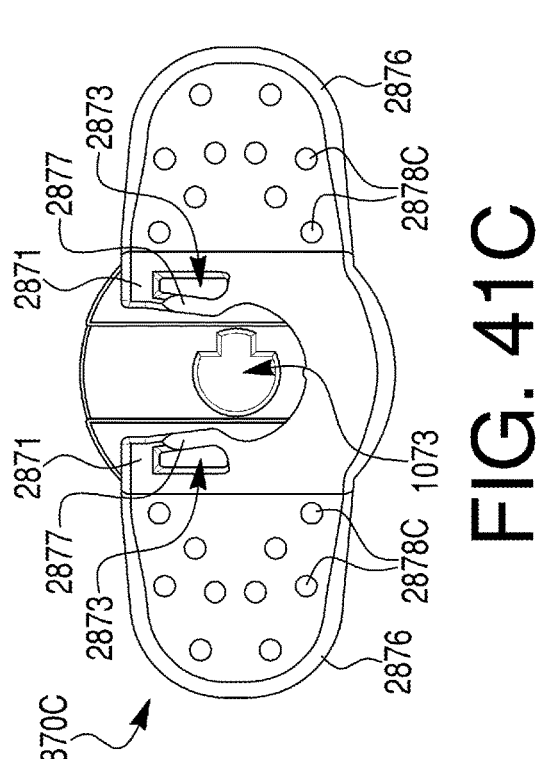
FIG. 41C

3200

Perform a leak test on the sterilization system ~3202

Precondition the sterilization system ~3204

Perform a sterilization phase ~3206

Perform a first aeration phase ~3208

Perform a second aeration phase ~3210 component always active/open/on
component sometimes active/open/on
component never active/open/on component always active/open/on component sometimes active/open/on component never active/open/on US IOI CASE COUNT, DISTRIBUTION COUNT AND REPORTING RATES FOR VIAL AND PFS SINCE LAUNCH OF PFS (DEC-2019)

A

| Year | Month | Vial Case Count | Vials Distributed Count | Reporting Rate |
|---|---|---|---|---|
| 2019 | Dec | 18 | 238,231 | 0.0076% |
| 2020 | Jan | 13 | 229,336 | 0.0057% |
| | Feb | 13 | 129,285 | 0.0101% |
| | Mar | 9 | 70,593 | 0.0127% |
| | Apr | 1 | 52,103 | 0.0019% |
| | May | 7 | 58,288 | 0.0120% |
| | Jun | 4 | 59,582 | 0.0067% |
| | Jul | 2 | 56,682 | 0.0035% |
| | Aug | 9 | 51,672 | 0.0174% |
| | Sep | 4 | 51,943 | 0.0077% |
| | Oct | 5 | 45,570 | 0.0110% |
| | Nov | 4 | 42,970 | 0.0093% |
| | Dec | 3 | 45,483 | 0.0066% |
| 2021 | Jan | 2 | 41,982 | 0.0048% |
| | Feb | 1 | 34,932 | 0.0029% |
| | Mar | 4 | 41,153 | 0.0097% |
| | Apr | 4 | 37,529 | 0.0107% |
| | May | 4 | 34,301 | 0.0117% |
| | Jun | 2 | 40,431 | 0.0049% |
| | Jul | 2 | 34,037 | 0.0059% |
| Total | | 111 | 1,396,103 | 0.0080% |

B

| Year | Month | PFC Case Count | PFC Distributed Count | Reporting Rate |
|---|---|---|---|---|
| 2019 | Dec | 0 | 16,535 | 0.0000% |
| 2020 | Jan | 2 | 36,533 | 0.0055% |
| | Feb | 6 | 101,089 | 0.0059% |
| | Mar | 1 | 157,888 | 0.0006% |
| | Apr | 2 | 148,264 | 0.0013% |
| | May | 1 | 182,307 | 0.0005% |
| | Jun | 8 | 214,193 | 0.0037% |
| | Jul | 7 | 211,493 | 0.0033% |
| | Aug | 6 | 218,656 | 0.0027% |
| | Sep | 11 | 239,882 | 0.0046% |
| | Oct | 5 | 234,494 | 0.0021% |
| | Nov | 3 | 225,755 | 0.0013% |
| | Dec | 3 | 236,375 | 0.0013% |
| 2021 | Jan | 7 | 240,363 | 0.0029% |
| | Feb | 6 | 226,730 | 0.0026% |
| | Mar | 6 | 278,848 | 0.0022% |
| | Apr | 2 | 264,872 | 0.0008% |
| | May | 4 | 255,037 | 0.0016% |
| | Jun | 14 | 305,867 | 0.0046% |
| | Jul | 1 | 264,857 | 0.0004% |
| Total | | 95 | 4,060,038 | 0.0023% |

FIG. 46B

METHODS FOR DELIVERING AGENTS WITH PRE-FILLED SYRINGES TO MINIMIZE INTRAOCULAR INFLAMMATION

CROSS REFERENCE TO RELATED APPLICATIONS

This application claims priority to U.S. Application No. 63/324,762, filed on Mar. 29, 2022; U.S. Application No. 63/263,006, filed on Oct. 25, 2021; and U.S. Application No. 63/241,656, filed on Sep. 8, 2021; all of which are incorporated by reference herein in their entireties.

FIELD OF DISCLOSURE

Aspects of the present disclosure relate to devices and methods for administering a drug or other fluid substance for treating a patient disorder while minimizing a likelihood of the patient experiencing undesirable or negative symptoms or effects as a result. More specifically, embodiments of the present disclosure relate to devices and methods for storing and/or delivering a drug substance to a patient using a pre-filled syringe that is sterilized by a sterilization method using vaporized chemicals to reduce the occurrence of undesirable side effects in the patient. In one example aspect, the present disclosure is directed to apparatus and methods of treating an angiogenic eye disorder in a patient. In some embodiments, the method may include administering a medicament (e.g., an anti-VEGF agent) to the patient with a pre-filled syringe, wherein such administration treats the angiogenic eye disorder. In some embodiments, the pre-filled syringe may be terminally sterilized with vaporized hydrogen peroxide. In another example aspect, the present disclosure is directed to methods and apparatus for reducing the probability of occurrence of an intraocular infection (IOI) in a patient who is being treated for an eye condition (e.g., an angiogenic eye disorder) with a therapeutic agent (e.g., an anti-VEGF agent), wherein the agent is administered to the patient via a terminally sterilized pre-filled syringe. It should be appreciated that inflammation may be a part of infection but does not guarantee the presence of an infection.

Introduction

Drug products, including fluid drug substances, may be deliverable to patients in a variety of ways, including via injection. A source of the injection, such as the type of delivery device administering the substance, may influence the accuracy of the substance's volume being delivered to the patient and a likelihood of the patient experiencing a clinical impact from the injection. Furthermore, a method of handling, sterilizing, storing, packaging, and/or transporting the delivery device may further influence a precision of the drug product's volume and a rate of probability that the patient will experience negative symptoms.

In many cases, maintaining the accuracy of the liquid drug product dose delivered to the patient and mitigating or otherwise reducing undesirable side effects are important. Medical professionals may have an interest in ensuring that a prescribed volume of a drug substance is consistently delivered to each patient, and that a pain or discomfort resulting from the drug delivery is minimized. Errors in delivering an accurate dose of a drug substance for injection or reducing associated symptoms from delivery may impact the resulting clinical effect on the patient.

SUMMARY

Disclosed herein are methods for treating a patient with sterilized drug delivery devices. In one embodiment of the present disclosure, method of treating an eye disorder in a patient includes administering a medicament to the patient with a prefilled syringe, wherein the administration of the medicament with the prefilled syringe is configured to treat the eye disorder and decrease a rate of likelihood of an ocular infection to the patient's eye.

In some aspects of the present disclosure, the medicament includes an anti-VEGF agent. The eye disorder in the patient includes an angiogenic eye disorder. The ocular infection includes intraocular inflammation or endophthalmitis. The administration of the medicament with the prefilled syringe reduces a bacterial content on at least one portion of the pre-filled syringe relative to bacterial content on a non-prefilled syringe. Prior to administering the medicament to the patient with the prefilled syringe, the method comprises: sterilizing the pre-filled syringe with vaporized chemicals to remove contaminants and other biological agents present on the pre-filled syringe. The vaporized chemicals include vaporized hydrogen peroxide (VHF)). The administration of the medicament with the prefilled syringe is configured to decrease the rate of likelihood of the ocular infection to the patient's eye relative to the administration of the medicament with a non-prefilled syringe with the medicament stored in a vial. The administration of the medicament with the prefilled syringe is configured to decrease a rate of likelihood for inflammation to at least one of a conjunctiva, a cornea, a sclera, an iris, a ciliary body, a lens, a retina, a choroid, or aqueous and vitreous humor in the patient's eye. The administration of the medicament with the prefilled syringe decreases a rate of likelihood for intraocular inflammation of tissue with the patient's eye caused by an infection from bacteria contacting the tissue. The administration of the medicament with the prefilled syringe is configured to decrease a rate of likelihood for causing redness, pain, blurred vision, and/or sensitivity to light to the patient's eye.

According to another embodiment of the present disclosure, a method of reducing a probability of an occurrence of an ocular infection in a patient being treated for an eye disorder with a medicament, the method comprising: administering the medicament to the patient's eye via a pre-filled syringe.

In some aspects of the present disclosure, the medicament includes an anti-VEGF antagonist, the eye disorder in the patient includes an angiogenic eye disorder, and the ocular infection includes intraocular inflammation (IOI) or endophthalmitis. Prior to administering the medicament to the patient's eye via the prefilled syringe, the method comprises: sterilizing the pre-filled syringe with vaporized chemicals to remove contaminants and other biological agents present on the pre-filled syringe. The vaporized chemicals include vaporized hydrogen peroxide (VHF)). Prior to administering the medicament to the patient's eye via the pre-filled syringe, the method comprises: reducing a degree of bacterial content on a portion of the pre-filled syringe by subjecting the pre-filled syringe to a terminal sterilization process. The portion of the pre-filled syringe is a needle. Administering the medicament via the prefilled syringe decreases a rate of likelihood for inflammation to at least one of a conjunctiva, a cornea, a sclera, an iris, a ciliary body, a lens, a retina, a choroid, or aqueous and vitreous humor in the patient's eye. Administering the medicament via the prefilled syringe decreases a rate of likelihood for intraocular inflammation of tissue with the patient's eye caused by an infection from bacteria contacting the tissue. Administering the medicament with the prefilled syringe decreases a rate of likelihood for causing redness, pain, blurred vision, and/or sensitivity to light to the patient's eye.

According to another embodiment of the present disclosure, a method of reducing intraocular inflammation in a patient receiving an injection, the method comprising: administering the injection to the patient via a prefilled syringe including a medicament configured to treat an eye disorder, wherein the administration reduces a rate of likelihood of the patient developing an intraocular infection in response to the injection from the pre-filled syringe as compared to patients receiving the injection from non-prefilled syringes.

In some aspects of the present disclosure, the medicament includes an anti-VEGF agent, and the eye disorder includes an angiogenic eye disorder. Prior to administering the injection to the patient via the prefilled syringe, the method comprises: sterilizing the pre-filled syringe via a terminal VHP sterilization process. Prior to administering the injection to the patient via the prefilled syringe, the method comprises: sterilizing the pre-filled syringe via a moist chemical sterilization process. Prior to administering the injection to the patient via the prefilled syringe, the method comprises: positioning the pre-filled syringe within a sterilization chamber configured to run sterilization cycles at a predefined temperatures and pressures for one or more time durations at user-defined intervals; and supplying vaporized hydrogen peroxide into the sterilization chamber during the sterilization cycles and at adjustable concentrations. Administering the injection to the patient via the prefilled syringe decreases a rate of likelihood for inflammation to at least one of an outer layer (e.g., a conjunctiva, a cornea), a middle layer (e.g., a sclera, a chloroid), or an inner layer (e.g., an iris, a ciliary body, a lens, a retina, an aqueous and vitreous humor) in the patient's eye. Administering the injection to the patient via the prefilled syringe decreases a rate of likelihood for intraocular inflammation of tissue within the patient's eye caused by an infection from bacteria contacting the tissue.

BRIEF DESCRIPTION OF THE DRAWINGS

The accompanying drawings, which are incorporated into and constitute a part of this specification, illustrate various exemplary embodiments and, together with the description, serve to explain principles of the disclosed embodiments. The drawings show different aspects of the present disclosure and, where appropriate, reference numerals illustrating like structures, components, materials, and/or elements in different figures are labeled similarly. It is understood that various combinations of the structures, components, and/or elements in various embodiments, other than those specifically shown, are contemplated and are within the scope of the present disclosure.

There are many embodiments described and illustrated herein. The described devices and methods are neither limited to any single aspect nor embodiment thereof, nor to any combinations and/or permutations of such aspects and/or embodiments. Moreover, each of the aspects of the described inventions, and/or embodiments thereof, may be employed alone or in combination with one or more of the other aspects of the described inventions and/or embodiments thereof. For the sake of brevity, certain permutations and combinations are not discussed and/or illustrated separately herein.

FIGS. 6A-6E depict a further exemplary delivery device according to additional embodiments of the present disclosure.

FIGS. 8A-8E depict a further exemplary delivery device according to embodiments of the present disclosure.

FIGS. 34-40C depict a further exemplary delivery device and method of using said delivery device, according to aspects of the present disclosure.

FIGS. 41A-41D depict exemplary flange pieces according to further embodiments of the present disclosure.

FIG. 46B depicts a data table of report rates of IOI in the United States from injections delivered with non-prefilled syringes (e.g. medicament stored in vials) relative to a data table of report rates of IOI from injections delivered with medicament stored in pre-filled syringes over a defined period.

Figure 1B:
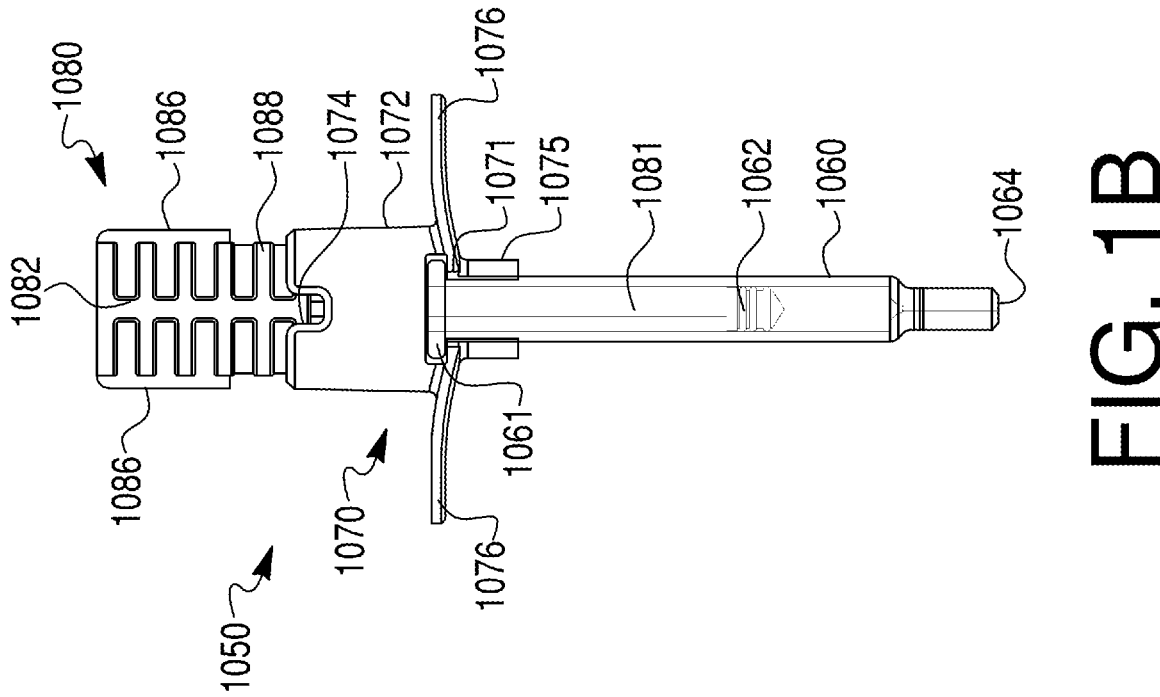
FIGS. 1A-1E depict an exemplary delivery device and components thereof, according to some embodiments of the present disclosure.

There are many embodiments described and illustrated herein. The present disclosure is neither limited to any single aspect nor embodiment thereof, nor to any combinations and/or permutations of such aspects and/or embodiments. Each of the aspects of the present disclosure, and/or embodiments thereof, may be employed alone or in combination with one or more of the other aspects of the present disclosure and/or embodiments thereof. For the sake of brevity, many of those combinations and permutations are not discussed separately herein.

DETAILED DESCRIPTION

As used herein, the terms "comprises," "comprising," "includes," "including," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "exemplary" is used in the sense of "example," rather than "ideal." Notably, an embodiment or implementation described herein as an "example" or "exemplary" is not to be construed as preferred or advantageous, for example, over other embodiments or implementations; rather, it is intended reflect or indicate the embodiment(s) is/are one "example," rather than "ideal." In addition, the terms "first," "second," and the like, herein do not denote any order, quantity, or importance, but rather are used to distinguish an element, a structure, a step or a process from another. Moreover, the terms "a" and "an" herein do not denote a limitation of quantity, but rather denote the presence of one or more of the referenced items. Additionally, the terms "about," "approximately," "substantially," and the like, when used in describing a numerical value, denote a variation of +/−10% of that value, unless specified otherwise.

As used in the present disclosure, the term "sterilization" refers to achieving a level of sterility appropriate for a formulated drug substance or drug product for commercial distribution and use. Such a level of sterility may be defined in, for example, regulatory guidelines or regulations, such as guidelines released by the U.S. Food and Drug Administration. In some embodiments, such a level of sterility may include, for example, a 6-log reduction in microbial populations of biological indicators placed on an outside or inside surface of a drug product (e.g., an outside surface of a syringe or an inside surface of a blister pack). In other embodiments, such a level of sterility may include, for example, a 9-log or 12-log reduction in microbial populations of biological indicators. Sterilization refers to achieving such an appropriate level of sterility while also achieving a sufficiently low level of residual sterilizing chemicals (e.g., vaporized hydrogen peroxide, ethylene oxide, etc.) for commercial distribution and use. Such a low level of residual sterilizing chemical may also be defined in regulatory guidelines or regulations.

As used in the present disclosure, the term "terminal sterilization" refers to the sterilization of a drug product in a container or packaging, such as in a primary packaging component, or in both primary and secondary packaging components, suitable for commercial distribution and use.

As used in the present disclosure, the term "medical product" refers to a product for medical use on a living animal. The term "medical product" includes, for example, drug products, formulated drug substances, medical implants, medical instruments, or combinations thereof. For example, the term "medical product" may refer to a syringe containing a formulated drug substance, such as a parenteral or an ophthalmic syringe. Other exemplary medical products include, e.g., suppository applicators and medication, transdermal drug delivery devices, medical implants, needles, cannulas, medical instruments, and any other product requiring sterilization prior to an intended medical use.

As used in the present disclosure, the term "vaporized chemical" refers to a chemical that has been converted into a substance that may be diffused or suspended in air. In some instances, a vaporized chemical may be a chemical that has been combined with water and then converted into a substance that may be diffused or suspended in air.

As used in the present disclosure, the term "fluid" refers to a liquid, semi-liquid, vapor, or gas including oxygen, hydrogen, nitrogen, or a combination thereof.

Embodiments of the present disclosure may be used with any type of fluid-containing products, such as liquid drug substances, liquid placebos, or other liquids that may be dispensed in a dose form. As used herein, the term "drug substance" or "formulated drug substance" may refer to a formulated substance or composition including an active ingredient or ingredients, such as, e.g., small or large molecules, such as pain medications, steroids, or biologics. The active ingredient may further include a protein, a nucleic acid, or a gene therapy medicament. The composition may further include an excipient, prepared for medical distribution and use. A formulated drug substance may include fillers, coloring agents, and other active or inactive ingredients.

As used herein, the term "biologic" may refer to a large molecule (e.g., having a size greater than 15 kDa, greater than 30 kDa, greater than 50 kDa, greater than 75 kDa, or greater than 100 kDa) created in a living system such as a cell. Biologics may include proteins (e.g., antibodies), nucleic acids, large sugars, etc. Unlike small molecules that may have well-defined chemical structures, biologics may have highly complex structures that cannot be easily quantified by laboratory methods. As used herein, the term "drug product" may refer to a volume of a drug substance apportioned into a primary packaging component for packaging, transportation, delivery, and/or administration to a patient. In other words, a drug product may include packaging for commercial distribution or use, such as a bottle, vial, or syringe. A drug product may refer to a dosage form that contains a formulated drug substance, such as a finished dosage form for an active ingredient.

The term "primary packaging component" refers to a packaging component for a drug product, such as a drug container, that is designed and manufactured to be in direct physical contact with the formulated drug substance. (See, for example, Guidance for Industry on Container Closure Systems for Packaging Human Drugs and Biologics, U.S. Department of Health and Human Services, Food and Drug Administration, Center for Drug Evaluation and Research, and Center for Biologics Evaluation and Research (May 1999), which is incorporated by reference herein.) Examples of primary packaging components include pre-fillable syringes, Luer syringes, cartridges, and vials made of glass, plastic, other polymers or co-polymers, and/or other materials.

As used herein, the terms "distal" and "distally" refer to a location (or portion of a device) relatively closer to, or in the direction of, a patient delivery site, and the terms "proximal" and "proximally" refer to a location (or portion of a device) relatively closer to, or in the direction of, a user end opposite a distal location/portion of a device.

As used herein, the term "body," when used in reference to a part of a device, may refer to a component of the device suitable for containing a volume of a drug substance. A body may include, e.g., a barrel (such as a syringe barrel), tube, cylinder, or other containing portion of a device. In some embodiments, a body may also include a distal end portion having a nozzle, needle, needle attachment site, and/or distal cap.

Embodiments of the present disclosure may be used with products typically having small dose volumes, such as, e.g., ophthalmic drug products. In some embodiments, devices of the present disclosure may be used with drug products including a large molecule, e.g., a molecular weight of 30 kDA or greater. In some embodiments, devices of the present disclosure may be used with drug products including a fragment of a large molecule. For example, in some embodiments, devices of the present disclosure may be used with drug products including an antigen-binding molecule. In some aspects, the antigen-binding molecule may be an antibody or antigen-binding fragment. In some embodiments, devices of the present disclosure may be suitable for use with drug products including ingredients such as, e.g., aflibercept, alirocumab, abicipar pegol, bevacizumab, brolucizumab, conbercept, dupilumab, evolocumab, tocilizumab, certolizumab, abatacept, rituximab, infliximab, ranibizumab, sarilumab, adalimumab, anakinra, trastuzumab, pegfilgrastim, interferon beta-la, insulin glargine [rDNA origin], epoetin alpha, darbepoetin, filigrastim, golimumab, etanercept, antigen-binding fragments of any of the above, or combinations of such binding domains, such as a bispecific antibody to VEGF or angiopoietin-2, among others.

In some embodiments, devices and aspects of the present disclosure can be used with any therapies for ophthalmic diseases, including for the treatment of patients with Diabetic Eye Disease, post-injection noninfectious Endophthalmitis, infectious Endophthalmitis, Neovascular (Wet) Age-related Macular Degeneration (AMD), Macular Edema following Retinal Vein Occlusion (RVO), Diabetic Macular Edema (DME), and Diabetic Retinopathy (DR). In particular, large molecule and small molecule antagonists of VEGF and/or ANG-2, such as aflibercept, ranibizumab, bevacizumab, conbercept, OPT-302, RTH258 (brolocizumab), abicipar pegol (a pegylated designed ankyrin repeating protein (DARPin)), RG7716, or fragments thereof and in any concentration. Intravitreal (IVT) administration of therapeutic agents may be an effective treatment for such eye disorders (e.g., macular degeneration, retinal vein occlusion, macular edema, retinopathy, etc.), however, IVT administration includes various challenges such as drug product development, administration procedure and adverse events. For example, providing accurate and precise delivery of small volumes (10-100 μL) requires precise design of container components. Accordingly, inaccuracies in a dosage delivery (e.g., over or under-dosing) may provide undesired adverse events or lack of efficacy resulting in unpredictable and variable clinical responses.

In some embodiments, devices and aspects of the present disclosure may provide accurate dose delivery while also providing a container closure system for maintaining the agent in a sterile, stable, and safe condition to increase an intended shelf-life and efficacy of the agent. IVT drug products are primarily presented in glass vials, however, pre-filled syringes offer a more convenient administration by reducing the number of steps required for dose preparation. Preassembling the agent in the devices of the present disclosure may minimize the steps necessary for preparing a dose for delivery to a patient. Product development studies may focus on primary container component characterization, material compatibility with the formulation, formulation stability, fill volume determination, extractable/leachable and terminal sterilization.

Additionally, careful selection of ancillary components such as disposable syringes and needles, and a detailed administration procedure that includes dosing instructions can ensure successful administration of the product. Despite significant efforts in improving the drug product and administration procedures, ocular safety concerns such as endophthalmitis, increased intraocular pressure and presence of silicone floaters have been reported. Devices and aspects of the present disclosure may provide detailed administration procedures (e.g., priming instructions, dosing instructions, etc.) to ensure successful administration of the agent to a patient to minimize such ocular safety concerns. In some embodiments, devices and aspects of the present disclosure can also be used for cosmetic applications or medical dermatology, such as treatment or diagnosis of allergic responses.

In some embodiments, devices and aspects of the present disclosure can be used to perform various eye injection procedures, such as, for example, intraocular treatments and surgeries involving an intravitreal injection of a drug product. Devices and aspects of the present disclosure may be used to dispense drug products of varying protein concentration and/or viscosity, including, for example, drug products having a viscosity ranging from about 1 centipoise to about 10 centipoise, from about 2 centipose to about 9 centipose, from about 3 centipose to about 8 centipose, from about 4 centipose to about 7 centipose, or from about 5 centipose to about 6 centipose. Drug products having still other viscosities also are contemplated. Providing a precise dose with a device of the present disclosure may be important given a possible variability in protein concentration or viscosity of a drug product being delivered to a patient. Devices and aspects of the present disclosure may be further used to dispense varying volumes and/or quantities of a drug product, such as, for example, volumes ranging from about 1 µL to about 200 µL, from about 10 µL to about 190 µL, from about 50 µL to about 150 µL, from about 75 µL to about 125 µL, from about 90 µL to about 110 µL, or about 100 µL. Devices of the present disclosure may be configured and operable to require application of a minimum force exceeding a threshold for performing one or more procedures, such as, for example, priming a device, delivering a dosage, and the like. By requiring application of the minimum force, devices of the present disclosure may promote control in administering a consistent dose of a drug product, and promote safety by minimizing inadvertent movement of the device's components, thereby potentially reducing pain, discomfort, and injury to a patient.

For some products in particular, e.g., ophthalmic or other drug products, dose accuracy may be particularly important. However, it is also contemplated that embodiments of the present disclosure may be applicable to any other liquid products or any other context for which precise methods for setting and administering a reliably accurate dose or delivery volume are beneficial.

In some embodiments, devices according to the present disclosure may be manufactured, packaged, filled, and/or otherwise prepared according to processes relevant to the products (e.g., drug products) of which they may be a part. For example, in some embodiments, devices according to the present disclosure may be sterilized, either before or after being filled and/or packaged. For example, in some embodiments, devices according to the present disclosure may be filled and packaged in, e.g., blister packaging, and/or may be terminally sterilized. For example, devices according to the present disclosure may be terminally sterilized using a chemical sterilization method, such as a method including ethylene oxide or hydrogen peroxide (e.g., vaporized hydrogen peroxide). In some embodiments, devices according to the present disclosure may be terminally sterilized using one or more of the exemplary sterilization methods described herein (see FIGS. 42-45C).

Dose delivery devices available on the market, such as pre-filled syringes or syringes for use with vials, may not necessarily assist with accurately loading a desired volume of a substance, priming the devices, expelling an excessive volume of drug substance from the devices, and/or removing air bubbles from the devices. In dose delivery devices containing a small volume of a drug substance in particular (e.g., about 500 µL or less, about 300 µL or less, about 250 µL or less, about 200 µL or less, about 150 µL or less, about 100 µL or less, about 50 µL or less, or about 25 µL or less, such as between about 25 µL and about 50 µL, between about 50 µL and about 100 µL, between about 25 µL and about 100 µL, between about 50 µL and about 150 µL, between about 100 µL and about 250 µL, between about 100 µL and about 150 µL, between about 150 µL and about 250 µL, between about 200 µL and about 250 µL, between about 200 µL and about 500 µL, or between about 250 µL and about 500 µL), it may also be difficult to confirm the presence of the correct dose of a drug substance in the device with the naked eye. Currently in the dose delivery device market, and specifically in the syringe market, there is a need for mechanisms that allow a user to set precisely for delivery a small volume of a product in a syringe (e.g., a pre-filled or fillable/refillable syringe), prime the syringe, remove air bubbles from the syringe, and/or confirm or be assured that the dose volume in the syringe is correct. Embodiments of the present disclosure may assist manufacturers, drug product providers, medical professionals, and/or patients with accurately making, filling, or otherwise preparing a dose administration device, priming the device, removing bubbles from the device, confirming the dose, and/or administering a dose from the device to a patient. Moreover, embodiments of the present disclosure may assist in preventing or mitigating errors or variation in device manufacture or use, such as errors or variation in placement of dose lines on devices, variation in device geometry (e.g., variation in syringe neck geometry), variations in component manufacturing tolerance, and/or variation or errors in setting a dose line prior to delivery of a product.

In some instances, embodiments of the present disclosure may be of particular assistance to individuals who may have difficulty setting doses with precision and accuracy. For example, embodiments of the present disclosure may assist elderly individuals, young children, or persons with physical or mental disabilities in setting accurate doses.

Described herein are various embodiments of dose delivery devices, and in particular, for syringes. In some instances, embodiments or aspects of embodiments disclosed herein may be used in conjunction with existing syringe body parts to modify off-the-shelf products, which may reduce the development and manufacturing time for the dose delivery devices. In other instances, embodiments or aspects of embodiments disclosed herein may be included in devices during their manufacture. The syringes described herein may be pre-filled or may be fillable/refillable.

Embodiments of the present disclosure may include syringes having rotating parts, threaded parts, springs, gears, detents, channels, grooves, and the like, that may allow a user to precisely control the movement of priming and dosage delivery elements such as, e.g., plungers and/or stoppers. Such parts may be intended to reduce human error and/or increase accuracy.

In some embodiments, visualization devices, such as magnifiers, may be provided with, attached to, or otherwise disposed on, delivery devices, in order to help enhance visibility of dose measurement markers on the devices. It is contemplated that aspects of one embodiment (such as sleeves, channels, blocking components, protrusions, detents, threaded parts, grips, visual, tactile, or auditory indicators, etc.) may be combined with aspects of one or more other embodiments, to create various combinations and permutations of features in a single device.

In some embodiments, devices according to the present disclosure may be depicted as including one type of plunger rod and plunger, or as including a general schematic representation of a plunger rod and plunger. For example, some devices according to the present disclosure may be depicted or described as including, e.g., a plunger rod having a ball-tipped end, which engages with a stopper such that the plunger rod and the stopper may be attached together. It is contemplated that multiple and/or different configurations of plunger rods and stoppers may be appropriate for each of the embodiments disclosed herein. For example, in some cases, the aforementioned ball-tipped plunger rod may be used with embodiments disclosed herein. In some embodiments, a plunger rod may not be affixed to a stopper, and instead may be disposed near, next to, or flush against a stopper such that pressure from the plunger rod towards the stopper may push the stopper, but withdrawal, twisting, or other movement of the plunger rod may not cause the stopper to likewise be withdrawn, twisted, or otherwise moved. As another example, in some embodiments, a plunger rod may be affixed to a stopper by threads, a clip, or an adhesive, or may be of a single piece with a stopper (e.g., may have been manufactured in a single mold with a stopper).

In some embodiments, devices according to the present disclosure may include various cosmetic features relevant to intended users of the devices. For example, devices according to the present disclosure may be manufactured and sold for use with pediatric, elderly, or differently-abled patients. In such cases, devices according to the present disclosure may include child-friendly coloring, cartoon images, or other cosmetic features to appeal to children, or high-contrast coloring, textured surfaces, or other features to enhance ease of identification and/or use. In some cases, devices according to the present disclosure may include lettering, labeling, or other features designed to be easily recognized by the intended users. For example, lettering on a pediatric device or a device for use by a disabled or differently-abled person or an elderly person may have larger, more accessible labeling so that it may be more easily recognized and read by the user(s) of the device. In some embodiments, lettering or labeling may be raised, molded, or embossed.

Referring now to FIGS. 1A-1E, views of a delivery device 1050 and component parts are depicted. Device 1050 includes a body 1060, and a blocking component in the form of a flange piece 1070 with a proximal collar 1072 surrounding an opening 1073 (shown in, e.g., FIGS. 4B-4E), through which a plunger rod 1080 may pass into body 1060. Plunger rod 1080 includes an actuation portion 1082 which may be actuated (e.g., pushed or twisted) to rotate plunger rod 1080, or to move plunger rod 1080 longitudinally into body 1060. Actuation portion 1082 may be sized and configured to fit (e.g., nest or otherwise fit) inside proximal collar 1072.

Device 1050 may be, for example, an injection device, such as a syringe, for dispensing a predetermined volume of a formulated drug substance. In some embodiments, device 1050 may be a pre-filled syringe. For example, a user may receive an assembled and packaged device 1050 ready for use, with a volume of formulated drug substance already disposed between a stopper 1062 in body 1060 and an expulsion end 1064 of body 1060. In some embodiments, an air bubble (not shown) may also be disposed between stopper 1062 and expulsion end 1064. In further embodiments, device 1050 may be a fillable syringe.

Body 1060 may be any suitable body configured for holding and expelling a predetermined volume of a formulated drug substance. In some embodiments, body 1060 may have, e.g., a hollow cylindrical portion. Body 1060 may be configured to hold any suitable volume of a formulated drug substance for delivering to, e.g., a patient, and (together with other components of device 1050) to expel a predetermined amount of the held volume through, e.g., expulsion end 1064 in a priming step and/or delivery step. In some embodiments, body 1060 may be configured to hold and (together with other components of device 1050) expel a relatively small volume of formulated drug substance (e.g., less than about 100 µl, such as less than about 80 µl, less than about 60 µl, less than about 40 µl, less than about 20 µl, less than about 10 µl, about 95 µl, about 90 µl, about 85 µl, about 80 µl, about 75 µl, about 70 µl, about 65 µl, about 60 µl, about 55 µl, about 50 µl, about 45 µl, about 40 µl, about 35 µl, about 30 µl, about 25 µl, about 20 µl, about 15 µl, about 10 µl, or about 5 µl). Device 1050, together with its other components, may be further configured to minimize a residual volume of the formulated drug substance remaining in body 1060 after delivering the predetermined small volume to the patient. In some embodiments, body 1060 may be pre-filled (e.g., prior to completed assembly, packaging, sterilization and/or shipment of device 1050 to users). In some embodiments, stopper 1062 may be configured to hold a predetermined volume of a formulated drug substance inside a cavity of body 1060.

Flange piece 1070 may be of any suitable size and/or shape to serve as a blocking component in delivery device 1050, to close, partially close, cover, or partially cover an end of body 1060 opposite expulsion end 1064, and/or to support and hold plunger rod 1080 in place inside body 1060. In some embodiments, flange piece 1070 may include a distal collar 1075 configured to engage with body 1060 and hold flange piece 1070 in place in relation to body 1060. For example, distal collar 1075 may include a lip 1071 that may slide under or otherwise in relation to a body flange 1061, to hold flange piece 1070 in place (e.g., to slidably couple flange piece 1070 to body 1060). In alternative embodiments, lip 1071 of distal collar 1075 may be made of a flexible or semi-flexible material, so that it may snap in place over body flange 1061. In further embodiments, distal collar 1075 or another portion of flange piece 1070 may be adhered to, molded to, or otherwise affixed to, body 1060, or may engage with body 1060 via a friction fit.

Flange piece 1070 may be or include a blocking component; i.e., part or all of flange piece 1070 may be sized and configured to control movement of plunger rod 1080 by blocking movement of plunger rod 1080 when plunger rod 1080 is in certain configurations relative to flange piece 1070. For example, flange piece 1070 may be configured to control rotational and longitudinal movement of plunger rod 1080, e.g., via opening 1073 (see, e.g., FIGS. 4B-4E) that complements the size and shape of parts of plunger rod b 1080 (e.g., neck 1084 and actuation portion 1082, and/or other portions of plunger rod 1080 as shown in FIGS. 4K-4O). As described in further detail herein, flange piece 1070 may be formed of various materials having a minimum strength and/or rigidity which may provide further control of a rotational or longitudinal movement of plunger rod 1080. For example, flange piece 1070 may be configured to resist proximal movement (or "pull back") of plunger rod 1080 (e.g., to inhibit disassembly of device 1050 by retracting plunger rod 1080) up to a predetermined force based at least in part on a material composition of flange piece 1070. It should be appreciated that flange piece 1070 may be configured such that applying a force exceeding the predetermined force may cause one or more of flange piece 1070 and plunger rod 1080 to break, thereby rendering device 1050 inoperable.

By way of further example, flange piece 1070 may be configured to resist rotational movement of plunger rod 1080 (e.g., to inhibit inadvertent rotation) up to a predetermined force based at least in part on a material composition of flange piece 1070. Additionally and/or alternatively, flange piece 1070 may be configured to resist distal movement of plunger rod 1080 to control a rate of dosage delivery (e.g., to inhibit inadvertent delivery) based at least in part on a material composition of flange piece 1070. Various other components of device 1050 other than flange piece 1070 may include a material composition providing a frictional interference to inhibit disassembly of device 1050, inadvertent rotation of plunger rod 1080, and/or inadvertent dosage delivery.

Figure 1A:
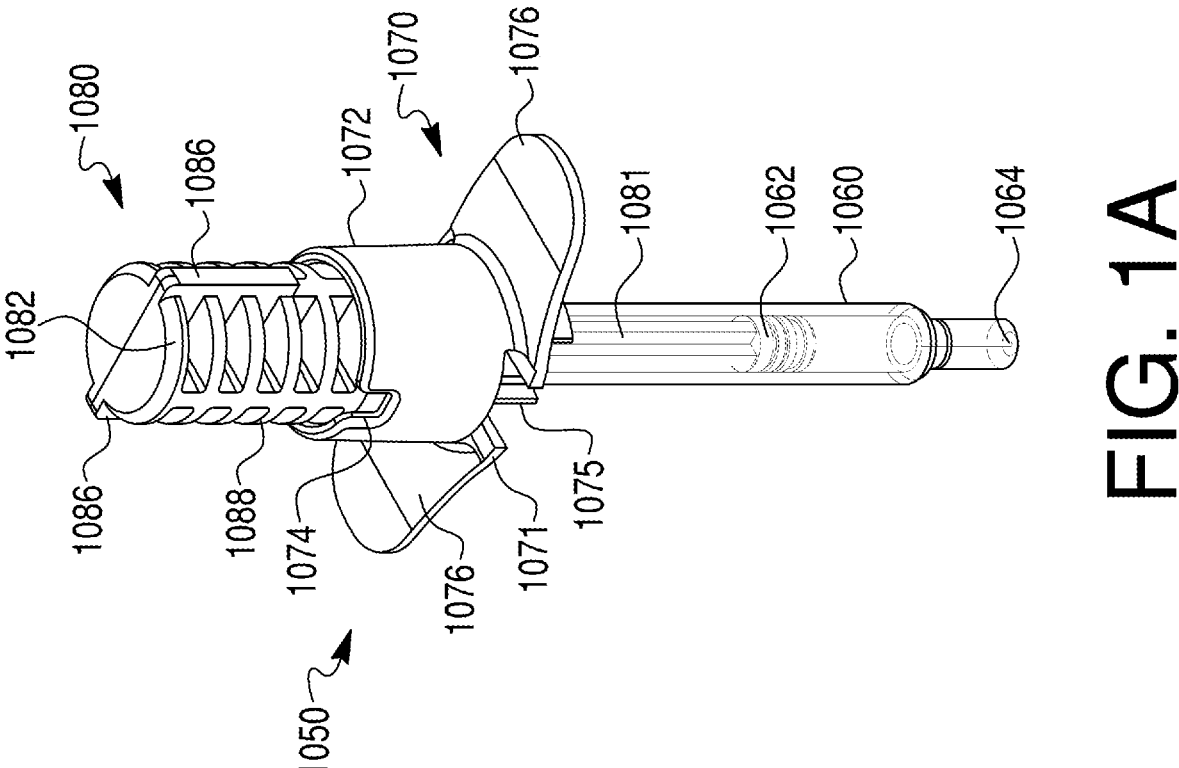

Proximal collar 1072 of flange piece 1070 may be sized and configured to accept part of actuation portion 1082 of plunger rod 1080, while blocking protrusions 1086 of plunger rod 1080 from moving distally past a predetermined point until plunger rod 1080 is rotated to a particular position. As shown in FIGS. 1A and 1B, collar 1072 may be cylindrical; in alternate embodiments, collar 1072 may have any suitable size or shape compatible with actuation portion 1082. Collar 1072 may also include cavities, e.g., slots 1074 into which protrusions 1086 of plunger rod 1080 may be received. Slots 1074 may have proximally-facing openings and may have a depth dimension parallel to a longitudinal axis of device 1050. A number and configuration of slots 1074 may correspond to a number and configuration of protrusions 1086 on plunger rod 1080. In some embodiments, slots 1074 may be disposed about a perimeter of collar 1072 in a radially symmetrical configuration. In further embodiments, collar 1072 may include only one slot 1074. The depth of slots 1074 may correspond to a distance plunger rod 1080 must move in order to push stopper 1062 towards expulsion end 1064, and dispense a predetermined volume of formulated drug substance from body 1060 through expulsion end 1064. Advantageously, the predetermined volume of formulated drug substance that is to be dispensed from body 1060 may be controlled during manufacturing, by, e.g., selecting a particular depth of slots 1074.

In some embodiments, device 1050 may be configured such that normal variations in manufacturing of other parts of device 1050 (e.g., body 1060 or plunger rod 1080) may not cause variations in the volume of formulated drug substance that is to be dispensed from body 1060. As such, the predetermined volume may be controlled by simply varying manufacture of flange piece 1070.

In some embodiments, flange piece 1070 may include one or more flanges 1076, which may be sized and configured to aid a user in holding device 1050 and/or expelling a formulated drug substance from device 1050. In some embodiments, as depicted in FIGS. 1A-1E, flange piece 1070 may include two flanges 1076 opposite to one another and extending perpendicularly from a longitudinal dimension of device 1050. In some embodiments, flange piece 1070 may include other arrangements of a flange or flanges, such as four flanges, or one circumferential flange extending radially outward from a central longitudinal axis of device 1050. In some embodiments, flange piece 1070 may extend radially outward from a central longitudinal axis of device 1050 farther than a circumference of body 1060. In such embodiments, flange piece 1070 may support device 1050 if device 1050 is placed on a surface, may prevent device 1050 from rolling on a flat surface, and/or may allow device 1050 to be picked up more easily. In still further embodiments, blocking component aspects of flange piece 1070 (e.g., collar 1072) may be separate from flange piece 1070, such that delivery device 1050 includes a separate flange piece and blocking component.

Plunger rod 1080 in general may be rotatable about a central longitudinal axis (e.g., in one direction or in both directions). In some embodiments, rotation of plunger rod 1080 may be accomplished by grasping and/or twisting actuation portion 1082 relative to flange piece 1070 and/or body 1060. In some embodiments, protrusions 1086 may assist a user in grasping and/or twisting actuation portion 1082 relative to flange piece 1070 and/or body 1060, by providing additional surface area that a user may grasp and/or push against to twist actuation portion 1082. In some embodiments, only a part or parts of plunger rod 1080 (e.g., actuation portion 1082 and/or a neck 1084) may be rotatable relative to flange piece 1070 and/or body 1060. In some embodiments, plunger rod 1080 may be configured to rotate relative to flange piece 1070 in response to applying a predetermined twisting force onto actuation portion 1082. A material composition of flange piece 1070 may be determinative of the predetermined twisting force required to rotate plunger rod 1080 relative to flange piece 1070. For example, flange piece 1070 may be formed of various materials having a predetermined rigidity that may generate frictional resistance against plunger rod 1080 to control rotational movement of plunger rod 1080 up to the predetermined force (e.g., to inhibit inadvertent rotation/accidental twisting of plunger rod 1080). Further, a material composition of flange piece 1070 may provide a frictional tolerance to control a distal translation of plunger rod 1080 up to a predetermined force (e.g., to inhibit inadvertent dosage delivery by device 1050).

A stem 1081 of plunger rod 1080 may have any thickness and cross-sectional shape suitable for fitting into body 1060, while maintaining sturdiness. For example, in some embodiments, stem 1081 may have as great a thickness, along at least one dimension, as can fit and slide into body 1060. Advantageously, such a thickness may help in preventing unwanted wobbling of plunger rod 1080 relative to the other components of device 1050. In further embodiments, stem 1081 may have a smaller thickness while still maintaining sturdiness (e.g., not bending, breaking, or warping during assembly and/or use of device 1050). In some embodiments, portions of stem 1081 may be configured to allow for plunger rod 1080 to rotate relative to flange piece 1070, whereas other portions of stem 1081 may not (see, e.g., FIGS. 4K-4S).

Plunger rod 1080 may also include a distal tip 1083 (see, e.g., FIG. 1D) sized and configured to push, attach to, or otherwise interface with stopper 1062. Tip 1083 may have any size or shape suitable to achieve this purpose. In some embodiments, for example, tip 1083 may be sized and configured to clip to stopper 1062 via an opening in stopper 1062. In further embodiments, tip 1083 may have a ball-shape configured to fit into an opening in stopper 1062. In yet further embodiments, tip 1083 may present a flat surface parallel to a proximal surface of stopper 1062, and may be configured to push stopper 1062 distally without attaching to stopper 1062. In further embodiments, tip 1083 may have any shaped surface suitable for pushing stopper 1062 distally.

In some embodiments, neck 1084 of plunger rod 1080 and opening 1073 of flange piece 1070 may have complementary geometries that restrict the extent and direction that plunger rod 1080 (or a part thereof) may rotate, depending on the specific longitudinal and/or rotational position of plunger rod 1080 relative to flange piece 1070. In some embodiments, actuation portion 1082 of plunger rod 1080 and collar 1072 may also include complementary geometries that control the extent and direction that plunger rod 1080 may move relative to flange piece 1070. For example, rotation and/or longitudinal movement of plunger rod 1080 may be restricted based on priming, preparing, and/or drug delivery steps of a method of using device 1050 (see, e.g., the method described with respect to FIGS. 4A-4F and the additional/alternative method described with respect to FIGS. 4G-4H and 4I-4J), and the corresponding position of plunger rod 1080 with respect to each step in such methods. For example, plunger rod 1080 may be restricted from being moved out of flange piece 1070 in a proximal direction (e.g., falling out or being pulled out) once device 1050 is assembled. Moreover, plunger rod 1080 may be restricted from rotation about a longitudinal axis before device 1050 is in a "primed" state, and/or after device 1050 is in a "delivery" state. Additionally, longitudinal movement of plunger rod 1080 in the proximal direction (e.g., to "back out" plunger rod 1080), may be restricted after device 1050 is in a "primed" and/or "delivery" state by complementary geometries of neck 1084 of plunger rod 1080 and opening 1073 of flange piece 1070 and/or of actuation portion 1082 of plunger rod 1080 and collar 1072 of flange piece 1070. Advantageously, this may prevent unwanted plunger rod back out in cases where plunger rod 1080 is not held inside body 1060 by, e.g., being affixed to stopper 1062. For example, in some embodiments, plunger rod 1080 may be configured to simply contact or rest against stopper 1062, such that proximal movement of plunger rod 1080 does not move stopper 1062 proximally. In such cases, proximal movement of plunger rod 1080 may be prevented by interaction between complementary geometries of plunger rod 1080 and flange piece 1070. Moreover, interaction between actuation portion 1082 of plunger rod 1080 and collar 1072 of flange piece 1070 may restrict longitudinal movement of plunger rod 1080 in a distal direction. As an example, plunger rod 1080 may be restricted from moving distally after the "primed" state but before the "delivery" state.

Upon being moved to the "delivery" state, protrusions 1086 on actuation portion 1082 may be longitudinally aligned with slots 1074 of collar 1072, allowing for distal movement of plunger rod 1080 to dispense a desired volume of a drug substance from body 1060. As such, plunger rod 1080 may include a number and configuration of protrusions 1086 such that each protrusion 1086 may move distally into a slot 1074 when plunger rod 1080 is in a particular position (e.g., a "delivery" state). In some embodiments, one, two, three, or more protrusions 1086 may extend from actuation portion 1082, corresponding to one, two, three, or more slots 1074, respectively. For example, as depicted, two protrusions 1086 may extend from the sides of actuation portion 1082 in a radially symmetrical configuration (corresponding to two slots 1074 in collar 1072). In some embodiments, radial symmetry of multiple protrusions 1086 (and slots 1074) may advantageously allow for protrusions 1086 to fit into slots 1074 in multiple configurations (e.g., depending on whether actuation portion 1082 is twisted in one direction or another). In such embodiments, actuation portion 1082 may be twisted in either direction based on, e.g., user preference, right-handedness or left-handedness, or other factors. In some embodiments, plunger rod 1080 may not be pulled proximally or backed out of body 1060 (e.g., towards actuation portion 1082) after plunger rod 1080 is in a "primed" state and/or after a desired volume of formulated drug substance has been delivered from device 1050 by depression of plunger rod 1080 into body 1060 (e.g., due to a geometry of neck 1084 and/or opening 1073).

In some embodiments, device 1050 may be configured for ease of use, and may include one or more features that aid a user by providing tactile or visual feedback. For example, one, two, or more components of device 1050 may have contrasting colors or textures. In some embodiments, for example, flange piece 1070 may have a different coloring than plunger rod 1080. As a further example, a single component of device 1050 may have two or more colors or textures. In some embodiments, for example, actuation portion 1082 may include a first color on a distal part of actuation portion 1082, that becomes covered by collar 1072 when device 1050 is primed, and a second color on a second portion of actuation portion 1082, that moves adjacent to collar 1072 when device 1050 is primed, to help indicate to a user that device 1050 has been properly primed. As a further example, in some embodiments, flange piece 1070 may have a different tactile feel than plunger rod 1080 and/or body 1060. For example, flange piece 1070 may be relatively rougher or smoother than plunger rod 1080 and/or body 1060. As yet another example, one or more components of device 1050 may have textures that aid in holding, gripping, identifying, or using device 1050. For example, flange piece 1070 may have a slightly rough or raised texture to aid a user in gripping flanges 1076, and/or to prevent a user's fingers from slipping off of the flanges 1076 during use. In some embodiments, some or all of flange piece 1070 may have a smooth-feeling surface. As another example, actuation portion 1082 of plunger rod 1080 may include a rough or raised texture to aid in gripping and rotating plunger rod 1080. For example, as depicted in FIGS. 1A-1I, 3A-3C, 3E, and 4A-4I, actuation portion 1082 may include circumferential ribbing on its side(s). Actuation portion 1082 may have any suitable number of ribs on its side(s) to provide texture. In further embodiments, actuation portion 1082 may have no ribbing on its side(s).

In some embodiments, device 1050 or one or more of its components may include colors, labels or markers, which may indicate contents or a status of device 1050, and/or which may direct or provide instructions to a user of device 1050. Examples include one or more labels to indicate a priming position versus a dosage delivery position of the plunger rod, one or more labels to indicate directions in which to rotate or otherwise move plunger rod 1080, and/or one or more labels to indicate an amount of formulated drug substance included in device 1050 (e.g., linear markings on body 1060). Labels may be, e.g., adhered or printed on components of device 1050, or may be embossed on, or molded as a part of, components of device 1050. In some embodiments, one or more textured labels (e.g., embossed or molded on device 1050) may also serve as a textured, rough, or raised surface to aid a user in gripping or using device 1050. One or more exemplary labels may include words, numerals, indicators, and/or symbols (e.g., lines, padlocks, arrows, diagrams, etc.).

In some embodiments, device 1050 may be configured to make one or more sounds during its use. For example, device 1050 may make a "clicking" noise upon completion of a priming step, or upon rotation of the plunger rod to a position suitable for dispensing a predetermined volume of a formulated drug substance. A "clicking" noise may be produced by, e.g., friction between two or more components (e.g., plunger rod 1080 and flange piece 1070), or a portion of one component contacting another portion (e.g., neck 1084 of plunger rod 1080 contacting opening 1073 of flange piece 1070). In some embodiments, device 1050 may include one or more detents or protrusions on adjacent surfaces of, e.g., plunger rod 1080 and flange piece 1070, which may produce a clicking sound when contacting one another (e.g., wings 1089 on neck 1084 contacting detents 1078 surrounding opening 1073, as shown in FIGS. 4T-4X). Such sounds may serve as auditory feedback to indicate that a user has reached a particular step in the use of device 1050.

In some embodiments, device 1050 may include additional features or components to control movement of plunger rod 1080 relative to body 1060. For example, as shown in FIG. 1F, flange piece 1070 may include an opening 1079 through which a pin 1077 may be disposed. Pin 1077 may be sized and configured to interface with actuation portion 1082 of plunger rod 1080 (e.g., to slide into an opening (not shown) in actuation portion 1082), such that when pin 1077 is inserted so as to engage actuation portion 1082, plunger rod 1080 may not be moved proximally or distally relative to body 1060 and flange piece 1070. In some embodiments, pin 1077 may also prevent rotational movement of plunger rod 1080 relative to flange piece 1070. Pin 1077 may be inserted upon filling and assembly of a device (e.g., device 1050 shown in FIGS. 1A and 1B), to prevent unwanted movement of plunger rod 1080 prior to its use. In some embodiments, pin 1077 may remain inserted during packaging, transportation, and delivery of device 1050. Before use of device 1050, pin 1077 may be removed or otherwise positioned so that it does not engage actuation portion 1082.

Figure 1H:
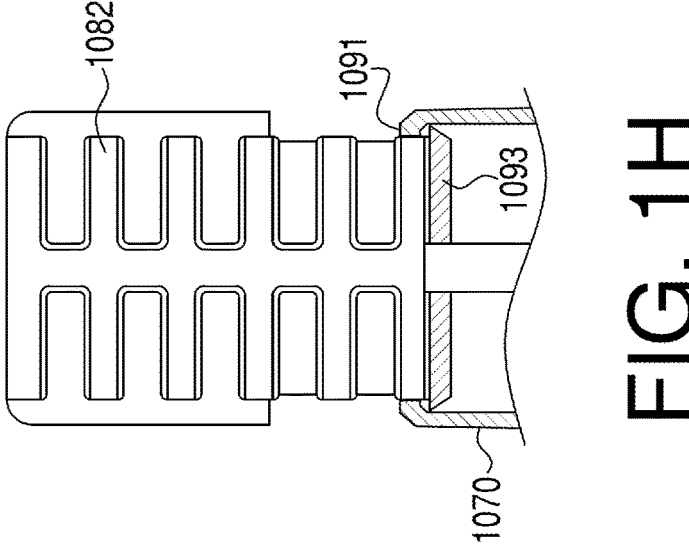
FIGS. 1F-2T depict additional aspects and embodiments of the exemplary delivery device of FIGS. 1A-1E.
Figure 1G:
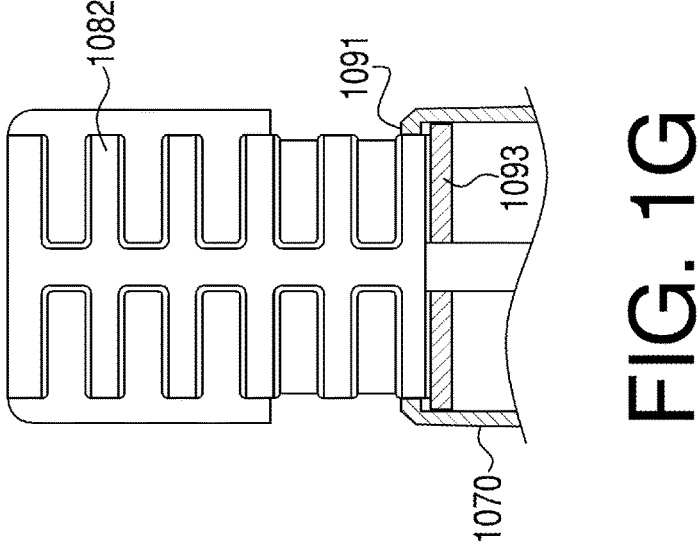
Figure 1F:
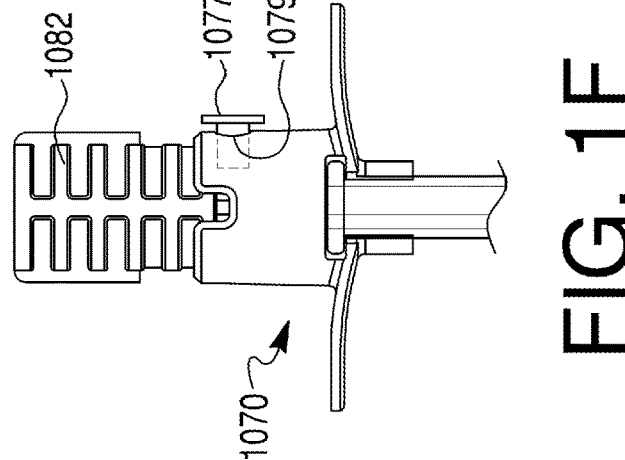

As shown in FIGS. 1G and 1H, in some embodiments, a protrusion 1093 may be disposed at a distal portion of actuation portion 1082, which may be located inside flange piece 1070 upon assembly of device 1050. An inward lip 1091 of flange piece 1070 may overhang protrusion 1093, such that actuation portion 1082 may not be pulled proximally out of flange piece 1070. In some embodiments, either protrusion 1093, lip 1091, or both may be disposed circumferentially about actuation portion 1082, such that lip 1091 blocks protrusion 1093 regardless of a rotational position of actuation portion 1082 relative to flange piece 1070. Protrusion 1093 and lip 1091 may have squared-off cross-sectional profiles, as shown in FIG. 1G, angled cross-sectional profiles, as shown in FIG. 1H, or any other suitable cross-sectional profiles. In some embodiments, a cross-sectional profile of protrusion 1093, lip 1091, or both may be selected to improve ease of manufacturing (e.g., machining or molding the shape of protrusion 1093 or lip 1091), or may be selected to improve assembly (e.g., insertion of plunger rod 1080 into and partially through flange piece 1070).

Figure 1J:
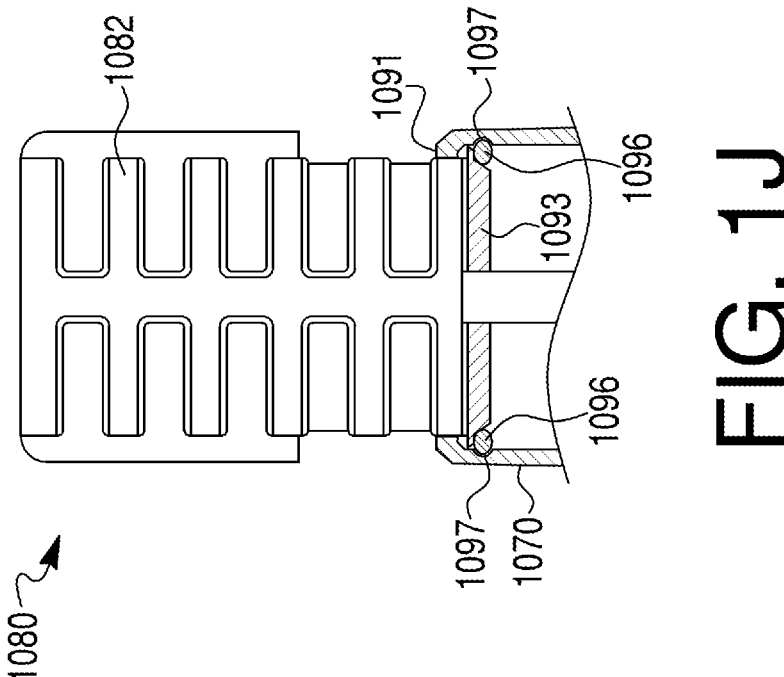
Figure 1I:
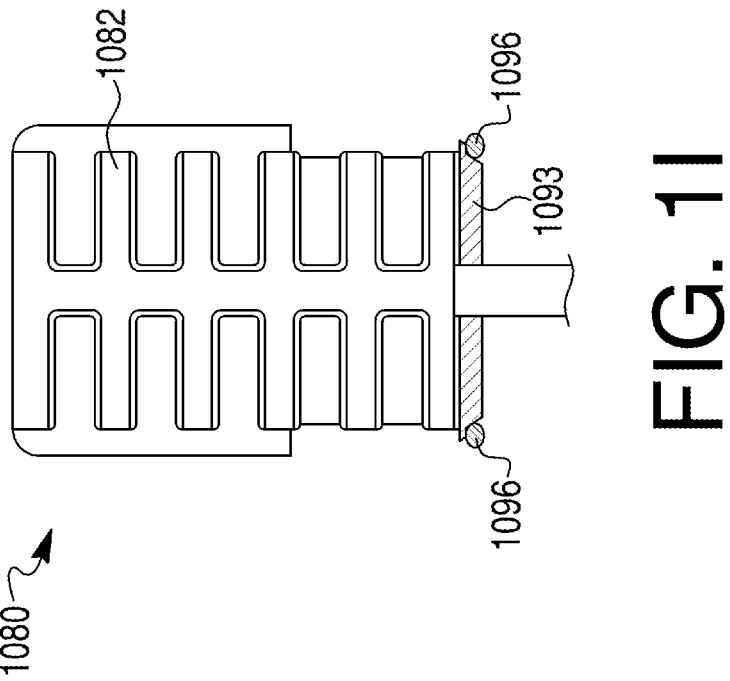

As shown in FIG. 1I, in some embodiments, actuation portion 1082 may include one or more projections 1096 extending radially outward from an exterior perimeter of protrusion 1093. For example, protrusion 1093 may include a pair of projections 1096 disposed about protrusion 1093 at opposite locations relative to one another. Projections 1096 may include various suitable sizes, shapes, and/or cross-sectional profiles. In some embodiments, projections 1096 may have a circular shape with a rounded exterior profile to facilitate movement of protrusion 1093 within flange piece 1070.

In the present example, projections 1096 may be positioned along a side of protrusion 1093 that longitudinally aligned with a corresponding side of actuation portion 1082 including protrusions 1086. In other examples, projections 1096 may be positioned along a side of protrusion 1093 that is offset (e.g., not in longitudinal alignment) with the side of actuation portion 1093 including protrusions 1086. Projections 1096 may be formed of various flexible materials, including, for example, a polymer such as plastic, rubber, etc. It should be appreciated that plunger rod 1080 may include additional and/or fewer projections 1096 on protrusion 1093, or other portions of actuation portion 1082, than those shown and described herein without departing from a scope of this disclosure.

FIG. 1J depicts a distal end portion of flange piece 1070 including one or more recesses 1097 along an interior surface. Recesses 1097 may be sized and shaped to receive projections 1096 when protrusion 1093 is received within flange piece 1070 and positioned adjacent and/or in contact with lip 1091. It should be appreciated that lip 1091 may be configured to require application of a hydrodynamic force onto plunger rod 1080 to receive projections 1096 and protrusion 1093 distally of lip 1091 and into flange piece 1070, thereby priming device 1050 and inhibiting retraction (e.g., proximal movement) of plunger rod 1080 relative to flange piece 1070. It should be appreciated that by inhibiting removal of plunger rod 1080 after an initial assembly into flange piece 1070, device 1050 may be configured to prevent reuse of device 1050 after an initial use, and/or to prevent inadvertent air intake forming bubbles within device 1050. In the present example, flange piece 1070 may include a plurality of recesses 1097 disposed about the distal end portion in an annular array relative to one another. The plurality of recesses 1097 may be spaced apart from one another about a circumference of flange piece 1070. In some embodiments, flange piece 1070 may include recesses 1097 having varying sizes and/or shapes relative to one another.

As described in further detail below, a subset of the plurality of recesses 1097 may be sized and shaped to receive and allow passage of projections 1096 therethrough upon movement of protrusion 1093 relative to flange piece 1070. A second subset of the plurality of recesses 1097 may be sized and shaped to receive and inhibit passage of projections 1096 therethrough such that protrusion 1093 is restricted from further movement relative to flange piece 1070, as explained in further detail below.

Figures 1K, 1L, 1M:
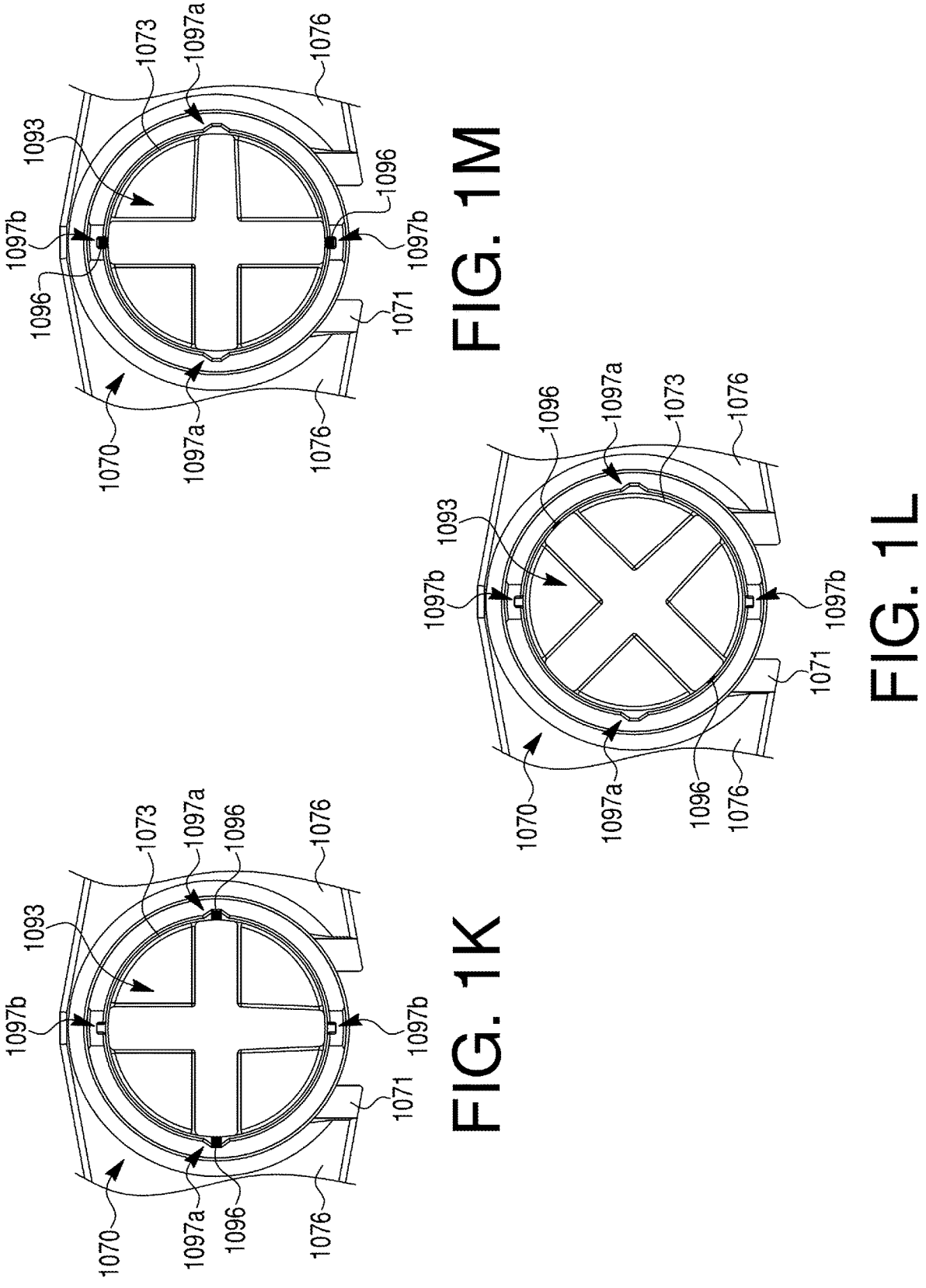

For example, as shown in FIG. 1K, flange piece 1070 includes a pair of widened recesses 1097a positioned about opening 1073 (with plunger rod 1080 received therethrough) at opposite locations relative to one another (e.g., spaced about 180 degrees apart from one another). Flange piece 1070 further includes a pair of narrowed recesses 1097*b* positioned about opening 1073 at opposite locations relative to one another (e.g., about 180 degrees from one another). A recess 1097*a* may be positioned about 90 degrees apart from an adjacent recess 1097*b*, along the circumference of flange piece 1070. Widened recesses 1097*a* may include a center wall transverse (e.g., perpendicular) to a longitudinal length of flanges 1076 and sidewalls that are angled relative to the center wall. Narrowed recesses 1097*b* may include a center wall parallel to the longitudinal length of flanges 1076 and sidewalls that are perpendicular to the center wall. It should be appreciated that widened recesses 1097*a* may form a larger opening for receiving projections 1096 relative to narrowed recesses 1097*b*. It should further be understood that sidewalls of recesses 1097*a*, 1097*b* may have a height that is parallel to a longitudinal length of device 1050.

In a first configuration seen in FIG. 1K, plunger rod 1080 is received through flange piece 1070 and protrusion 1093 is oriented relative to opening 1073 such that projections 1096 are received within widened recesses 1097*a*. The angled sidewalls of widened recesses 1097*a* may provide clearance to facilitate movement of projections 1096 out of widened recesses 1097*a* in response to a rotation of plunger rod 1080 relative to flange piece 1070. In this instance, projections 1096 may move along the angled sidewalls of widened recesses 1097*a* as protrusion 1093 rotates relative to opening 1073.

As seen in FIG. 1L, projections 1096 may abut against the interior surface of flange piece 1070 defining opening 1073 as protrusion 1093 rotates. Projections 1096 may generate a frictional interference against flange piece 1070 while moving between adjacent recesses 1097. FIG. 1M shows protrusion 1093 positioned relative to opening 1073 with projections 1096 aligned with and received in narrowed recesses 1097*b*. In this instance, plunger rod 1080 may be configured to generate an audible and/or tactile feedback in response to narrowed recesses 1097*b* receiving projections 1096. For example, a "click" or "snap" noise may be generated in response to a release of pressure applied to projections 1096 by the interior surface of flange piece 1070 when projections 1096 are received in narrowed recesses 1097*b*. Additionally and/or alternatively, an audible feedback may be produced in response to projections 1096 expanding and striking one or more walls defining narrowed recesses 1097*b* when received therein.

It should be appreciated that a frictional interference between projections 1096 and flange piece 1070 may be removed upon receipt of projections 1096 within narrowed recesses 1097*b*. The sidewalls of narrowed recesses 1097*b* may provide a physical restriction that inhibits further movement of projections 1096. In this instance, plunger rod 1080 may be fixed relative to flange piece 1070 such that protrusion 1093 is inhibited from further rotation relative to opening 1073 when projections 1096 are received within narrowed recesses 1097*b*.

Figure 1N:
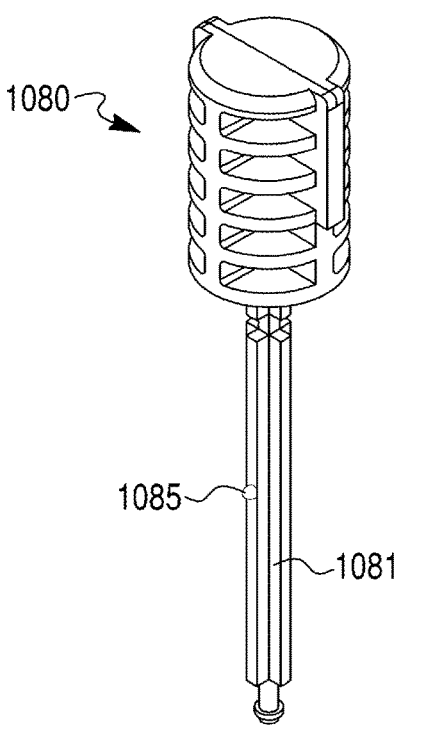
Figure 1O:
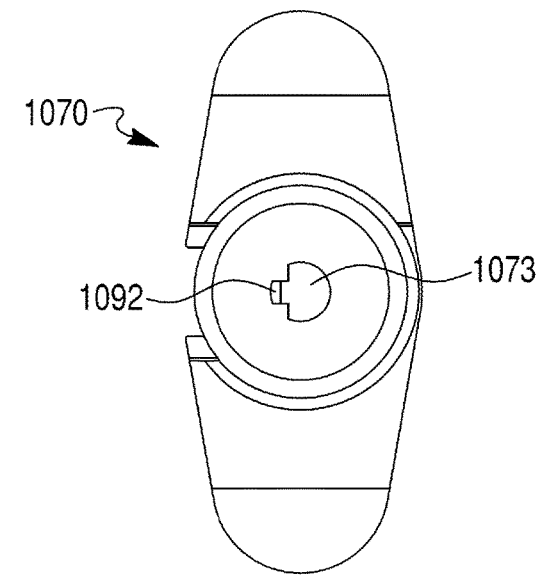
Figure 1P:
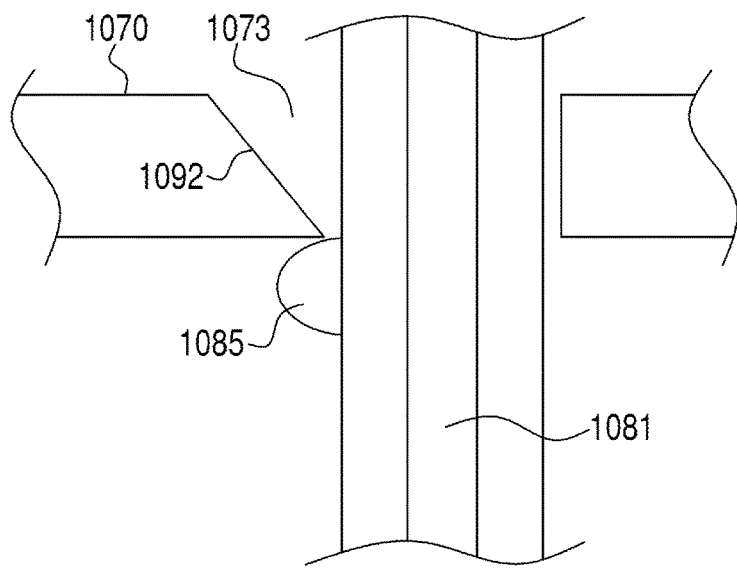

As shown in FIGS. 1N-1P, in some embodiments, plunger rod 1080 may additionally or alternatively include a protrusion 1085 on stem 1081, which may be configured to interact with opening 1073 of flange piece 1070, such that protrusion 1085 may only move distally through opening 1073. A side 1092 of opening 1073 may be angled to allow for distal passage of protrusion 1085, and to block proximal passage of protrusion 1085, as stem 1081 moves through opening 1073. Protrusion 1085 and/or side 1092 may have any suitable shape or configuration to achieve this purpose. In some embodiments, a shape or configuration of protrusion

1085 and/or side 1092 may be selected to improve ease of manufacturing (e.g., machining or molding the shape of protrusion 1085 and/or flange piece 1070).

Figure 1R:
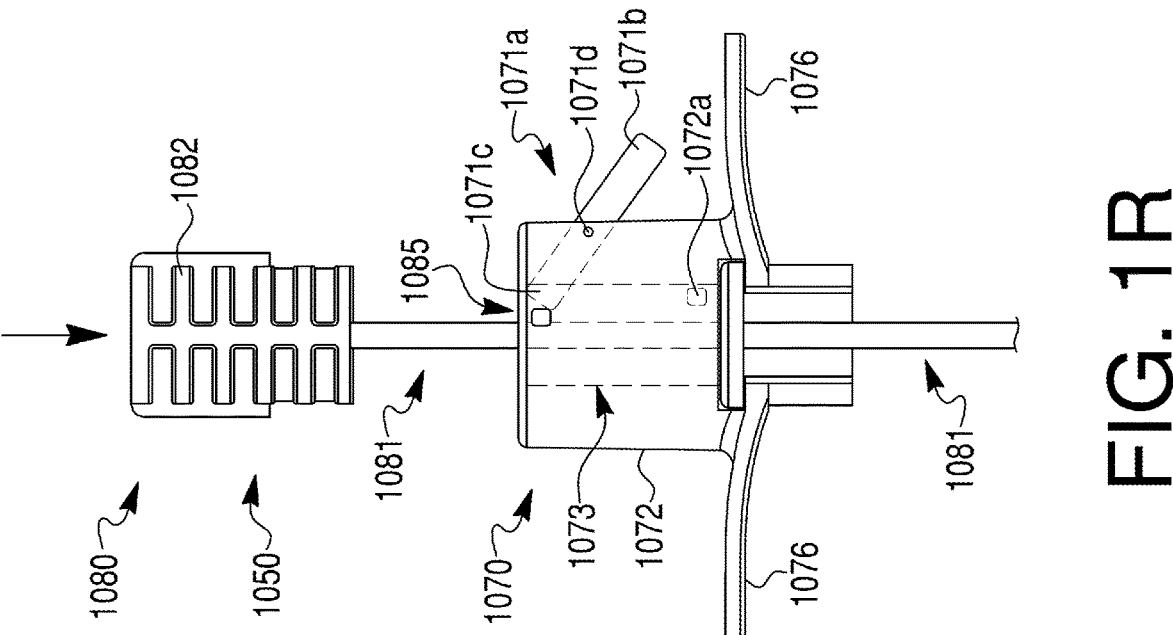
Figure 1Q:
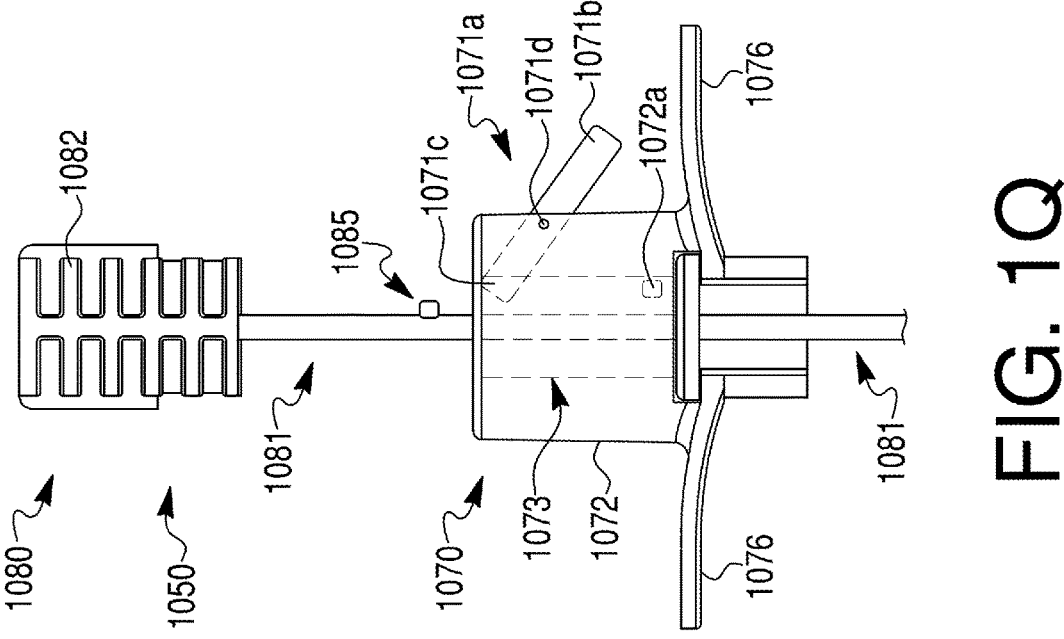

In other embodiments, flange piece 1070 may include a movable lever 1071*a* as seen in FIGS. 1Q-1T. Movable lever 1071*a* may include a first end 1071*b* extending outwardly from collar 1072 and a second end 1071*c* disposed within collar 1072. Movable lever 1071*a* may be movable (e.g., pivotable) about a rotation pin 1071*d*. Second end 1071*c* may be positioned within opening 1073 such that movable lever 1071*a* is configured to interact with protrusion 1085 upon receipt of plunger rod 1080 in flange piece 1070. Referring initially to FIG. 1Q, plunger rod 1080 may be configured to prime device 1050 by translating stem 1081 distally through flange piece 1070 until encountering movable lever 1071*a*.

As seen in FIG. 1R, second end 1071*c* may abut against protrusion 1085 when movable lever 1071*a* is in an obstructing position. Second end 1071*c* may be configured to inhibit translation of plunger rod 1080 relative to flange piece 1070 when plunger rod 1080 is in a primed position. It should be appreciated that a distance between second end 1071*c* and protrusion 1085 may define a priming distance for moving plunger rod 1080 to prime device 1050. Movable lever 1071*a* may be configured to move (e.g., pivot) relative to collar 1072 and about rotation pin 1071*d* to displace second end 1071*c* from the obstruction position. The pivoting axis, along which rotation pin 1071*d* extends, may be substantially perpendicular to the longitudinal axis along which plunger rod 1080 extends.

Figure 1T:
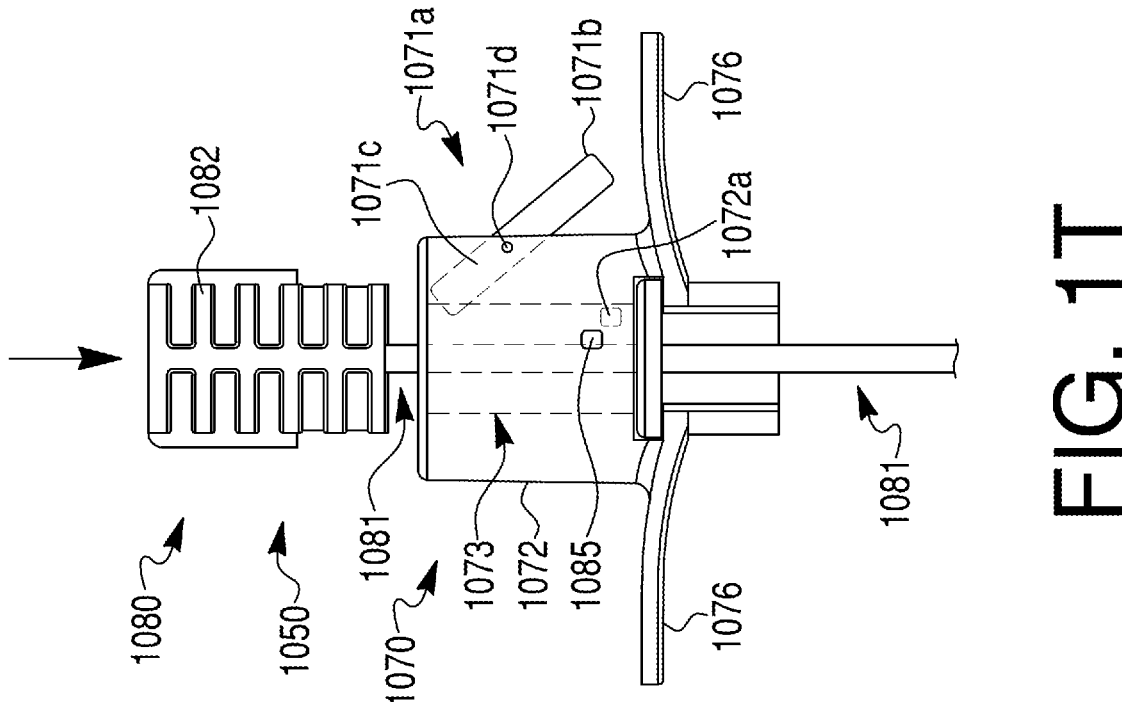
Figure 1S:
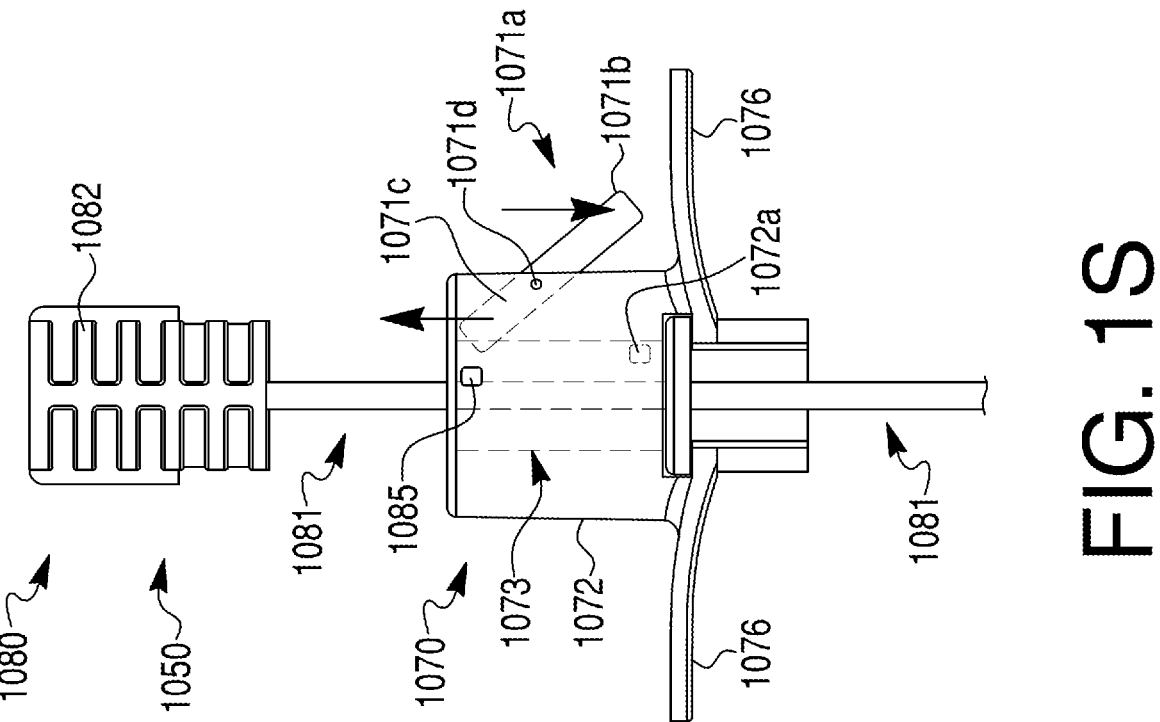

For example, as seen in FIG. 1S, movable lever 1071*a* may be actuated in response to moving first end 1071*b* distally toward flange 1076 and about rotation pin 1071*d*. In some embodiments, first end 1071*b* may be actuated in response to receiving a distally-directed force applied thereto by, for example, a user of device 1050. Second end 1071*c* may be moved in a proximal direction away from flange 1076 and relative to rotation pin 1071*d* in response to first end 1071*b* moving distally, thereby causing second end 1071*c* to disengage protrusion 1085.

Accordingly, as shown in FIG. 1T, movable lever 1071*a* may allow plunger rod 1080 to translate relative to flange piece 1070 until protrusion 1085 encounters an abutment 1072*a* positioned at a distal end of opening 1073. Abutment 1072*a* may cause plunger rod 1080 to settle into a dose completion position of plunger rod 1080 when protrusion 1085 is engaged thereto. It should be appreciated that a distance between second end 1071*c* and abutment 1072*a* may define a dosage delivery distance for moving plunger rod 1080 to dispense a controlled volume of substance from device 1050.

Figure 1V:
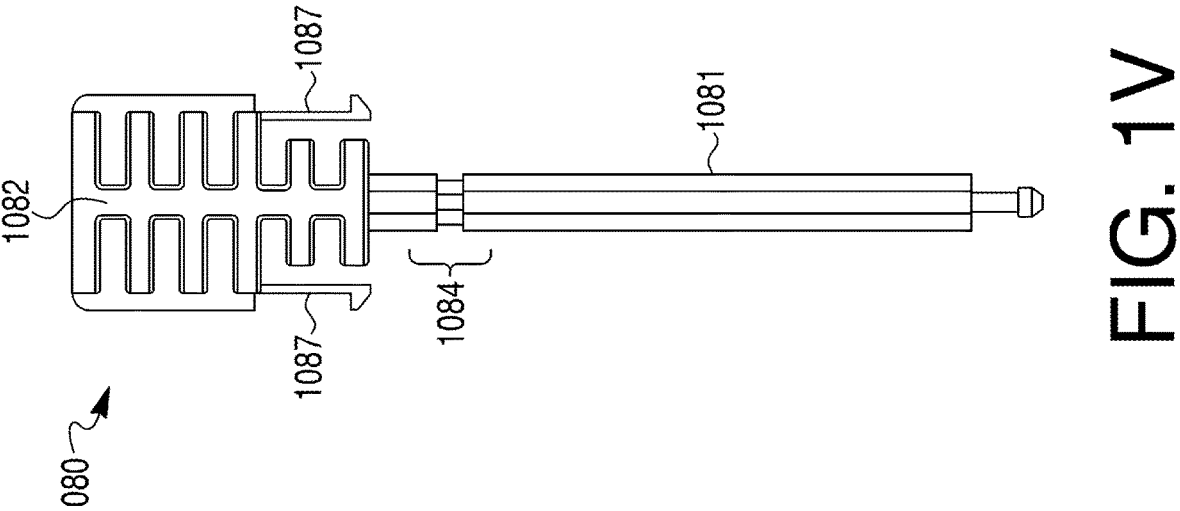
Figure 1U:
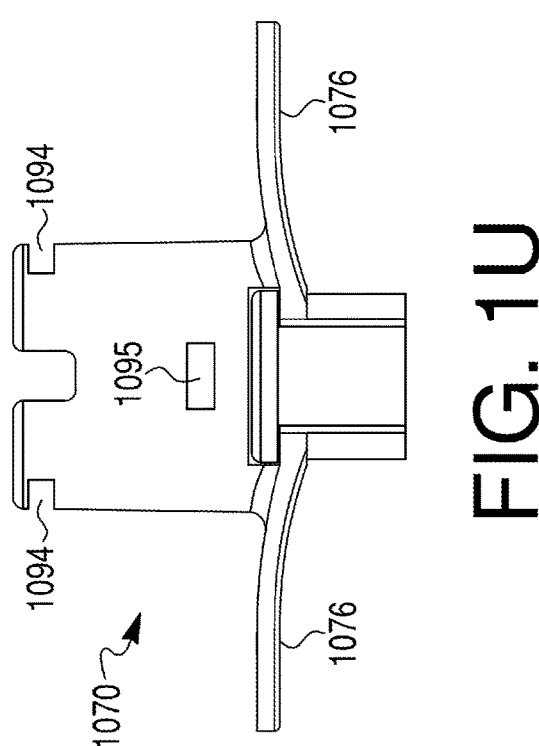

As shown in FIGS. 1U and 1V, in some embodiments, actuation portion 1082 of plunger rod 1080 may additionally or alternatively include one or more extensions 1087 configured to interface with side openings 1094, 1095 in collar 1072 of flange piece 1070. Extensions 1087 may extend distally from actuation portion 1082, and may have an angled or rounded distal portion sized and configured to be pushed inward toward a central axis of plunger rod 1080 when actuation portion 1082 is pushed distally into collar 1072. The angled or rounded distal portion of each extension 1087 may include a hook or clip shaped part 1087*a*. Extensions 1087 may additionally be made of a flexible material, allowing them to be pushed inward into collar 1072 and spring back outwards when no longer being restricted by a side of collar 1072. Side openings 1094, 1095 in collar 1072 may be sized and configured to receive hook or clip shaped part 1087*a* of an extension 1087, such that once an extension 1087 reaches a side opening 1094 or 1095, a hook or clip shaped part 1087*a* may spring outward into the side opening 1094 or 1095 and thereafter prevent proximal movement of plunger rod 1080. A number of extensions 1087 may coincide with a number of each of side openings 1094 and side openings 1095, such that each extension 1087 may be received in a corresponding side opening 1094 or 1095 simultaneously as plunger rod 1080 moves distally relative to flange piece 1070.

Specifically, first side openings 1094 may be configured to receive hook or clip shaped parts 1087*a* of extensions 1087 upon assembly of device 1050, to prevent proximal movement of plunger rod 1080 once plunger rod 1080 is inserted to a ready-to-use position. As hook or clip shaped part 1087*a* of each extension 1087 is received in first side openings 1094, it may make a "clicking" sound as it interfaces with collar 1072, thereby providing auditory and/or tactile feedback, indicating that the device is in a ready-to-use position. In some embodiments, first side openings 1094 may each extend around a partial circumference of collar 1072, such that the hook or clip shaped parts 1087*a* of extensions 1087 may be received inside openings 1094 in a range of rotational positions of plunger rod 1080 relative to flange piece 1070. Second side openings 1095 may be configured to receive hook or clip shaped parts 1087*a* of extensions 1087 once device 1050 is in a "delivery" configuration (e.g., after priming and additional rotation of actuation portion 1082 to align protrusions 1086 with slots 1074). In the embodiment depicted in FIGS. 1U and 1V, extensions 1087 are longitudinally aligned with protrusions 1086, and, as depicted in FIGS. 3C-3F, side openings 1095 are likewise longitudinally aligned with slots 1074, to allow for distal movement of actuation portion 1082 further into collar 1072 when device is in the "delivery" configuration. It should be appreciated that device may be transitioned to the "delivery" configuration in response to applying a distally-directed force onto actuation portion 1082, to overcome an engagement of side openings 1094 with extensions 1087, and a rotative force to overcome a frictional force between an interior of collar 1072 and extensions 1087. However, in other embodiments, it is contemplated that extensions 1087 and side openings 1094, 1095 may be in any suitable complementary configuration to assist in controlling proximal movement of plunger rod 1080.

Figure 1W:
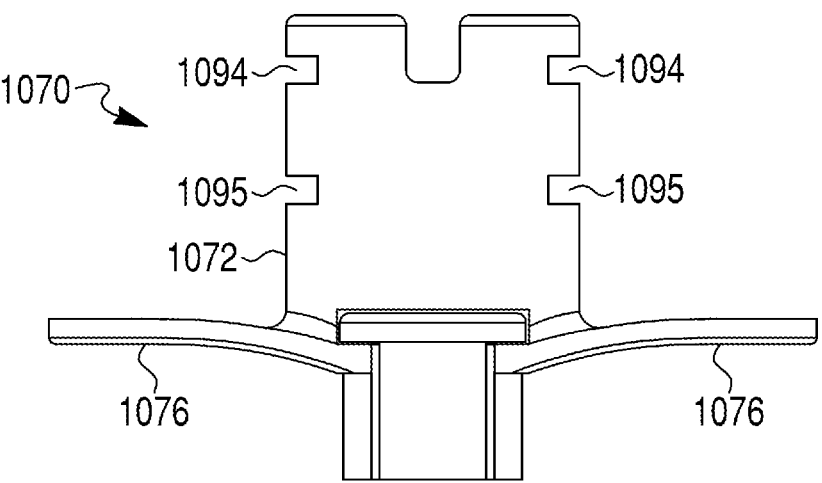

In other embodiments, as shown in FIG. 1W, side openings 1094 may be positioned along collar 1072 in longitudinal alignment with side openings 1095. Device 1050 may be primed upon receiving hook or clip shaped parts 1087*a* of extensions 1087, initially positioned proximally of side openings 1094, within side openings 1094. In some instances, a feedback (e.g., tactile, auditory, etc.) may be generated in response to extensions 1087 being received within side openings 1094. It should be understood that a proximal end of collar 1072 may resist distal advancement of plunger rod 1080 relative to flange piece 1070 in response to hook or clip shaped parts 1087*a* being engaged to collar 1072 at side openings 1094. Applying a distally-directed force onto plunger rod 1080 may cause extensions 1087 to be released from side openings 1094 and translated distally through collar 1072 until received within side openings 1095.

It should be appreciated that the distally-directed force required to deflect extensions 1087 inwardly and to release hook or clip shaped parts 1087*a* from side openings 1094 may correspond to a minimum priming and hydrodynamic force. Accordingly, plunger rod 1080 may be maintained in a constant radial orientation during a priming step and delivery step of device 1050. In other embodiments, additional and/or fewer side openings may be included along a circumferential wall of collar 1072 in longitudinal alignment and/or offset (e.g., not longitudinally aligned) with side openings 1094, 1095.

Figure 1X:
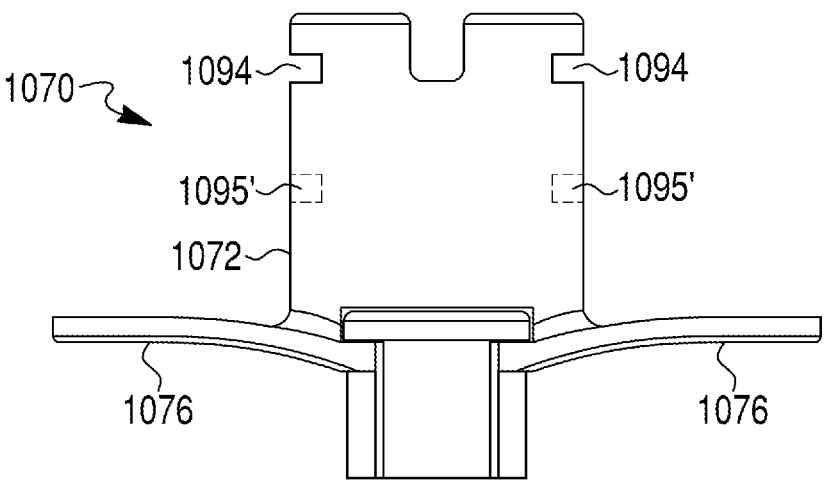

As seen in FIG. 1X, flange piece 1070 may alternatively include one or more inner projections 1095' in lieu of side openings 1095 shown and described above. In this instance, plunger rod 1080 may be preassembled into flange piece 1070 with extensions 1087 (FIG. 1V) squeezed into collar 1072 and positioned relatively proximal to side openings 1094. Device 1050 may be primed by pushing plunger rod 1080 distally through flange piece 1070 until extensions 1087 are received within side openings 1094. In some instances, a feedback (e.g., tactile, auditory, etc.) may be generated in response to extensions 1087 being received within side openings 1095. In further embodiments, side openings 1094 may be flared and/or extensions 1087 may have a distally-tapering profile to facilitate further distal advancement of plunger rod 1080 from a primed position to a dose completion position.

Further translation of plunger rod 1080 relative to flange piece 1070 may cause extensions 1087 to bend radially-inward toward one another, thereby allowing plunger rod 1080 to translate distally to deliver a dose from device 1050. Plunger rod 1080 may continue to translate distally relative to collar 1072 until hook or clip shaped parts 1087*a* (FIG. 1V) encounter inner projections 1095'. Inner projections 1095' may be configured to contact extensions 1087 and fix plunger rod 1080 to the dose completion position, and/or prevent further distal movement of plunger rod 1080 relative to flange piece 1070. Accordingly, further movement (e.g., proximal and/or distal) of plunger rod 1080 relative to flange piece 1070 may be inhibited by inner projections 1095' engaging hook or clip shaped parts 1087*a* within collar 1072. Inner projections 1095' may include complimentary hooks or clip-shaped parts that are sized and/or shaped to interact with hook or clip shaped parts 1087*a* or extensions 1087. It should be appreciated that a distance between side openings 1094 and inner projections 1095' may define a dosage delivery distance to dispense a controlled volume of substance from device 1050.

Figures 2A, 2B:
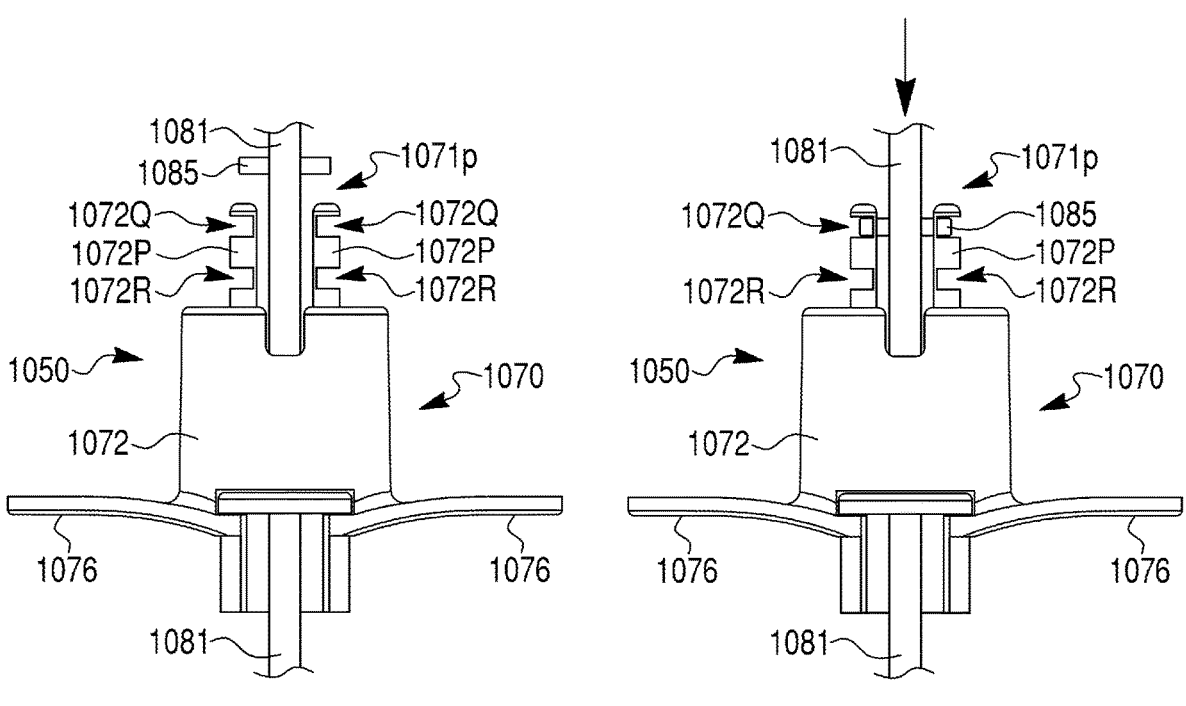
Figure 2C:
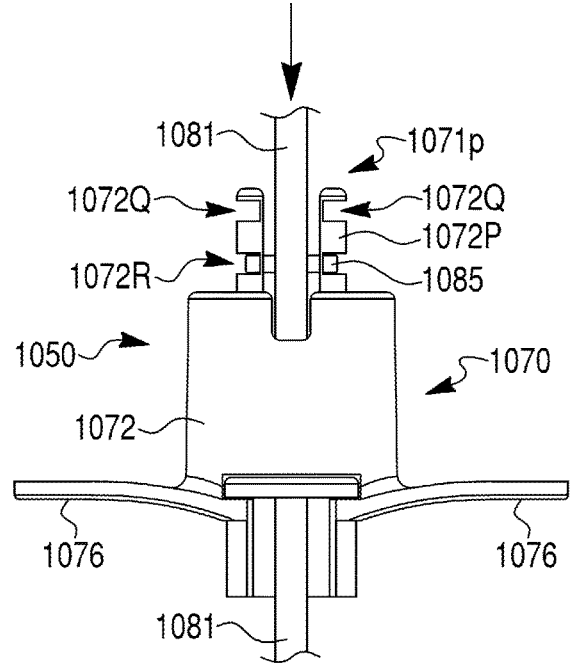

In other embodiments, as shown in FIGS. 2A-2C, flange piece 1070 may include a fixed sleeve 1072P extending proximally from collar 1072. Fixed sleeve 1072P may have a circular cross-section defining an inner channel with an opening at each terminal end of the fixed sleeve 1072P. The inner channel of fixed sleeve 1072P may extend through a longitudinal length of fixed sleeve 1072P and may be longitudinally aligned with opening 1073 (FIG. 10) such that a respective longitudinal axis of the inner channel and opening 1073 are coaxial with one another. Fixed sleeve 1072P may be sized, shaped, and configured to receive stem 1081. In some embodiments, fixed sleeve 1072P may be integral with collar 1072, while in other embodiments fixed sleeve 1072P may be a separate component assembled onto flange piece 1070.

Fixed sleeve 1072P may include a plurality of openings that are sized and shaped to receive protrusion 1085. For example, fixed sleeve 1072P may include a pair of proximal openings 1072Q and a pair of distal openings 1072R longitudinally spaced apart from one another by an offset distance. Further, the pair of proximal openings 1072Q are located at the same longitudinal position as one another, and the pair of distal openings 1072R are located at the same longitudinal position as one another. As described in further detail below, the longitudinal offset between proximal openings 1072Q and distal openings 1072R may define a dosage delivery distance for moving plunger rod 1080 to dispense a controlled volume of substance from device 1050. Alternatively, the longitudinal offset between openings 1072Q, 1072R may define a priming distance of device 1050 such that protrusion 1085 may be initially received within proximal openings 1072Q during an assembly of device 1050 to inhibit proximal retraction of plunger rod 1080. In this instance, a dosage delivery distance may correspond to a longitudinal offset between a distal end of actuation portion 1082 and a bottom surface of collar 1072 when protrusion 1085 is received within distal opening 1072R. Although not shown, it should be appreciated that an additional set of openings may be included on fixed sleeve 1072P (e.g., proximal of proximal openings 1072Q, distal of proximal openings 1072Q, and/or distal of distal openings 1072R) to further define a priming distance and/or dosage delivery distance.

A proximal end of fixed sleeve 1072P may include an angled interface 1071P defining a proximal opening of fixed sleeve 1072P. Angled interface 1071P may be tapered radially-inward toward the inner channel of fixed sleeve 1072P and configured to guide stem 1081 and protrusion 1085 into the inner channel. In the present example, protrusion 1085 may extend radially outward from stem 1081 in opposing lateral directions and may be compressible and/or formed of a flexible/deformable material, such that protrusion 1085 is configured to retract or deform radially inward into and/or toward stem 1081 in response to a force being applied thereto. In other embodiments, protrusion 1085 may be configured to at least partially deform fixed sleeve 1072P to facilitate movement of protrusion 1085 toward and/or between openings 1072Q, 1072R. In this instance, fixed sleeve 1072P may be formed of a flexible material operable to flex radially-outward when applying a distally-directed force onto stem 1081, thereby causing protrusion 1085 to apply a radial force onto fixed sleeve 1072P.

Still referring to FIG. 2A, fixed sleeve 1072P may be configured to receive plunger rod 1080 through the inner channel and allow stem 1081 to pass through collar 1072 to prime device 1050. Protrusion 1085 may be received within fixed sleeve 1072P in response to encountering angled surface 1071P and compressing radially inward relative to stem 1081 until plunger rod 1080 is moved distally enough so that protrusion 1085 is received by proximal openings 1072Q. As shown in FIG. 2B, protrusion 1085 may be configured to expand radially outward (decompress) when longitudinally aligned with proximal openings 1072Q to lock stem 1081 relative to flange piece 1070. In this instance, device 1050 may be in a primed position such that further translation of stem 1081 distally relative to fixed sleeve 1072P and flange piece 1070 may deliver a dose from device 1050. Alternatively, device 1050 may be preassembled with protrusion 1085 received in proximal openings 1072Q such that translation of stem 1081 distally relative to fixed sleeve 1072P may prime device 1050 until protrusion 1085 is received within distal openings 1072R.

As seen in FIG. 2C, while protrusion 1085 is positioned within proximal openings 1072Q applying a distally-directed force onto stem 1081 may cause fixed sleeve 1072P to compress (or deform) protrusion 1085 radially inward, thereby allowing stem 1081 to translate distally relative to fixed sleeve 1072P. Alternatively, protrusion 1085 may be manually compressed (or deformed) by applying a radially inward-directed force through proximal openings 1072Q. Protrusion 1085 may move distally through an inner channel of fixed sleeve 1072P and may be received by distal openings 1072R. As stem 1081 translates distally relative to collar 1072, device 1050 may transition from the primed position to a dose completion position when protrusions 1085 are received within distal openings 1072R, thus delivering the dose.

It should be appreciated that a volume of the dose delivered by device 1050 may be controlled based on the longitudinal offset distance between proximal openings 1072Q and distal openings 1072R. In some embodiments, fixed sleeve 1072P may include additional openings for receiving protrusion 1085 after priming and delivering a dose to inhibit proximal retraction of stem 1081 (e.g., pull back of plunger rod 1080) relative to flange piece 1070. For example, protrusion 1085 may be received within proximal openings 1072Q during an assembly of device 1050 at a manufacturing stage such that distal openings 1072R may define a priming position and a third set of openings (not shown) distal to distal opening 1072R may define a dosage delivery position. Alternatively, a bottom, interior surface of flange piece 1070 distal to distal opening 1072R may define the dosage delivery position of plunger rod 1080.

In some embodiments, as seen in FIGS. 2D-2G, flange piece 1070 may include a movable sleeve 1072S extending distally and proximally from collar 1072. Movable sleeve 1072S may have a circular cross-section defining an inner channel with an opening at each terminal end of movable sleeve 1072S. The inner channel of movable sleeve 1072S may extend through a longitudinal length of movable sleeve 1072S. Movable sleeve 1072S may be sized, shaped, and configured to be received through opening 1073, and the inner channel of movable sleeve 1072S may be sized to receive stem 1081. Movable sleeve 1072S may be fixed relative to collar 1072 when in a preassembled configuration and may be movable relative to collar 1072 upon engagement with plunger rod 1080.

Movable sleeve 1072S may include a plurality of openings that are sized and shaped to receive protrusion 1085. For example, movable sleeve 1072S may include a proximal opening 1072U at a proximal end of movable sleeve 1072S and a distal opening 1072T at a distal end of movable sleeve 1072S. A proximal end of movable sleeve 1072S may further include an angled interface 1071S defining a proximal opening of movable sleeve 1072S. Angled interface 1071S may be tapered radially-inward toward the inner channel of movable sleeve 1072S and configured to guide stem 1081 and protrusion 1085 into the inner channel of movable sleeve 1072S. In some embodiments, protrusion 1085 may extend radially outward from stem 1081 in opposite directions and may be compressible such that protrusion 1085 is configured to compress into and/or toward stem 1081 in response to a force being applied thereto.

Figure 2E:
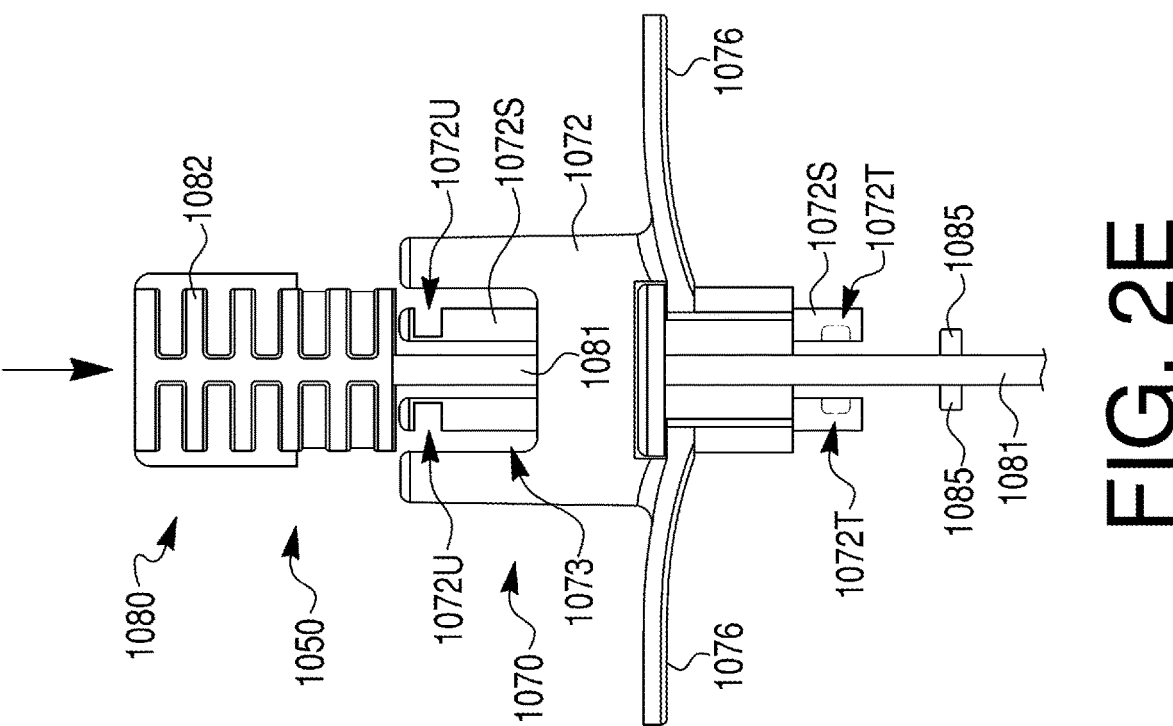
Figure 2D:
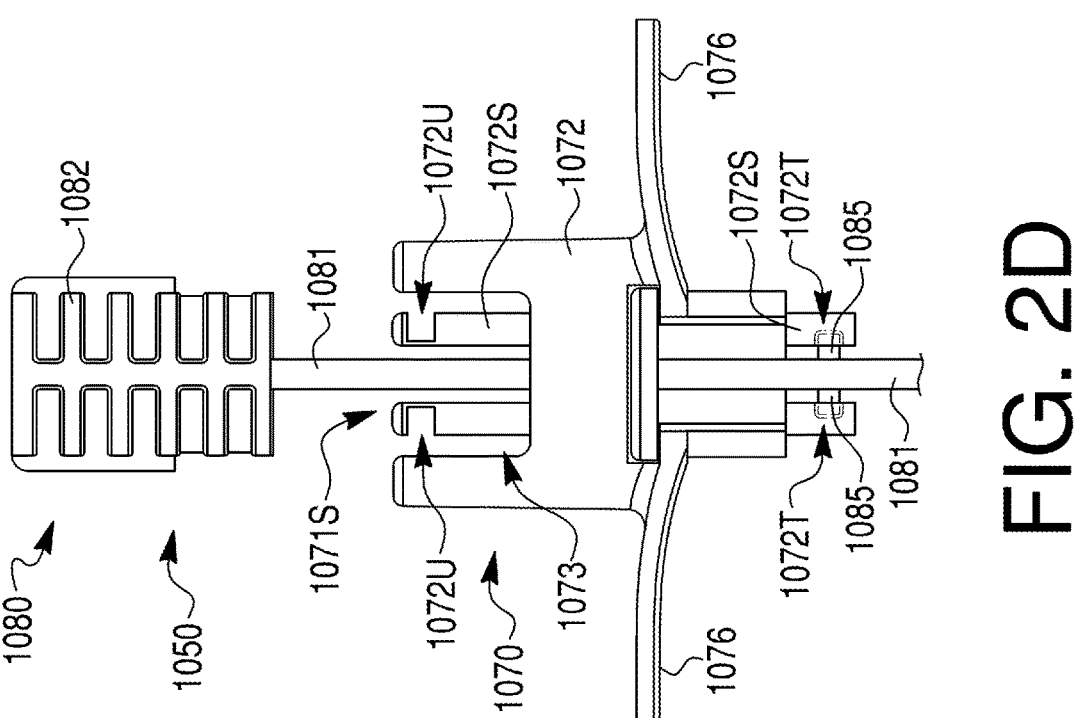

Still referring to FIG. 2D, the proximal end of movable sleeve 1072S may be positioned adjacent to a proximal end of collar 1072 and a distal end of movable sleeve 1072S may be positioned adjacent to a distal end of collar 1072 when in the preassembled position. Plunger rod 1080 may be received through the inner channel of movable sleeve 1072S with stem 1081 extending through collar 1072. Protrusion 1085 may be received within distal opening 1072T such that plunger rod 1080 may be fixed to movable sleeve 1072S. Protrusion 1085 may be configured to exit distal opening 1072T and expand laterally outward in response to plunger rod 1080 translating relative to movable sleeve 1072S.

For example, as shown in FIG. 2E, applying a distally-directed force onto actuation portion 1082 may cause protrusion 1085 to compress radially inward, thereby allowing stem 1081 to translate distally relative to movable sleeve 1072S. In this instance, protrusion 1085 may exit distal opening 1072T and expand upon translating distally from a distal end of movable sleeve 1072S. Device 1050 may transition from a preassembled state to a primed state, in response to stem 1081 translating distally relative to collar 1072, until actuation portion 1082 abuts against a proximal end of movable sleeve 1072S. In this instance, device 1050 may be in a primed state and further translation of stem 1081 relative to collar 1072 may be inhibited by the presence of movable sleeve 1072S.

Figure 2F:
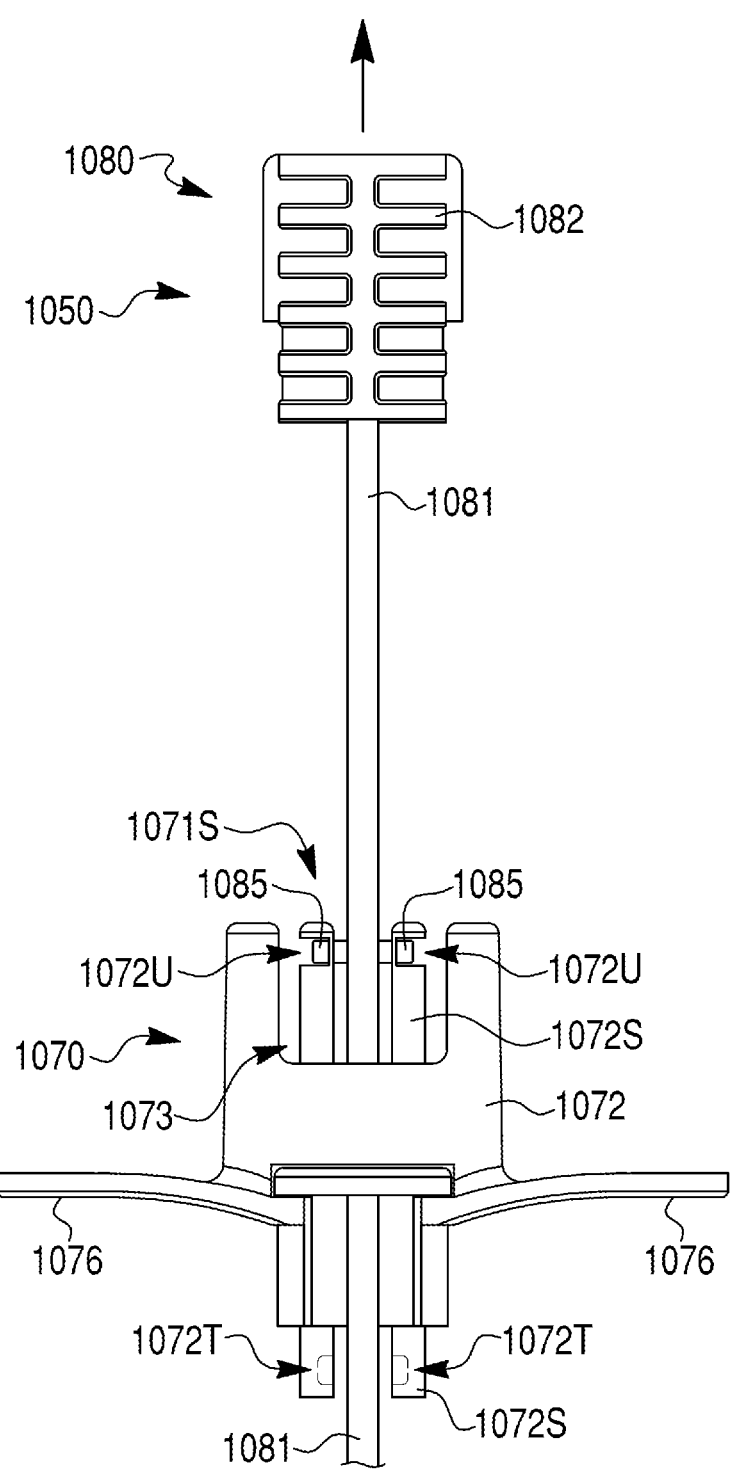

Referring now to FIG. 2F, plunger rod 1080 may couple to movable sleeve 1072S in response to proximal translation of stem 1081 relative to collar 1072 until protrusion 1085 engages proximal opening 1072U. It should be understood that protrusion 1085 may be in a compressed state when translating through an inner channel of movable sleeve 1072S and may expand into proximal opening 1072U upon longitudinal alignment therewith. With protrusion 1085 engaged to proximal opening 1072U, a distal translation of plunger rod 1080 relative to flange piece 1070 may provide a simultaneous movement of movable sleeve 1072S relative to collar 1072. It should be appreciated that a collective length of movable sleeve 1072S and plunger rod 1080 may be greater than a longitudinal length of plunger rod 1080 alone.

Figure 2G:
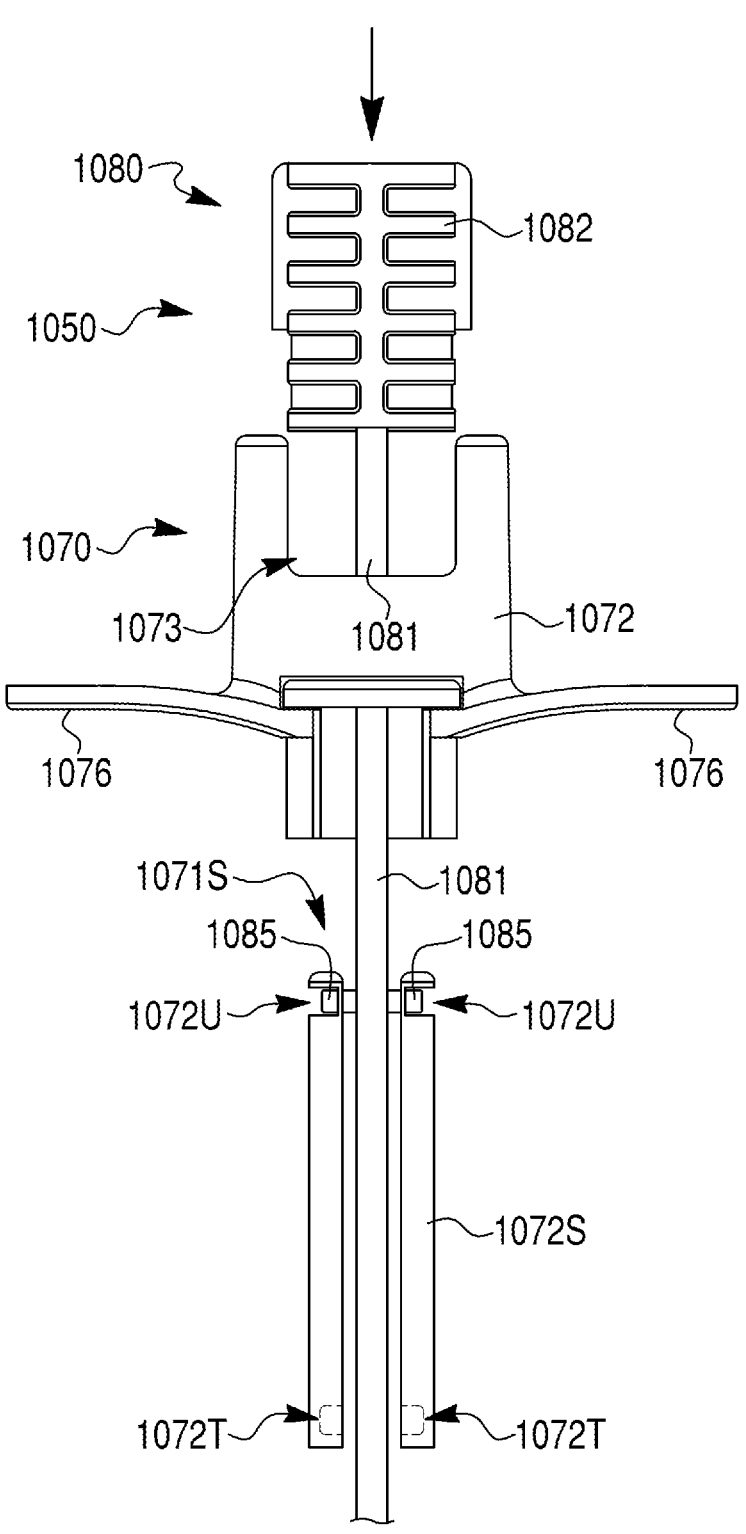

As seen in FIG. 2G, plunger rod 1080 may be configured to move movable sleeve 1072S through a channel of flange piece 1070 by a predetermined distance until actuation portion 1082 encounters a proximal end of collar 1072. Plunger rod 1080 may be configured to deliver a dose from device 1050 in response to translating movable sleeve 1072S distally relative to collar 1072. It should be appreciated that the dosage delivered by device 1050 may be controlled based on the predetermined distance between actuation portion 1082 and collar 1072 when protrusion 1085 is received within proximal opening 1072U. In some embodiments, flange piece 1070 may be configured to inhibit proximal movement of movable sleeve 1072S relative to collar 1072 when protrusion 1085 is received within proximal opening 1072U. Although not shown, flange piece 1070 may include one or more blocking components operable to restrict proximal retraction of movable sleeve 1072S from opening 1073.

In other embodiments, as seen in FIGS. 2H-2M, plunger rod 1080 may include at least one protrusion 1085W positioned on actuation portion 1082. In the example, protrusion 1085W may be positioned at or adjacent a distal end of actuation portion 1082 such that protrusion 1085W may be received within flange piece 1070 in response to translation of plunger rod 1080 into collar 1072.

Figure 2I:
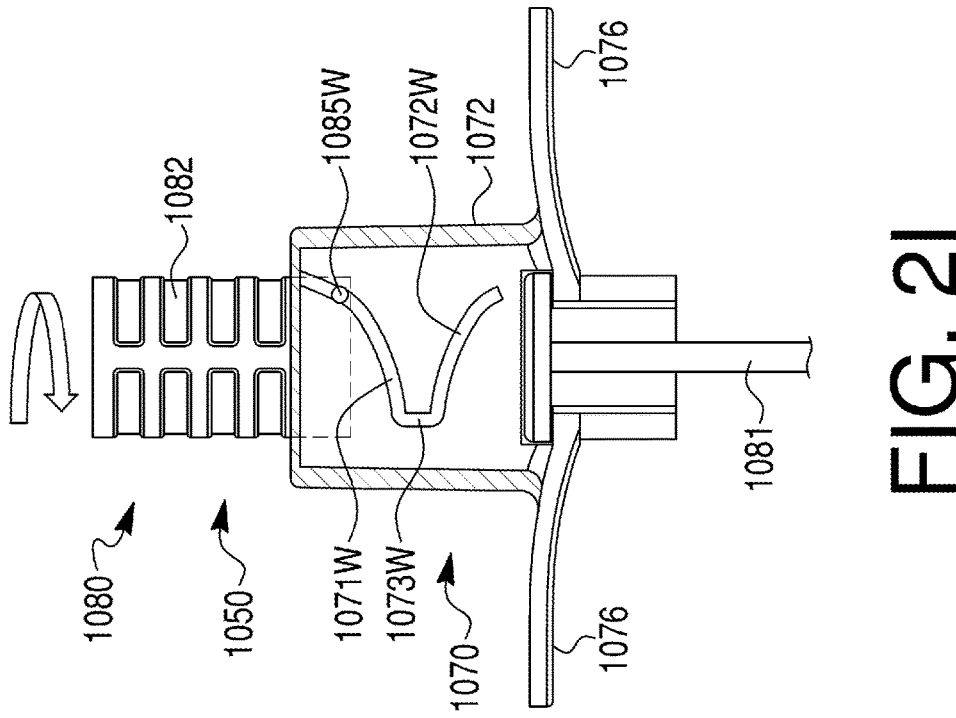
Figure 2H:
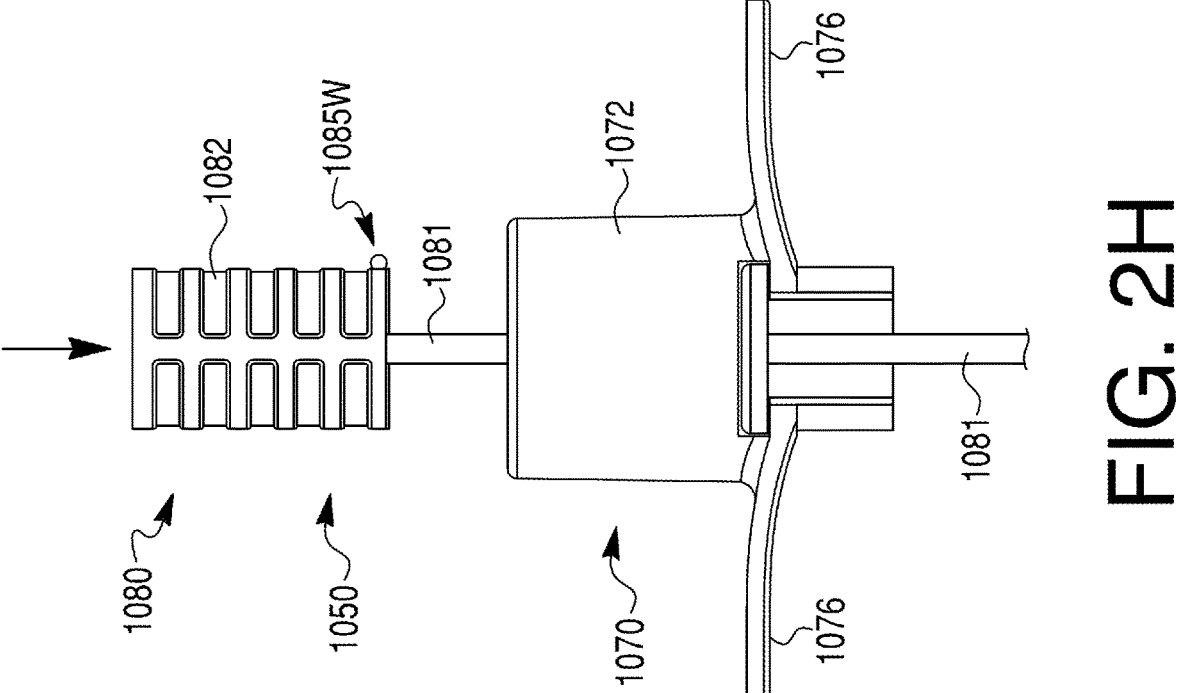
Figure 2K:
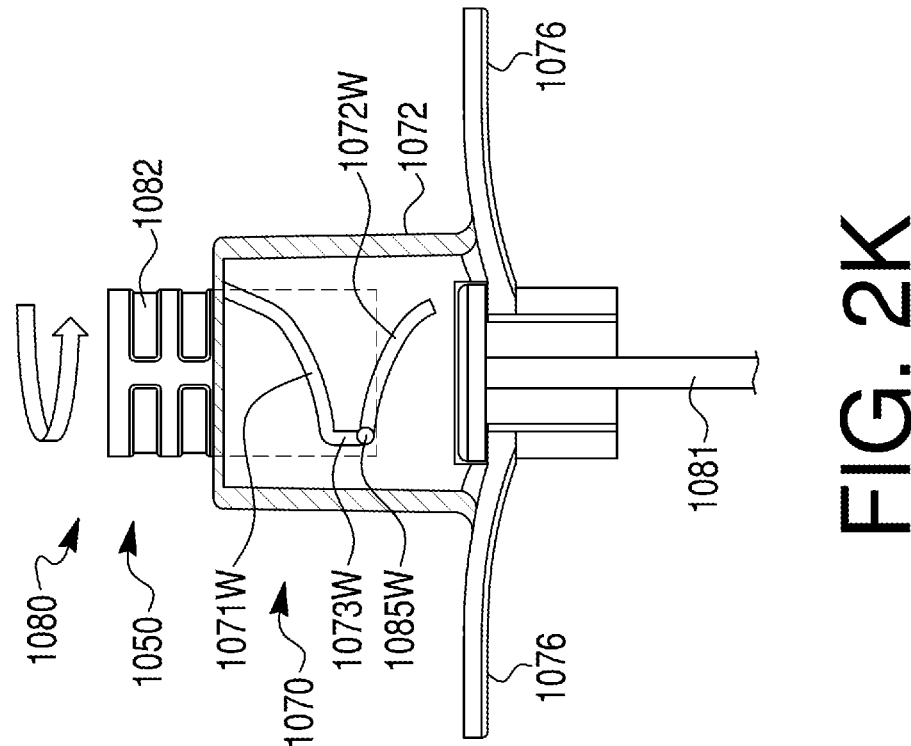

As seen in FIG. 2K, flange piece 1070 may include one or more channels formed along an inner surface of collar 1072. In particular, collar 1072 may include a first (proximal) helical channel 1071W formed along an interior of collar 1072 and having a first curvature, and a second (distal) helical channel 1072W formed along the interior of collar 1072 and having a different and/or opposite curvature than the first helical channel 1071W. For example, when viewed from the proximal end of actuation portion 1082, first helical channel 1071W may be concave, while second helical channel 1072W may be convex when viewed from the same vantage point. Or, first helical channel 1071W may be convex when viewed from the proximal end of actuation portion 1082, while second helical channel 1072W is concave from the same vantage point. Further, second helical channel 1072W may be longitudinally spaced apart from first helical channel 1071W. First helical channel 1071W may be connected with second helical channel 1072W by an intermediate, third channel 1073W extending therebetween.

Third channel 1073W may extend along or substantially parallel to a longitudinal axis of collar 1072. It should be understood that a size, shape, and/or orientations of the one or more channels on collar 1072 are merely exemplary such that other suitable configurations may be included without departing from a scope of this disclosure. As described in detail below, the plurality of channels 1072 are configured to receive protrusion 1085W. In some embodiments, first helical channel 1071W and second helical channel 1072W may be threaded and configured to mesh with a corresponding component of plunger rod 1080 (e.g., protrusion 1085W). Opposite rotational movement may be required for protrusion 1085W to traverse through first helical channel 1071W and second helical channel 1072W. For example, a first rotational movement of actuation portion (e.g., clockwise) may cause protrusion 1085W to traverse first helical channel 1071W, while an opposing rotational movement (e.g., counterclockwise) may cause protrusion 1085W to traverse through second helical channel 1072W.

Referring to FIG. 2H, with plunger rod 1080 in a ready position, protrusion 1085W may be received within collar 1072 in response to a distal translation of actuation portion 1082 toward flange piece 1070. As seen in FIG. 2I, protrusion 1085W may be received within first helical channel 1071W and moved therethrough in response to a rotation of plunger rod 1080 (e.g., in a first direction) relative to flange piece 1070. It should be appreciated that plunger rod 1080 may be configured to translate axially in a distal direction relative to flange piece 1070 as plunger rod 1080 rotates within collar 1072, due to the curvature of first helical channel 1071W. For example, plunger rod 1080 may translate a first distance defined by a configuration of first helical channel 1071W until reaching a terminal end of first helical channel 1071W. The first distance may correspond to a priming step of device 1050 such that device 1050 may be at least partially primed upon protrusion 1085W moving through first helical channel 1071W.

Figure 2J:
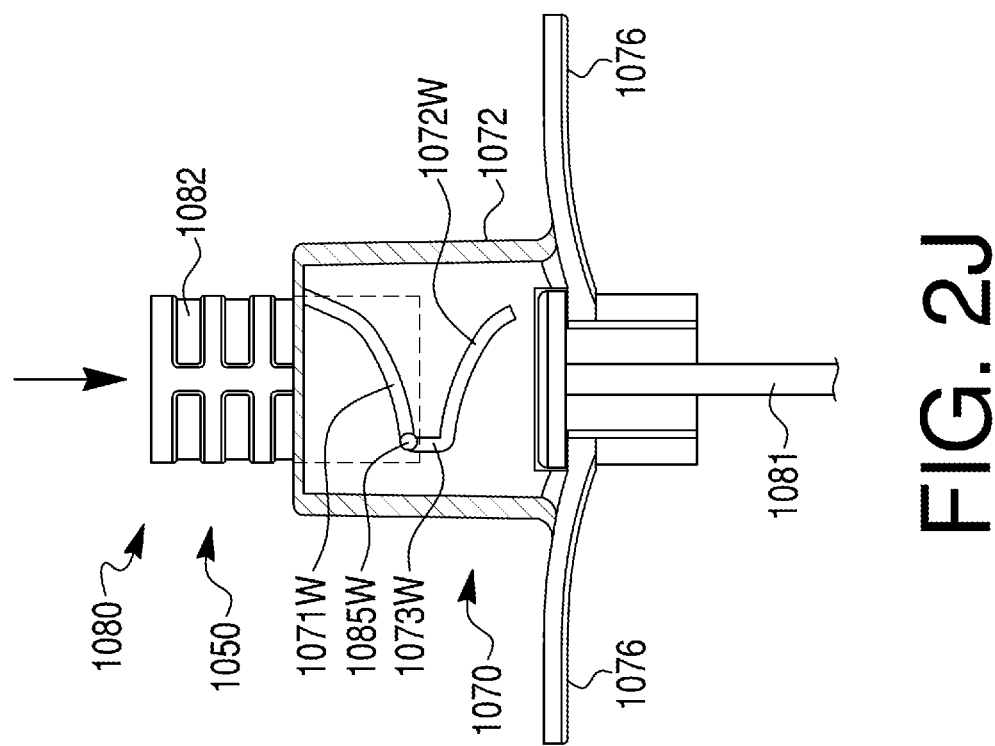

Referring now to FIG. 2J, protrusion 1085W may be positioned at a terminal end of first helical channel 1071W and a proximal (e.g., top) end of third channel 1073W. In some embodiments, plunger rod 1080 may experience a tactile feedback formed by the terminal end of first helical channel 1071W. Plunger rod 1080 may be translated distally through third channel 1073W to complete a priming step of device 1050, as shown in FIG. 2K. It should be understood that first helical channel 1071W and third channel 1073W may collectively define a priming distance of device 1050 such that plunger rod 1080 is in a primed position when protrusion 1085W translates through third channel 1073W.

With protrusion 1085W received within second helical channel 1072W, plunger rod 1080 may be rotated in the second direction (opposite of the first direction) to translate plunger rod 1080 distally by a second distance that is defined by a configuration of second helical channel 1072W. The second distance may be less than, greater than, and/or substantially equal to the longitudinal dimension of second helical channel 1072W, depending on the particular application and need. Plunger rod 1080 may be rotated in the second direction and translated by the second distance until reaching a terminal end of second helical channel 1072W to deliver a dose from device 1050. It should be understood that the second distance may correspond to a dosage delivery step of device 1050 such that device 1050 may deliver the dose upon protrusion 1085W moving through second helical channel 1072W and arriving at a dose completion position.

In other embodiments, as seen in FIGS. 2L-2O, plunger rod 1080 may include a protrusion, a knob, and/or a thread 1085X positioned on actuation portion 1082. In the example, thread 1085X may be positioned about a circumference of actuation portion 1082 and along a distal end such that thread 1085X may be received within flange piece 1070 in response to translation of plunger rod 1080 into collar 1072.

Flange piece 1070 may further include a threaded portion 1072X disposed within opening 1073 and forming a helical path that is configured to receive thread 1085X. In the example, threaded portion 1072X may be positioned along a proximal portion of opening 1073 such that a distal portion of opening 1073 may include a non-threaded portion 1071X. As described in further detail herein, threaded portion 1072X may define a longitudinal distance corresponding to a priming step of device 1050 and non-threaded portion 1071X may define a distance corresponding to a dosage delivery step of device 1050.

Figure 2M:
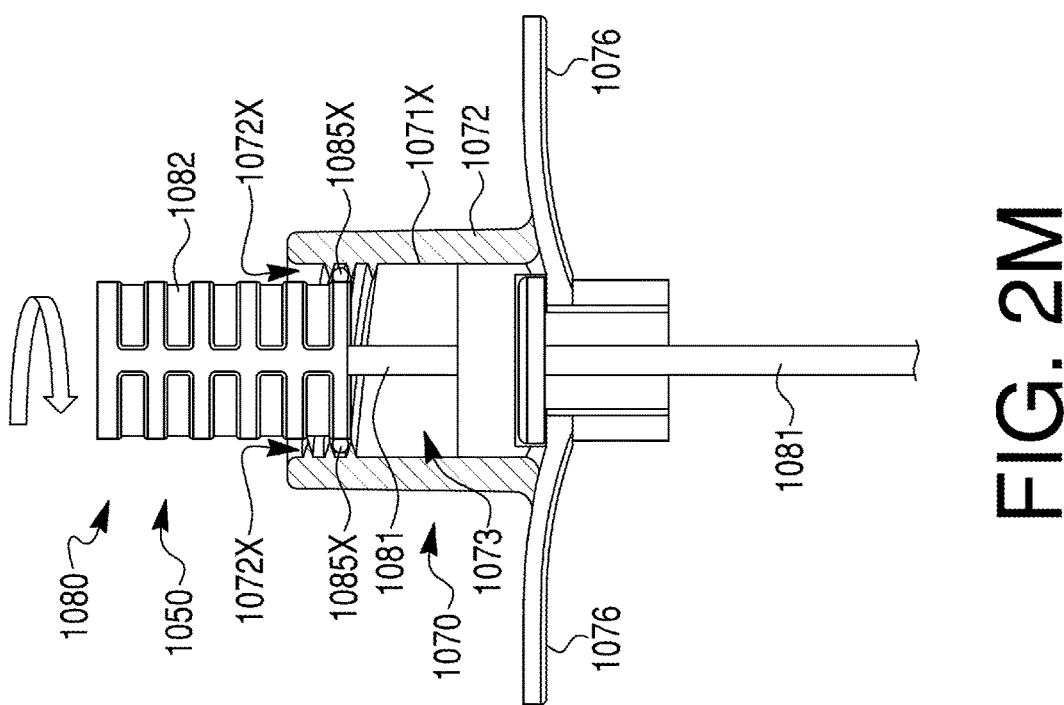
Figure 2L:
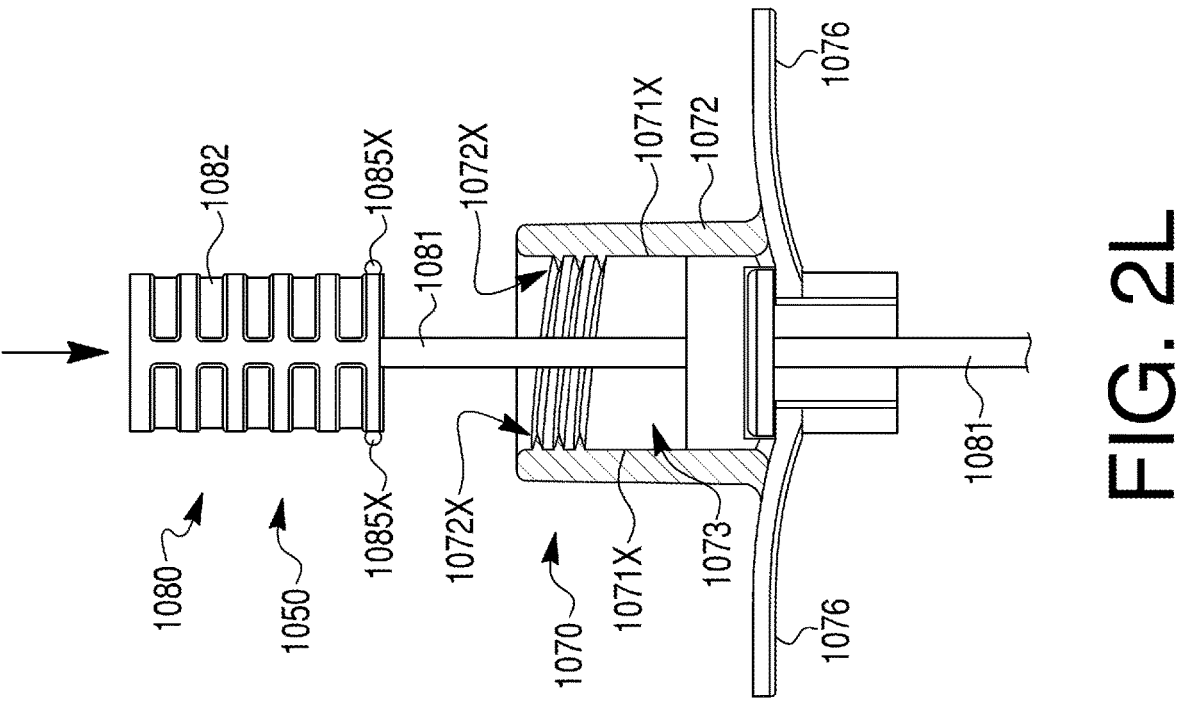

For example, as seen in FIG. 2L, actuation portion 1082 may be translated distally toward flange piece 1070 until thread 1085X encounters a distal end of collar 1072. Rotation of plunger rod 1080 in a first direction (e.g., clockwise or counter clockwise) may cause thread 1085X to engage threaded portion 1072X. As shown in FIG. 2M, rotation of plunger rod 1080 may provide axial/longitudinal translation of actuation portion 1082 into collar 1072 as thread 1085X moves through the helical path of threaded portion 1072X. It should be appreciated that rotation and translation of thread 1085X through threaded portion 1072X may transition device 1050 from a ready position (FIG. 2L) to a primed position (FIG. 2N). With thread 1085X disengaged from threaded portion 1072X and positioned along non-threaded portion 1071X, device 1050 may be in the primed position. In some instances, a feedback (e.g., tactile, auditory, etc.) may be generated in response to thread 1085W exiting threaded portion 1072X and/or entering non-threaded portion 1071X.

Figure 2O:
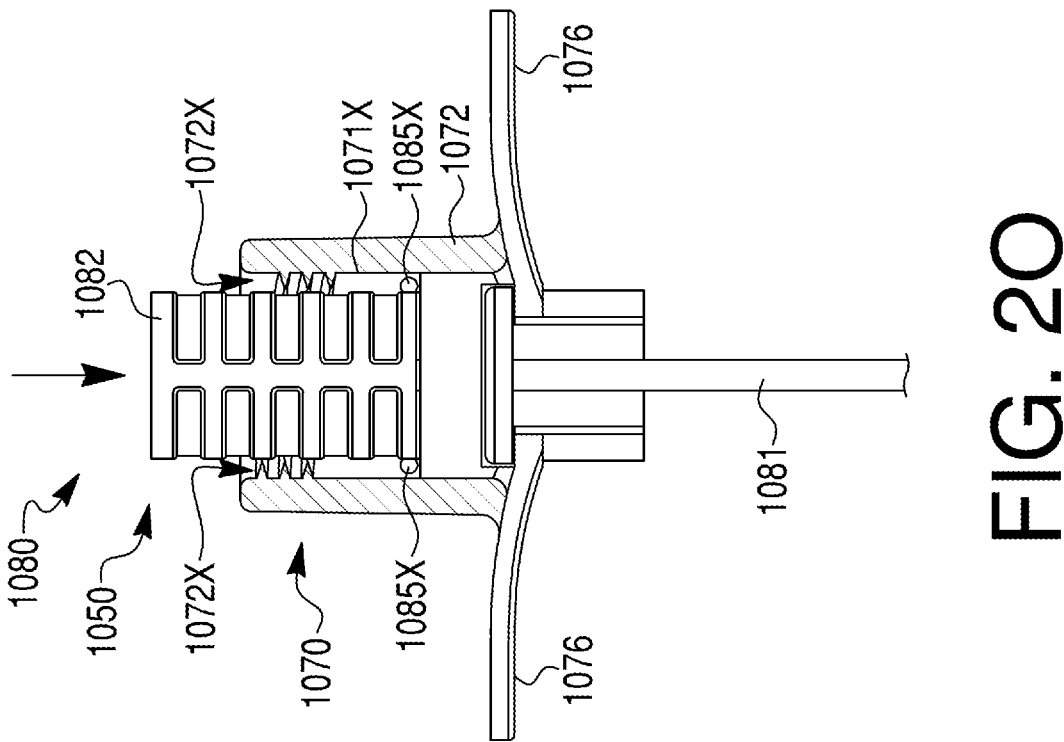
Figure 2N:
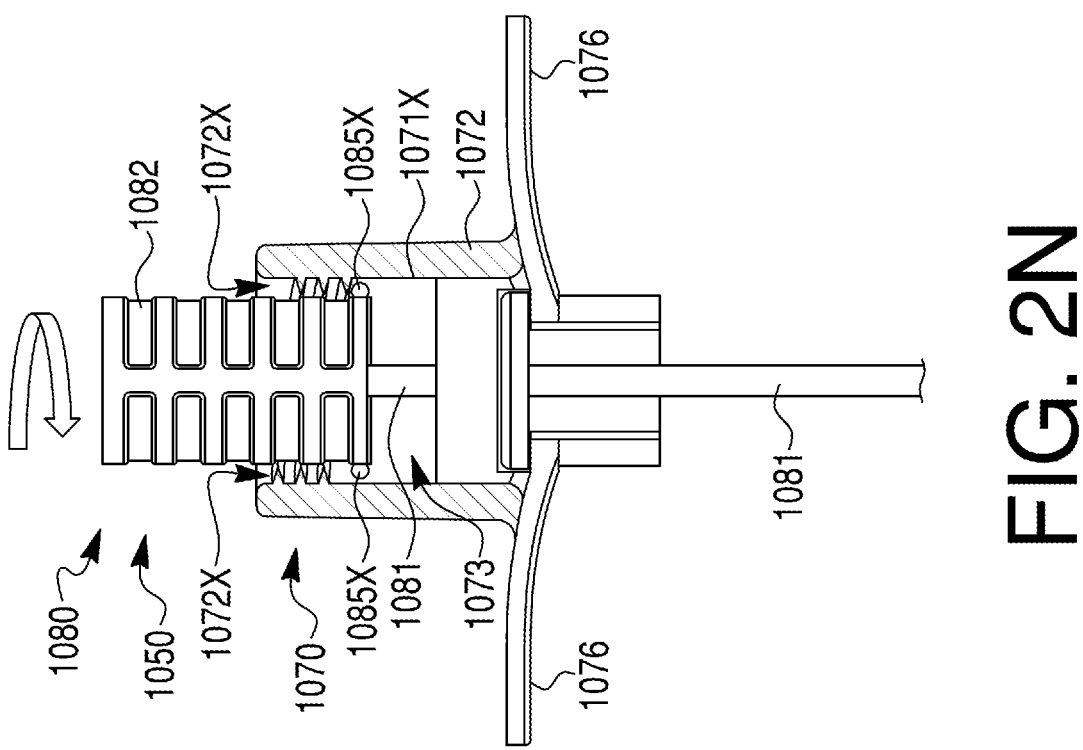

In this instance, as shown in FIG. 2O, actuation portion 1082 may be translated distally relative to flange piece 1070 to deliver a dose from device 1050 by application of a distally-directed force against actuation portion 1082. Thread 1085X may move through the distal portion of opening 1073 when thread 1085X is positioned within non-threaded portion 1071X. A longitudinal length of non-threaded portion 1071X defined between a distal end of thread portion 1072X and a distal end of opening 1073 may control a dosage delivery of device 1050. Device 1050 may complete delivery of a dose when actuation portion 1082 engages a proximally-facing and distal surface of collar 1072 and plunger rod 1080 arrives at the dose completion position.

FIGS. 2P-2T illustrate further embodiments of a flange piece that may be configured and operable similar to flange piece 1070 shown and described above except for the differences explicitly noted herein. It should be understood that like reference numerals are used to identify like components and the flange pieces described below may be readily incorporated with one or more components of device 1050 shown and described above.

Figures 2P, 2Q, 2R:
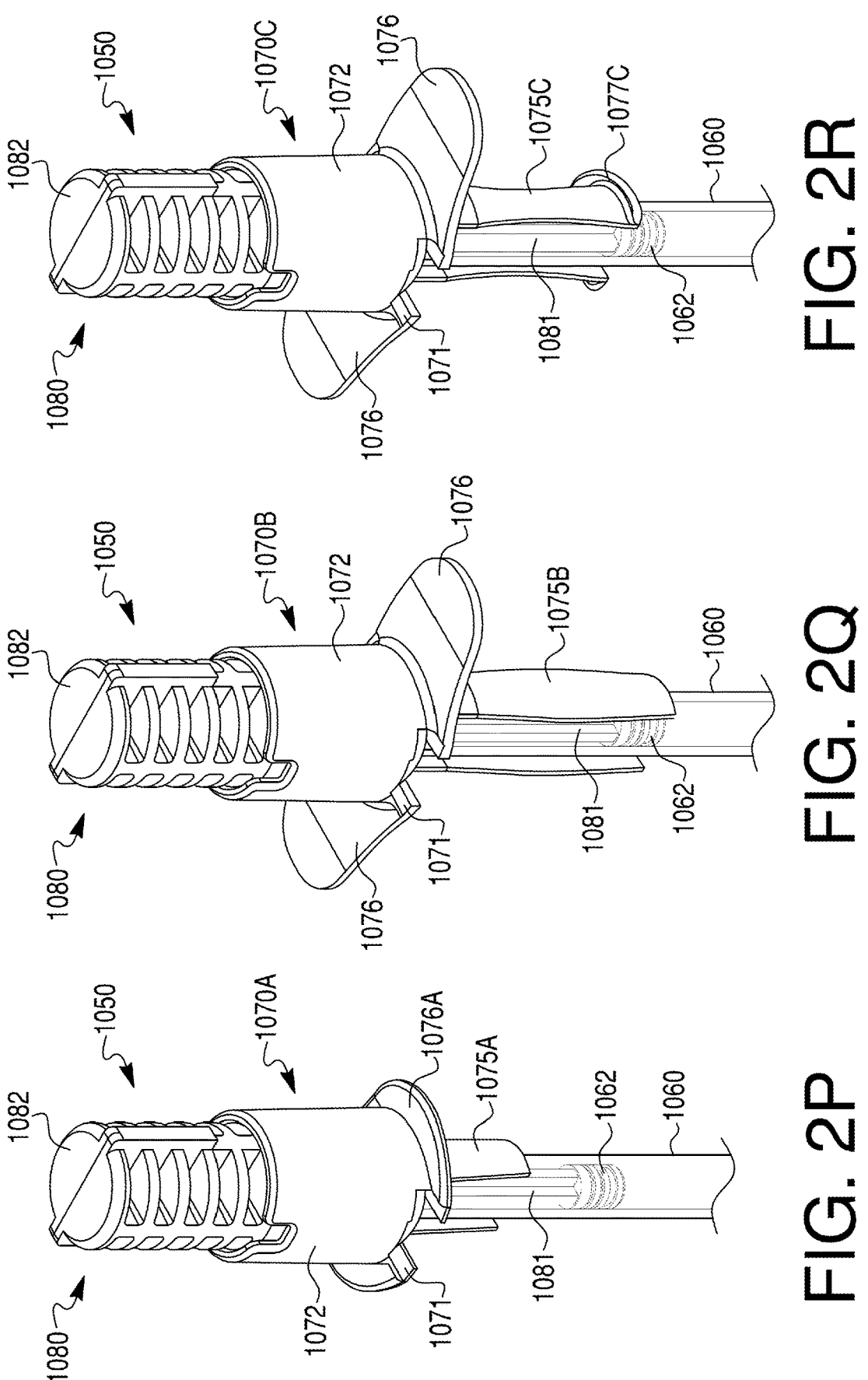
Figure 24A:
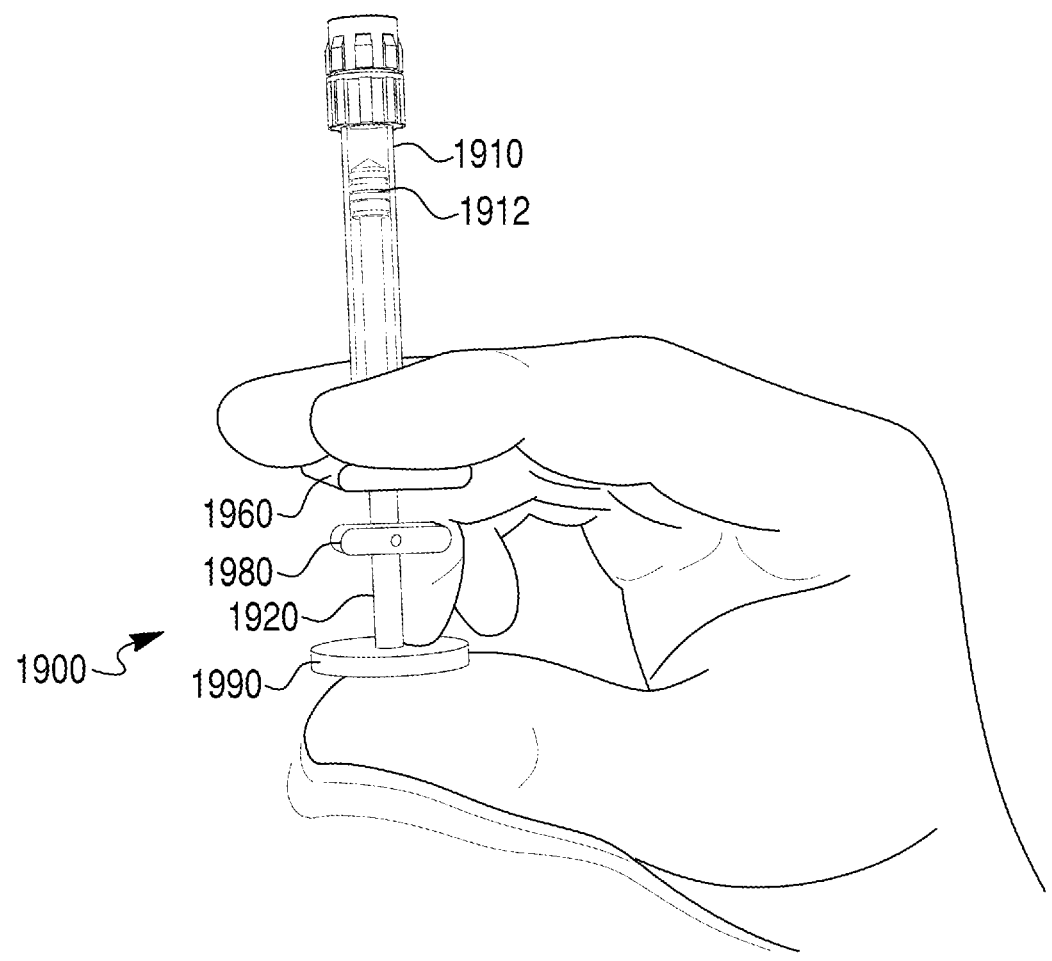
FIGS. 24A-24E depict a further exemplary delivery device and method of using said delivery device, according to aspects of the present disclosure.

For example, referring initially to FIG. 2P, a flange piece 1070A may include one or more flanges 1076A that may be sized and configured to aid a user in holding device 1050 and/or expelling a formulated drug substance from device 1050. Flanges 1076A may be further sized and/or shaped to allow a user to hold device 1050 with a plurality of hand/grip positions, arrangements, and/or orientations. By way of illustrative example, flanges 1076A may be sized and/or shaped such that flange piece 1070A may be held similar to a writing instrument (e.g., pencil, pen, etc.) without requiring use of flanges 1076A, or sized in accordance with the example shown in FIG. 24A such that flanges 1076A may abut against one or more fingers of a user. Flange piece 1070A may include a pair of flanges 1076A extending radially outwardly from collar 1072 in opposite radial directions relative to one another. Flanges 1076A may extend transversely from collar 1072 (e.g., flanges 1076A may include an angled surface that is sloped radially-inward in a distal direction) and configured to inhibit a user's fingers from slipping off of flange piece 1070A during use of device 1050.

Flanges 1076A may be coupled to one another to form a semi-circular profile with a minimal radius relative to collar 1072. Accordingly, flanges 1076A may form a slim profile to facilitate visualization of a target treatment site at a distal end of device 1050 (not shown) when using device 1050 from a perspective proximal of finger flange 1070A. It should be understood that flange piece 1070A may include various other quantities and/or arrangements of flanges 1070A than those shown and described herein without departing from a scope of this disclosure. In other embodiments, flanges 1076 may include various other suitable sizes and/or shapes.

Flange piece 1070A may further include a distal collar 1075A extending distally from collar 1072 and configured to engage body 1060 to hold flange piece 1070A in a fixed position relative to body 1060. Distal collar 1075A may be adhered to, molded, or otherwise affixed to body 1060, or may engage body 1060 via a friction fit. In the example, distal collar 1075A includes a longitudinal length that is generally less than a longitudinal length of collar 1072. In some embodiments, distal collar 1075A may be sized sufficiently small enough to facilitate adequate exposure of body 1060 for user grasp and/or manipulation during use of device 1050. Additionally, distal collar 1075A may include a material composition that is similar to and/or different from collar 1072. For example, distal collar 1075A may be formed of a flexible material such that distal collar 1075A may be configured to flex radially-outward when receiving body 1060 into flange piece 1070A and flex radially-inward once body 1060 is fully received to facilitate a snap-fit connection (without breaking distal collar 1075A). It should be appreciated that, in other embodiments, flange piece 1070A may omit distal collar 1075A entirely.

In other embodiments, as seen in FIG. 2Q, a flange piece 1070B may include a distal collar 1075B that is substantially longer than distal collars 1075, 1075A shown and described above. For example, distal collar 1075B may be enlarged with a longitudinal length that is greater than a longitudinal length of collar 1072. In the example, distal collar 1075A may be sized sufficiently large enough to encompass a substantial length of body 1060. In this instance, an exterior surface of distal collar 1075B may provide an interface for a user to grasp and/or manipulate during use of device 1050. Additionally, distal collar 1075B may include an expanded diameter that exceeds a diameter of body 1060 to provide an enhanced surface area for grasping flange piece 1070B. Stated differently, distal collar 1075B may have a widened size and/or shape to facilitate ease in gripping and/or manipulating device 1050. In the present example, distal collar 1075B may have a barrel-shape with a convex outer surface when viewed from an exterior of device flange piece 1070B.

Alternatively, as seen in FIG. 2R, a flange piece 1070C may include a distal collar 1075C that is substantially similar to distal collar 1075B and includes a longitudinal length that is greater than a longitudinal length of collar 1072. In the example, an exterior surface of distal collar 1075C may be configured to provide an interface for a user to grasp and/or manipulate during use of device 1050. Distal collar 1075C may include a slim profile with a diameter that is greater than a diameter of body 1060 such that distal collar 1075C does not substantially increase a profile of body 1060. Stated differently, distal collar 1075C may have a narrowed size relative to distal collar 1075B. In some embodiments, distal collar 1075C may include a terminal lip 1077C that extends radially outward at a distal end. Terminal lip 1077C may be sized, shaped, and configured to enhance gripping and/or manipulation of distal collar 1075C. In the present example, distal collar 1075C may have a flared-shape with a concave outer surface when viewed from an exterior of device flange piece 1070C.

Figure 2T:
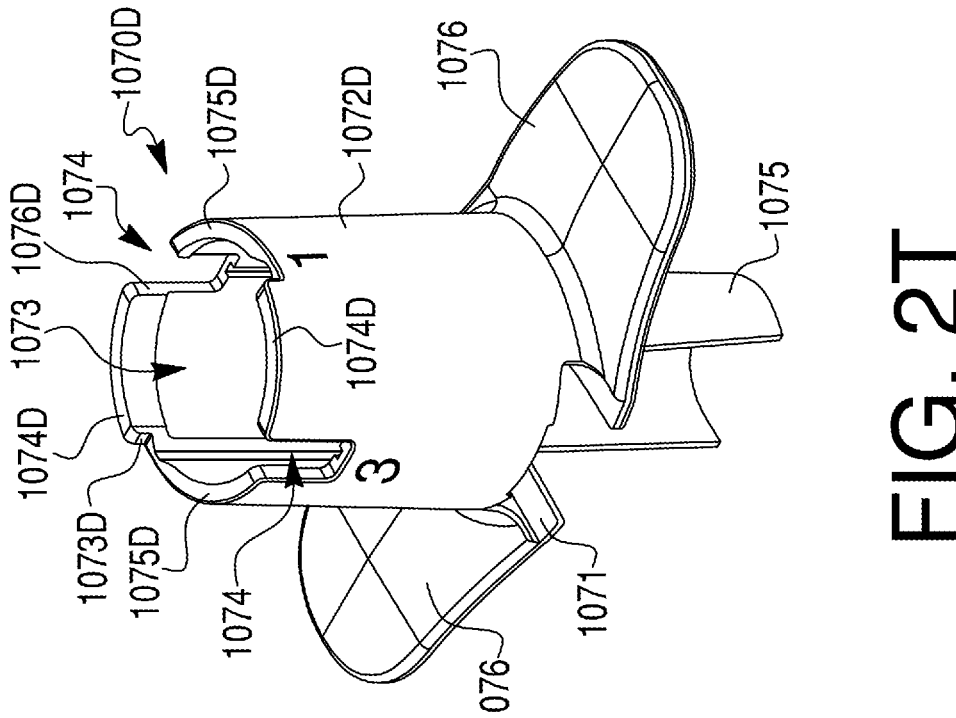
Figure 2S:
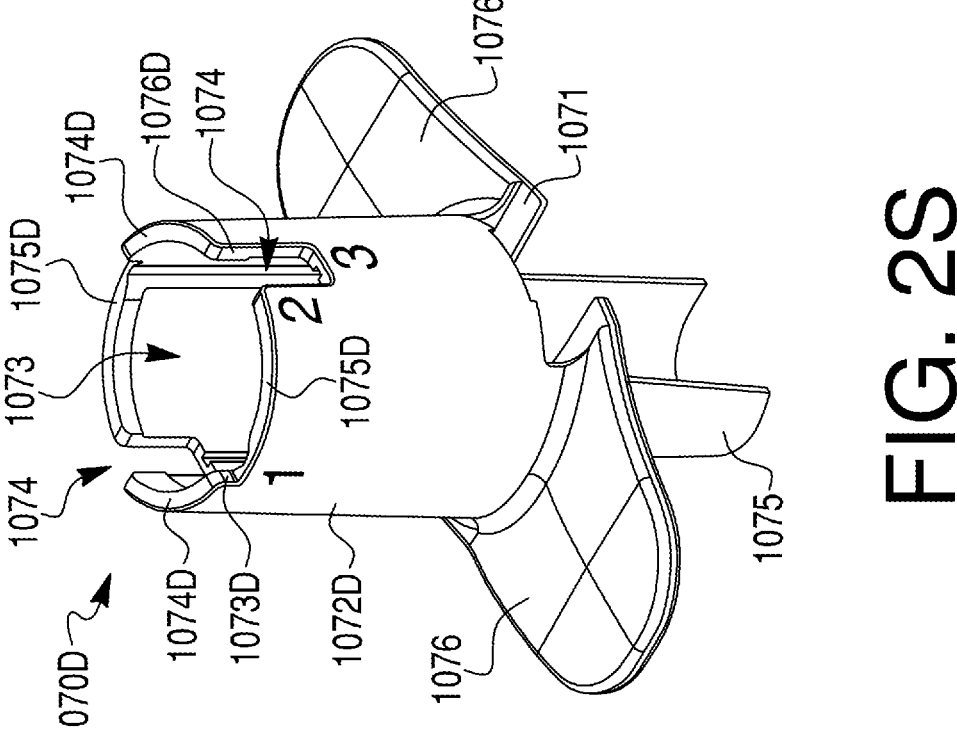

In other embodiments shown in FIGS. 2S-2T, a flange piece 1070D may include a collar 1072D having a proximal lip 1074D. Proximal lip 1074D may define an irregular surface configured to interface with plunger rod 1080 when actuation portion 1082 is received by collar 1072D. For example, proximal lip 1074D may include a pair of recessed surfaces 1075D positioned along opposing sides from one another along proximal lip 1074D. In other words, recessed surfaces 1075D may be separated from one another by surfaces and/or portions of proximal lip 1074D that are not recessed. In the example, recessed surfaces 1075D may be positioned adjacent to slots 1074 and may define a pathway for moving plunger rod 1080 relative to collar 1072D for priming and delivering a dose from device 1050. In some embodiments, recessed surfaces 1075D may include a spiral configuration (e.g., have a distally-directed slope) such that recessed surfaces 1075D may be tapered in a distal direction between a first ledge 1073D and a second ledge 1076D.

In some embodiments, flange piece 1070D may include visualization mechanisms, such as, for example, one or more labels or markings disposed on collar 1072D to provide instructions to a user of device 1050. For example, the one or more labels (e.g., numbering) may indicate directions in which to rotate or otherwise move plunger rod 1080 relative to flange piece 1070D to prime and deliver a dosage from device 1050. By way of example, the one or more labels may include markings that indicate a start position (e.g., "1"), a priming position (e.g., "2"), and a dosage delivery position (e.g., "3") of protrusions 1086 relative to proximal lip 1074D. The one or more labels may be adhered, printed, embossed, and/or molded onto collar 1072D.

As described in greater detail herein, flange piece 1070D may be configured to allow movement of plunger rod 1080 in a single direction when priming and delivering a dosage from device 1050. In exemplary use, plunger rod 1080 (not shown) may initially be received through flange piece 1070D and actuation portion 1082 may be positioned against collar 1072D with protrusions 1086 positioned along a first end of recessed surfaces 1075D at marking "1" and opposite of slot 1074. Protrusions 1086 may only be rotated in a single direction along recessed surface 1075D, toward marking "2," due to first ledge 1073D inhibiting protrusions 1086 from moving in an opposite direction away from marking "2".

When protrusions 1086 are received along recessed surfaces 1075D at marking "2," second ledge 1076D may further prevent protrusions 1086 from moving past slots 1074 and passing by marking "3". It should be appreciated that a configuration of proximal lip 1074D is exemplary such that flange piece 1070D may include various other sizes, shapes, and/or configurations of proximal lip 1074D and/or recessed surfaces 1075D than those shown and described herein to facilitate movement of plunger rod 1080 during use of device 1050.

In other embodiments, the components of device 1050 may include one or more color indicators in lieu of and/or in addition to the markings described above to provide instructions to a user of device 1050. For example, device 1050 may include colors, symbols (e.g., arrows), and the like indicating a direction in which to rotate or otherwise move plunger rod 1080 relative to flange piece 1070D to prime and deliver a dosage. In one embodiment, an exterior surface of plunger rod 1080 may be provided with different colors along various portions of actuation portion 1082 to indicate a respective start position (e.g., green), priming position (e.g., yellow), and dosage delivery position (e.g., red) of plunger rod 1080 relative to collar 1072D. The one or more color indicators may be printed or molded onto plunger rod 1080. In other embodiments, the various portions of plunger rod 1080 may include different textures in lieu of and/or in addition to the color indicators described above to provide instructions to a user of device 1050.

Components of device 1050 may be made of any suitable material, and each component may be made from the same or different materials as other components. It should be appreciated that, in some embodiments, one or more components of device 1050 (e.g., flange piece 1070, proximal collar 1072, plunger rod 1080, actuation portion 1082, and more) may be formed of a flexible material having sufficient flexibility to prevent breakage during flexing. In some embodiments, the one or more components of device 1050 may be rigid and have enough strength to maintain shape and provide support. In other embodiments, one or more components of device 1050 (or at least a portion of a component) may having a varying rigidity along a longitudinal length or lateral width such that the component may have a variable flexibility. In still further embodiments, the one or more components of device 1050 may have sufficient flexibility to prevent breakage during flexing while also having sufficient rigidity and strength to maintain shape and provide support. In some embodiments, such features may further provide a user feedback (e.g., tactile, audible, visual, etc.) when flexing and/or interacting with other components of device 1050. For example, each of body 1060, flange piece 1070, and plunger rod 1080 may be made of a material including a polymer, such as a plastic. In some embodiments, one or more of body 1060, flange piece 1070, and plunger rod 1080 may include multiple different materials (e.g., glass, rubber, and/or plastic). In some embodiments, for example, the cylindrical portion of body 1060 may be made of glass, Plexiglas, or any other suitable polymer (e.g., cyclic olefin polymer or cyclic olefin copolymer) or other material, and stopper 1062 may be made of, e.g., plastic, rubber, or other polymer or copolymer. By way of further example, flange piece 1070 may include a polypropylene homopolymer, an ABS (Acrylonitrile, Butadiene, and Styrene) polymer, ABS polycarbonate blend, and other suitable materials. In some embodiments, plunger rod 1080 may include an ABS polycarbonate blend. Such materials may provide greater tolerances for manufacturing (e.g., injection molding) flange piece 1070 and/or plunger rod 1080, or facilitate an increased reproducibility of said components of device 1050. As described in greater detail above, in some embodiments, one or more components of device 1050 may be formed of a flexible and/or deformable material composition providing greater tolerances for flexing or deforming said components (e.g., without breaking) when priming or delivering a dose from device 1050.

In some embodiments, a portion of body 1060 configured to contain a formulated drug substance may be made of a transparent or translucent material. In some embodiments, flange piece 1070 and plunger rod 1080 may be made of the same, similar, or different materials, such as similar or different plastics (e.g., each having a similar or different hardness). In some embodiments, parts of device 1050 may include elastic materials. For example, parts of device 1050 may include rubber or plastic configured to allow a user to better grip device 1050, or to create an airtight or otherwise sealing fit between two components of device 1050 (e.g., between body 1060 and stopper 1062). In some embodiments, some or all of plunger rod 1080 (e.g., actuation portion 1082 and/or extensions 1087, or alternately the entirety of plunger rod 1080) may be made of a material having some flexibility, e.g., to allow for bending of extensions 1087. One or more of the materials listed above (e.g., plastic, rubber, polymers, or copolymers) may have such characteristics. In some embodiments, some or all of device 1050 may be suitable for sterilization, e.g., heat or chemical sterilization (see FIGS. 42-45C).

Figure 3A:
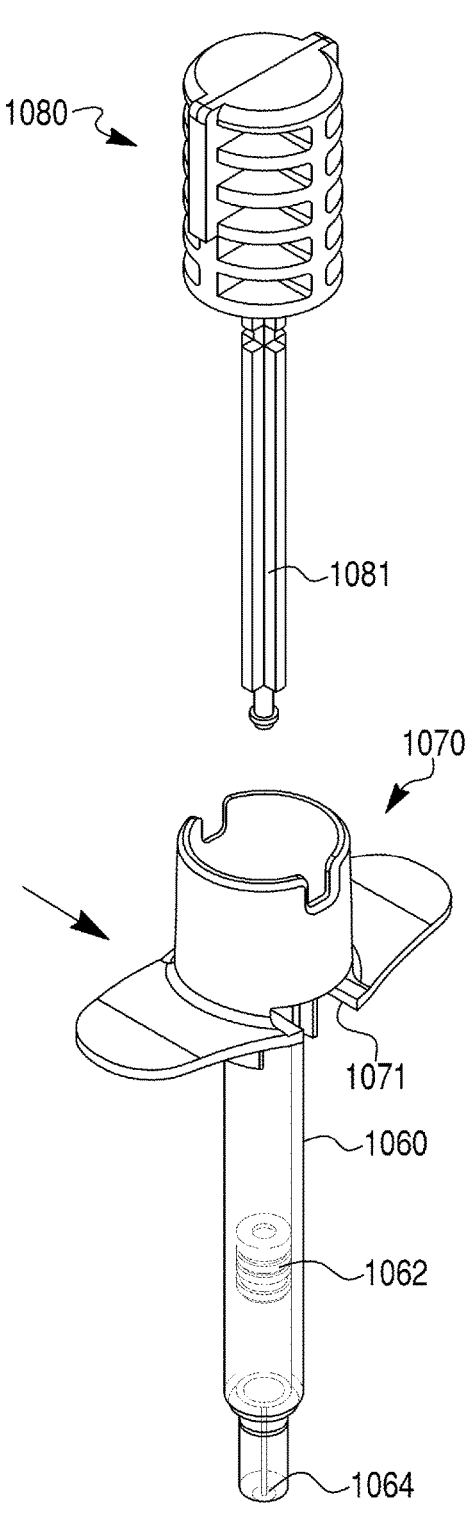
FIGS. 3A and 3B depict an exemplary method of assembling the delivery device depicted in FIGS. 1A-1E, according to aspects of the present disclosure.
Figure 3B:
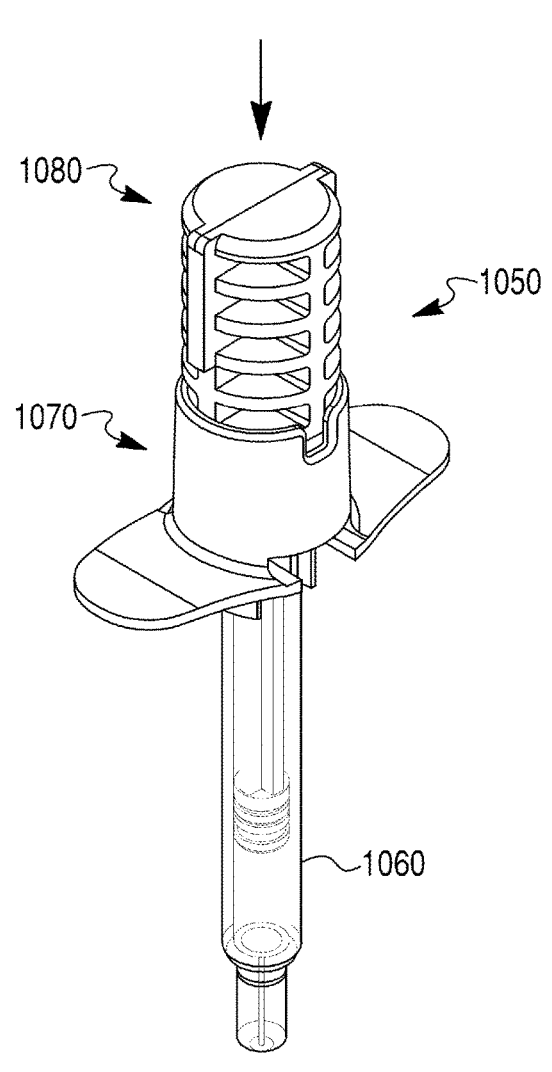
Figure 3C:
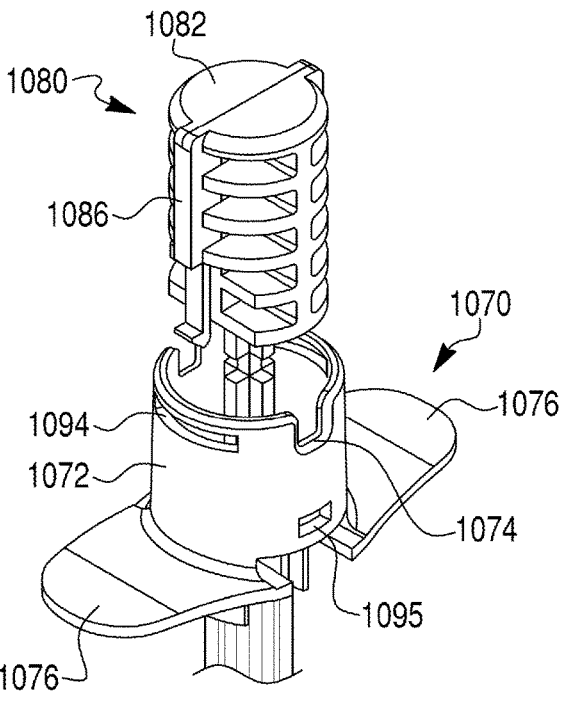
FIGS. 3C-3F depict an exemplary method of assembling an embodiment of the delivery device depicted in FIGS. 1A-1E, according to aspects of the present disclosure.
Figure 3E:
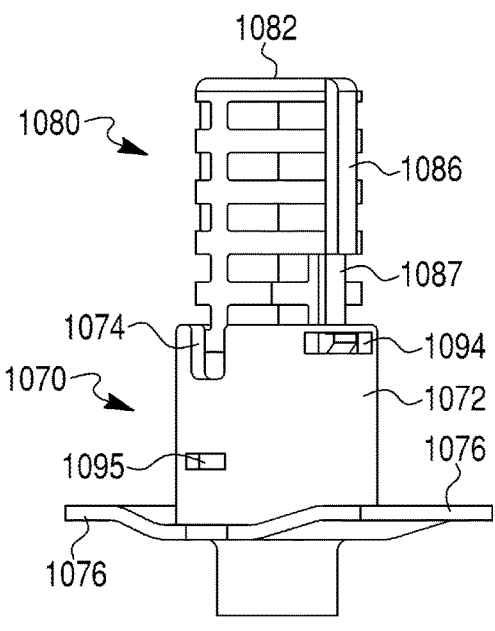
Figure 3D:
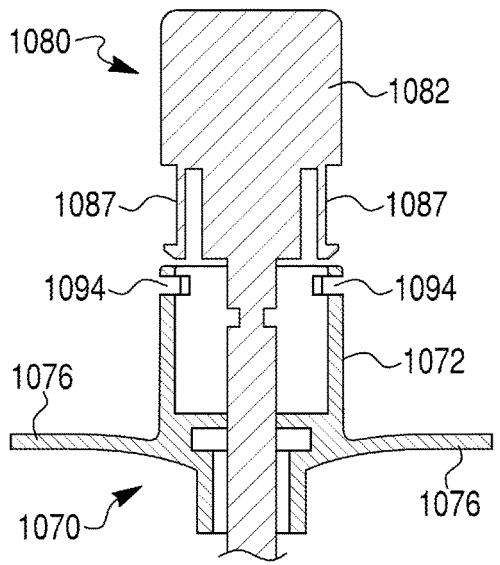
Figure 3F:
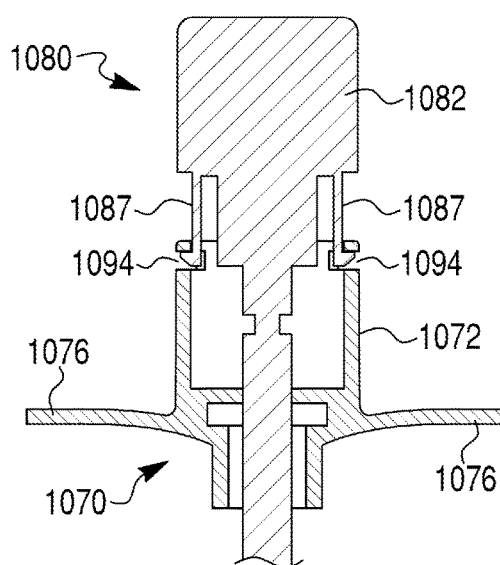

FIGS. 3A and 3B depict an exemplary method of assembling the delivery device depicted in FIGS. 1A-1E. Flange piece 1070 may be assembled to body 1060, as shown in FIG. 3A. The assembly of flange piece 1070 to body 1080 may include sliding, snapping, adhering, or otherwise affixing the two components together. As depicted in FIG. 3A, flange piece 1070 may be slid onto body 1060, e.g., such that lip 1071 of flange piece 1070 engages with body flange 1061. Plunger rod 1080 may be inserted through the assembled flange piece 1070 and body 1060, such that a distal end of plunger rod 1080 contacts stopper 1062. The assembled device 1050 may then be in a configuration suitable for packaging, sterilization (see FIGS. 42-45C), and/or use.

FIGS. 3C-3F depict an exemplary method of assembling device 1050 in which actuation portion 1082 includes extensions 1087 and collar 1072 includes side openings 1094. In such an embodiment, plunger rod 1080 may be inserted through flange piece 1070 until the hook or clip portions of extensions 1087 are received within side openings 1094, at which point the assembled device 1050 may be in a configuration suitable for packaging, sterilization, and/or use. It should be appreciated that side openings 1094 may be configured to inhibit a proximal retraction of plunger rod 1080 relative to flange piece 1070 once the hook or clip portions of extensions 1087 are received therein. Side openings 1094 may function as a first lock when device 1050 is placed into an initial assembly state to prevent disassembly of device 1050.

As described in further detail herein (see FIGS. 4G-4J), side openings 1095 may be configured to inhibit a proximal retraction of plunger rod 1080 once the hook or clip portions of extensions 1087 are received therein. Side openings 1095 may function as a second lock when device 1050 is placed in a dosage delivery state to prevent extracting patient fluid after completion of drug/medicament delivery. It should be appreciated that side openings 1094, 1095 may generate a feedback indicating a relative position of plunger rod 1080 to flange piece 1070, such as, for example, an audible feedback, a tactile feedback, and the like. In some embodiments, device 1050 may include additional and/or fewer side openings 1094, 1095 than those shown and described herein to increase and/or decrease a quantity of locks on device 1050.

In some embodiments, assembling device 1050 may include pre-filling body 1060 before combining it with flange piece 1070 and stopper 1080; for example, a predetermined amount of drug substance may be disposed in body 1060 between stopper 1062 and needle end 1064. In some embodiments, an alternate order of assembly of the components of device 1050 may be employed, depending on contemplated variations in the structures of components of device 1050. For example, in an embodiment (not shown) in which flange piece 1070 is configured to be assembled to body 1060 using a snap-fit interface, plunger rod 1080 may be first inserted through flange piece 1070, and the combined flange piece 1070 and plunger rod 1080 may be assembled to body 1060, e.g., such that flange piece 1070 snaps over a proximal body flange 1061 of body 1060 and plunger rod 1080 is inserted into body 1060.

Figures 4A, 4B, 4C:
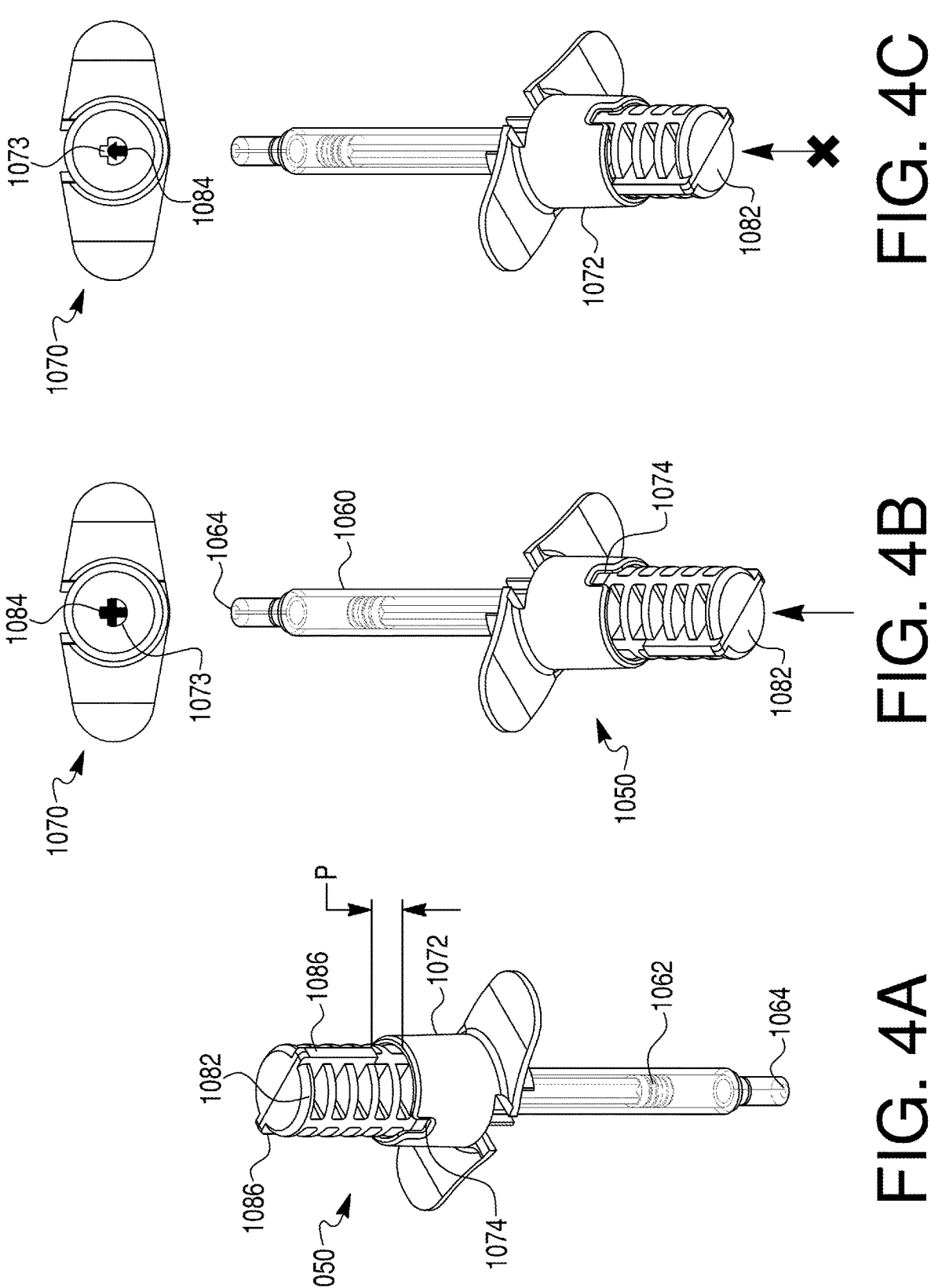
FIGS. 4A-4F depict an exemplary method of using the delivery device depicted in FIGS. 1A-1E, according to aspects of the present disclosure.

FIGS. 4A-4F depict an exemplary method of using device 1050, according to aspects of the present disclosure. In a pre-use configuration depicted in FIG. 4A, device 1050 may hold a volume of a drug substance in between stopper 1062 and expulsion end 1064. A priming distance p may exist between protrusions 1086 and a proximal end of proximal collar 1072, and protrusions 1086 may be non-aligned with slots 1074. In a priming step depicted in FIG. 4B, plunger rod 1080 may be moved longitudinally further into body 1060. For example, a user may press actuation portion 1082 partially into proximal collar 1072 of flange piece 1070. In some embodiments, device 1050 may be held in an inverted position during this step, to ensure that air trapped in body 1060 may be expelled via expulsion end 1064, as stopper 1062 is pushed distally by plunger rod 1080. In the pre-use configuration of FIG. 4A and during the priming step shown in FIG. 4B, plunger rod 1080 may be prevented from rotating about the longitudinal axis of the syringe, due to the geometries of opening 1073 in flange piece 1070, and neck 1084 of plunger rod 1080 (as shown in the top cross-sectional view in FIG. 4B). As shown in FIG. 4C, the priming step may be stopped when protrusions 1086 of plunger rod 1080 abut a proximal end of proximal collar 1072. When the priming step is completed, neck 1084 of plunger rod 1080 may be positioned longitudinally with respect to opening 1073 of flange piece 1070, such that it may now be rotatable with respect to flange piece 1070. For example, when the priming step is completed, a narrower portion of neck 1084 may be disposed inside opening 1073 than when device was in a pre-use configuration.

Figure 4F:
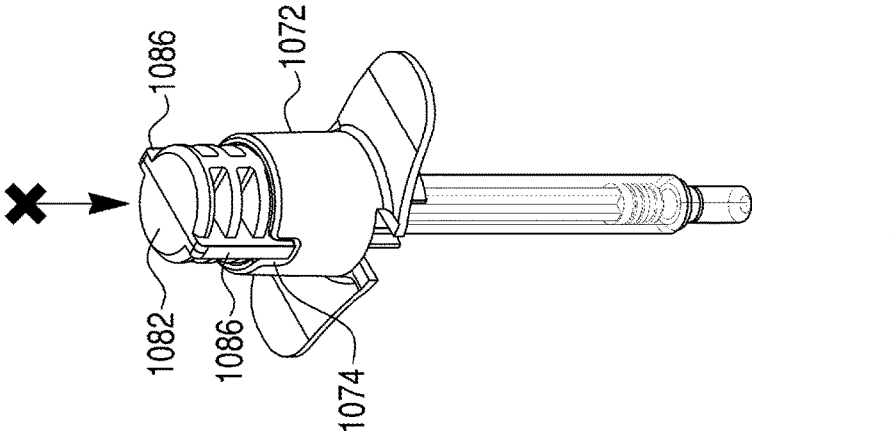
Figure 4E:
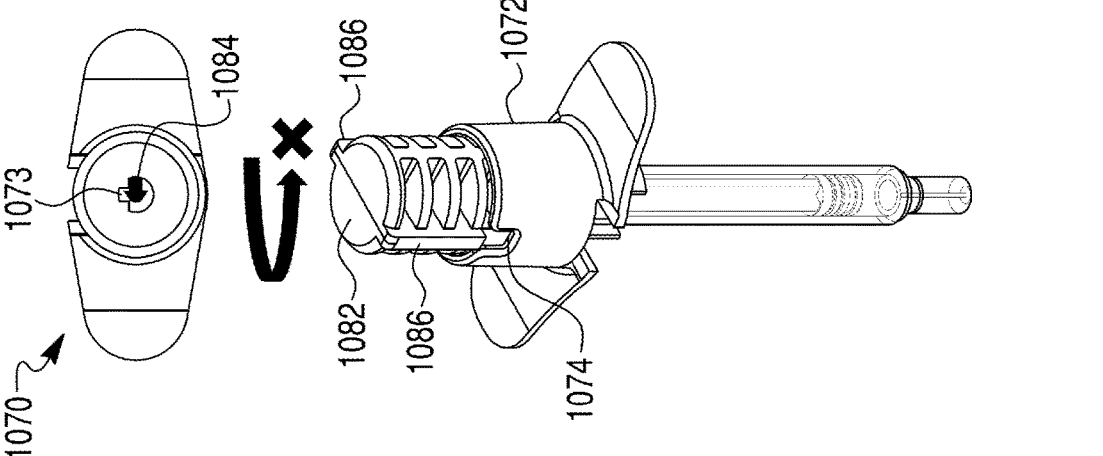
Figure 4D:
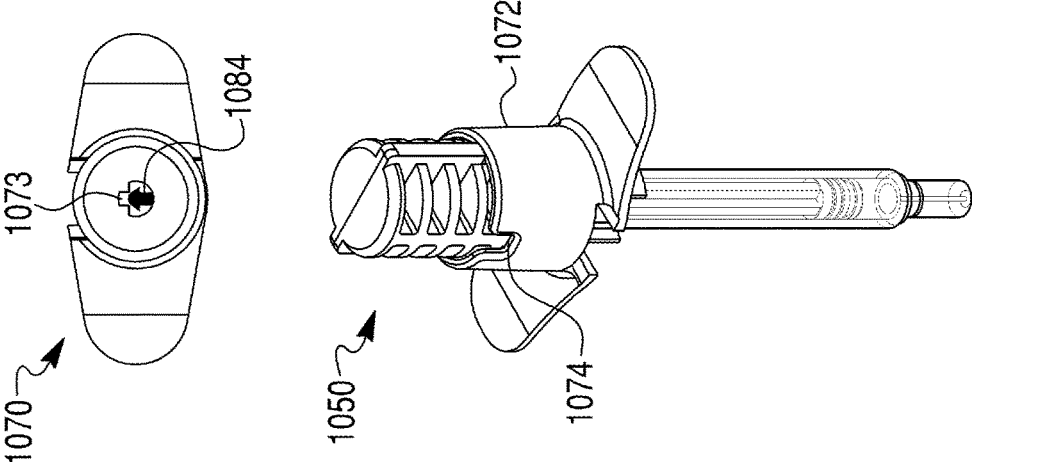

As depicted in FIG. 4D, device 1050 may be in a primed configuration. In a dispensing preparation step depicted in FIG. 4E, plunger rod 1080 may be rotated about a longitudinal axis to align protrusions 1086 with slots 1074. To do so, a user may grasp and twist actuation portion 1082. In some embodiments, as has been described elsewhere, it may be possible to twist actuation portion 1082 in either direction to align protrusions 1086 and slots 1074. In other embodiments, actuation portion 1082 may be rotatable only in one direction. In some embodiments, once protrusions 1086 are aligned with slots 1074, further rotation of plunger rod 1080 relative to flange piece 1070 may be stopped by, e.g., contact between the geometries of neck 1084 and opening 1073. Thus, aligning protrusions 1086 and slots 1075 may lock device 1050 in a ready-to-dispense configuration. In some embodiments, rotation of actuation portion 1082 may align protrusions 1086 with slots 1074, and may allow plunger rod 1080 to remain longitudinally stationary relative to flange piece 1070 (e.g., no proximal or distal movement of plunger rod 1080 is caused by rotation of actuation portion 1082). As depicted in FIG. 4F, in a dispensing step, plunger rod 1080 may be moved longitudinally further into body 1060. For example, a user may press actuation portion 1082 distally into proximal collar 1072 of flange piece 1070, such that protrusions 1086 slide into slots 1074. Once protrusion 1086 abut distal ends of slots 1074, further distal movement of plunger rod 1080 is stopped. The dispensing step may ensure that a predetermined volume of a drug substance inside body 1060 is dispensed from device 1050. In some embodiments, when protrusions 1086 abut distal ends of slots 1074, stopper 1062 does not "bottom out" or abut an interior of expulsion end 1064 in body 1060. Advantageously, by ensuring that a predetermined volume of a drug substance inside body 1060 is dispensed from device 1050 before stopper 1062 can bottom out, any variations in the manufacture of expulsion end 1064 (e.g., altering the exact size or shape of expulsion end 1064) are less likely to affect the predetermined volume of drug substance that is delivered from device 1050. Indeed, in some embodiments, the predetermined volume of drug substance that is delivered from device 1050 may not be affected by typical variations in manufacturing of any component of device 1050, particularly in any component except for flange piece 1070. Advantageously, this may allow for the existence of different or larger tolerances in manufacturing variation in several components of device 1050 (e.g., variations in formation of a glass body 1060 or other glass components), without affecting the predetermined volume of drug substance to be delivered from device 1050.

Figure 4G:
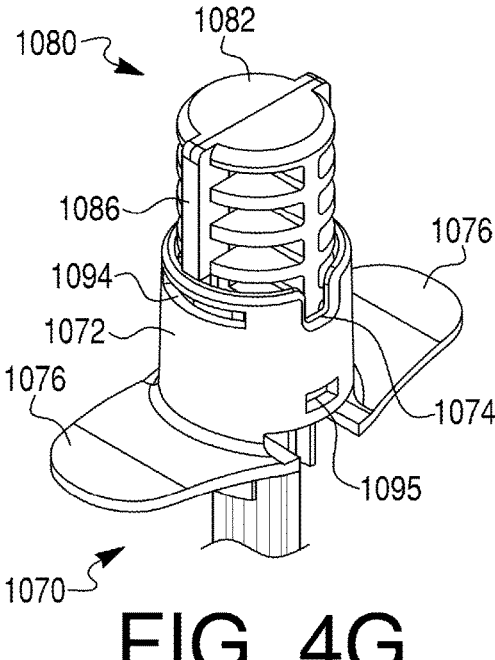
FIGS. 4G-4J depict an exemplary method of using an embodiment of the delivery device depicted in FIGS. 1A-1E, according to aspects of the present disclosure.
Figure 4I:
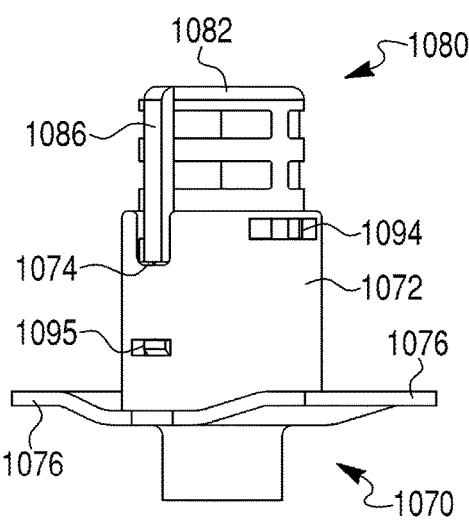
Figure 4H:
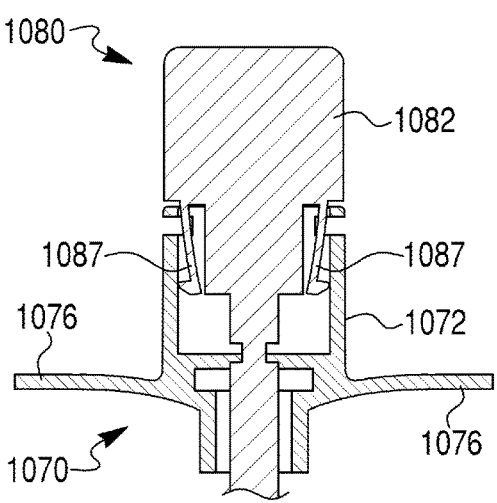
Figure 4J:
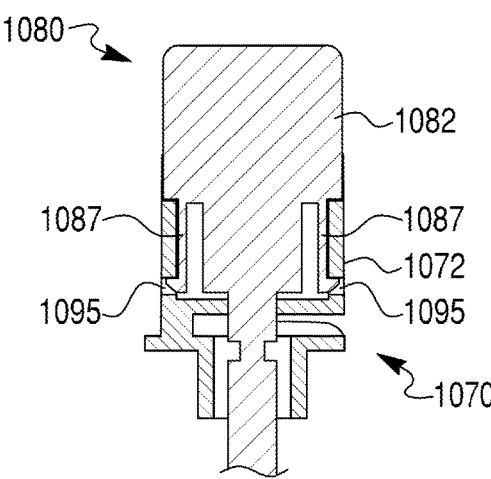

In some embodiments, after one or more steps in the use of device 1050, a user may be prevented from re-doing a step, and/or from reversing one or more steps. For example, geometries of, e.g., plunger rod neck 1084 and opening 1073 may prevent a user from pulling plunger rod 1080 proximally (e.g., out of) body 1060, from rotating plunger rod 1080 preemptively (e.g., before the priming step shown in FIG. 4C), and/or from over-rotating plunger rod 1080 during a dispensing preparation step (e.g., shown in FIG. 4E). In particular, FIGS. 4G-4J depict steps in the use of an embodiment of device 1050 having extensions 1087 on actuation portion 1082 and corresponding side openings 1094, 1095 in collar 1072 of flange piece 1070. FIGS. 4G and 4H depicts device 1050 as actuation portion 1082 is being pushed distally into collar 1072. Due to their angled distal portions, extensions 1087 are pushed inward into collar 1072. Once plunger rod 1080 has been rotated to a "delivery" position and actuation portion 1082 is further pushed distally into collar 1072 to deliver a predetermined volume of drug substance from device 1050, extensions 1087 may be received into side openings 1095 (shown in FIGS. 4I and 4J), thereafter restricting proximal movement of plunger rod 1080. Advantageously, restricting proximal movement of plunger rod 1080 may prevent inadvertent withdrawal of material into device 1050 from, e.g., a site into which a drug substance is delivered. In some embodiments, device 1050 may include either side openings 1094, or side openings 1095. In other embodiments, as shown in FIGS. 4G-4J, device 1050 may include both side openings 1094 and side openings 1095.

Figure 4K:
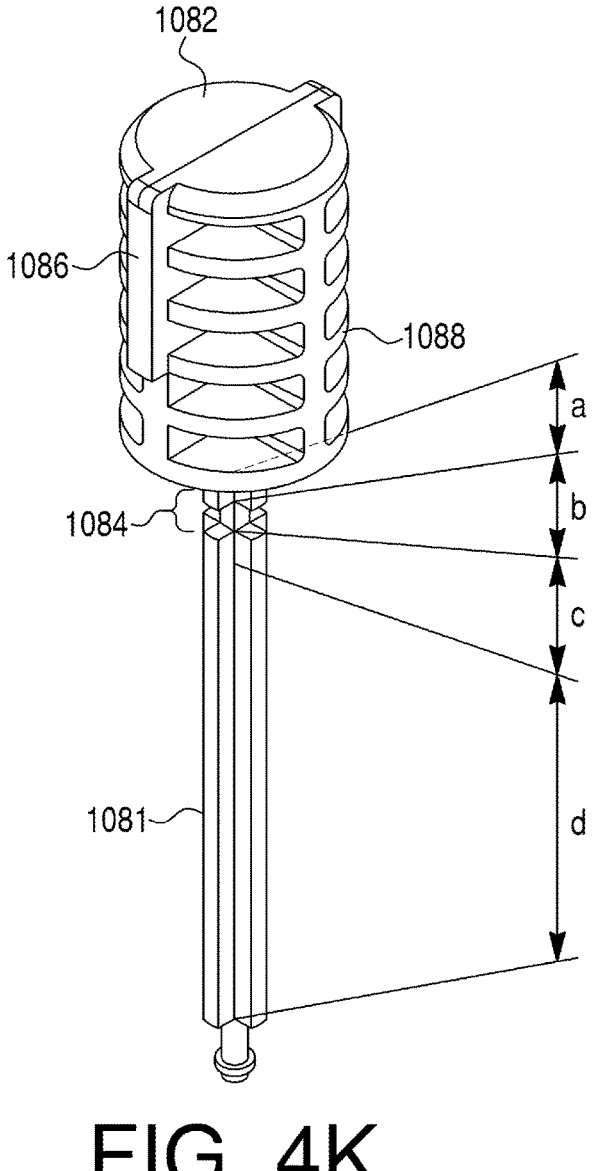
FIGS. 4K-4S depict exemplary aspects of plunger rods for use in embodiments of the delivery device depicted in FIGS. 1A-1E.
Figure 4L:
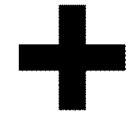
Figure 4M:
Figure 4N:
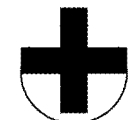
Figure 4Q:
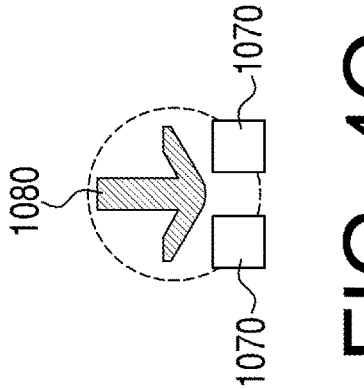
Figure 4S:
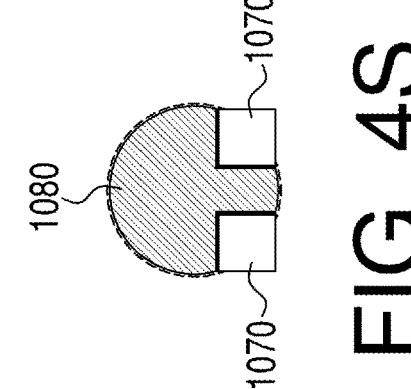
Figure 4P:
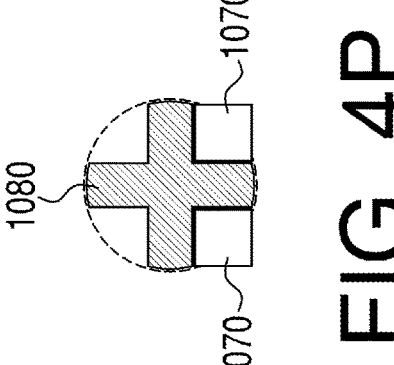
Figure 4R:
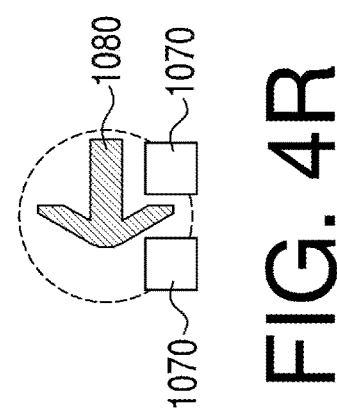
Figure 4O:
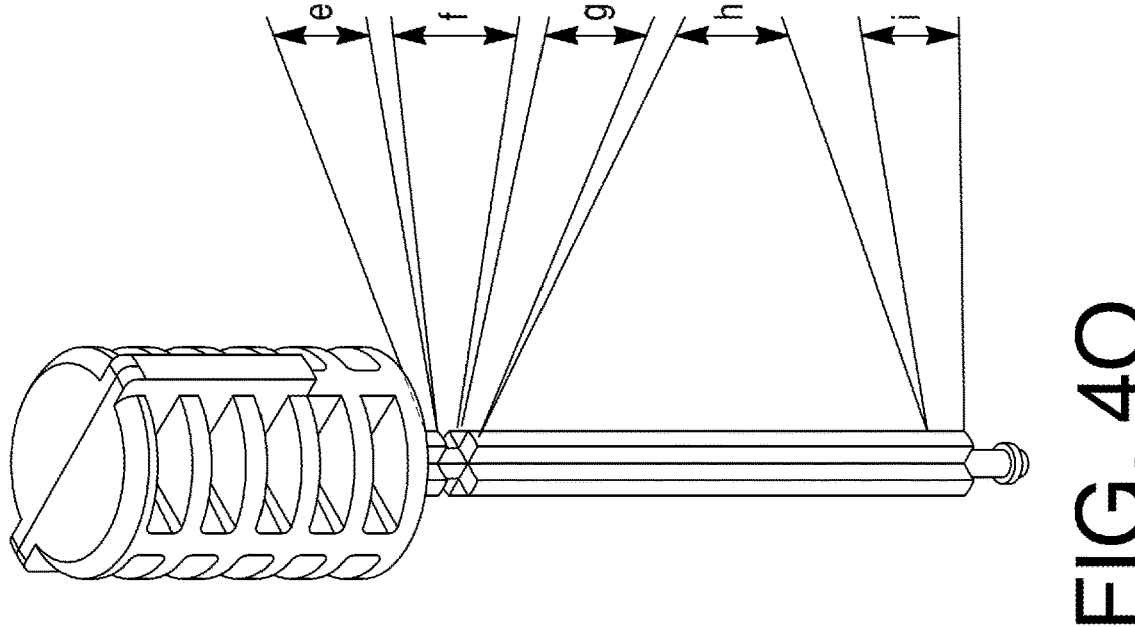

FIGS. 4K and 4O depicts in further detail exemplary aspects of a geometry of neck 1084, which may help to control movement of plunger rod 1080. For example, a proximal-most portion a of neck 1084 and stem 1081 (indicated by section d in FIG. 4K) may both have a first cross-sectional shape, as shown in FIG. 4L. This shape may allow for corresponding portions of plunger rod 1080 to move proximally/distally through an opening (e.g., opening 1073) of a blocking component (e.g., flange piece 1070), but may prevent rotation of plunger rod 1080 about a longitudinal axis. A narrow portion b of neck 1084 may have a smaller cross-sectional shape, as shown in FIG. 4M. This shape, when disposed in an opening (e.g., opening 1073) of a blocking component (e.g., flange piece 1070) may allow for unidirectional or bidirectional rotation of plunger rod 1080 about a longitudinal axis. It should be appreciated that the respective portion of neck 1084 allowing for transitional rotation of plunger rod 1080 (e.g., at narrow portion b) may have a geometry with the smallest cross-sectional shape to allow greater space for such movement, relative to the cross-sectional shapes of other portions of plunger rod 1080. A third portion c of neck 1084 may have a larger cross-sectional shape, as shown in FIG. 4N, which may correspond directly with the size and shape of an opening (e.g., opening 1073) of a blocking component (e.g., flange piece 1070). As such, proximal or distal movement of this portion of neck 1084 through opening 1073 may only be possible when plunger rod 1080 is in a specific rotational orientation relative to flange piece 1070. Moreover, plunger rod 1080 will not be rotatable while portion c of neck 1084 is disposed within opening 1073. This may ensure that, e.g., plunger rod 1080 is in a desirable position relative to flange piece 1070 (e.g., priming is complete and portion c is no longer disposed within opening 1073) before plunger rod 1080 may be rotated. Together, the various cross-sectional shapes of neck 1084 and the size and shape of opening 1073 may combine to create a specific sequence of movements of plunger rod 1080 needed to prime and deliver a drug substance from device 1050. In the example, a distal portion of opening 1073 may have the greatest cross-sectional profile relative to an intermediate and/or proximal portion of opening 1073 to accommodate the varying geometries of plunger rod 1080 therethrough (e.g., neck 1084, stem 1081, etc.).

In a further embodiment depicted in FIG. 4, a proximal-most portion e of neck 1084 and a majority portion h of stem 1081 may both have a first cross-sectional shape, as shown in FIG. 4P. This shape may allow for corresponding portions of plunger rod 1080 to move proximally/distally through an opening (e.g., opening 1073) of a blocking component (e.g., flange piece 1070), but may prevent rotation of plunger rod 1080 about a longitudinal axis. A narrow portion f of neck 1084 may have a smaller winged (or arrow-shaped) cross-sectional shape, as shown in FIG. 4Q (in a pre-rotation configuration relative to flange piece 1070) and FIG. 4R (in a post-rotation configuration relative to flange piece 1070). This "winged" shape, when disposed in an opening (e.g., opening 1073) of a blocking component (e.g., flange piece 1070) may allow for unidirectional or bidirectional rotation of plunger rod 1080 about a longitudinal axis, and may restrict or resist "backwards" rotation of plunger rod 1080 in the opposite direction after rotation has been completed (as described further with respect to FIGS. 4T-4X). Portions g and l of plunger rod 1080 may have a larger cross-sectional shape, as shown in FIG. 4S, which may correspond directly with the size and shape of an opening (e.g., opening 1073) of a blocking component (e.g., flange piece 1070). As such, proximal or distal movement of these portions of plunger rod 1080 through opening 1073 may only be possible when plunger rod 1080 is in a specific rotational orientation relative to flange piece 1070. Moreover, plunger rod 1080 will not be rotatable while portions g or l of plunger rod 1080 are disposed within opening 1073. This may ensure that, e.g., plunger rod 1080 is in a desirable position relative to flange piece 1070 at certain steps during assembly and use of device 1050, allowing for precise assembly and use of device 1050. Additionally, the "larger" cross sectional area of portions g and l may assist in preventing plunger rod "back-out", as they will not be able to move proximally through opening 1073 unless in a particular rotational position relative to flange piece 1070. For example, after rotation of plunger rod 1080 from a "primed" position to a "delivery" position, portion g of plunger rod 1080 may not be able to move through opening 1073, thus preventing plunger rod "back-out" at that stage of use of device 1050. Together, the various cross-sectional shapes of plunger rod 1080 and the size and shape of opening 1073 may combine to create a specific sequence of movements of plunger rod 1080 needed to assemble, prime, and deliver a drug substance from device 1050.

Figure 4T:
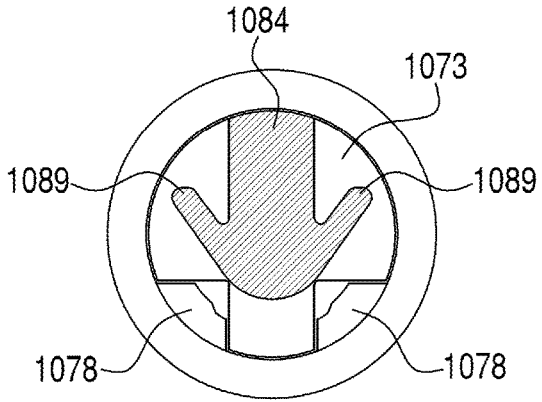
FIGS. 4T-4X depict views of an exemplary neck portion of a plunger rod and opening of a flange piece in embodiments of the delivery device depicted in FIGS. 1A-1E.
Figure 4U:
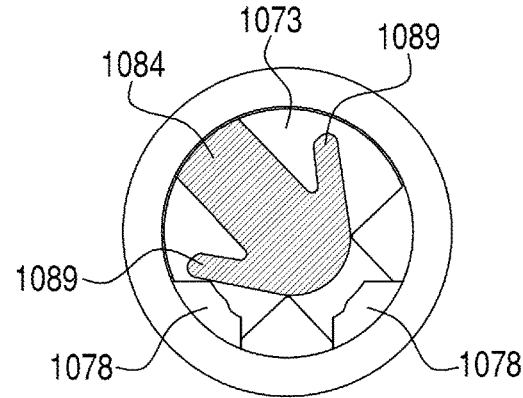
Figure 4V:
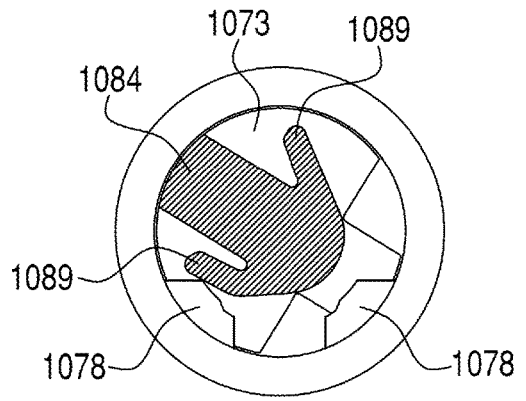
Figure 4W:
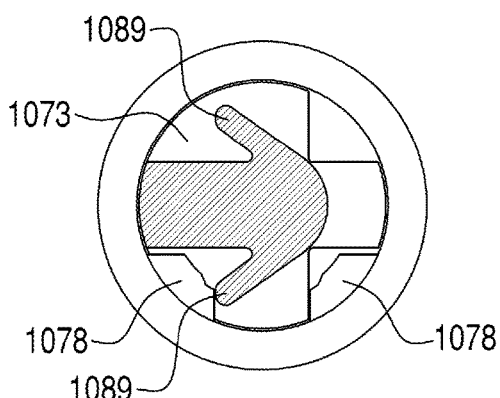
Figure 4X:
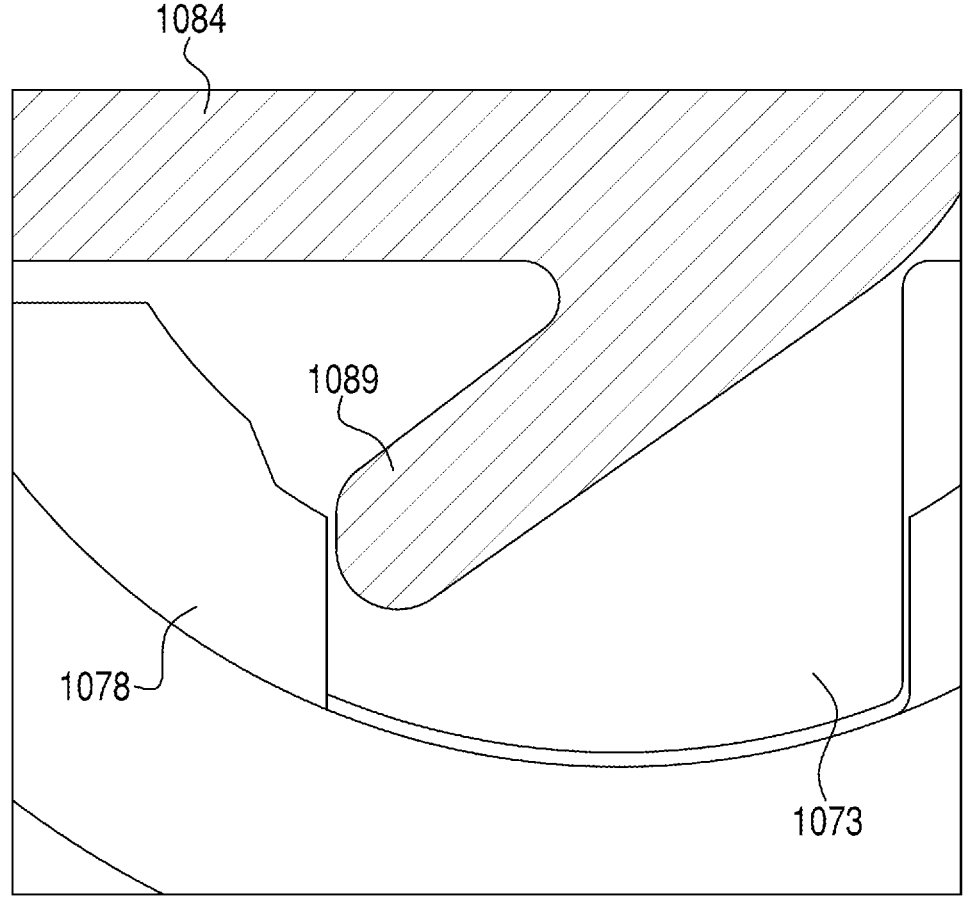

FIGS. 4T-4X depict in further detail specific interactions between a wing-shaped part of neck 1084 and opening 1073 in flange piece 1070. Flange piece 1070 may include detents 1078 either adjacent to or within opening 1073, which may interface with wings 1089 on neck 1084. FIG. 4T depicts a cross-sectional view of neck 1084 inside opening 1073 in a pre-rotation configuration (e.g., after device 1050 has been primed but before plunger rod 1080 has been rotated to a "delivery" configuration relative to flange piece 1070). FIG. 4U depicts that, as plunger rod 1080 is rotated about a longitudinal axis, one of wings 1089 may contact one of detents 1078 (depending on the direction of rotation). As rotation continues, one of detents 1078 may cause one of wings 1089 to be compressed towards the remainder of neck 1084. When rotation is complete, the one of wings 1089 has passed the one of detents 1078 and has expanded. This expansion of a wing 1089 past detent 1078 may cause an auditory "click" feedback and/or a tactile feedback to indicate that rotation is complete, and may thereafter prevent "backwards" rotation of plunger rod 1080 relative to flange piece 1070. Wings 1089 and detents 1078 may be configured to interact in a similar fashion regardless of whether plunger rod 1080 is rotated in a clockwise or counterclockwise direction, thereby allowing for bidirectional rotation of plunger rod 1080 to move plunger rod 1080 from a "primed" position to a "delivery" position. As shown in further detail in FIG. 4X, each wing 1089 may have a rounded shape to allow for ease of rotation in one direction, and the expansion of a wing 1089 past a detent 1078 may place the wing 1089 in a position relative to detent 1078 that greatly resists or otherwise prohibits rotation in the opposite direction. Detent 1078 may have any suitable contour configured to assist unidirectional movement of a wing 1089 past detent 1078.

Advantageously, the various configurations of plunger rod 1080 described herein may allow for modeling, molding, and/or manufacturing one piece (e.g., plunger rod 1080) or two pieces (e.g., plunger rod 1080 and flange piece 1070) in order to achieve several goals—e.g., control desired plunger rod movement and assembly, reduce user error, prevent plunger rod back-out, and minimize a number of disparate parts needing to be manufactured and handled in order to assemble device 1050.

Figures 4Y, 4Z:
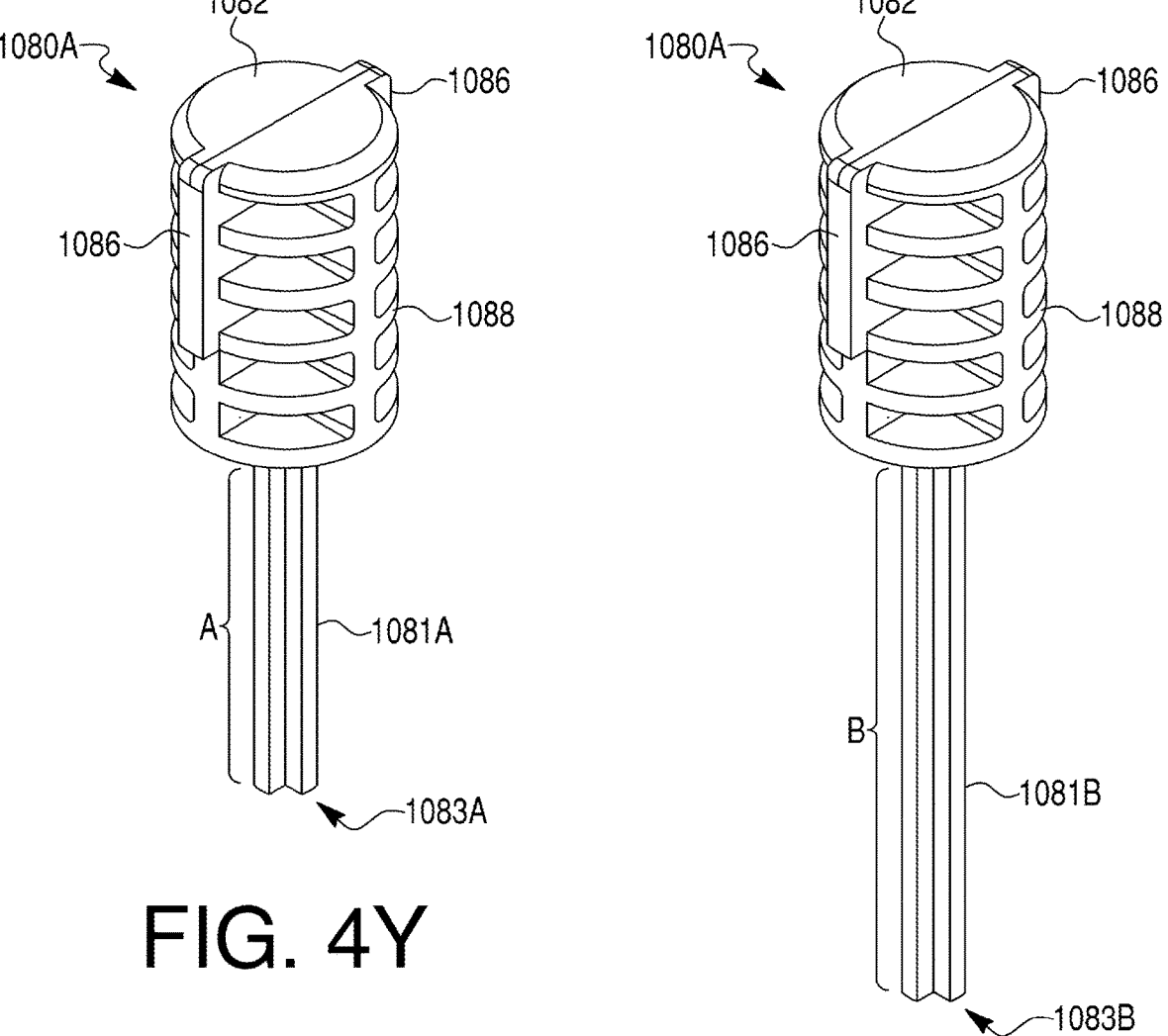
FIGS. 4Y-4Z depict exemplary aspects of plunger rods for use in embodiments of the delivery device depicted in FIGS. 1A-1E.

In some embodiments, as seen in FIGS. 4Y-4Z, device 1050 may include a pair of plunger rods in one kit, interchangeable with a single actuation portion 1082, or coupled to separate actuation portions 1082. For example, referring initially to FIG. 4Y, device 1050 may include a first plunger rod 1080A that is substantially similar to plunger rod 1080 shown and described above except for the differences explicitly noted herein. First plunger rod 1080A may include a stem 1081A having a longitudinal length A defined between a distal end of actuation portion 1082 and a tip 1083A. As described in detail below, longitudinal length A may define a priming distance for moving plunger rod 1080A relative to flange piece 1070 for priming device 1050. Tip 1083A may have a flat and/or planar interface that may be configured to inhibit engagement of stopper 1062 when first plunger rod 1080A is received within body 1060.

Referring now to FIG. 4Z, device 1050 may further include a second plunger rod 1080B that is substantially similar to plunger rod 1080. Second plunger rod 1080B may include a stem 1081B extending distally from actuation portion 1082 and having a longitudinal length B defined between a distal end of actuation portion 1082 and a tip 1083B. Tip 1083B is substantially similar to tip 1083A described above. Longitudinal length B of stem 1083B is relatively greater than longitudinal length A of stem 1081A and may define a dosage delivery distance for moving plunger rod 1080A relative to flange piece 1070 to deliver a dose from device 1050.

First plunger rod 1080A may be configured to prime device 1050 in response to translating stem 1081A through collar 1072 and into body 1060 (see FIGS. 1A-1B). In this instance, tip 1083A may contact and push stopper 1062 distally by the priming distance. It should be understood that the priming distance of device 1050 may be controlled based on a size of longitudinal length A of first plunger rod 1080A. Upon priming device 1050, first plunger rod 1080A may be removed from body 1060 and flange piece 1070 without retracting stopper 1062 due to a flattened-interface of tip 1083A. Accordingly, stopper 1062 may remain at a fixed position relative to body 1060 upon retraction of first plunger rod 1080A.

Second plunger rod 1080B may be configured to deliver a dose from device 1050 in response to translating stem 1081B through collar 1072 and into body 1060 (see FIGS. 1A-1B), after the priming step described above using stem 1081A. In this instance, tip 1083B may contact and push stopper 1062 distally by the dosage delivery distance. It should be understood that the dosage delivery distance of device 1050 may be controlled based on a size of longitudinal length B of second plunger rod 1080B. The dosage delivery distance may be substantially equal to the difference in length between stem 1081B and stem 1081A.

Figures 5A, 5B, 5C:
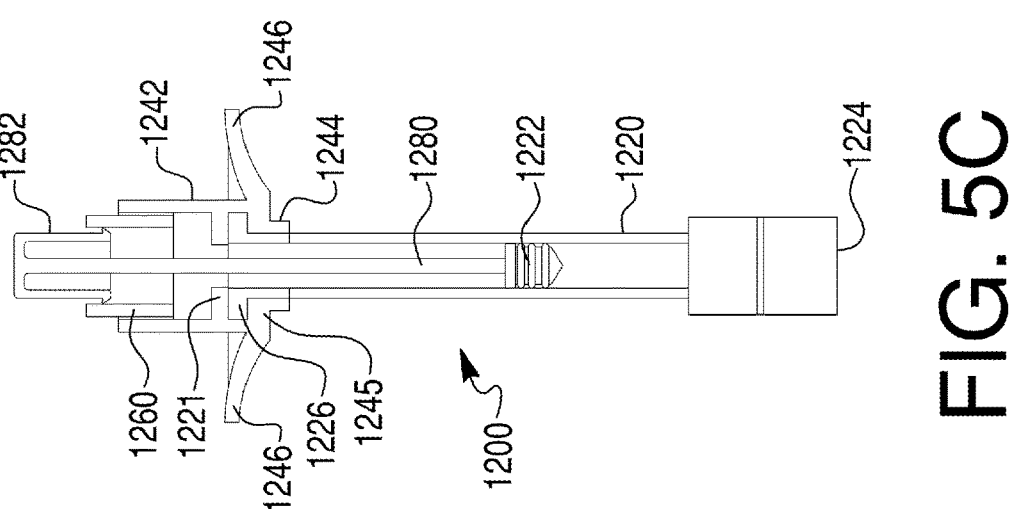
FIGS. 5A-5C depict another exemplary delivery device according to additional embodiments of the present disclosure.
Figure 6E:
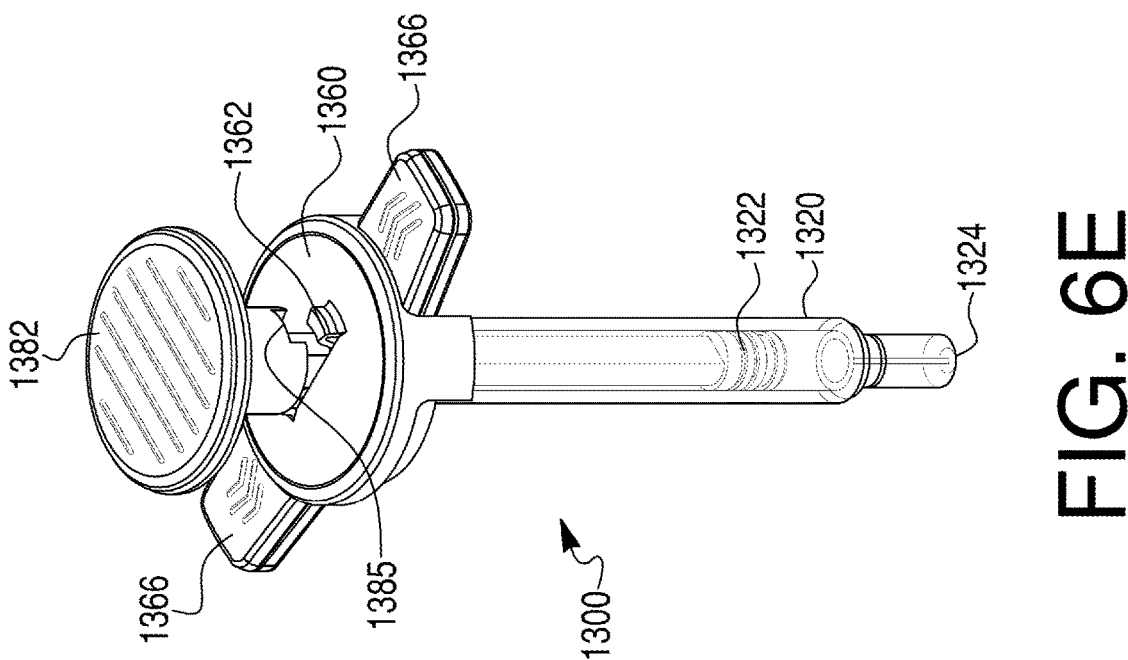
Figure 6D:
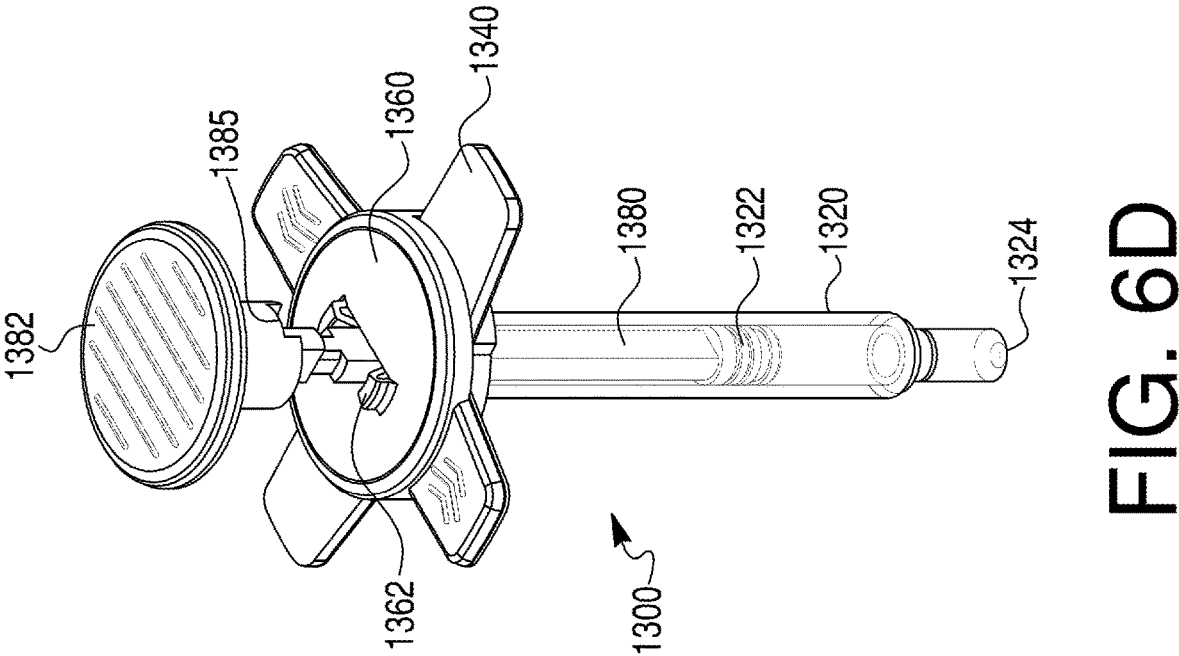

FIGS. 5A-5C depict another exemplary delivery device 1200 according to additional embodiments of the present disclosure. Device 1200 includes a body 1220, and a flange piece 1240 with a proximal collar 1242, in which an inner collar 1260 may be disposed. Together, proximal collar 1242 and inner collar 1260 may form a blocking component for device 1200. A plunger rod 1280 may pass through inner collar 1260 and flange piece 1240, into body 1060. Plunger rod 1280 may share a longitudinal axis with a central axis of proximal collar 1242 and inner collar 1260, and may have an actuation portion 1282 sized and configured to fit (e.g., nest or otherwise fit) inside inner collar 1260.

Device 1200 may be, for example, an injection device, such as a syringe, for dispensing a predetermined volume of a formulated drug substance. Generally, device 1200 may share size, capacity, material, preparation, assembly, manufacturing, operation, or use characteristics with device 1050, or with other delivery devices disclosed herein. As with device 1050, device 1200 may be configured for ease of use and may include one or more features that aid a user by providing tactile, auditory, or visual feedback (e.g., using any of the features described elsewhere herein).

Body 1220 may have any or all of the same characteristics as, e.g., body 1060 of device 1050, or as any syringe body known in the art. For example, in some embodiments, body 1220 may be pre-fillable or pre-filled (e.g., fillable or filled with a drug substance prior to completed assembly, packaging, sterilization and/or shipment of device 1200 to users). In some embodiments, a stopper 1222 may be configured to be inserted into body 1220 and may be configured to hold a predetermined volume of a formulated drug substance inside body 1200, between stopper 1222 and an expulsion end 1224.

Flange piece 1240 may be of any suitable size and/or shape to close, partially close, cover, or partially cover an end of body 1220 opposite expulsion end 1224, and/or to support and hold plunger rod 1280 in place inside body 1220. In some embodiments, flange piece 1240 may share some characteristics with flange piece 1070 of device 1050. For example, flange piece 1240 may include a distal collar 1244 configured to engage with body 1220 and hold flange piece 1240 in place in relation to body 1220. For example, distal collar 1244 may include a lip 1245 that may slide over a body flange 1226, to hold flange piece 1240 in place. In alternative embodiments, lip 1245 of distal collar 1244 may be made of a flexible or semi-flexible material, so that it may snap in place over body flange 1226. In further embodiments, distal collar 1244 or another portion of flange piece 1240 may be adhered to, molded to, or otherwise affixed to, body 1220, or may engage with body 1220 via a friction fit.

In some embodiments, flange piece 1240 may include one or more flanges 1246, which may be sized and configured to aid a user in holding device 1200 and/or expelling a formulated drug substance from device 1200. In some embodiments, as depicted in FIGS. 1A-1E, flange piece 1240 may include two flanges 1246 opposite to one another and extending perpendicularly from a longitudinal dimension of device 1200. In some embodiments, flange piece 1240 may include other arrangements of a flange or flanges, such as four flanges, or one circumferential flange extending radially outward from a central longitudinal axis of device 1200. In some embodiments, flange piece 1240 may extend radially outward from a central longitudinal axis of device 1200 farther than a circumference of body 1220. In such embodiments, flange piece 1240 may support device 1200 if device 1200 is placed on a surface, may prevent device 1200 from rolling on a flat surface, and/or may allow device 1200 to be picked up more easily.

In some embodiments, flange piece 1240 and inner collar 1260 may be sized and configured to serve as a blocking component in device 1200, e.g., by limiting and/or directing rotational and longitudinal movement of plunger rod 1280. Proximal collar 1242 of flange piece 1240 may be sized and configured to accept part of inner collar 1260, while blocking protrusions 1262 from moving distally until inner collar 1260 is rotated to a particular position. In turn, inner collar 1260 may be sized and configured to receive part or all of an actuation portion 1282 of plunger rod 1280. As shown in FIGS. 5A-5C, proximal collar 1242, inner collar 1260, and actuation portion 1282 may all have generally cylindrical shapes; in alternate embodiments, each of proximal collar 1242, inner collar 1260, and actuation portion 1282 may have any suitable size or shape that allows for actuation portion 1282 to fit (e.g., nest) within inner collar 1260, and inner collar 1260 to fit within proximal collar 1242.

Plunger rod 1280 and inner collar 1260 may be in general rotatable about a shared central longitudinal axis (e.g., in one direction or in both directions). Moreover, both plunger rod 1280 and inner collar 1260 may be movable along the central longitudinal axis, e.g., in a distal direction to prime device 1200 and/or deliver a volume of drug substance from distal end 1224 of body 1220. Actuation portion 1282 of plunger rod 1280 may include a distal geometry which, when actuation portion 1282 is moved distally into inner collar 1260, interfaces with inner collar 1260 to prevent proximal movement (e.g., back-out) of plunger rod 1280 from inner collar 1260. For example, actuation portion 1282 may include a wedge-shaped distal portion that, when it passes a distal portion of inner collar 1260, expands distally from inner collar 1260 so that actuation portion 1282 can no longer move freely in relation to inner collar 1260.

Flange piece 1240 may include cavities, such as slots 1248, into which protrusions 1262 of inner collar 1260 may slide when inner collar 1260 is rotated to a particular position. As with slots 1074 of device 1050, slots 1248 may have a depth dimension parallel to a longitudinal axis of device 1200, and the depth of slots 1248 may correspond to a distance plunger rod 1280 must move distally in order to push stopper 1222 towards expulsion end 1224, and dispense a predetermined volume of formulated drug substance from body 1220 through expulsion end 1224.

In some embodiments, device 1200 may have additional features. For example, in some embodiments, a neck of plunger rod 1280 may have a geometry complementary to an opening of flange piece 1240 that restricts the extent and direction that plunger rod 1280 may rotate or move longitudinally, similar to neck 1084 and opening 1073 of device 1050. For example, rotation and/or longitudinal movement of plunger rod 1280 may be restricted based on priming, preparing, and/or drug delivery steps during use of device 1200. As another example, plunger rod 1280 may be prevented from being pulled or backed out of body 1220 at any point during preparation or use of device 1200.

In a contemplated method of use of device 1200, device 1200 may be filled with a predetermined volume of drug substance. The predetermined volume of drug substance may be greater than a volume of drug substance suitable for delivery to a patient. In some embodiments, device 1200 (e.g., body 1220) may contain both a predetermined volume of drug substance and an air bubble (not shown) that should be removed prior to delivery of the drug substance to a patient. In some embodiments, device 1200 may be a pre-filled syringe. In order to prime device 1200 (e.g., removing an air bubble if any and ensuring that a suitable volume of the drug substance will be delivered to a patient), a user may push actuation portion 1282 of plunger rod 1280 into inner collar 1260. A geometry of actuation portion 1282 may interact with inner collar 1260 (e.g., a distal wedge or clip of actuation portion 1282 may expand on a distal side of inner collar 1260) to secure actuation portion 1282 in and/or to inner collar 1260 and to prevent back-out of plunger rod 1280. At this point, device 1200 may be in a "primed" state. Subsequently, inner collar 1260 may be rotated about a longitudinal axis, until protrusions 1262 become longitudinally aligned with slots 1248. At this point, device 1200 may be in a "delivery" state. To deliver a predetermined volume of drug substance from device 1200, inner collar 1260, together with actuation portion 1282 and plunger rod 1280, may then be moved distally until protrusions 1262 abut a distal end of slots 1248. The distance traveled by plunger rod 1280 in this step may push stopper 1222 distally by a distance required to dispense the predetermined volume of drug substance from expulsion end 1224 of device 1200.

Referring now to FIGS. 6A-6E, views of a delivery device 1300 and component parts are depicted. Delivery device 1300 includes a blocking component comprising a distal flange piece 1340 and a proximal flange piece 1360, a plunger rod 1380, and a body 1320. Distal flange piece 1340 and proximal flange piece 1360 each include flanges (1346 and 1366, respectively). The flanges 1366 of proximal flange piece 1360 optionally may include a texture 1365. Distal flange piece 1340 includes a channel which may allow for distal flange piece 1340 and body 1320 to be slidably assembled. Proximal flange piece 1360 includes a clip which may allow for proximal flange piece 1360 and distal flange piece 1340 to be movably affixed to one another, such that they may still be rotatable relative to one another about a longitudinal axis of delivery device 1300 see, e.g., FIGS. 6D and 6E). Proximal flange piece 1360 includes clips 1362 bordering a central opening through which plunger rod 1380 may pass. Plunger rod 1380 includes an actuation portion 1382, which optionally may include a texture 1381. Plunger rod 1380 further includes a distal neck shape 1384, a proximal neck shape 1387, and a proximal stop 1386 having a cavity 1385, all of which are configured to interface with distal flange piece 1340 and proximal flange piece 1360 in a plurality of configurations to allow for controlled priming and delivery of a predetermined volume of a drug substance using delivery device 1300. Plunger rod 1380 further includes a distal tip 1383 at a distal end of a stem 1389, where tip 1383 is configured to interface with stopper 1322. Tip 1383 may have any suitable size, shape, and mode of attaching to, affixing to, or pushing stopper 1322 as has been described with respect to, e.g., tip 1083 of plunger rod 1080. As with stem 1081, stem 1389 may have any size and configuration suitable to fit inside body 1320. In some embodiments, step 1389 may be sized and configured to provide sufficient size (e.g., thickness), stability and/or rigidity to reduce a likelihood of undesirable bending, wobbling, or breaking.

Body 1320 (depicted in FIGS. 6D and 6E) may have any or all of the same characteristics as, e.g., body 1060 of device 1050, or as any syringe body known in the art. For example, in some embodiments, body 1320 may be pre-fillable or pre-filled. A stopper 1322 may be configured to be inserted into body 1320 and may be configured to hold a predetermined volume of a formulated drug substance inside body 1320, between stopper 1322 and an expulsion end 1324.

Delivery device 1300 may be, for example, an injection device, such as a syringe, for dispensing a predetermined volume of a formulated drug substance. Generally, delivery device 1300 may share size, capacity, material, preparation, assembly, or manufacturing characteristics with device 1050, device 1200, or with other delivery devices disclosed herein. As with devices 1050 and 1200, delivery device 1300 may be configured for ease of use and may include one or more features that aid a user by providing tactile, auditory, or visual feedback (e.g., textures 1365, 1381, other textures, labels, colors, or tactile or auditory feedback, or using any of the other features described elsewhere herein). As with devices 1050 and 1200, such features are optional, and one or more such features may be combined to improve ease of use.

Proximal flange piece 1360 and distal flange piece 1340 may be of any suitable size and/or shape to serve as a blocking component in delivery device 1300, to close, partially close, cover, or partially cover an end of body 1320 opposite expulsion end 1324, and/or to support and hold plunger rod 1380 in place inside body 1320. In some embodiments, proximal flange piece 1360 and distal flange piece 1340 may each include one or more flanges, which may be sized and configured to aid a user in holding device 1300 and/or expelling a formulated drug substance from expulsion end 1324. In some embodiments, as depicted in FIGS. 6A-6E, flange pieces 1360, 1340 may each include two flanges 1366, 1346 respectively, where each pair of flanges is opposite to one another and extending perpendicularly from a longitudinal dimension of device 1300. In general, other arrangements of a flange or flanges, such as one flange on each of flange pieces 1360, 1340, are possible. Each of flange pieces 1340, 1360 may extend radially outward from a central longitudinal axis of device 1300 farther than a circumference of body 1320, to, e.g., support device 1300 if device 1300 is placed on a surface, prevent device 1300 from rolling on a flat surface, and/or allow device 1300 to be picked up more easily.

Flange pieces 1360 and 1340 may, in combination, form a central opening having a changeable size and/or shape depending on a relative position of proximal flange piece 1360 and distal flange piece 1340. For example, in the configuration depicted in FIG. 6D, proximal flange piece 1360 and distal flange piece 1340 may combine to form an opening sized and configured to allow for distal passage of distal neck portion 1384 of plunger rod 1380, but to block passage of proximal neck portion 1387. In the second configuration depicted in FIG. 6E (e.g., where flanges 1346 and 1366 are in alignment), the central opening formed by flange pieces 1360 and 1340 may be sized and configured to allow for distal passage of proximal neck portion 1387. Proximal stop 1386 may be of a size and shape that is too large to pass through the central opening formed by flange pieces 1360 and 1340 in any combination. In some embodiments, distal flange 1340 may be assembled with body 1320 and plunger rod 1380 such that distal flange 1340 is not movable relative to body 1320 and not rotatable relative to plunger rod 1380. Proximal flange 1360 may, in contrast, be assembled to distal flange 1340 (and body 1320) such that it is rotatable about a longitudinal axis in relation to distal flange 1340, body 1320, and plunger rod 1380, which may pass through central opening 1368. Specifically, proximal flange 1360 may be rotatable relative to distal flange 1340 from a first configuration in which flanges 1346, 1366 are offset from one another (see FIG. 6D), to a second configuration in which flanges 1346, 1366 overlay one another (see FIG. 6E). One of ordinary skill in the art will understand that in alternate embodiments, distal flange 1340 may be rotatable in relation to other parts of device 1300, while proximal flange 1360 may not be rotatable. In yet further embodiments, both proximal flange 1360 and distal flange 1340 may be assembled with body 1320 and plunger rod 1380 such that they are both rotatable relative to other components of device 1300.

Clips 1362 of proximal flange piece 1360 may overhang and be biased towards opening 1368. In a pre-use configuration (depicted in FIG. 6D), clips 1362 may be compressed by plunger rod 1380. They may be positioned on proximal flange piece 1360 such that, upon distal movement of plunger rod 1380 such that distal neck portion 1384 passes through opening 1368, they expand inward to abut the sides of distal neck portion 1384. Once clips 1362 expand in this manner, they may block proximal movement of plunger rod 1380, e.g., to prevent plunger rod back-out (see, e.g., FIG. 7C). A cavity 1385 may be positioned on proximal stop 1386 for each clip 1362, such that when plunger rod 1380 is moved distally into body 1320 to a fullest desired extent, each clip 1362 may fit into a cavity 1385.

Figures 7A, 7B, 7C:
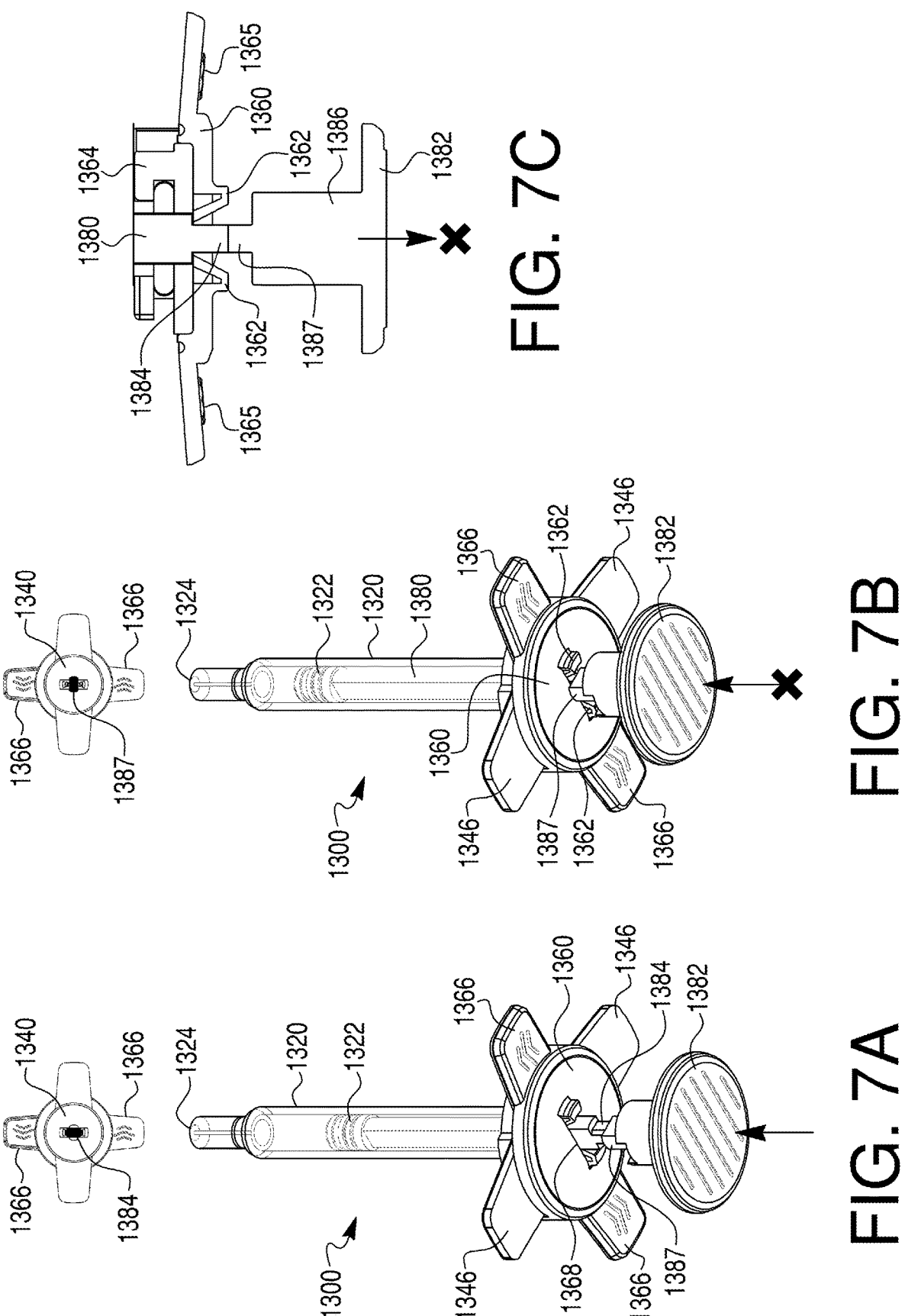
FIGS. 7A-7F depict an exemplary method of using the delivery device depicted in FIGS. 6A-6E, according to aspects of the present disclosure.

FIGS. 7A-7F depict an exemplary method of using device 1300, according to aspects of the present disclosure. In a pre-use configuration depicted in FIG. 7A, device 1300 may hold a volume of a drug substance in between stopper 1322 and expulsion end 1324. Flange pieces 1340 and 1360 may be in a pre-use configuration, in which flanges 1346, 1366 are offset from one another. Plunger rod 1380, which may abut or be assembled to stopper 1322, may be partially inserted into body 1320 through flange pieces 1340, 1360. Proximal flange piece 1360 may be prevented from rotating about the longitudinal axis of the syringe, due to the geometries of plunger rod 1380 and flange piece 1360. In a priming step depicted in FIG. 7B, plunger rod 1380 may be moved longitudinally further into body 1320, until distal movement is blocked by the abutment of proximal neck portion 1385 against a surface of proximal flange piece 1360. For example, a user may press actuation portion 1382 towards proximal flange piece 1360. In some embodiments, device 1300 may be held in an inverted position during this step, to ensure that air trapped in body 1320 may be expelled via expulsion end 1324, as stopper 1322 is pushed distally by plunger rod 1380. In the "primed" configuration, distal neck portion 1384 may be disposed in opening 1368 of proximal flange piece 1360. Moreover, as depicted in FIG. 7C, once the priming step is stopped, clips 1362 may be released from their compressed configuration such that they may expand inwards and abut a side of distal neck portion 1384. As distal neck portion 1384 may be comparatively narrower than the part of plunger rod 1380 previously disposed in opening 1368, the expansion of clips 1362 may prevent proximal movement (e.g., back-out) of plunger rod 1380.

Figures 7D, 7E, 7F:
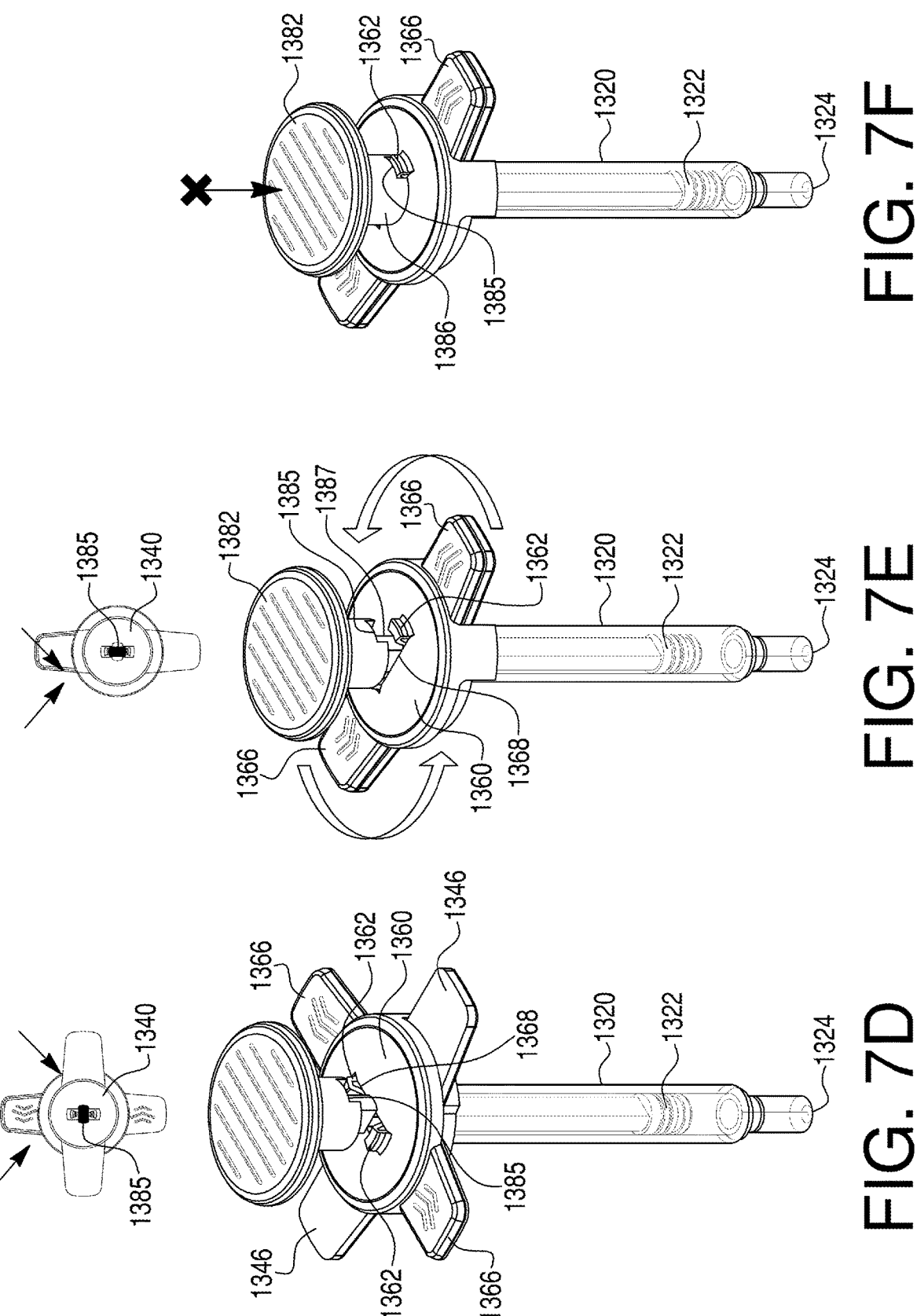

As depicted in FIG. 7D, device 1300 may be in a primed configuration. In a dispensing preparation step depicted in FIG. 7E, proximal flange piece 1360 may be rotated about a longitudinal axis to align flanges 1366 and flanges 1346, and to change (e.g., enlarge) a shape of the central opening formed by the combined openings of proximal flange piece 1360 and distal flange piece 1340. To do so, a user may grasp and twist proximal flange piece 1360. In some embodiments, it may be possible to twist proximal flange piece in either direction to align flanges 1366 and flanges 1346. In other embodiments, proximal flange piece 1360 may be rotatable only in one direction. In some embodiments, once flanges 1366 and flanges 1346 are aligned (as shown in, e.g., FIG. 7E), further rotation of plunger rod 1080 relative to flange piece 1070 may be stopped by, e.g., clip 1362 abutting against flange 1346. Thus, device 1300 may be locked in a ready-to-dispense configuration. As depicted in FIG. 7F, in a dispensing step, plunger rod 1380 may be moved longitudinally further into body 1320. For example, a user may press actuation portion 1382 distally, until each of clips 1362 enter a cavity 1385 in a proximal stop 1386, and/or until proximal stop 1386 abuts a proximal surface of proximal flange piece 1360. The dispensing step may ensure that a predetermined volume of a drug substance inside body 1320 is dispensed from device 1300.

In some embodiments, after each successive step in the use of device 1300, a user may be prevented from re-doing a step, and/or from reversing one or more steps. For example, geometries of, e.g., plunger rod 1380 and the combined openings of proximal flange piece 1360 and distal flange piece 1340 may prevent a user from pulling plunger rod 1380 proximally (e.g., out of) body 1320, from rotating plunger rod 1380, from rotating proximal flange piece 1360 preemptively (e.g., before completion of the priming step shown in FIGS. 7B and 7C), and/or from over-rotating flange piece 1360 during a dispensing preparation step (e.g., shown in FIG. 7E).

FIGS. 8A-8G depict a further exemplary delivery device 1400 and component parts Delivery device 1400 includes a plunger rod 1480, a blocking component 1460, a flange piece 1440, and a body 1420. Plunger rod 1480 includes an actuation portion 1482 and a protrusion 1484. Blocking component 1460 may be a rotatable alignment component that is configured to partially or fully surround plunger rod 1480, and includes three connected channels 1462, 1464, 1468 sized and configured to allow for passage of protrusion 1484. Flange piece 1440 includes a proximal collar 1442 having a channel 1447 into which tabs 1461 of blocking component 1460 may slidably fit, a distal collar 1444 including a channel 1445 into which a flange 1421 of body 1420 may fit (e.g., may be slidably assembled), and flanges 1446.

Body 1420 (depicted in FIGS. 8D and 8E) may have any or all of the same characteristics as, e.g., body 1060 of device 1050, or as any syringe body known in the art. For example, in some embodiments, body 1420 may be pre-fillable or pre-filled. A stopper 1422 may be configured to be inserted into body 1420 and may be configured to hold a predetermined volume of a formulated drug substance inside body 1420, between stopper 1422 and an expulsion end 1424.

Delivery device 1400 may be, for example, an injection device, such as a syringe, for dispensing a predetermined volume of a formulated drug substance. Generally, delivery device 1400 may share size, capacity, material, preparation, assembly, or manufacturing characteristics with device 1050, device 1200, device 1300, or with other delivery devices disclosed herein. As with other devices disclosed herein, delivery device 1400 may be configured for ease of use and may include one or more features that aid a user by providing tactile, auditory, or visual feedback, using any of the features described elsewhere herein.

Blocking component 1460 may be of any suitable size and/or shape to assist in controlling proximal and distal movement of plunger 1480 in device 1400.

Flange piece 1440 may be of any suitable size and shape to close, partially close, cover, or partially cover an end of body 1420 opposite expulsion end 1424, and/or to support and hold blocking component 1460 and plunger rod 1480 in relation to body 1420. For example, proximal collar 1442 and channel 1447 may be sized and configured to hold blocking component 1460, and distal collar 1444 and channel 1445 may be sized and configured to hold a flange 1421 of body 1420, such that blocking component 1460 is held stationary in relation to body 1420. Further, blocking component 1460 may be sized and configured to plunger rod 1480 inside body 1420, and to limit movement of plunger rod 1480 with respect to body 1420. Flange piece 1440 may include one or more flanges 1446, which may be sized and configured to aid a user in holding device 1400 and/or expelling a formulated drug substance from expulsion end 1424. In some embodiments, as depicted in FIGS. 8A-8E, flange piece 1440 may include two flanges 1446, opposite to one another. In general, other arrangements of a flange or flanges, such as one flange or three flanges, are possible. Flange piece 1440 may extend radially outward from a central longitudinal axis of device 1400 farther than a circumference of body 1420, to, e.g., support device 1400 if device 1400 is placed on a surface, prevent device 1400 from rolling on a flat surface, and/or allow device 1400 to be picked up more easily.

Channels 1462, 1464, 1468 in blocking component 1460 together form a path through which protrusion 1484 may travel, to allow for controlled movement of plunger rod 1480. A first channel 1462 may allow for sufficient distal movement of plunger rod 1480 to prime device 1400. A second channel 1464 may allow for movement of the plunger rod between a "primed" state and a "delivery" state. Channel 1464 may have a path requiring rotation of plunger rod 1480 about a longitudinal axis of device 1400 (as opposed to distal movement of plunger rod 1480), such that the likelihood of plunger rod 1480 being accidentally or unintentionally moved to a "delivery" state may be reduced. Channel 1464 may provide a path of any suitable length (corresponding to any suitable angle of rotation of plunger rod 1480) to ensure adequate separation between the "primed" state and the "delivery" state. A third channel 1468 may allow for sufficient distal movement of plunger rod 1480 to dispense a predetermined volume of drug substance from device 1400.

Figure 8E:
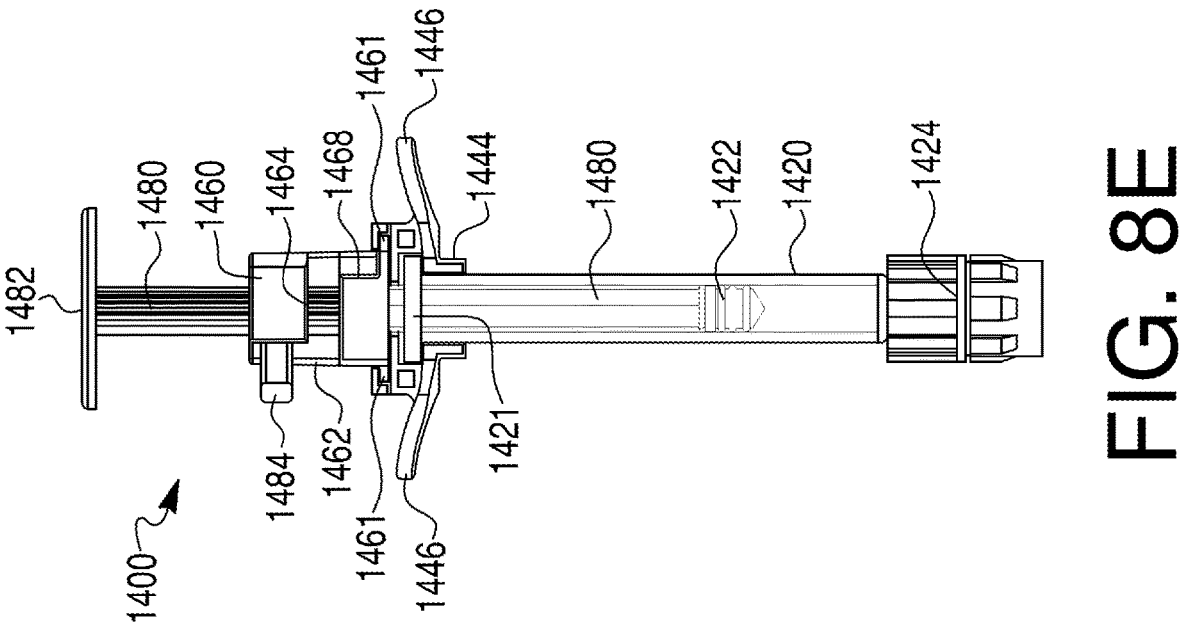
Figure 8D:
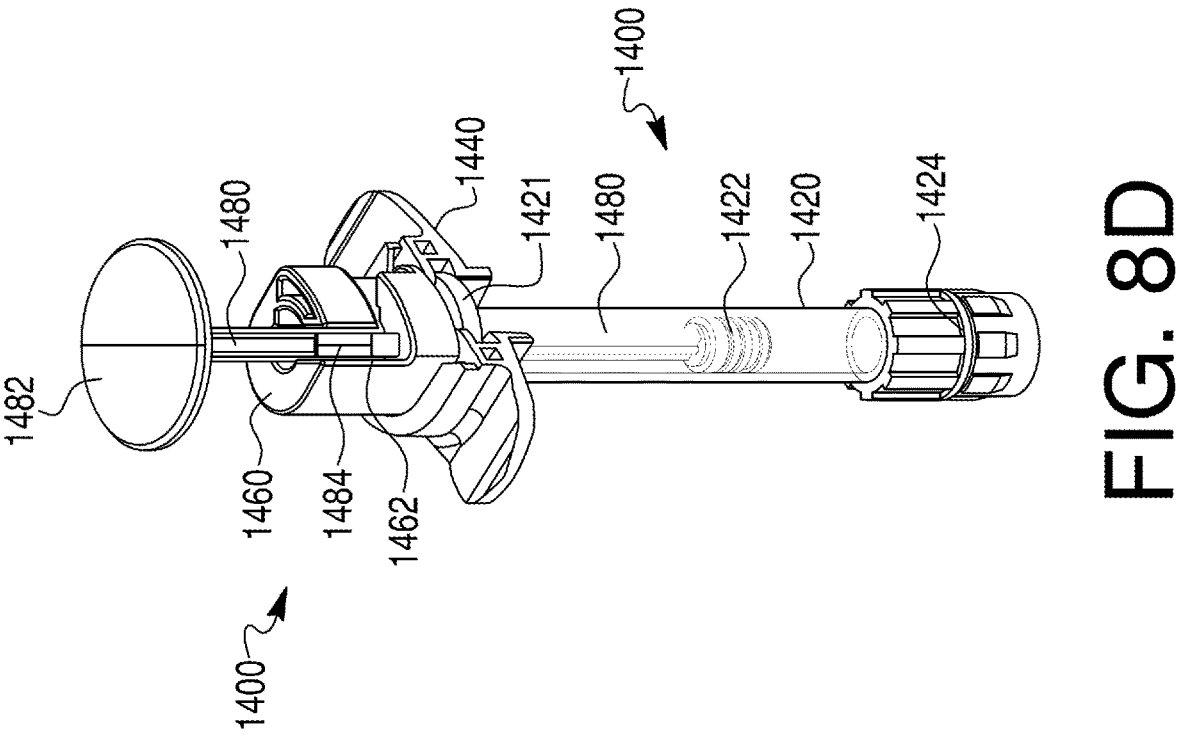
Figure 8F:
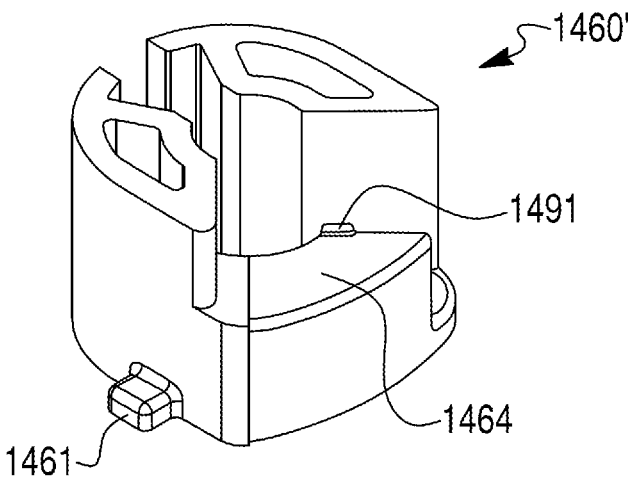
FIGS. 8F and 8G depict a blocking component of the delivery device depicted in FIGS. 8A-8E according to embodiments of the present disclosure.
Figure 8G:
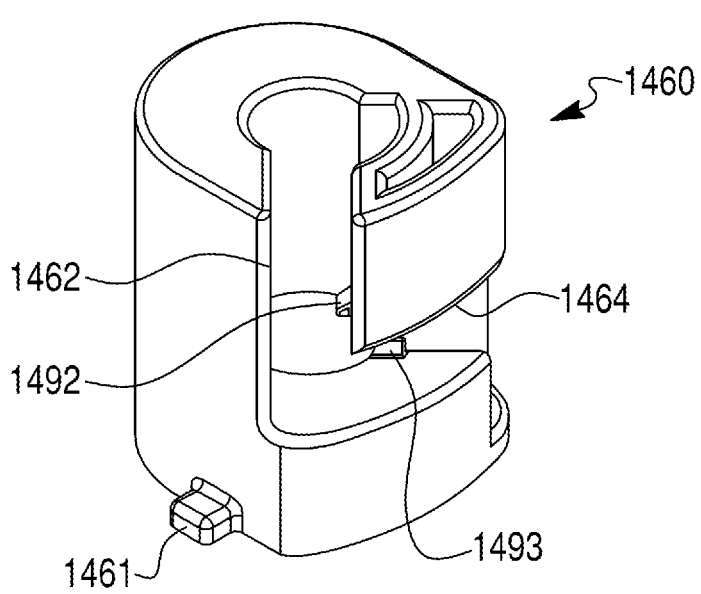

One or more of each channel 1462, 1464, 1468 may include one or more detents, as shown in FIGS. 8F and 8G. For example, a cross sectional view of blocking component 1460 in FIG. 8F shows an interior of channel 1464 having a small detent 1491 disposed on one side. FIG. 8G depicts two larger detents 1492, 1493 in channels 1462, 1464, respectively. Each detent may provide resistance to the movement of protrusion 1484 through channels 1462, 1464, and/or 1468 to provide auditory feedback and/or to prevent unintended movement of protrusion 1484. In some embodiments, detents 1491, 1492, 1493 may be angled on one side, to allow for passage of protrusions 1484 in one direction, but not in the other direction. Detents such as those shown in FIGS. 8F and 8G may be suitable for inclusion in any device disclosed herein, as well as in device 1400.

FIGS. 9A-9E depict an exemplary method of using device 1400, according to aspects of the present disclosure. In a pre-use configuration depicted in FIG. 9A, device 1400 may hold a volume of a drug substance in between stopper 1422 and expulsion end 1424. Plunger rod 1480 may be partially inserted into body 1420 such that protrusion 1484 of plunger rod 1480 is disposed in a proximal end portion of channel 1462. In a priming step depicted in FIG. 9B, plunger rod 1480 may be moved longitudinally further into body 1420, until distal movement is blocked by the abutment of protrusion 1484 against a distal end of channel 1462. For example, a user may press actuation portion 1482 distally through blocking component 1460. In some embodiments, device 1400 may be held in an inverted position during this step, to ensure that air trapped in body 1420 may be expelled, as stopper 1422 is pushed distally by plunger rod 1480. In the "primed" configuration, depicted in FIG. 9C, protrusion 1484 of plunger rod 1480 may be disposed at a first end of channel 1464.

Figure 9B:
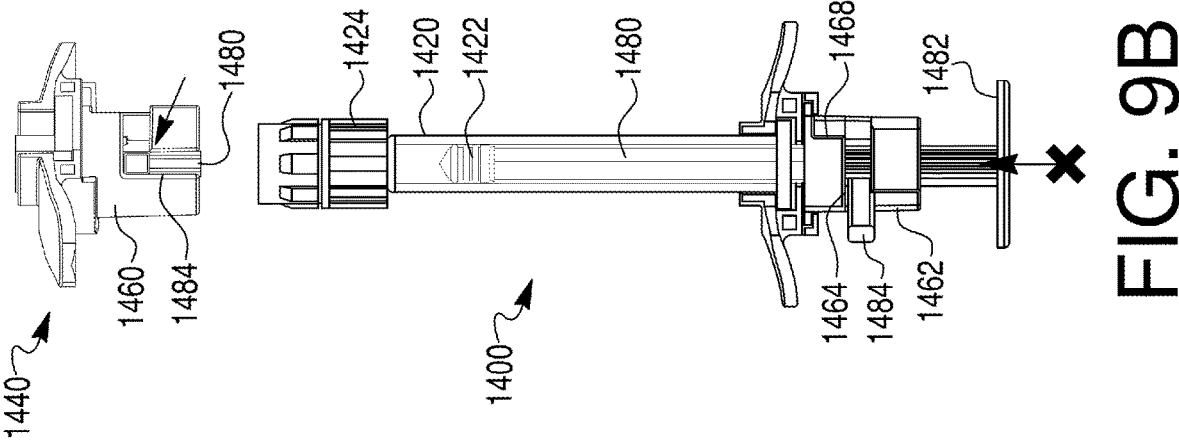
FIGS. 9A-9E depict an exemplary method of using the delivery device depicted in FIGS. 8A-8E, according to aspects of the present disclosure.
Figure 9A:
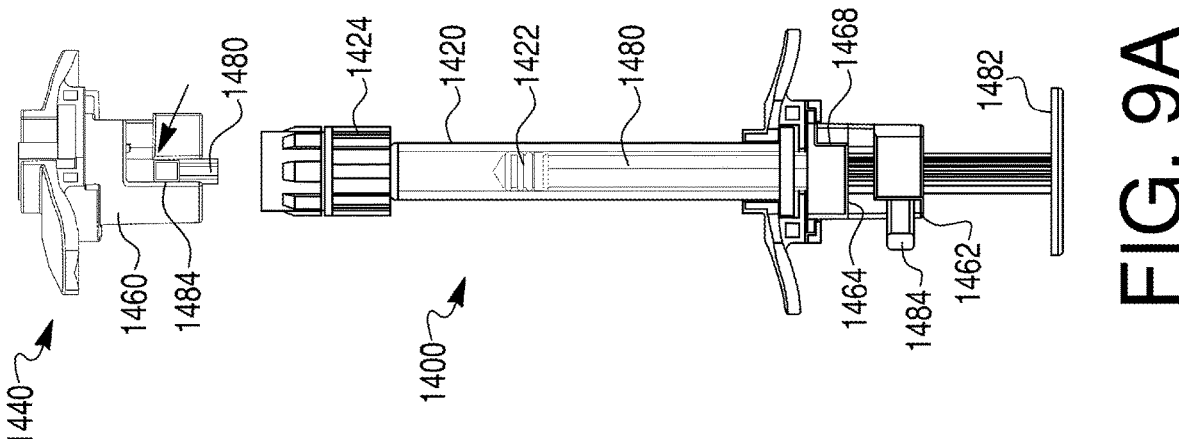
Figure 9E:
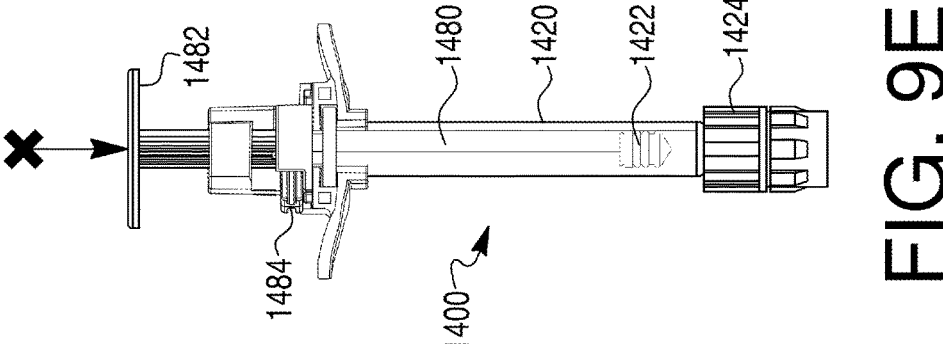
Figure 9D:
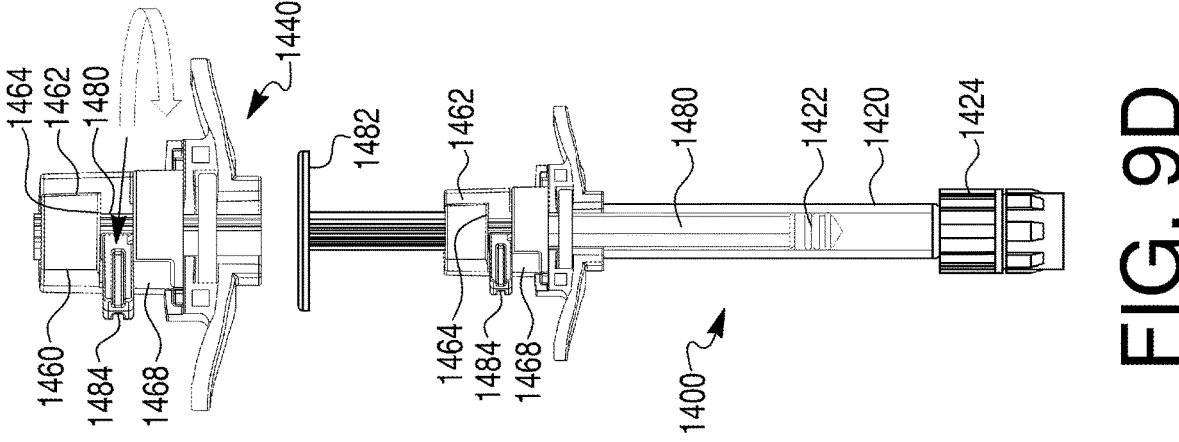
Figure 9C:
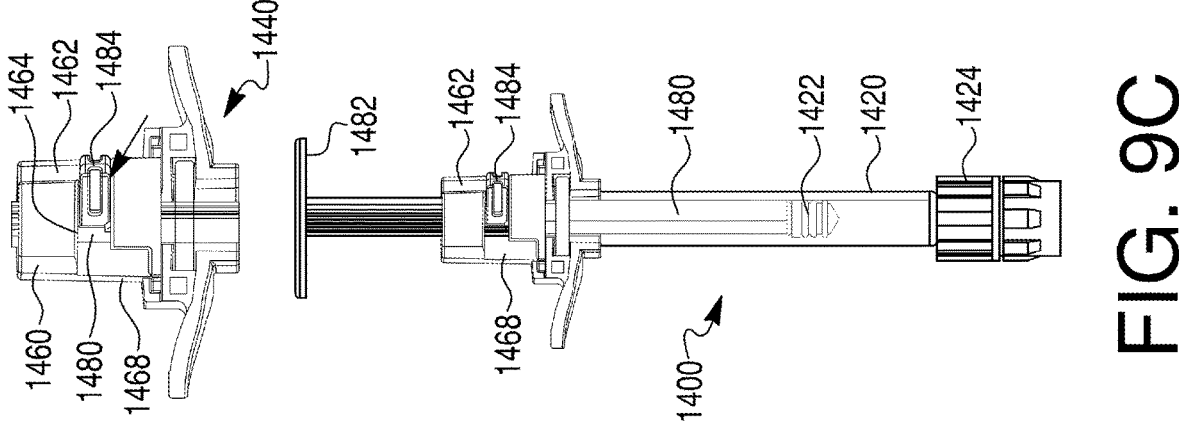

In a dispensing preparation step depicted in FIG. 9D, plunger rod 1480 may be rotated about a longitudinal axis such that protrusion 1484 is moved from a first end of channel 1464 to a second end of channel 1464. For example, a user may grasp and twist actuation portion 1482 of plunger rod 1480. Device 1400 may then be in a ready-to-dispense configuration, wherein protrusion 1484 is disposed at a proximal end of channel 1468. As depicted in FIG. 9E, in a dispensing step, plunger rod 1480 may be moved longitudinally further into body 1420. For example, a user may press actuation portion 1482 distally, until protrusion 1484 abuts a distal end of channel 1468. The dispensing step may ensure that a predetermined volume of a drug substance inside body 1420 is dispensed from device 1400.

In some embodiments, after each successive step in the use of device 1050, a user may be prevented from re-doing a step, and/or from reversing one or more steps. For example, geometries of, e.g., plunger rod 1480, protrusion 1484, and/or channels 1462, 1464, 1468 may prevent a user from pulling plunger rod 1480 proximally (e.g., out of) body 1420.

Figure 10A:
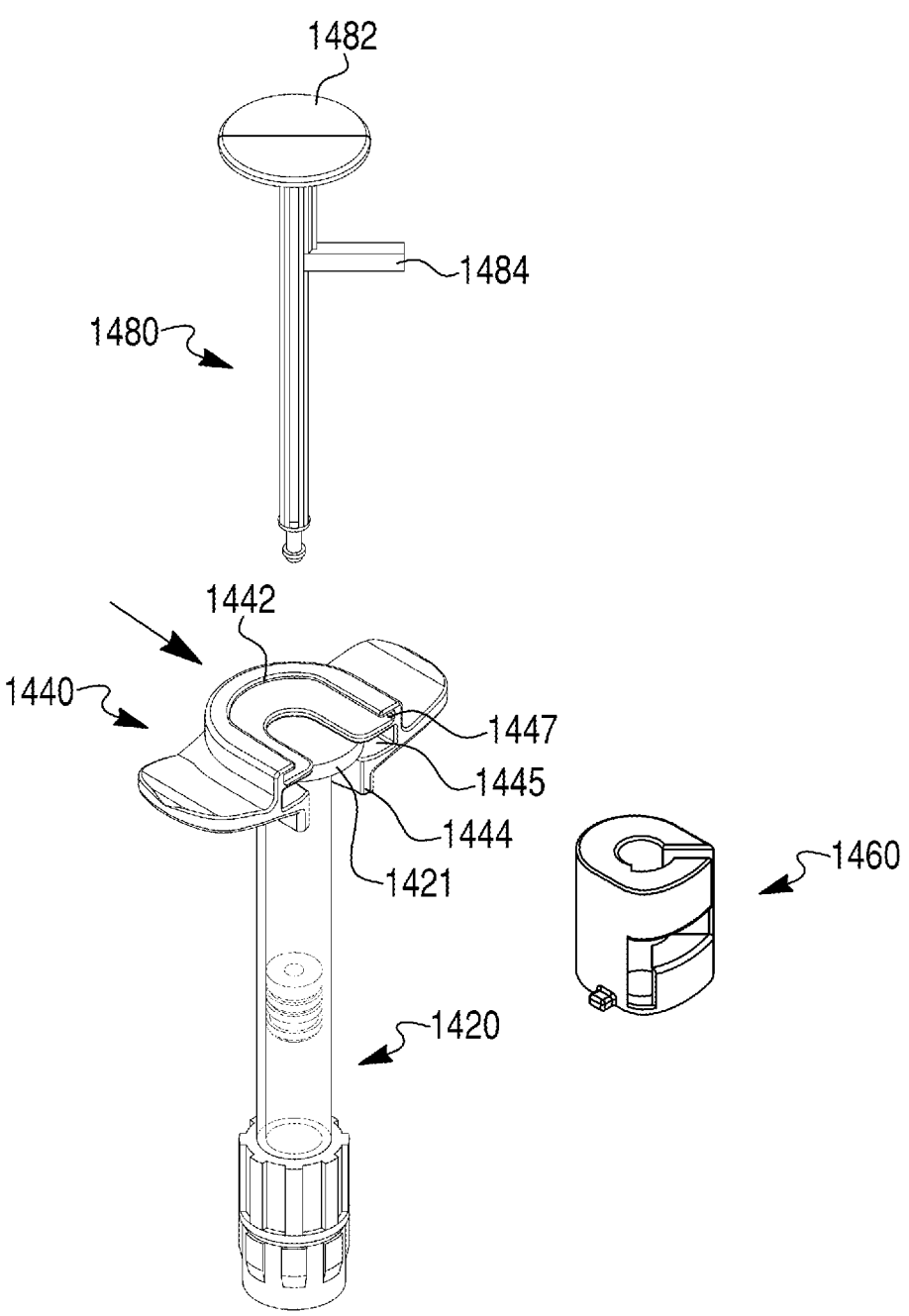
FIGS. 10A-10C depict an exemplary method of assembling the delivery device depicted in FIGS. 8A-8E, according to aspects of the present disclosure.
Figure 10B:
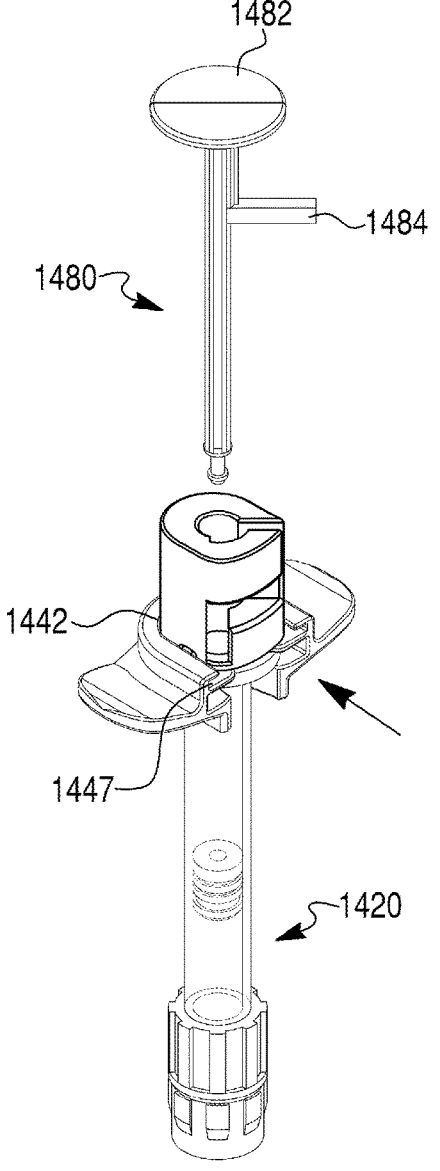
Figure 10C:
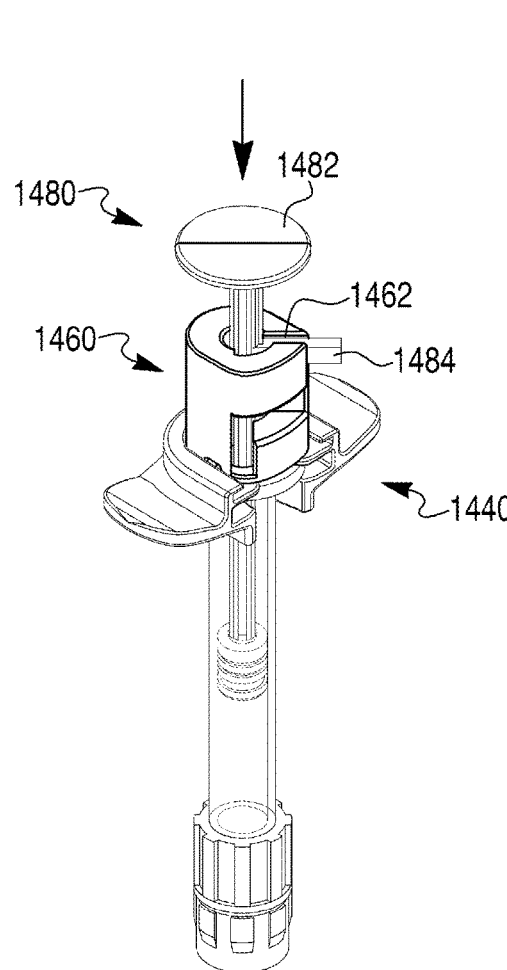

FIGS. 10A-10C depict an exemplary method of assembly of device 1400. As depicted in FIG. 10A, flange piece 1440 may be slidably assembled to body 1420 such that flange 1421 fits into channel 1445 and collar 1444 partially surrounds body 1420. As depicted in FIG. 10B, blocking component 1460 may be slidably assembled to flange piece 1440, such that tabs 1461 rest within channels 1447 and blocking component 1460 abuts proximal collar 1442. As depicted in FIG. 10C, plunger rod 1480 may then be inserted into the combined blocking component 1460, flange piece 1440, and body 1420, such that protrusion 1484 is disposed within channel 1462 of body 1460.

Figure 10E:
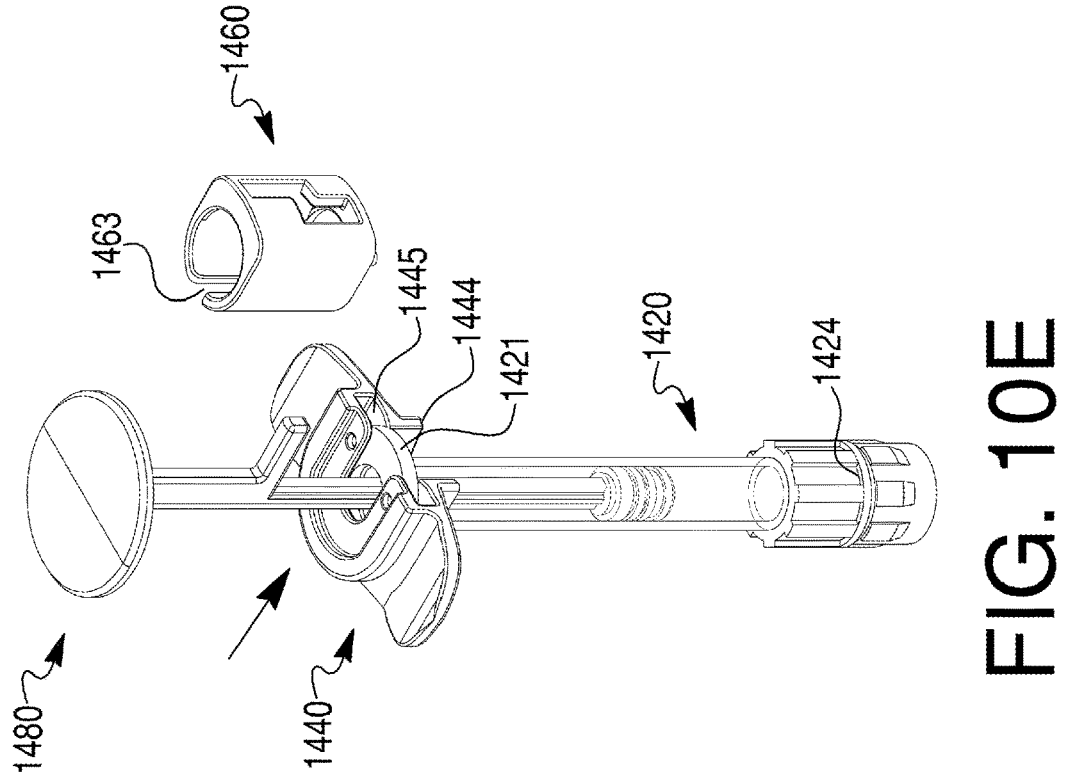
FIGS. 10D-10G depict another exemplary method of assembling a variation of the delivery device depicted in FIGS. 8A-8E, according to aspects of the present disclosure.
Figure 10D:
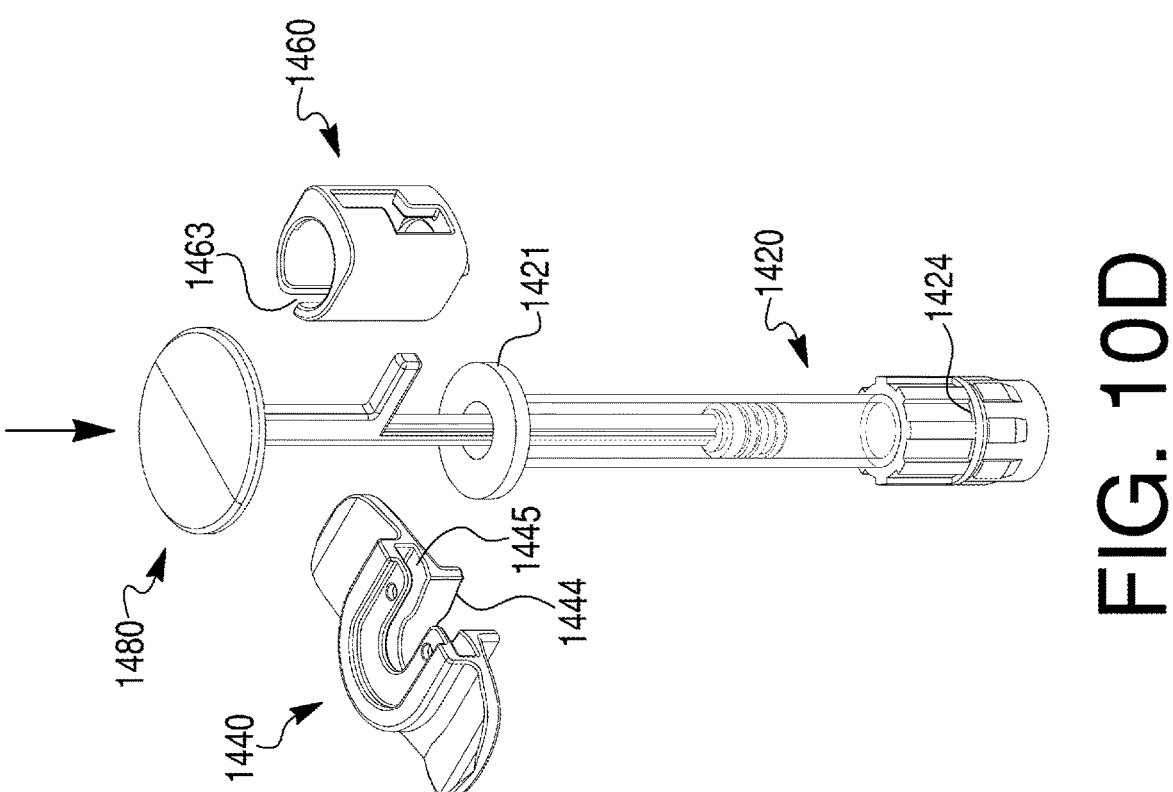
Figure 10G:
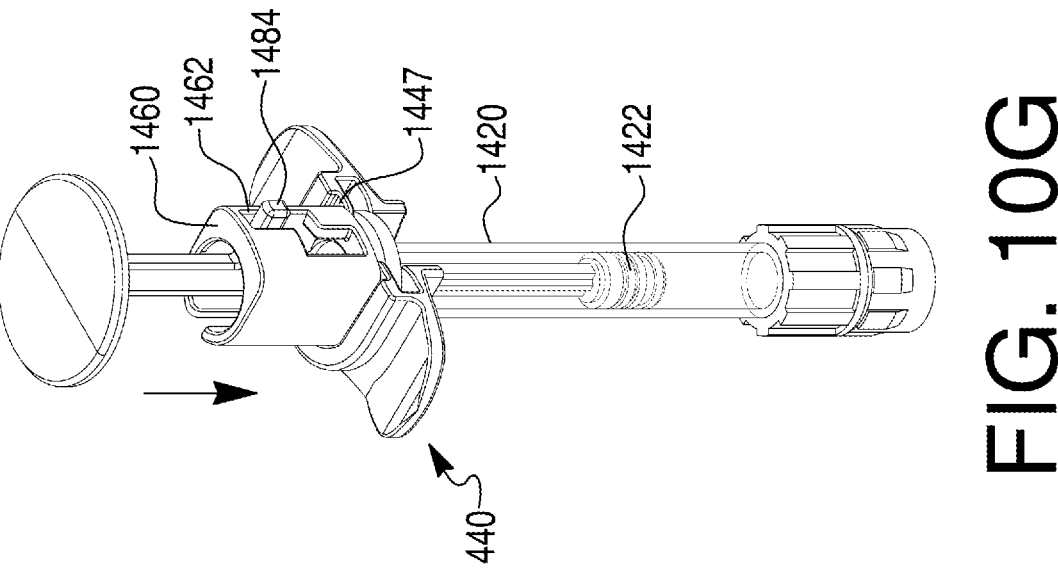
Figure 10F:
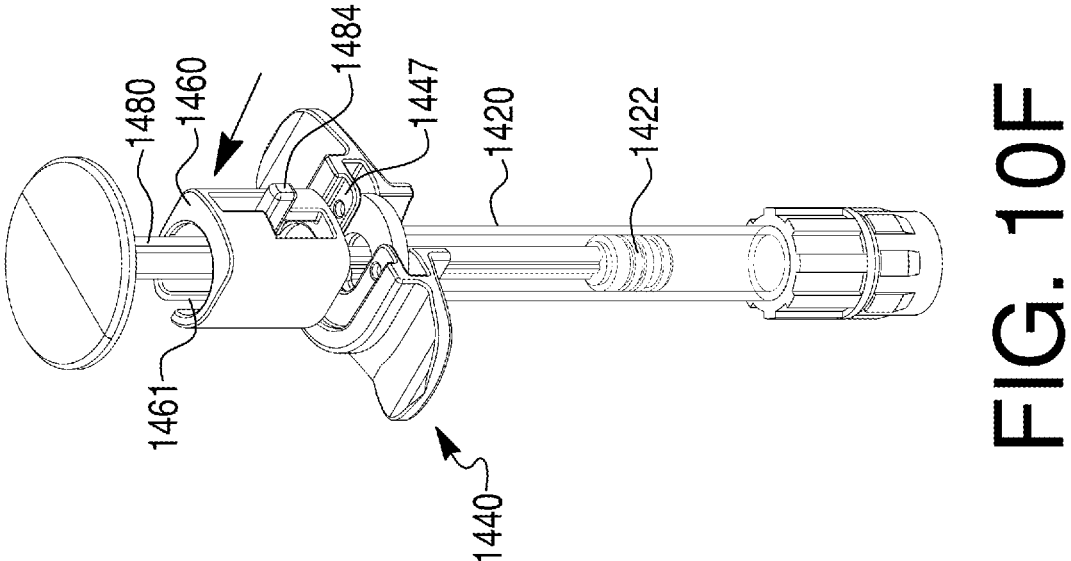
Figure 11C:
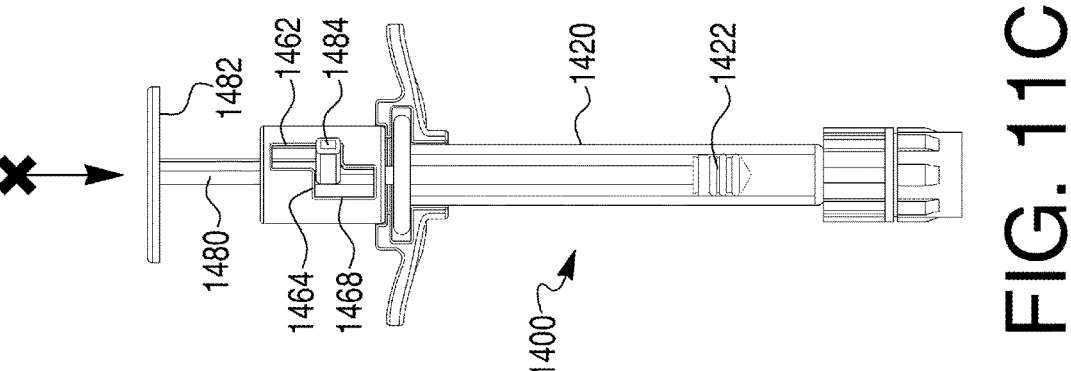
FIGS. 11A-11E depict an exemplary method of using the delivery device depicted in FIGS. 10D-10G according to aspects of the present disclosure.
Figure 11B:
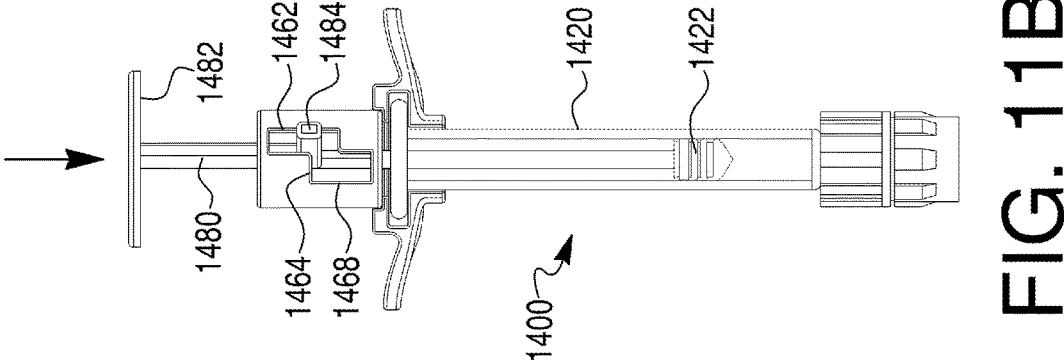
Figure 11A:
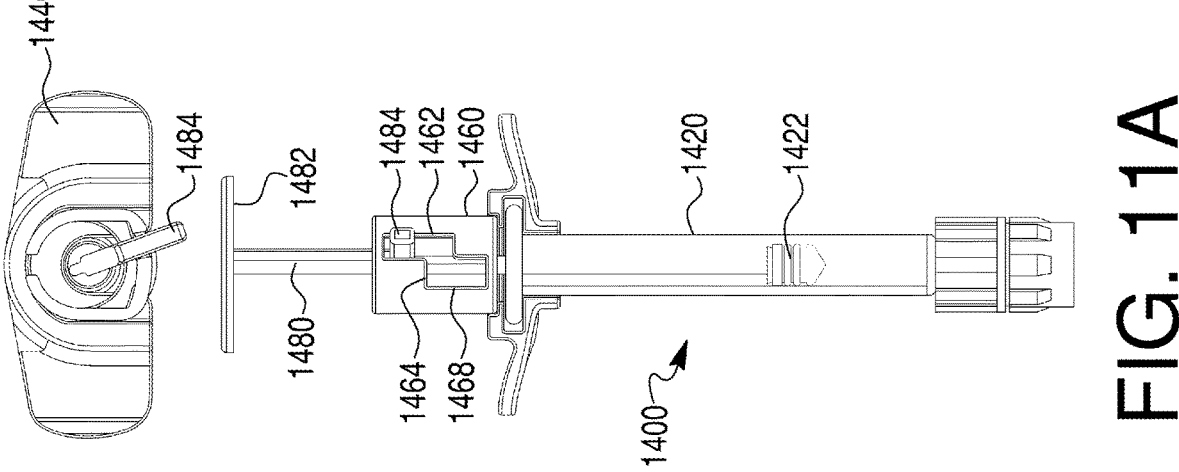
Figure 11E:
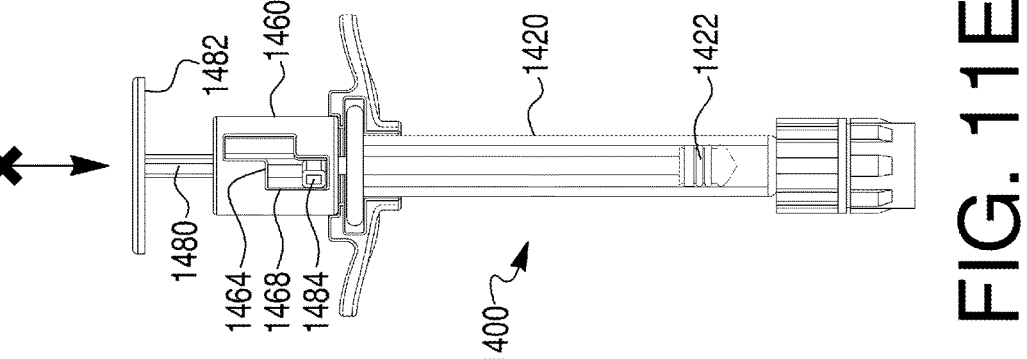
Figure 11D:
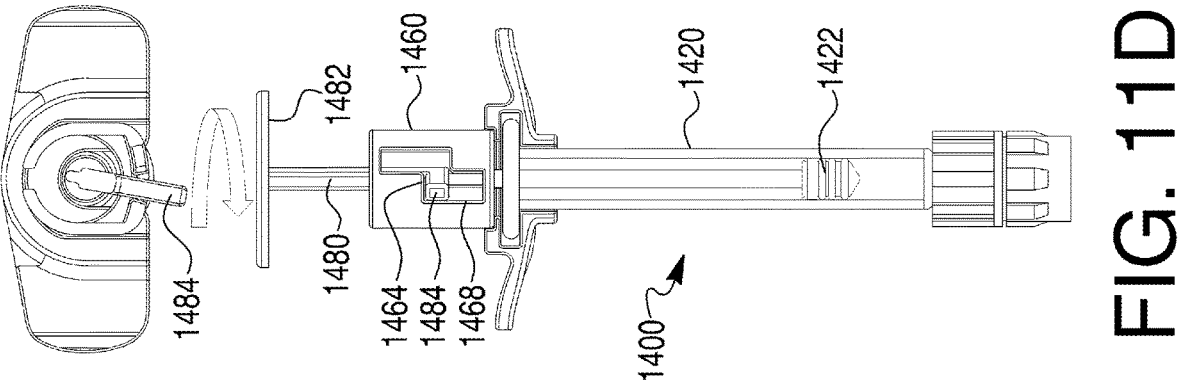
Figure 12A:
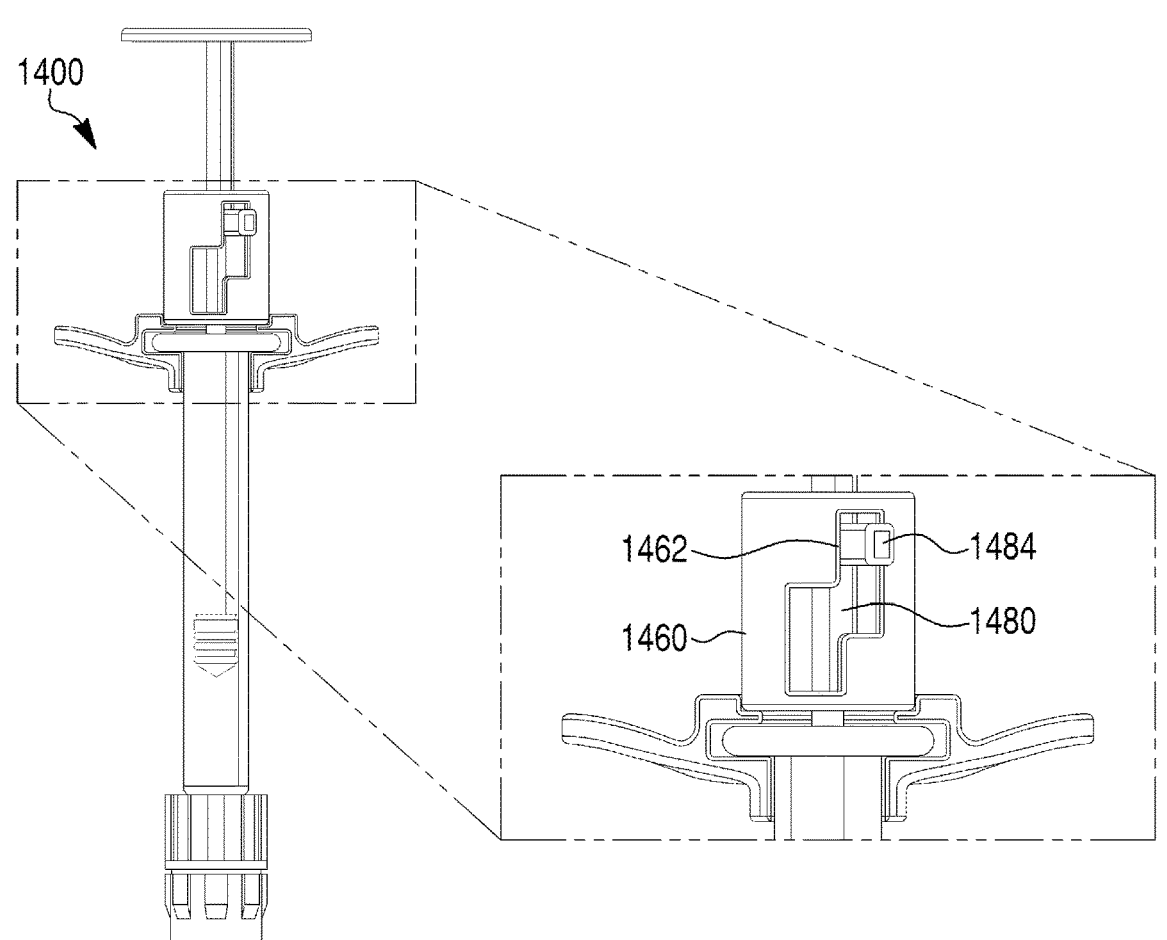
FIGS. 12A-12D depict a close-up view of aspects of the exemplary method depicted in FIGS. 11A-11E.
Figure 12B:
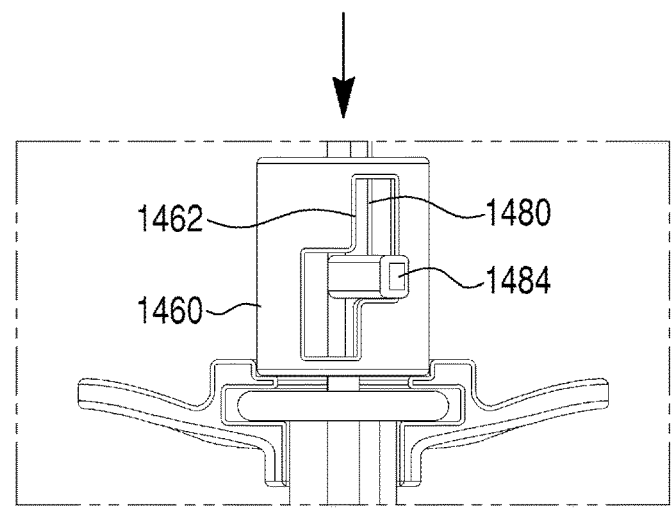
Figure 12C:
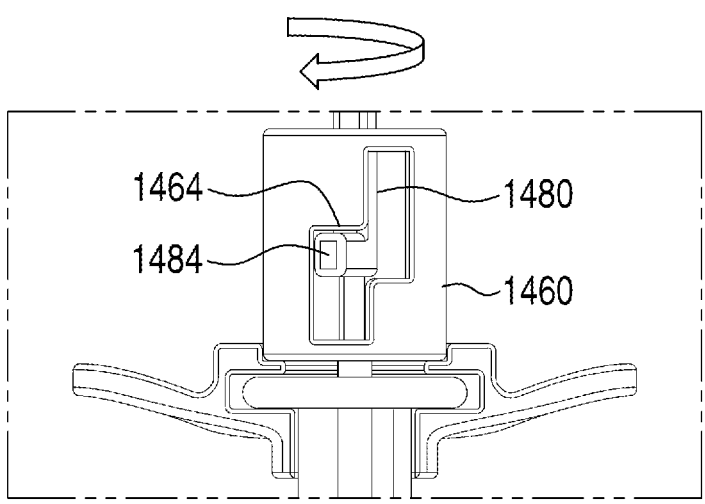
Figure 12D:
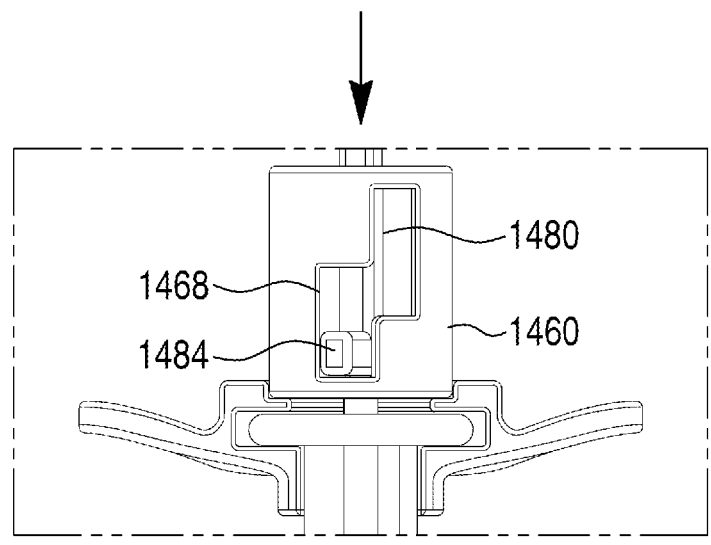

FIGS. 10D-10G, 11A-11E, and 12A-12D depict a variation on a configuration and method of use of device 1400, and to avoid redundancy will not be described in great detail. FIGS. 10D-10G depict an alternate method of assembly of device 1400, where blocking component 1460 includes an opening 1463 through which plunger rod 1480 may fit. In this embodiment, the channels within blocking component 1460 (e.g., channels 1462, 1468) may be closed on a proximal and distal end, to prevent back-out or over-insertion of plunger rod 1480 relative to body 1420. As depicted in FIG. 10E, plunger rod 1480 may be partially inserted into body 1420, and flange piece 1440 may be slidably assembled to body 1420 such that flange 1421 fits into channel 1445 and collar 1444 partially surrounds body 1420. As depicted in FIG. 10F, blocking component 1460 may be assembled to plunger rod 1480, such that protrusion 1484 is disposed within one of the channels in blocking component 1460. As depicted in FIG. 10G, blocking component 1460 may then be assembled to flange piece 1440 such that it is disposed in channel 1447. Blocking component may be affixed to flange piece 1440 in any suitable manner (e.g., using clips, adhesive, a friction fit, a dovetail connection, etc.). FIGS. 12A-12D depict a close-up view of protrusion 1484 moving through the channels of blocking component 1460, per the method of use shown in FIGS. 11A-11E.

Figure 13B:
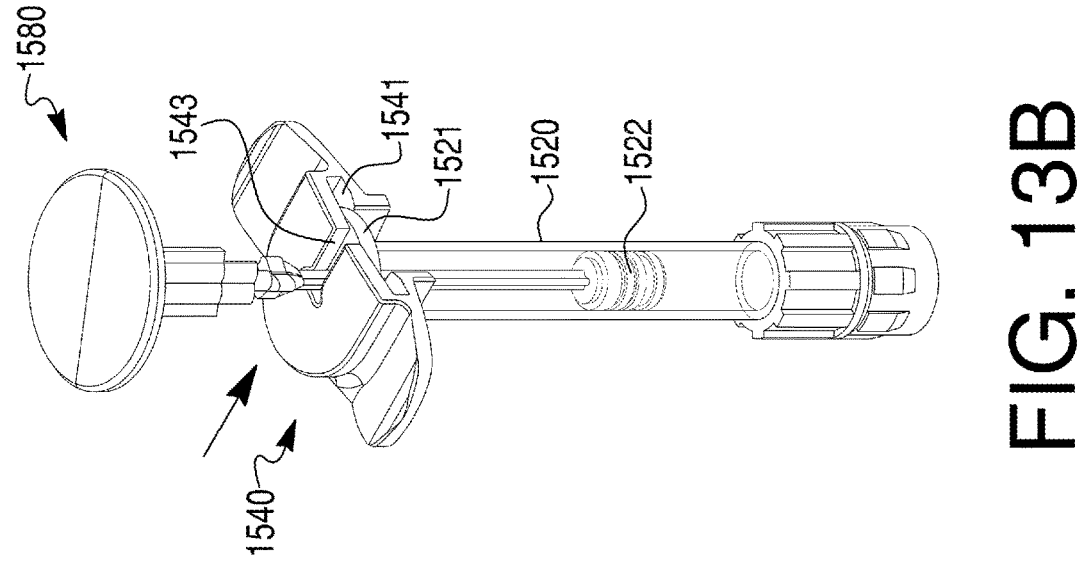
FIGS. 13A and 13B depict a further exemplary delivery device and method of assembling said delivery device, according to additional embodiments of the present disclosure.
Figure 13A:
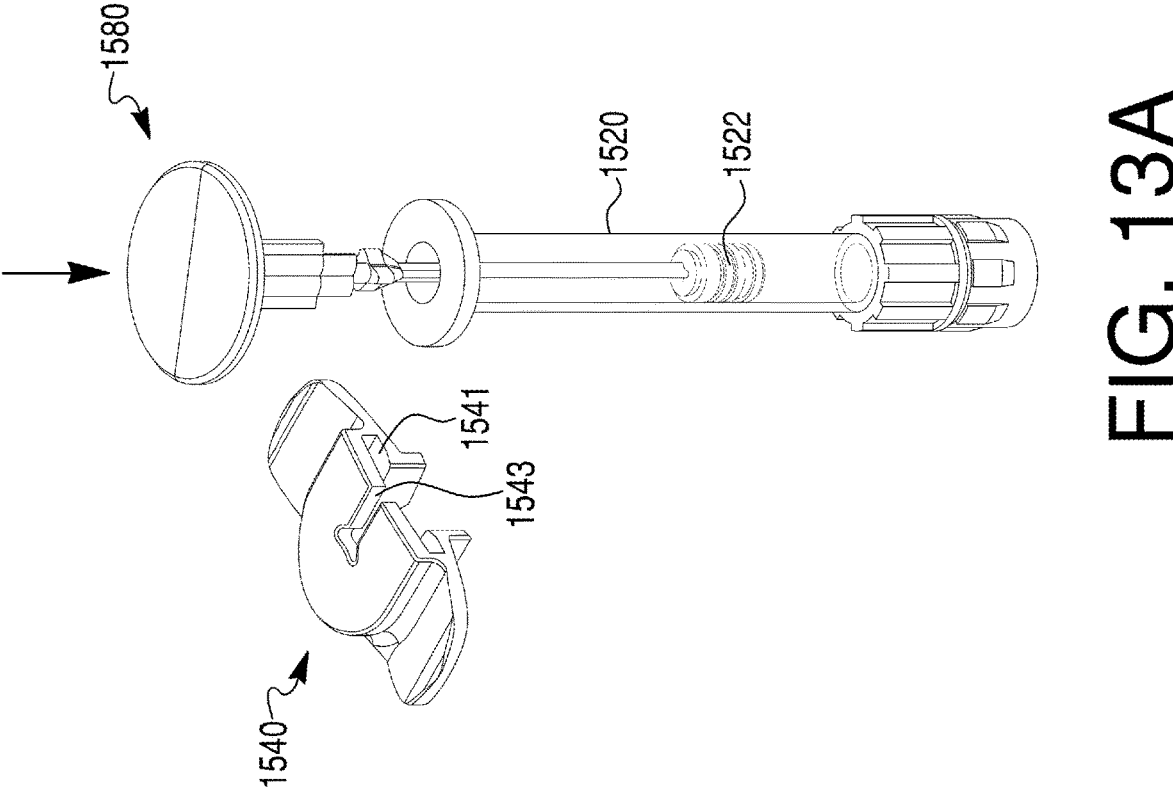

FIGS. 13A and 13B depict a further exemplary delivery device 1500, and a method of assembling said delivery device, according to additional embodiments of the present disclosure. Device 1500 includes a plunger rod 1580, a blocking component in the form of flange piece 1540, and a body 1520. To assemble device 1500, plunger rod may be inserted into body 1520 (e.g., as shown in FIG. 13A), such that it abuts or attaches to a stopper 1522 in body 1520, and flange piece 1540 may be slidably assembled to 1521, e.g., by sliding a channel 1541 on to a flange 1521 of body 1520 (e.g., as shown in FIG. 13B). An opening 1543 may allow for flange piece 1540 to be assembled to body 1520 around plunger rod 1580. It is contemplated that, depending on the size, shape, and structure of each component of device 1500, alternate methods of assembly are possible.

Delivery device 1500 may be, for example, an injection device, such as a syringe, for dispensing a predetermined volume of a formulated drug substance. Generally, delivery device 1500 may share size, capacity, material, preparation, assembly, or manufacturing characteristics with device 1050, device 1200, device 1300, or with other delivery devices disclosed herein. As with other devices disclosed herein, delivery device 1500 may be configured for ease of use and may include one or more features that aid a user by providing tactile, auditory, or visual feedback, using any of the features described elsewhere herein.

Figures 14A, 14B, 14C:
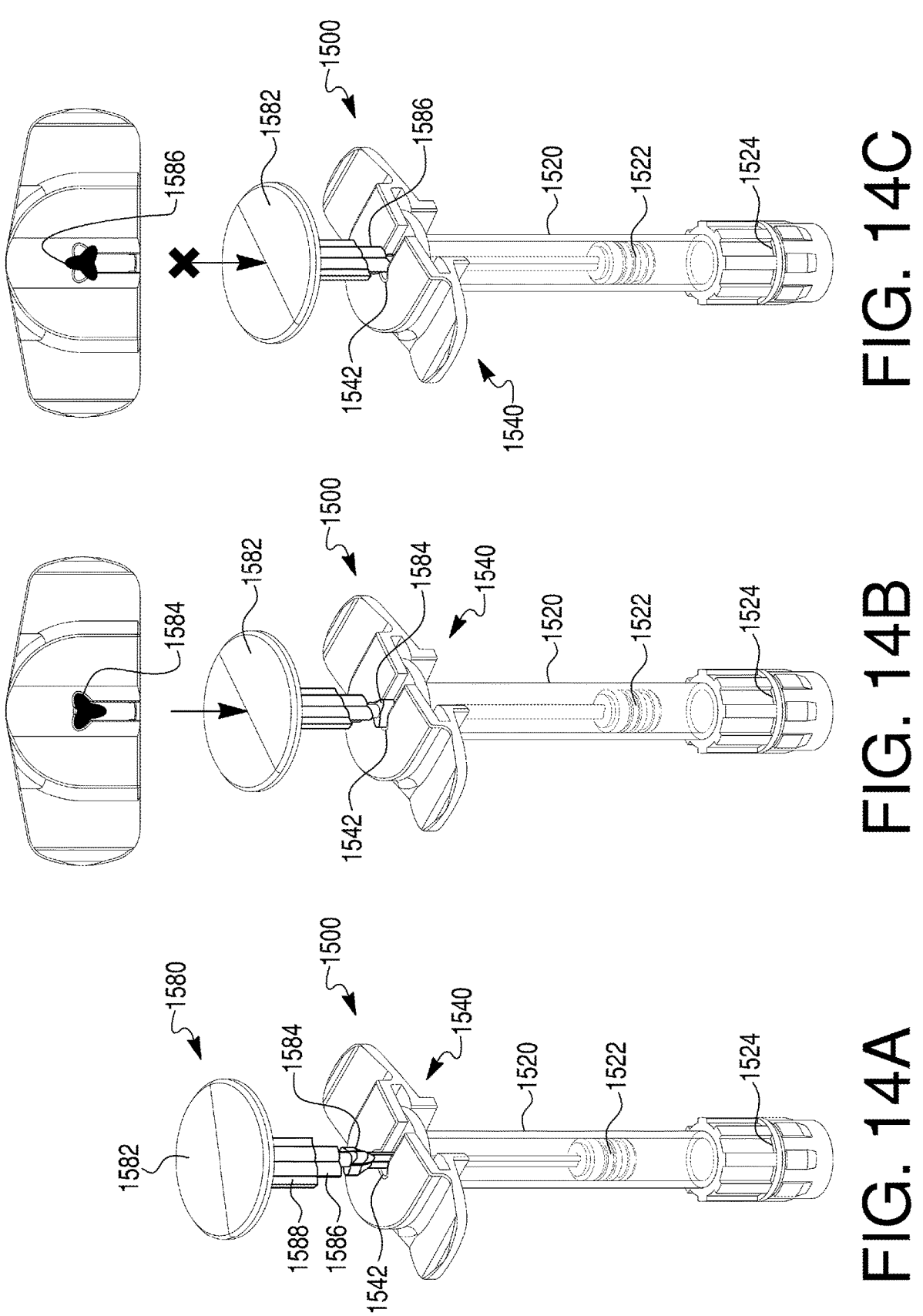
FIG. 14A-14F depict a method of using the delivery device depicted in FIGS. 12A and 12B.

FIG. 14A-14F depict a further view of device 1500 and a method of using device 1500. As shown in FIG. 14A, plunger rod 1580 may include an actuation portion 1582, a proximal stop 1588, a proximal neck portion 1586, and a distal neck portion 1584. Body 1520 may have any or all of the same characteristics as, e.g., body 1060 of device 1050, or as any syringe body known in the art. For example, in some embodiments, body 1520 may be pre-fillable or pre-filled. Stopper 1522 may be configured to be inserted into body 1520 and may be configured to hold a predetermined volume of a formulated drug substance inside body 1520, between stopper 1522 and an expulsion end 1524.

Flange piece 1540 may be of any suitable size and shape to partially close, cover, or partially cover an end of body 1520 opposite expulsion end 1524, and/or to support and hold plunger rod 1580 in body 1520. An opening 1542 may have a size and shape configured to allow passage of plunger rod 1580 in two different configurations. Distal neck portion 1584 and proximal neck portion 1586 may have similar shapes, but may be rotationally offset from one another (e.g., such that once distal neck portion 1584 passes through opening 1542, plunger rod 1580 must be rotated about a longitudinal axis to allow proximal neck portion 1587 to pass. Distal neck portion 1584 may include, e.g., a tapered distal side, which may assist in orienting plunger rod 1580 such that distal neck portion 1584 may pass through opening 1542. This may increase the ease of, e.g., a priming step.

FIG. 14A depicts a pre-use configuration of device 1500. In such a configuration, device 1500 may hold a volume of a drug substance in between stopper 1522 and expulsion end 1524. Plunger rod 1580 may be partially inserted into body 1520 such that distal neck portion 1584 is positioned proximally from flange piece 1540. In a priming step depicted in FIG. 14B, plunger rod 1580 may be moved longitudinally further into body 1520, until distal movement is blocked by the abutment of proximal neck portion 1586 against opening 1542 (as shown in FIG. 14C). For example, a user may press actuation portion 1582 until distal neck portion passes through opening 1542. In some embodiments, device 1500 may be held in an inverted position during this step, to ensure that air trapped in body 1520 may be expelled, as stopper 1522 is pushed distally by plunger rod 1580. In the "primed" state, depicted in FIG. 14D, proximal neck portion 1586 may be disposed against a surface of flange piece 1540.

Figures 14D, 14E, 14F:
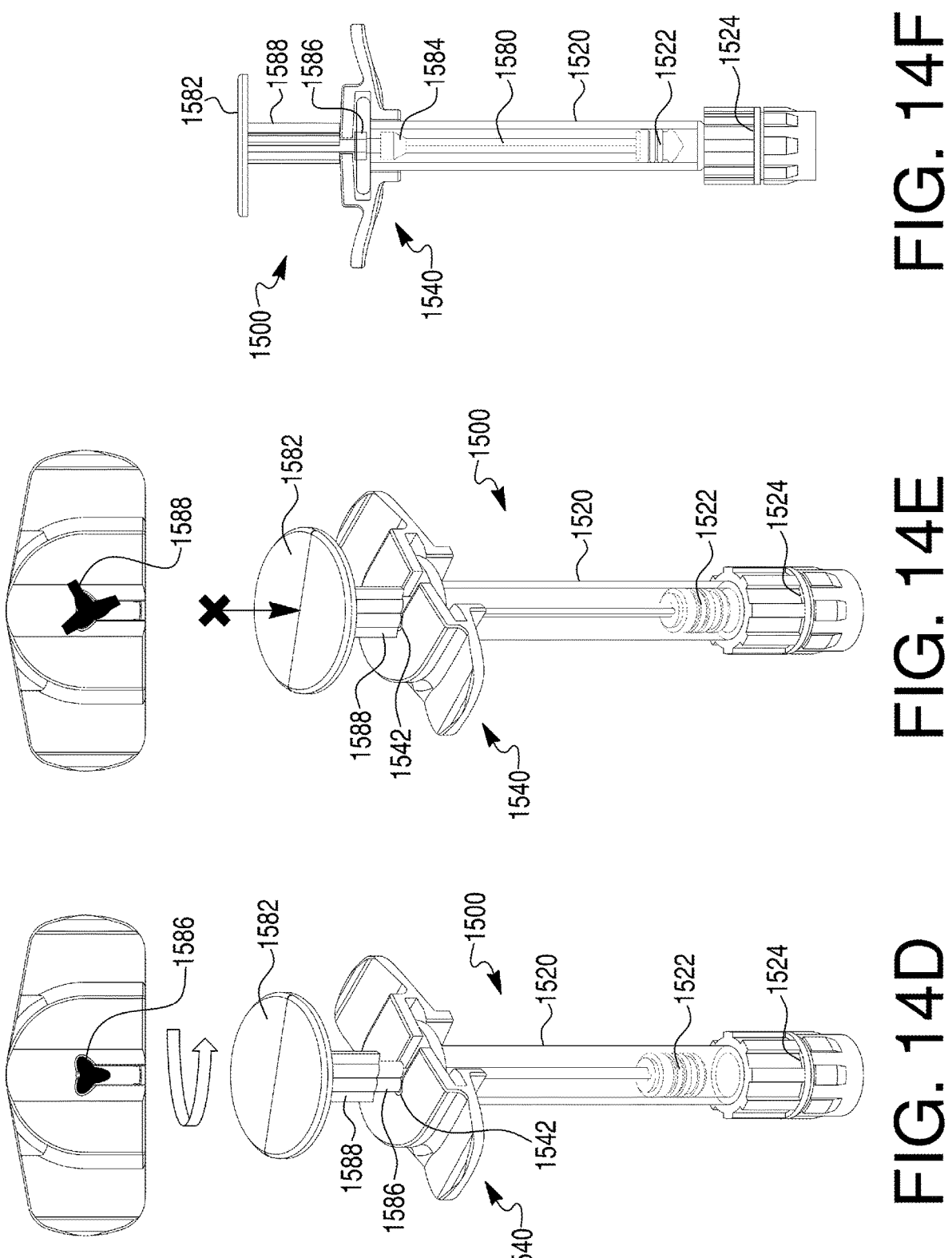
Figure 16B:
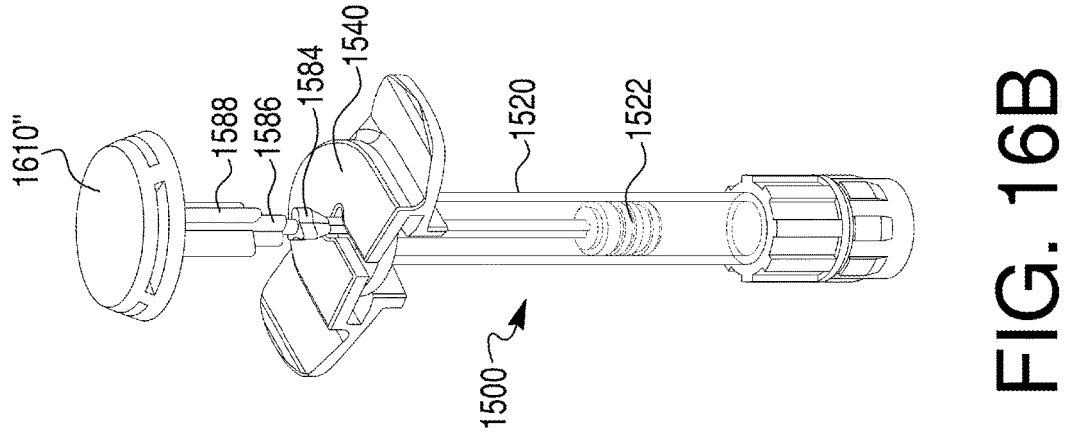
FIGS. 15A-15B, and 16A-16B depict exemplary plunger rod dials according to further embodiments of the present disclosure.

In a dispensing preparation step depicted in FIG. 14D, plunger rod 1580 may be rotated about a longitudinal axis such that the shape of proximal neck portion 1586 aligns with opening 1542. For example, a user may grasp and twist actuation portion 1582 of plunger rod 1580. Device 1500 may then be in a ready-to-dispense configuration. As depicted in FIG. 14E, in a dispensing step, plunger rod 1580 may be moved longitudinally further into body 1520. For example, a user may press actuation portion 1582 distally, until proximal stop 1588 abuts a surface of flange piece 1540. The dispensing step may ensure that a predetermined volume of a drug substance inside body 1520 is dispensed from device 1500.

In some embodiments, after each successive step in the use of device 1500, a user may be prevented from re-doing a step, and/or from reversing one or more steps. For example, geometries of, e.g., plunger rod 1580, distal neck portion 1584, proximal neck portion 1586, and opening 1542 may interface with one another to prevent a user from pulling plunger rod 1580 proximally (e.g., out of) body 1520.

Additional variations on blocking components, dosage control components, and the like will now be described.

Figure 15B:
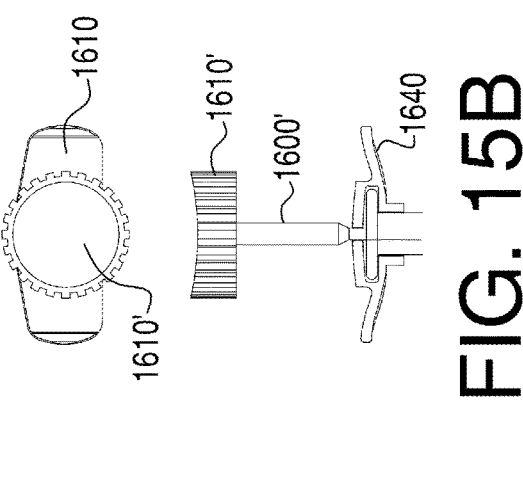
Figure 15A:
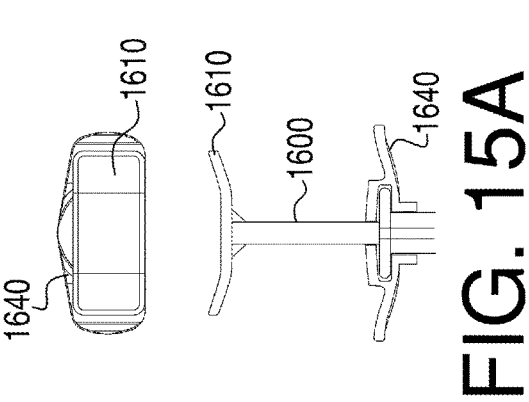
Figure 16A:
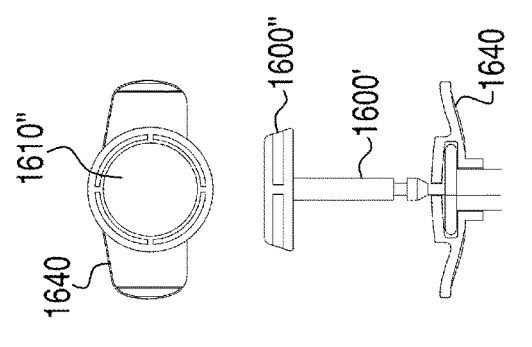

FIGS. 15A-23C depict exemplary plunger rod dials according to further embodiments of the present disclosure. For example, FIG. 15A depicts a plunger rod 1600 having an actuation portion 1610. Actuation portion 1610 may have a shape generally corresponding to a flange piece 1640. Plunger rod 1600 may be rotatable with respect to flange piece 1640 and/or a body of the device. A device may be in a configuration suitable for delivery of a desired amount of a drug substance when, e.g., a shape of plunger rod 1610 is generally aligned with shape of 1640 (as shown in, e.g., the top view of FIG. 15A). As another example, FIG. 15B depicts an actuation portion 1610' with a ridged side, to allow for ease of rotation of plunger rod 1600' with respect to flange piece 1640 and/or a remainder of the syringe. FIG. 16A depicts an actuation portion 1610'' with a ribbed side, again to allow for ease of rotation of plunger rod 1600. FIG. 16B depicts an exemplary combination of actuation portion 1610'' with device 1500. One of ordinary skill in the art will understand that any of the actuation portions or other features described herein may be combined with devices described herein.

Figure 18B:
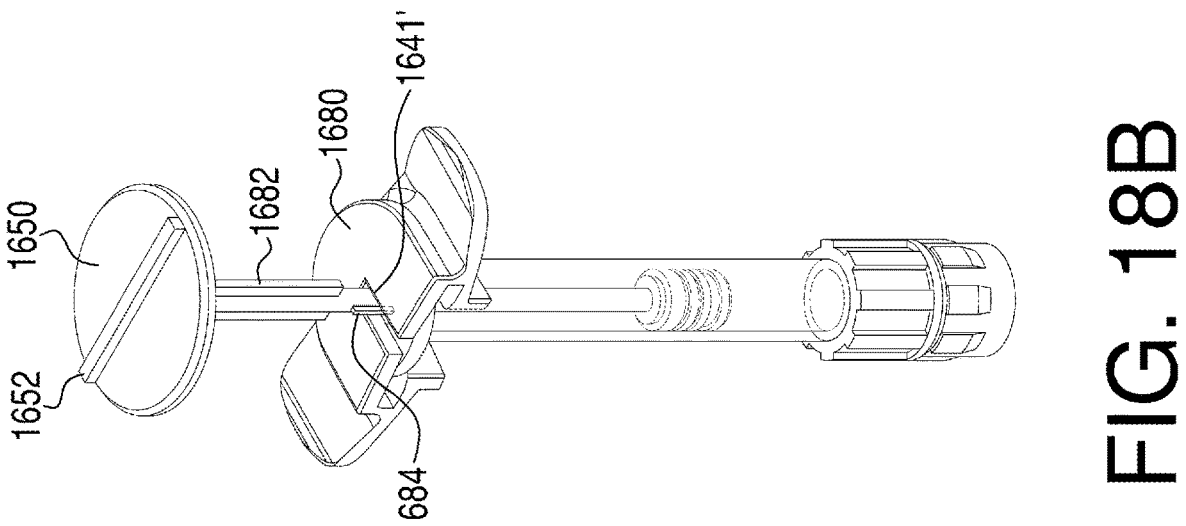
FIGS. 18A and 18B depict a further exemplary plunger rod and dial according to additional embodiments of the present disclosure.
Figure 18A:
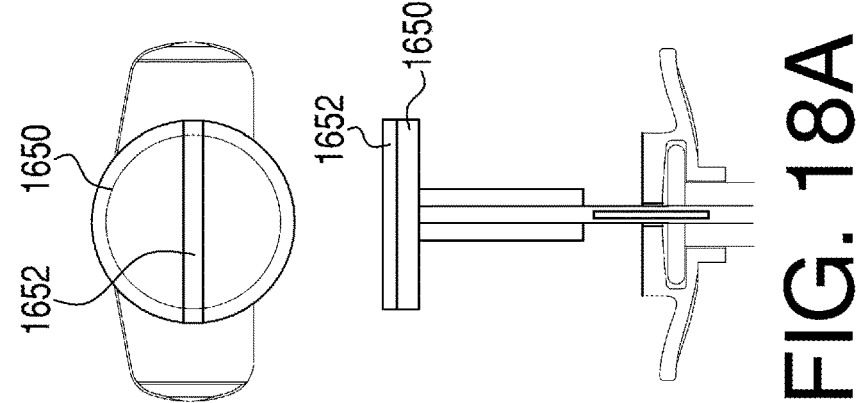
Figure 17:
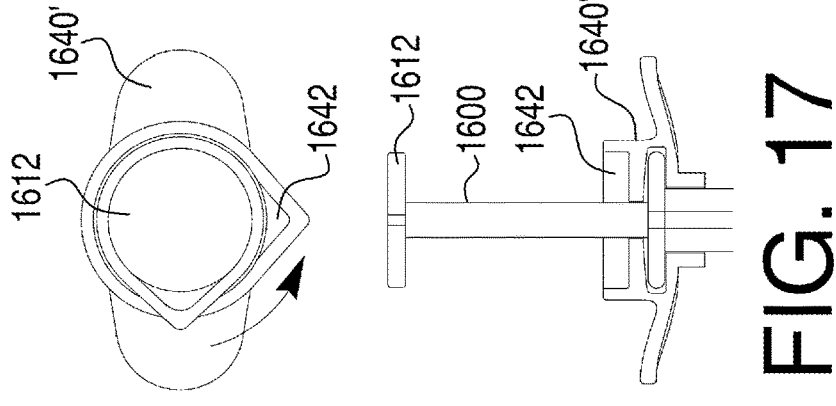
FIG. 17 depicts an exemplary plunger rod and dial according to further embodiments of the present disclosure.

FIG. 17 depicts an exemplary plunger rod and dial according to further embodiments of the present disclosure. An actuation portion 1612 may be sized and configured to fit into a collar 1642 of a flange piece 1640' in only a particular configuration. A depth of collar 1642 may correspond to, e.g., a distance that plunger rod 1600 must travel to dispense a predetermined volume of a drug substance from a drug delivery device. In one embodiment, actuation portion 1612 may be moved distally until it abuts collar 1642, and then may be rotated until its shape corresponds with the shape of collar 1642 so that it may be pushed into collar 1642 in a dispensing step. FIGS. 18A and 18B depict a further exemplary plunger rod and dial, which combine exemplary features that allow for precision dose delivery. The plunger rod may include, e.g., protrusions 1684 and 1682, which may each fit through an opening 1641' in a flange piece 1680 in a particular configuration. Each of protrusions 1682 and 1684 may correspond to a distance required to deliver a desired volume of a drug substance from a device and/or prime the device. Actuation portion 1650 may include a raised portion 1652, which may aid a user in twisting the plunger rod in relation to flange piece 1680.

Figure 19A:
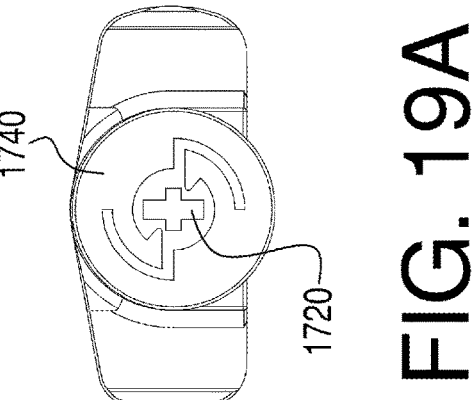
FIGS. 19A and 19B depict an exemplary rotation lock mechanism according to additional embodiments of the present disclosure.
Figure 19B:
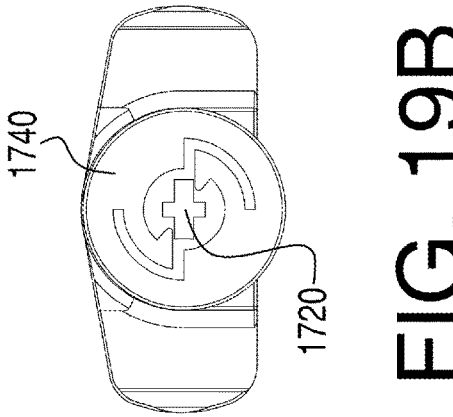

FIGS. 19A and 19B depict a top view of a flange piece 1740 and a plunger rod 1720. Flange piece 1740 and plunger rod 1720 may have a cross-sectional shape allowing for limited rotation of plunger rod 1720 relative to flange piece 1740 in a single direction. For example, flange piece 1740 may have inner protrusions that may interact with an irregular cross-sectional shape of plunger rod 1720 to resist a first portion of plunger rod 1720 as it rotates past the inner protrusions, and to stop a second portion of plunger rod 1720 when it abuts the inner protrusions.

Figure 20:
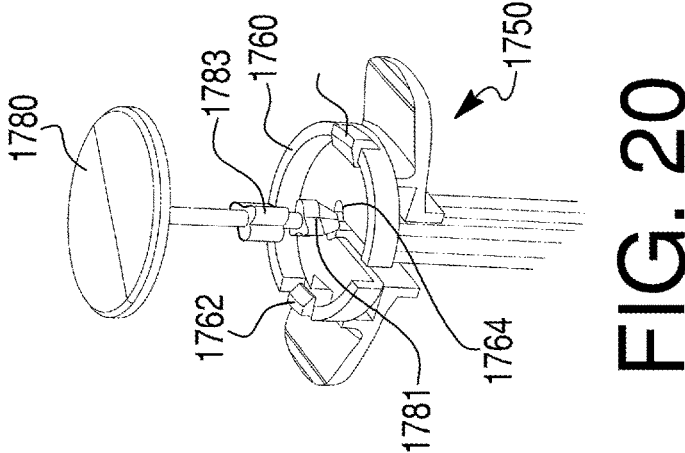
FIG. 20 depicts an exemplary plunger rod snap feature according to additional embodiments of the present disclosure.

FIG. 20 depicts an exemplary flange piece 1750 with a well 1760 having clips 1762. A plunger rod actuation portion 1780 may be pushed distally into well 1760 until clips 1762 overlay actuation portion 1780, to hold actuation portion 1780 in place and, e.g., prevent back-out of the plunger rod. The plunger rod includes a distal protrusion 1781 and a proximal protrusion 1783, each of which is sized to fit through an opening 1764 when the plunger rod is rotated to a particular position. Distal protrusion 1781 includes a tapered distal side, which may assist in orienting the plunger rod into the position required to advance the plunger rod distally such that distal protrusion 1781 passes through opening 1764. This may increase the ease of, e.g., a priming step. In some embodiments, a height of well 1760 and/or actuation portion 1780 may correspond to a height that a plunger rod must travel to dispense a predetermined volume of a drug substance. Thus, a device may be primed when actuation portion 1780 abuts a proximal side of well 1760, and may deliver a predetermined volume of a drug substance as actuation portion 1780 travels distally into well 1760.

Figure 21:
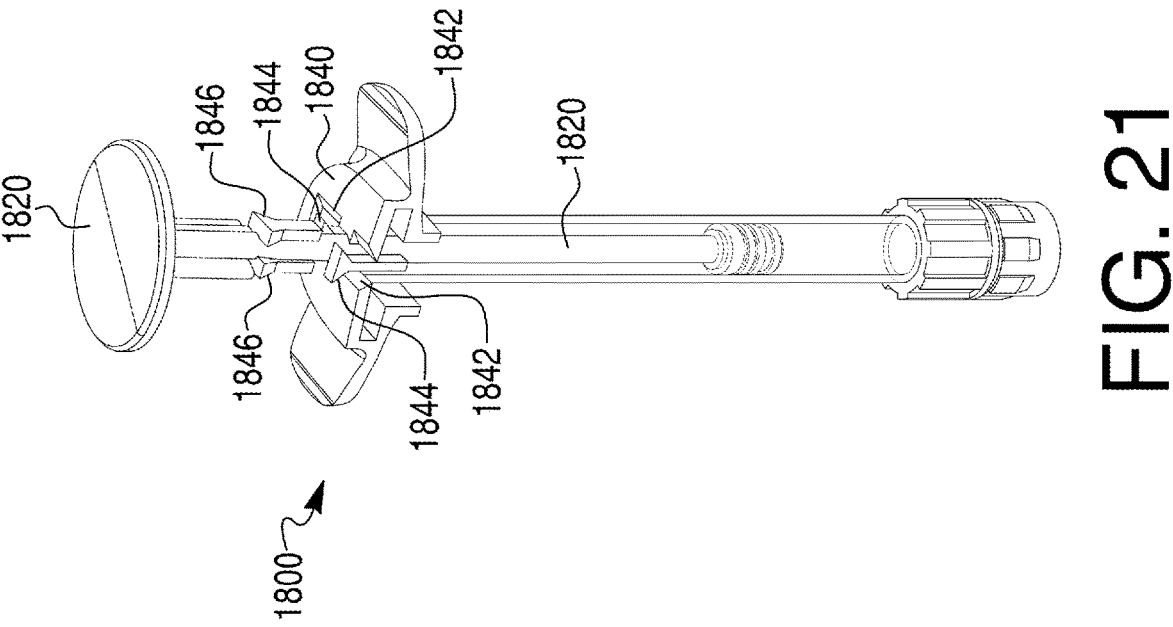
FIG. 21 depicts an exemplary plunger rod with a bump feature according to additional embodiments of the present disclosure.

FIG. 21 depicts an exemplary device 1800 with a plunger rod 1820 and a complementary flange piece 1840. Plunger rod 1820 may include, e.g., protrusions 1844, 1846 having an angled or wedge shape, corresponding to a shape of one or more openings 1842 in flange piece 1840. The wedge or angled shapes of protrusions 1844, 1846 and openings 1842 may suffice to resist distal movement of plunger rod 1820 when a protrusion 1844 or 1846 abuts a side of opening 1842, but may be able to move past one another given enough force. The resistance provided by the abutment of protrusions 1844, 1846 against the sides of openings 1842 may suffice to indicate to a user that a particular step in the use of device 1800 is completed. A user may then apply enough force to move plunger rod 1820 past the resistance and continue to a next step (e.g., from a completed priming step to a delivery-ready step).

Figure 22:
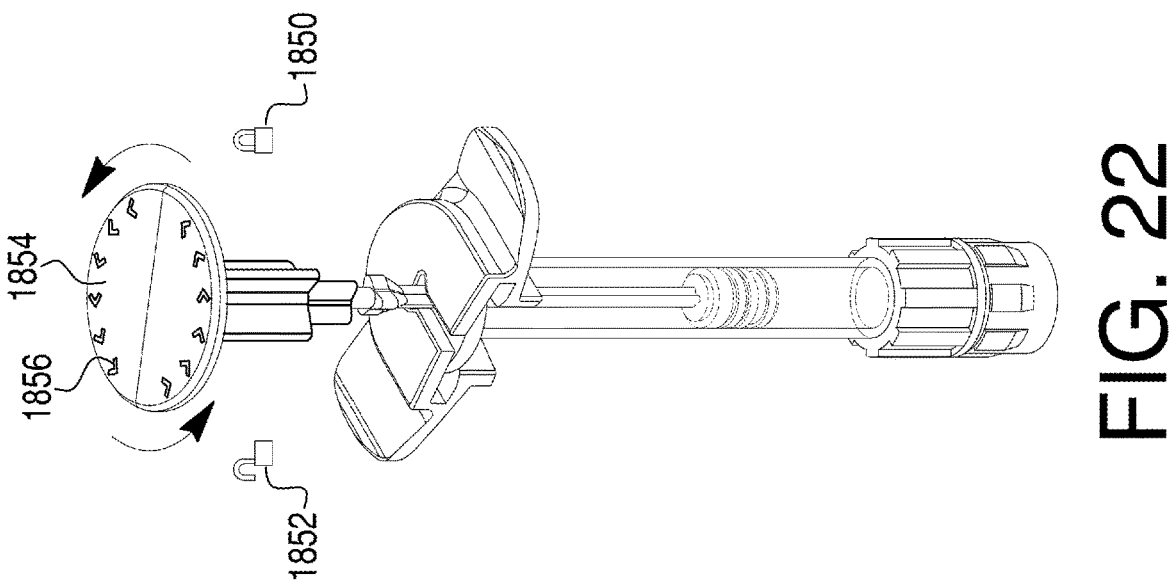
FIG. 22 depicts exemplary visual feedback features according to some embodiments of the present disclosure.

As has been described elsewhere, any of the devices disclosed herein may be combined with labels, auditory feedback, and/or tactical feedback in the form of symbols (e.g., in FIG. 22 depicted as lock and unlock symbols 1850, 1852, chevrons 1856 on actuation portion 1854). Rotation of a plunger rod also may be accompanied by a "clicking" sound.

Figure 23C:
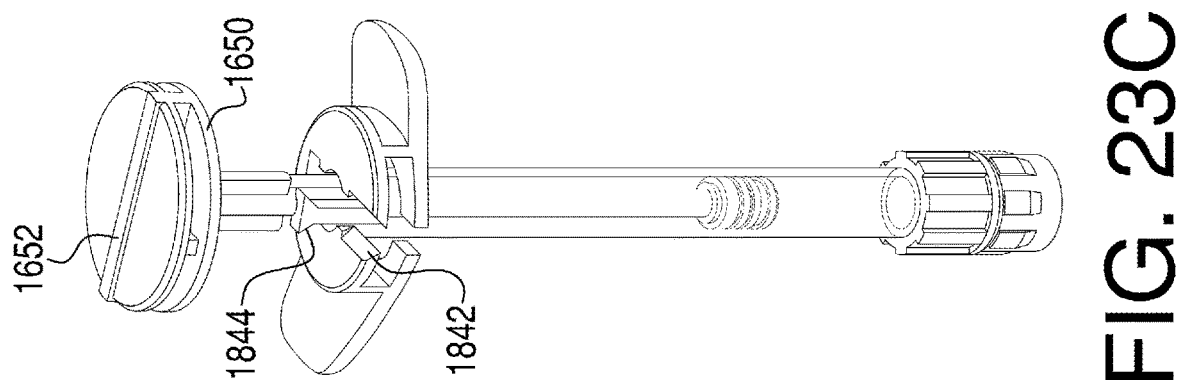
FIGS. 23A-23C depict a further exemplary delivery device according to aspects of the present disclosure.
Figure 23B:
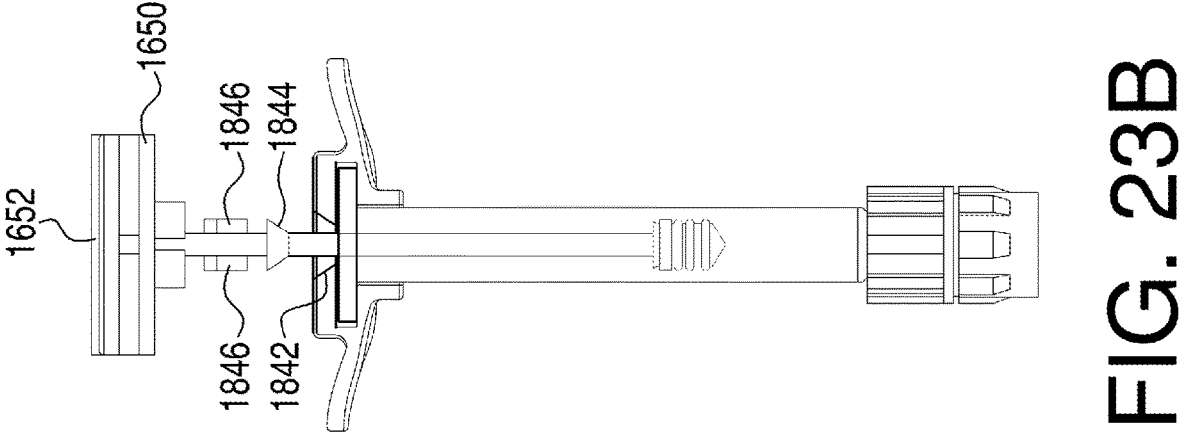
Figure 23A:
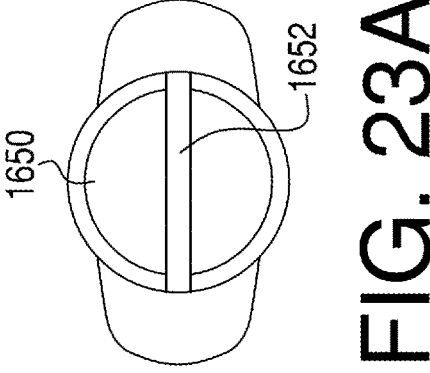

FIGS. 23A-23C depict a further exemplary combination of components in a delivery device. For example, a plunger rod actuation portion 1650 may include, e.g., ribbed sides and a raised portion 1652, to assist in twisting the actuation portion. A device with these characteristics may include, e.g., openings 1842 and corresponding angled protrusions 1844, 1846 (described with respect to FIG. 21).

Figures 24B, 24C, 24D, 24E:
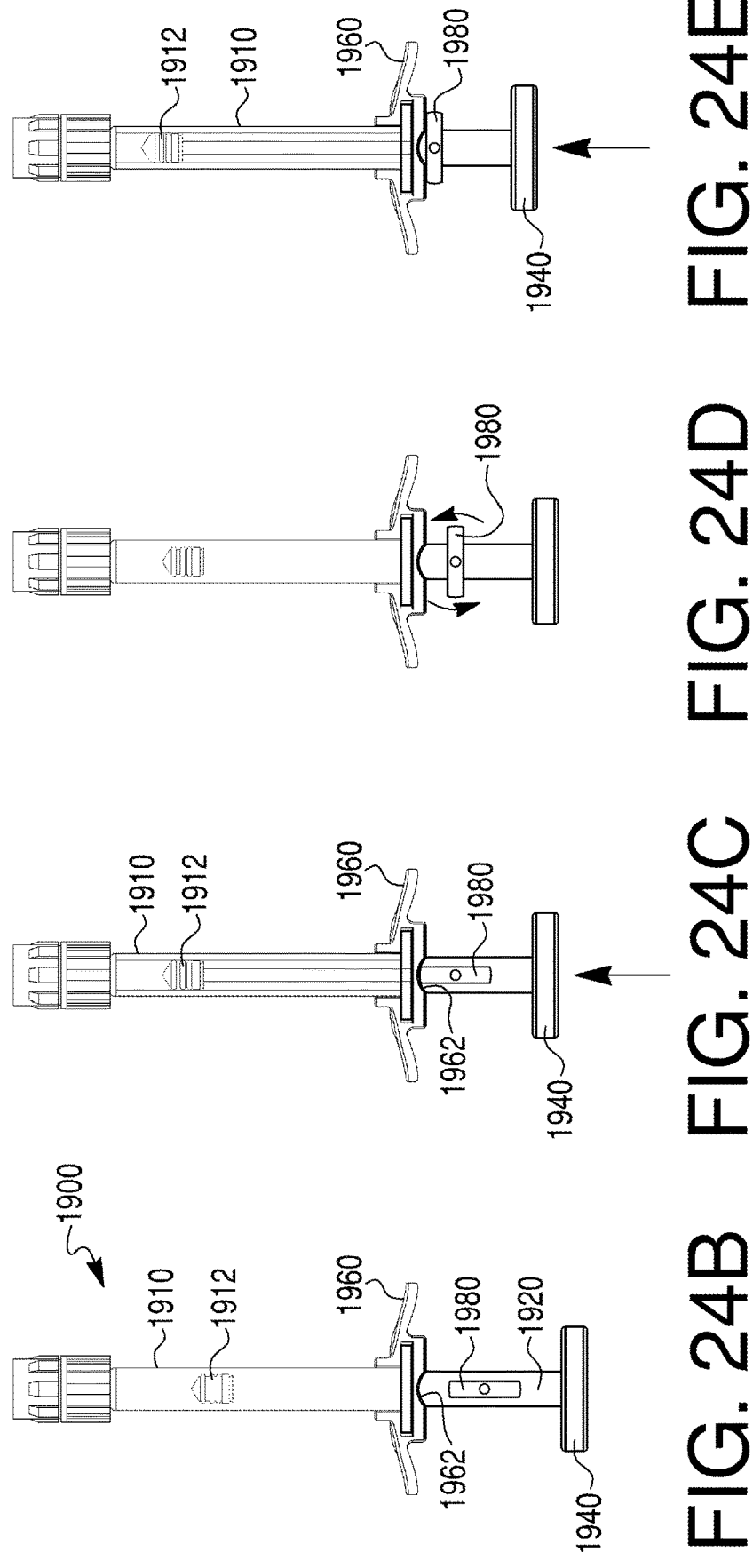

FIGS. 24A-24E depict a further exemplary delivery device 1900 and a method of using device 1900. Device 1900 may include an actuation portion 1940 and a blocking component 1980 depicted on a plunger rod 1920. Plunger rod 1240 may abut a stopper 1912 in a body 1910. Blocking component 1980 may be rotatable relative to plunger rod 1920. In a pre-use configuration depicted in FIG. 24B, blocking component 1980 may be in a first position with respect to plunger rod 1920 and flange piece 1960. In a priming step depicted in FIG. 24C, plunger rod 1920 may be moved longitudinally further into body 1910, until distal movement is blocked by the abutment of blocking component 1980 against a recess 1962 in flange piece 1960. For example, a user may press actuation portion 1940 distally towards flange piece 1960. In a dispensing preparation step depicted in FIG. 24D, blocking component 1980 may be rotated such that a shorter dimension of blocking component 1980 faces flange piece 1960. Recess 1962 may be curved to allow for ease of rotation of blocking component 1980. A distance between blocking component 1980 and flange piece 1960 after blocking component 1980 is rotated may correspond to a distance that plunger rod 1920 may move to dispense a predetermined volume of a drug substance from device 1900. As depicted in FIG. 24E, in a dispensing step, plunger rod 1920 may be moved longitudinally further into body 1910, until the rotated blocking component 1980 abuts flange piece 1960 in a second position. For example, a user may press actuation portion 1940 distally, until protrusion blocking component abuts flange piece 1960. The dispensing step may ensure that a predetermined volume of a drug substance inside body 1910 is dispensed from device 1900.

Figures 25A, 25B:
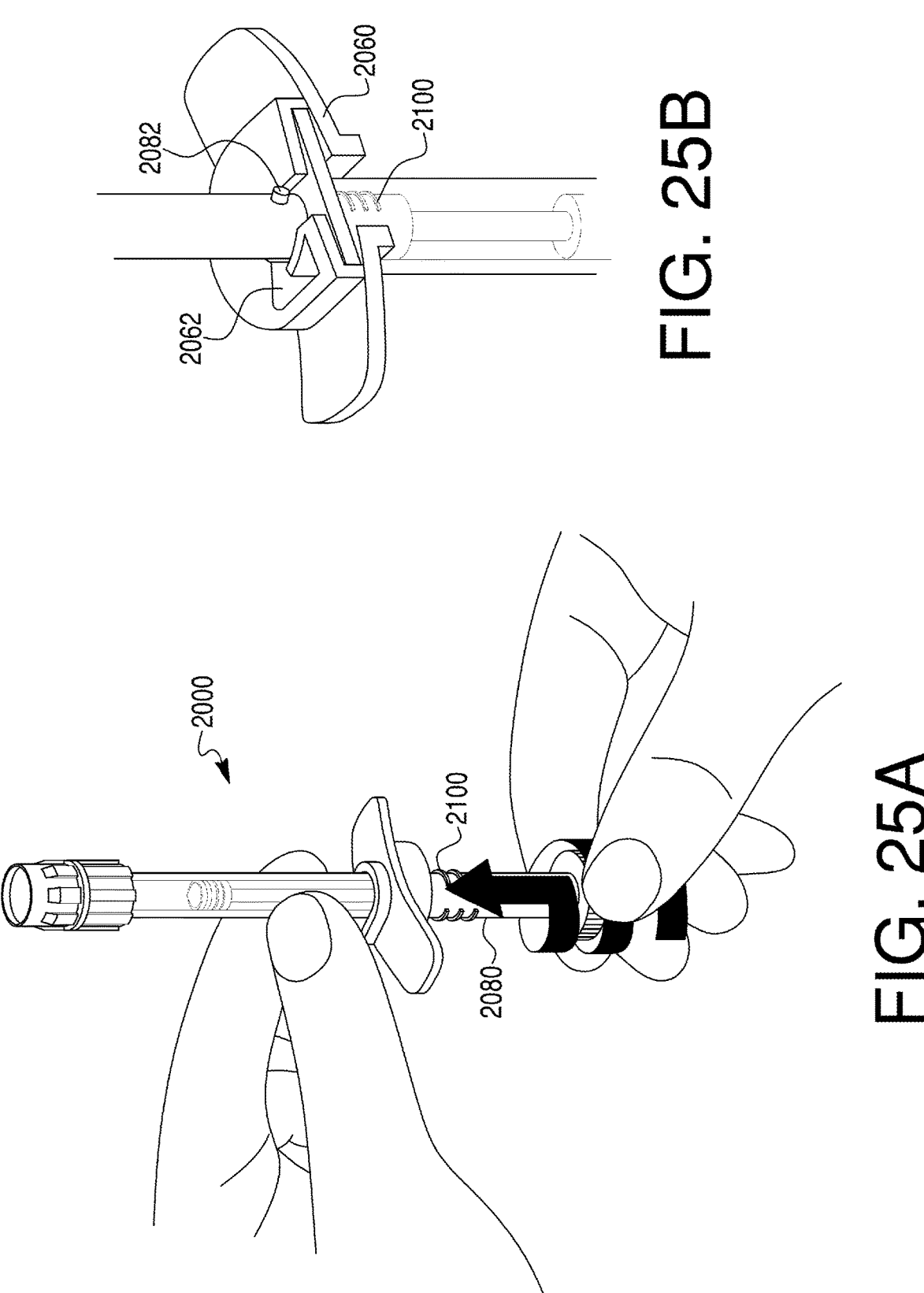
FIGS. 25A-25E depict a further exemplary delivery device and method of using said delivery device, according to aspects of the present disclosure.
Figure 25E:
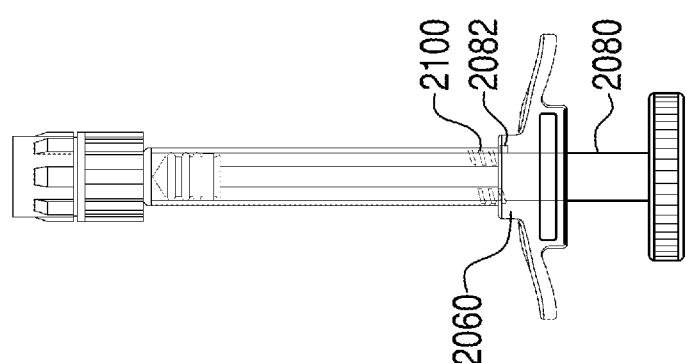
Figure 25D:
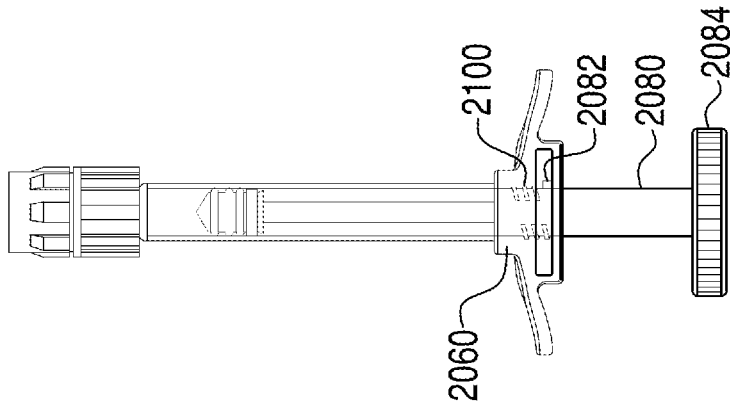
Figure 25C:
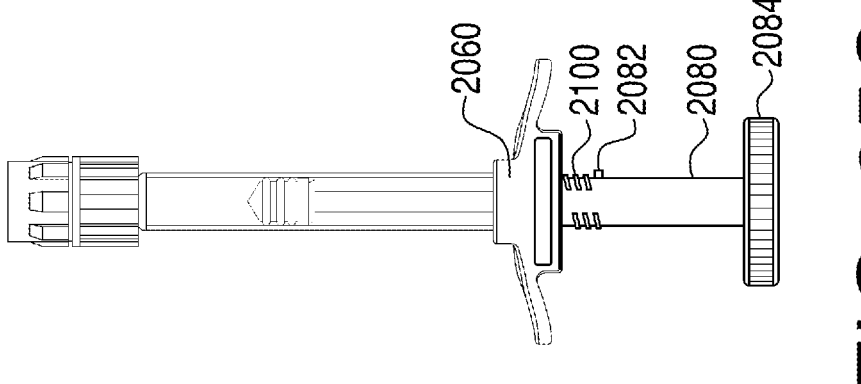

FIGS. 25A-25E depict a further exemplary delivery device 2000, and a method of using delivery device 2000. A plunger rod 2080 of device 2000 may include threads 2100, corresponding to inner threads (not pictured) in a flange piece 2062. As depicted in FIG. 25A, plunger rod 2080 may be rotatable relative to other portions of device 2000. Plunger rod 2080 may also include a protrusion 2082 located proximally from threads 2100 (see, e.g., FIG. 25B), which may correspond to an opening 2062 in a flange piece 2062, such that plunger rod 2080 must be in a particular configuration and position to allow protrusion 2082 to pass into and/or through flange piece 2060. In a pre-use configuration depicted in FIG. 25C, threads 2100 and protrusion 2082 may be positioned proximally to flange piece 2060. In a priming step, plunger rod 2080 may be rotated with respect to the inner threads of flange piece 2060 until threads 2100 pass through flange piece 2060 and/or protrusion 2082 prevents further rotation or distal movement of plunger rod 2080. In a dispensing preparation step, protrusion 2082 may be moved towards opening 2062. In a dispensing step, protrusion 2082 may be moved through opening 2062 to further advance plunger rod 2080, and to dispense a predetermined volume of a drug substance inside the body of device 2000.

Figure 26B:
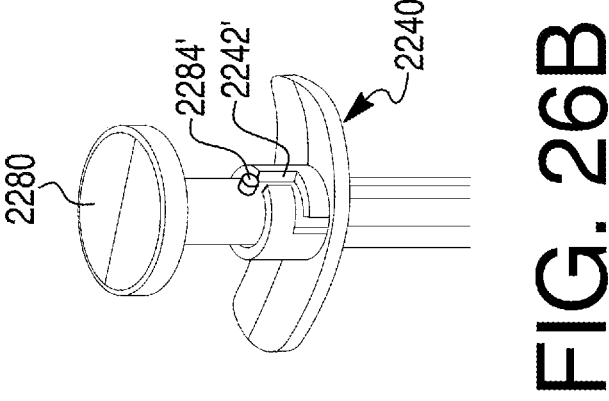
FIGS. 26A-26G depict further exemplary delivery devices and a method of using one such delivery device, according to aspects of the present disclosure.
Figure 26A:
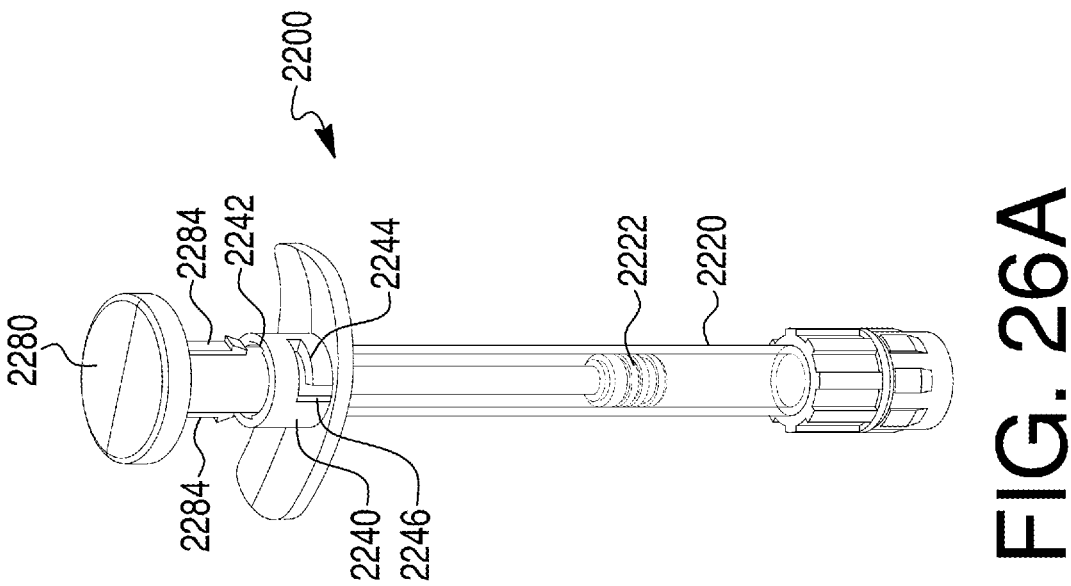
Figure 26E:
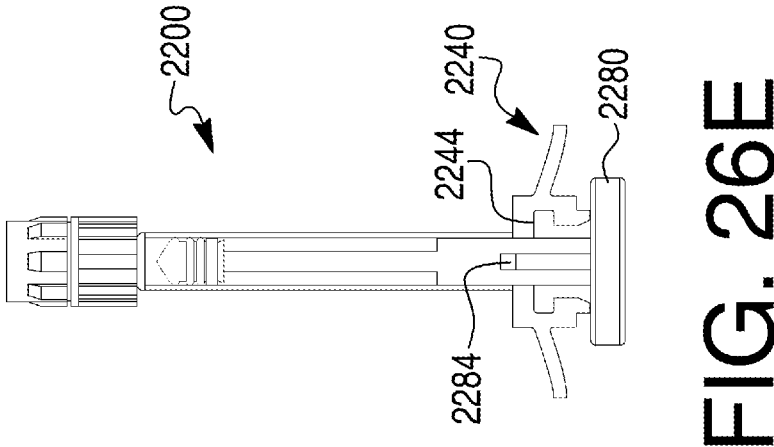
Figure 26D:
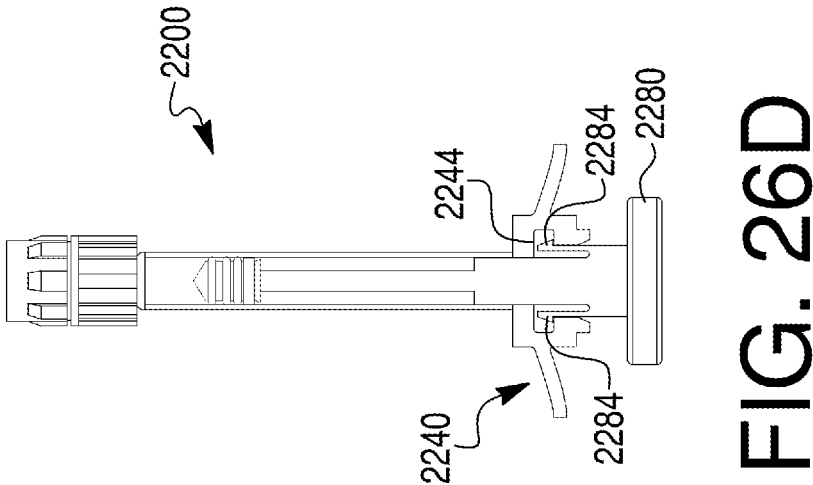
Figure 26C:
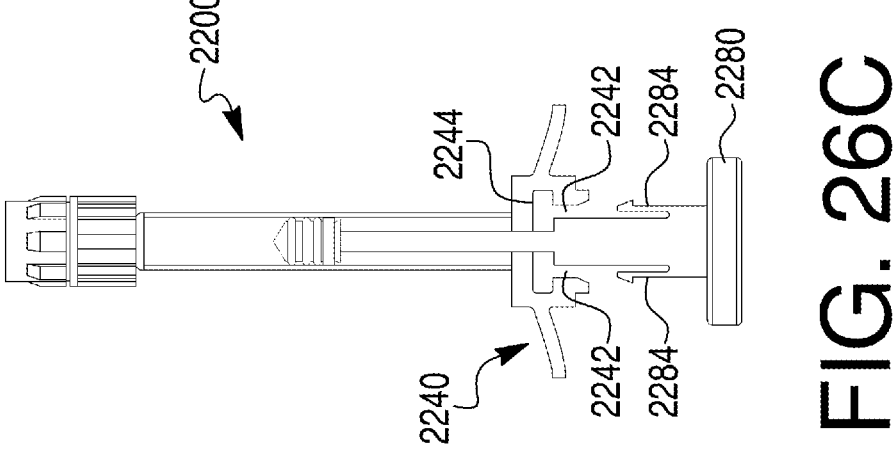

FIGS. 26A-26E depict a delivery device 2200 having further variations on dosage control components. For example, device 2200 includes a plunger rod 2280 with one or more clips 2284, each of which may be configured to slide distally into a channel 2242 of a flange piece 2240 and, once having slid distally, to resist sliding proximally out of channel 2242 (e.g., to prevent or resist back-out of plunger rod 2280). Flange piece 2240 may further have a second channel 2244 and a third channel 2246, through which each of clips 2284 may slide in delivery preparation and dosage delivery steps, as has been previously described. Alternately, as shown in FIG. 26B, channel 2242' may have an open proximal end through which a protrusion 2284' may move, allowing for proximal and/or distal movement of a plunger rod 2280 relative to flange piece 2240'. As depicted in FIG. 26C, in a pre-use configuration, clips 2284 may be disposed proximally to channels 2242 of flange piece 2240. In a priming step, plunger rod 2280 may be moved distally into a body of device 2200, until clips 2284 move into channels 2242 and abut a distal end of channels 2242. In a dispensing preparation step, plunger rod 2280 may be rotated relative to flange piece 2240. In a dispensing step, plunger rod 2280 may be moved further distally into a body of device 2200 to dispense a predetermined volume of the drug substance from device 2200.

Figure 26G:
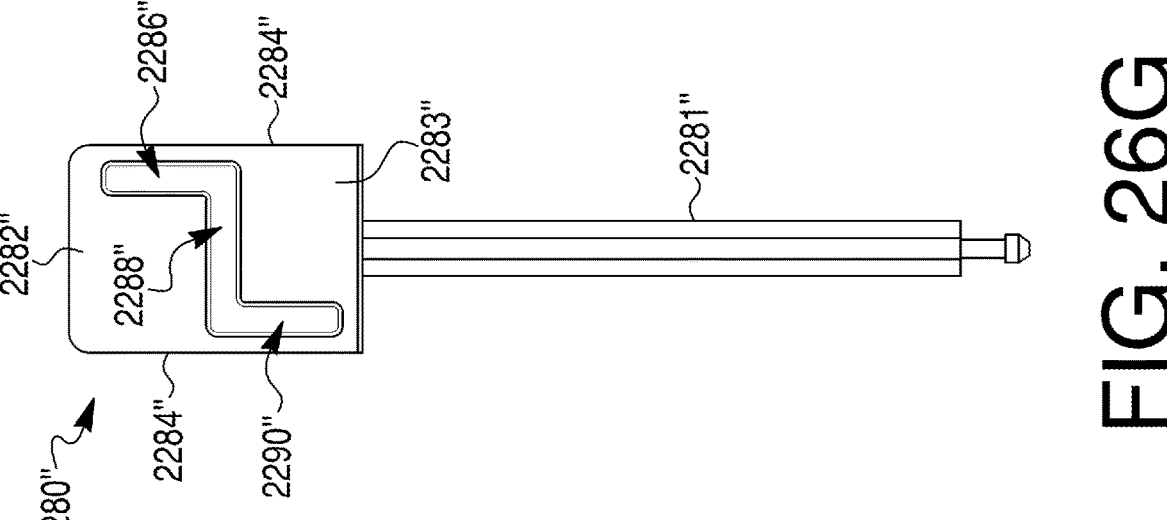
Figure 26F:
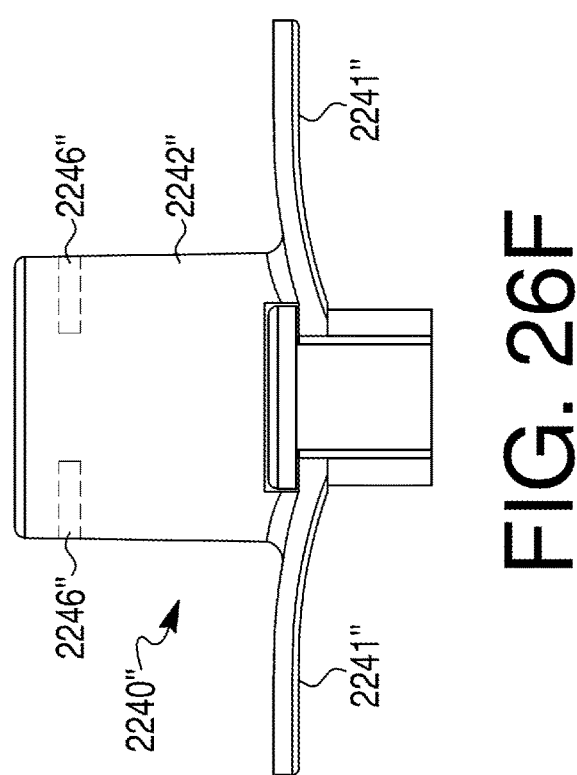

In other embodiments, as shown in FIGS. 26F-26G, a flange piece 2240" may include one or more projections 2246" disposed within a collar 2242". In the present example, collar 2242" may include a pair of projections 2246" extending radially inward from an interior surface of collar 2242" and in opposite directions relative to another. For example, projections 2246" may be disposed approximately 180 degrees away from one another. It should be appreciated that flange piece 2240" may include additional and/or fewer projections 2246" than those shown and described herein without departing from a scope of this disclosure. Flange piece 2240" may be configured to engage a plunger rod 2080" in response to plunger rod 2280" receiving projections 2246".

As seen in FIG. 26G, a plunger rod 2280" may include an actuation member 2284" defined by a proximal end 2282" and a distal end 2283". Plunger rod 2280" may include a series of channels along opposing sides of actuation member 2284", such as, for example, a first channel 2286", a second channel 2288", and a third channel 2290" positioned between proximal end 2282" and distal end 2283". First channel 2286" is offset from third channel 2290" and connected to third channel 2290" by second channel 2288" positioned therebetween. As described in detail below, first channel 2286" may define a longitudinal and axial priming path of plunger rod 2280", second channel 2288" may define a circumferential path of plunger rod 2280", and third channel 2290" may define a longitudinal and axial dose completion path. It should be appreciated that an opposing surface and/or side of actuation member 2284" (not shown) includes a substantially similar series of interconnected first channel 2286", second channel 2288", and third channel 2290" as seen in FIG. 26G. In the present example, first channel 2286" and third channel 2290" may be aligned parallel relative to one another.

First channels 2286", second channels 2288", and third channels 2290" may be sized, shaped, and configured to receive at least one of the pair of projections 2246". With plunger rod 2280" coupled to flange piece 2240", projections 2246" may protrude and slide through first channels 2286", second channels 2288", and third channels 2290" to prime and deliver a dosage from device 2200 (FIG. 26A) as described in detail above. In some embodiments, first channels 2286" may have an open end at proximal end 2282" through which projections 2246" may be received in. In some embodiments, first channels 2286" may have a closed proximal end and projections 2246" may be at least partially flexible and/or deformable such that projections 2246" may be configured to flex radially-outward when being received at the proximal end of first channels 2286". In other embodiments, first channels 2286" may have a sloped, chamfered, and/or tapered end to facilitate guiding projections 2246" toward second channels 2288". In this instance, the sloped end may inhibit retraction (e.g., proximal movement) of plunger rod 2280" relative to flange piece 2240". A longitudinal length of first channels 2286" may define an axial priming path (e.g., an amount or extent priming) that is configured to facilitate proximal and/or distal movement of plunger rod 2280" relative to flange piece 2240". For example, projections 2246" may be disposed at a proximal end of first channels 2286" and proximally of second channels 2288" when device 2200 is in an assembly state. In a priming step, plunger rod 2280" may move distally relative to flange piece 2240" until projections 2246" are positioned within second channels 2288" and at a distal end of first channels 2286". Second channels 2288" may define a circumferential path of plunger rod 2280".

In a dispensing preparation step, plunger rod 2280" may be rotated relative to flange piece 2240" to translate projections 2246" laterally through the circumferential path of second channels 2288" and toward a dose completion path defined by third channels 2290". In some embodiments, plunger rod 2280" and/or flange piece 2240" may be configured to generate a user feedback (e.g., tactile, audible, visual, etc.) when device 1050 is in the dispensing preparation step. In a dispensing step, plunger rod 2280" may move distally into a body of device 2200 to dispense a controlled volume of substance by translating projections 2246" through third channels 2290". A longitudinal length of third channels 2290" may define a dosage delivery path (e.g., a dosage amount). It should be appreciated that the axial priming path (length of first channels 2286") may vary relative to the dosage delivery path (length of third channels 2290"). In other embodiments, plunger rod 2280" may include additional and/or fewer channels along actuation member 2284" (e.g., corresponding to a quantity of projections 2246" on flange piece 2240"), or have various other relative channel configurations, than those shown and described herein.

Figure 27C:
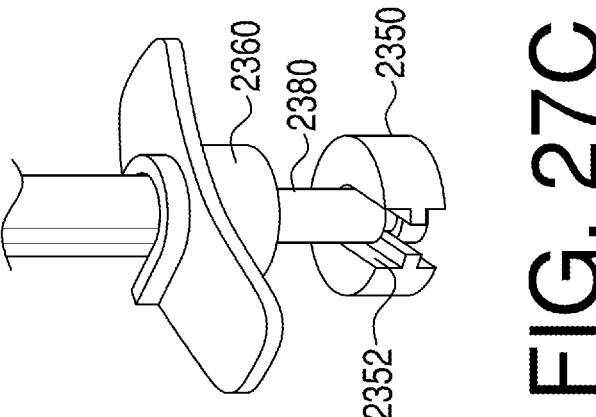
FIGS. 27A-27H depict a further exemplary delivery device and method of using said delivery device, according to aspects of the present disclosure.
Figure 27B:
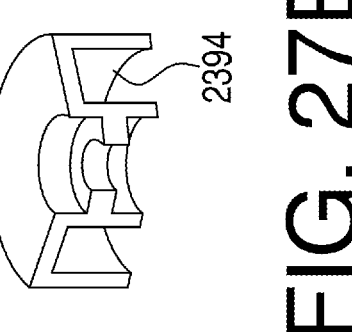
Figure 27A:
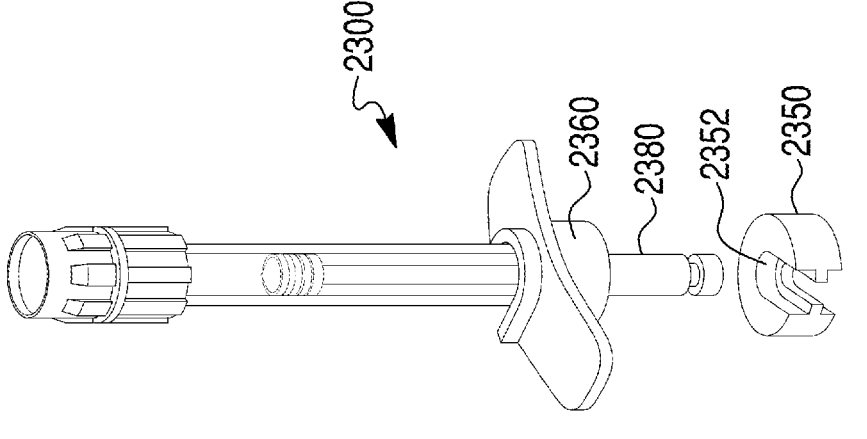
Figures 27D, 27E, 27F:
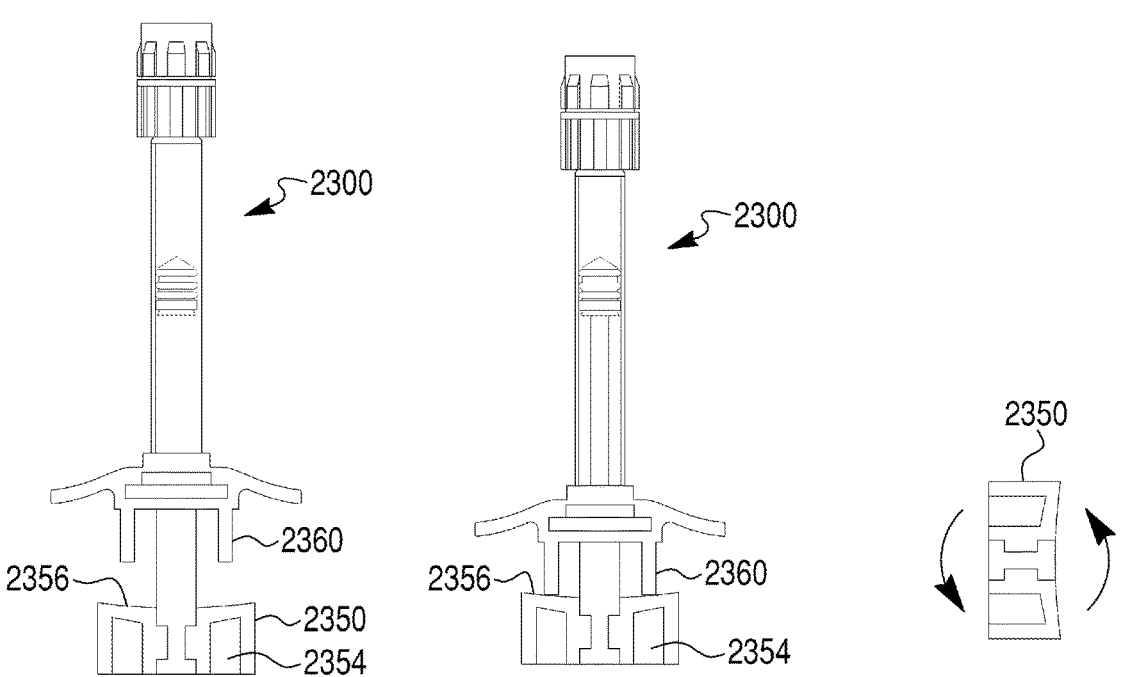
Figures 27G, 27H:
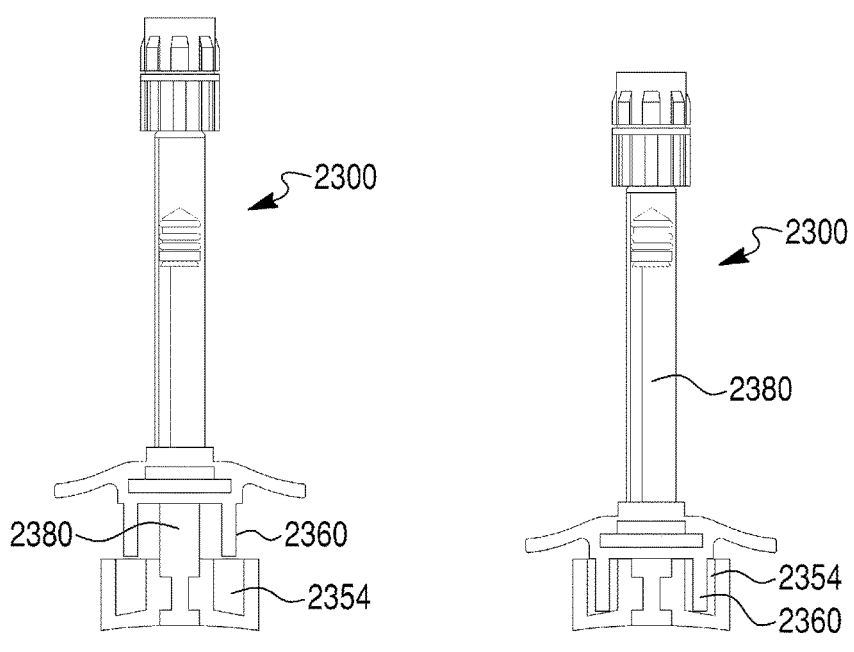

FIGS. 27A-27H depict an exemplary delivery device 2300 and method of using delivery device 2300. An actuation portion 2350 may also serve as a blocking component of device 2300. Actuation portion 2350 may be slidably coupled to plunger rod 2380 in two configurations, via a channel 2352. As depicted in FIG. 27B, one side of actuation portion 2350 may include a channel 2354. A depth of channel 2354 may correspond to a distance that a plunger rod may move to dispense a predetermined volume of a drug substance once device 2300 has been primed. As depicted in FIG. 27C and FIG. 27D, in a pre-use configuration, actuation portion 2350 may be assembled onto plunger rod 2380 such that a flat side of actuation portion 2350 faces a collar 2360 of device 2300. In a priming step, actuation portion 2350 may be used to move plunger rod 2380 distally until the flat side 2356 of actuation portion 2350 abuts a proximal side of collar 2360. To prepare for a dosage delivery step, actuation portion 2350 may be removed from plunger rod 2380, and may be rotated or flipped and reassembled with plunger rod 2380 such that channel 2354 faces collar 2360, as depicted in FIGS. 27F and 27G. In a dosage delivery step, actuation portion 2350 may be used to push plunger rod 2380 further distally, until a proximal end of collar 2360 abuts an inner end of channel 2354. This movement of plunger rod 2380 may be sufficient to dispense a predetermined dose of a drug substance from device 2300.

Figure 28C:
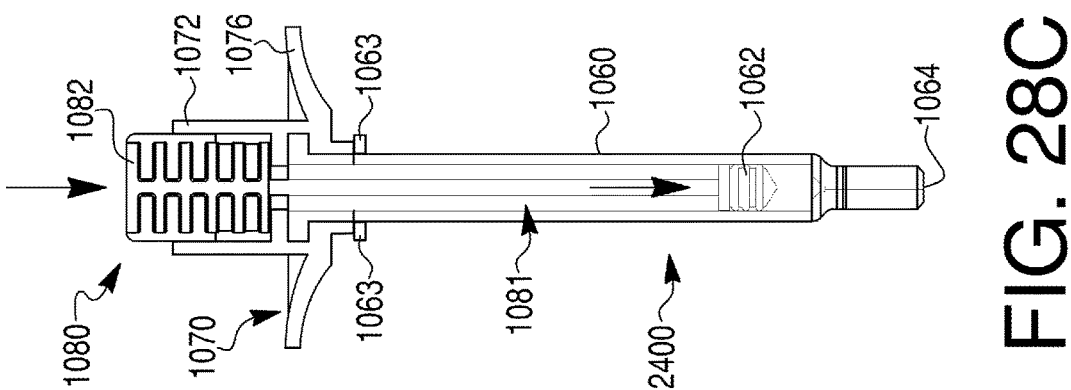
FIGS. 28A-28Z depict further exemplary delivery devices and methods of using said delivery devices, according to aspects of the present disclosure.
Figure 28B:
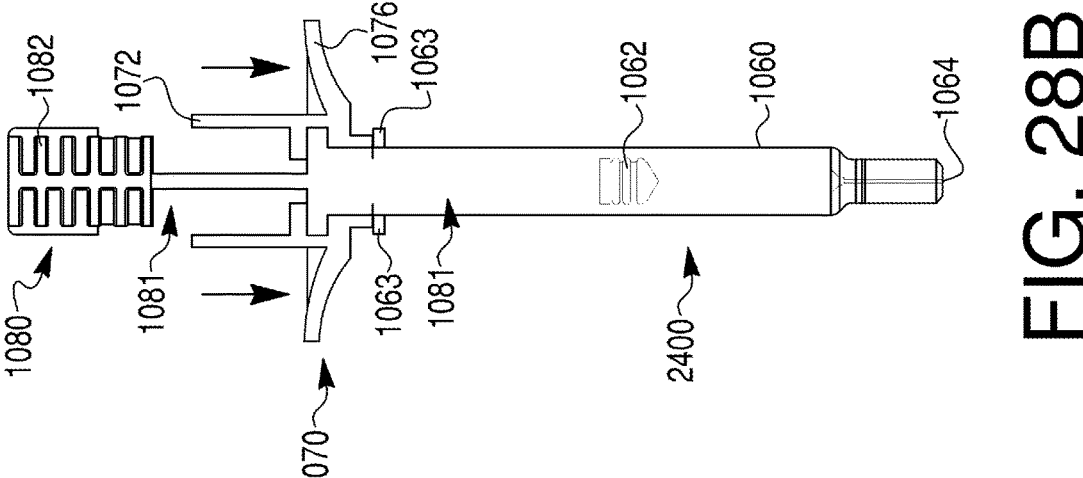
Figure 28A:
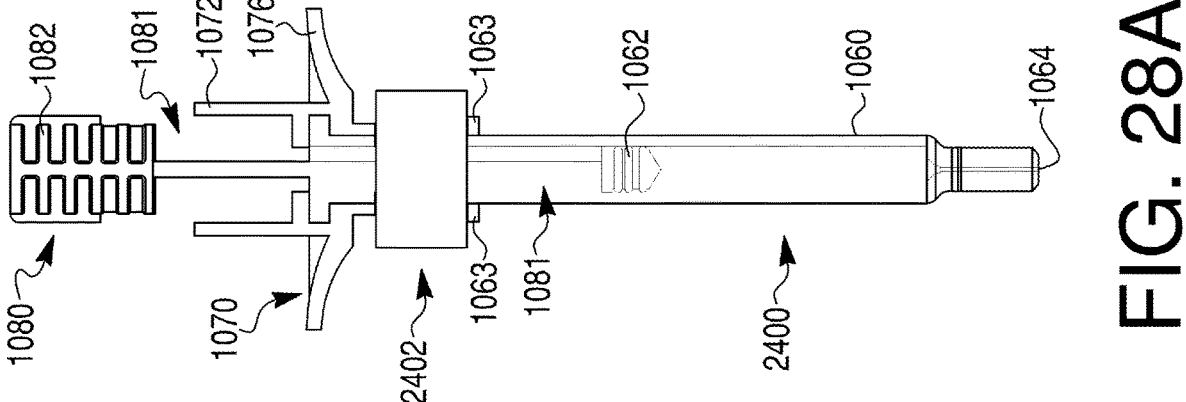

FIGS. 28A-28C depict an exemplary delivery device 2400 and method of using delivery device 2400. Delivery device 2400 may include substantially similar features as those shown and described above such that like reference numerals are used to identify like components. As shown in FIG. 28A, delivery device 2400 may include a removable clip 2402 coupled to body 1060 at a position distal to flange piece 1070. Removable clip 2402 may be an obstruction and/or blocking component configured to inhibit movement of flange piece 1070 relative to body 1060. Removable clip 2402 is selectively removable such that removable clip 2402 may be configured to disengage body 1060 in response to manual actuation of removable clip 2402.

By way of illustrative example, removable clip 2402 may have a body that wraps about an exterior of body 1060 and is configured to selectively deform (e.g., break, tear, etc.) upon application of a force thereto to decouple removable clip 2402 from body 1060. In other examples, removable clip 2402 may have a flexible body that is configured to bend in response to a radially-outward force being applied thereto, thereby disengaging removable clip 2402 from body 1060. By way of further example, removable clip 2402 may have a body that is configured to selectively transition between a closed configuration encapsulating a circumference of body 1060 therein and an open configuration permitting removal of body 1060 from the body of removable clip 2402. Removable clip 2402 may include various other suitable sizes, shapes, and/or configurations than those shown and described herein without departing from a scope of the present disclosure.

Delivery device 2400 may include a radial wall 1063 extending laterally outward from an exterior of body 1060, thereby forming an obstruction along body 1060. As seen in FIG. 28A, radial wall 1063 may be configured to inhibit distal translation of removable clip 2402 along body 1060. In some embodiments, radial wall 1063 may be an add-component attached to body 1060, while in other embodiments, radial wall 1063 may be integrally formed onto body

1060. Referring now to FIG. 28B, flange piece 1070 and plunger rod 1080 may be configured to translate distally along body 1060 to prime delivery device 2400 upon removal of removable clip 2402 from body 1060. In this instance, plunger rod 1080 may remain stationary relative to flange piece 1070, as the combined assembly of flange piece 1070 and plunger rod 1080 moves relative to body 1060. In other embodiments, plunger rod 1080 may remain stationary as flange piece 1070 translates distally along body 1060 to prime delivery device 2400. For example, at least a portion of flange piece 1070 may extend into body 1060 (e.g., and behind stopper 1062) when priming device 2400. In this instance, plunger rod 1080 may be translated separately to deliver a dosage from delivery device 2400.

With flange piece 1070 translated from a proximal position (FIG. 28A) to a distal position (FIG. 28B), delivery device 2400 may be in a primed position. It should be appreciated that body 1060 may be configured to limit movement by flange piece 1070 to a defined distance based on a location of radial wall 1063, which may correspond to a priming distance of delivery device 2400. Accordingly, a priming distance of delivery device 2400 may be controlled by adjusting a range of movement of flange piece 1070 along body 1060.

As seen in FIG. 28C, plunger rod 1080 may be translated distally relative to body 1060 in response to applying a distally-directed force onto actuation portion 1082. In this instance, stem 1081 may move relative to flange piece 1070, thereby causing stopper 1062 to move within body 1060 to deliver a dose. It should be appreciated that an extent that plunger rod 1080 translates relative to flange piece 1070 may define a dosage delivery distance of delivery device 2400. The dosage delivery distance may be controlled based on a gap formed between collar 1072 and actuation portion 1082.

Figure 28F:
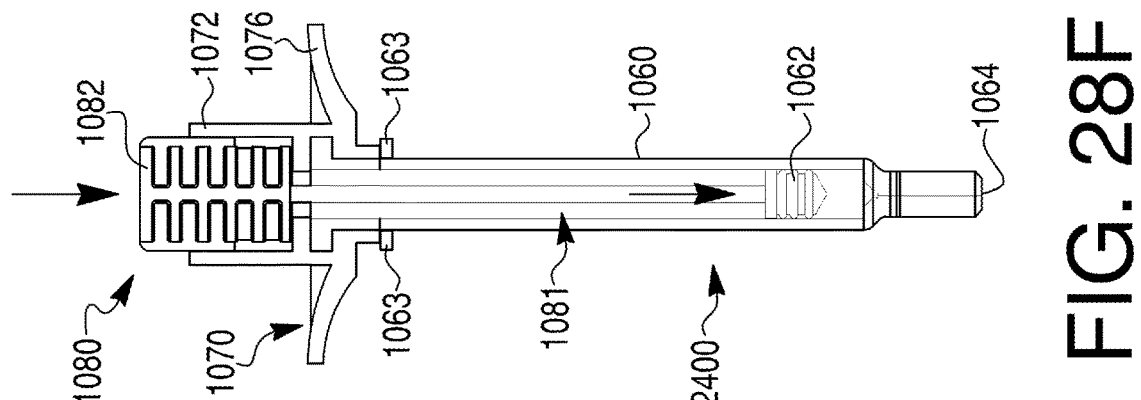
Figure 28E:
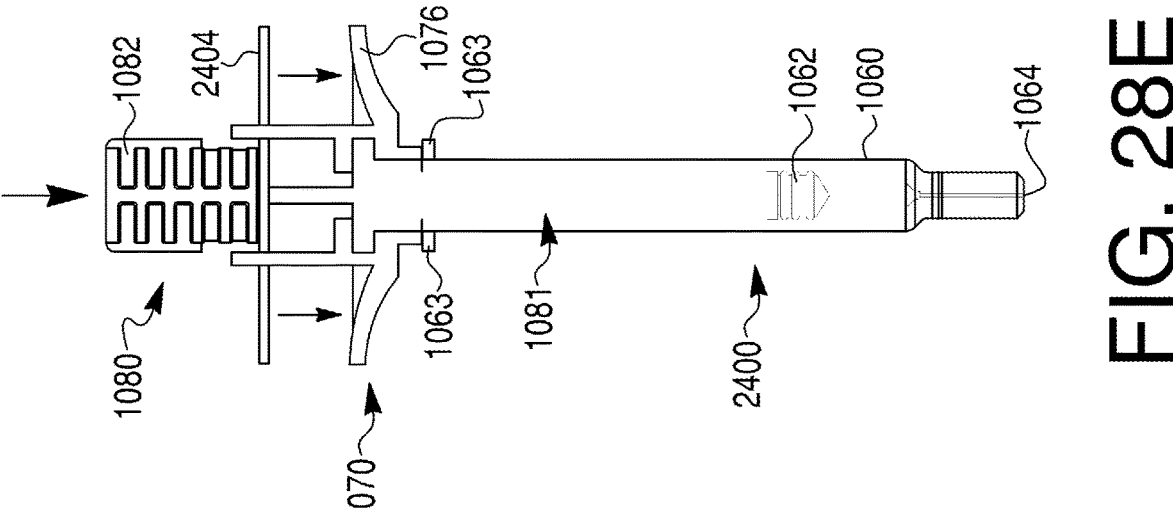
Figure 28D:
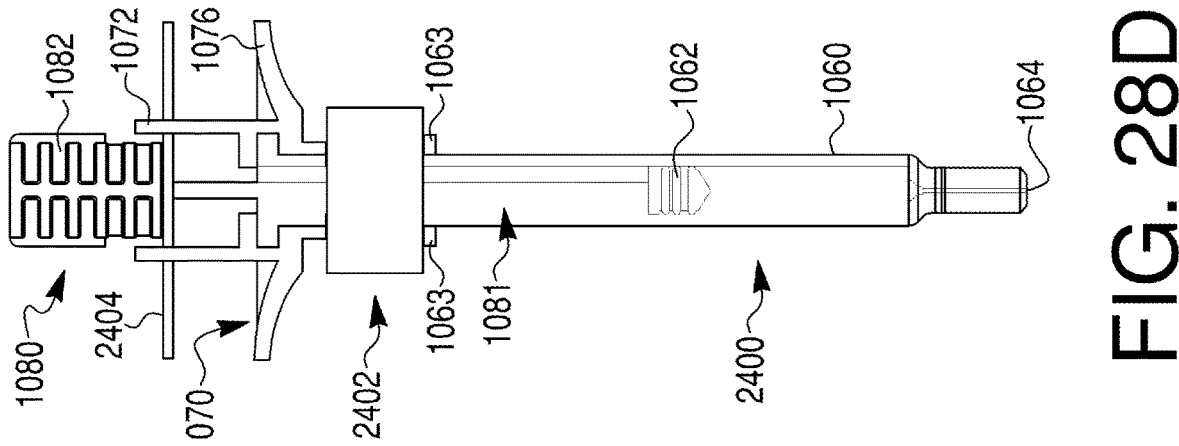

In other embodiments, as seen in FIGS. 28D-28F, delivery device 2400 may further include a locking component, such as, for example, a removable rod 2404 coupled to flange piece 1070. Referring specifically to FIG. 28D, removable rod 2404 may be received through a proximal end of collar 1072, such as, for example, through one or more lateral apertures (not shown) formed through collar 1072. Removable rod 2404 may be configured to inhibit movement of plunger rod 1080 relative to flange piece 1070, such as, for example, preventing receipt of actuation portion 1082 into collar 1072. Removable rod 2404 may be selectively removable and configured to disengage collar 1072 upon manual actuation of removable rod 2404. It should be appreciated that delivery device 2400 may include various other locking components in addition to and/or in lieu of removable of 2404, such as, for example, a pin, a tab, a bar, and the like.

For example, referring now to FIG. 28E, flange piece 1070 and plunger rod 1080 (e.g., stem 1081 and actuation portion 1082) may be configured to translate distally along body 1060 to prime delivery device 2400 in response to removal of removable clip 2402 from body 1060. Plunger rod 1080 may remain stationary relative to flange piece 1070 as the assembly of flange piece 1070 and plunger rod 1080 moves relative to body 1060. With flange piece 1070 translated from a proximal position (FIG. 28D) to a distal position (FIG. 28E), delivery device 2400 may be in a primed position. It should be appreciated that body 1060 may be configured to limit movement by flange piece 1070 to a defined distance based on a location of radial wall 1063 along body 1060, which may correspond to a priming distance of delivery device 2400.

As seen in FIG. 28F, removable rod 2404 may be disengaged from collar 1072 such that plunger rod 1080 is no longer inhibited from moving distally relative to flange piece 1070. Actuation portion 1082 may be translated into collar 1072 to move stem 1081 and stopper 1062 within body 1060 to deliver a dose. An extent that plunger rod 1080 translates relative to flange piece 1070 may define a dosage delivery distance of delivery device 2400.

Figure 28I:
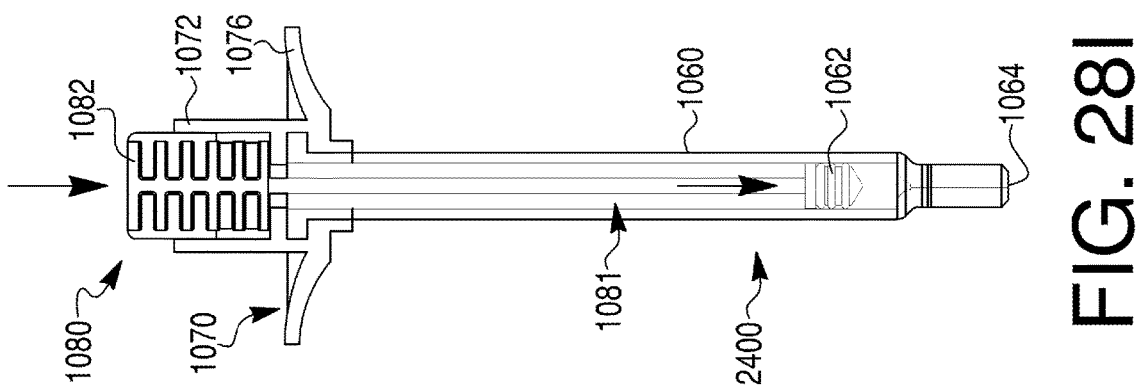
Figure 28H:
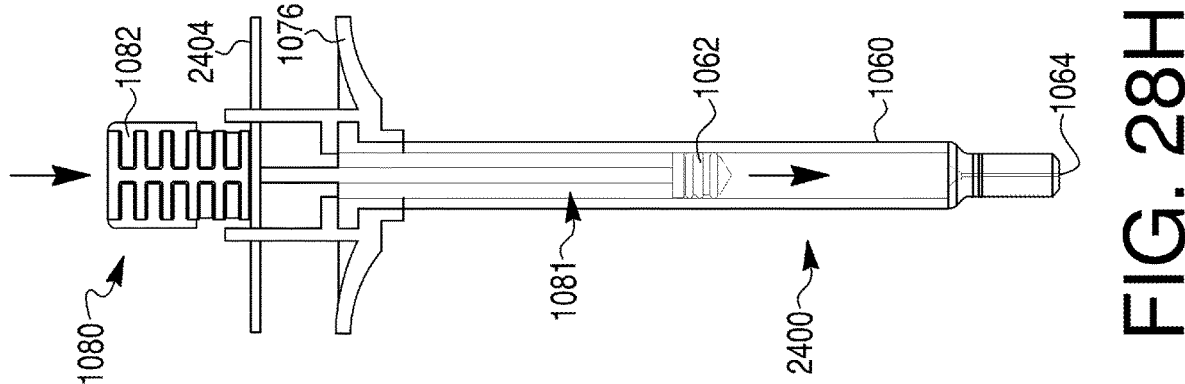
Figure 28G:
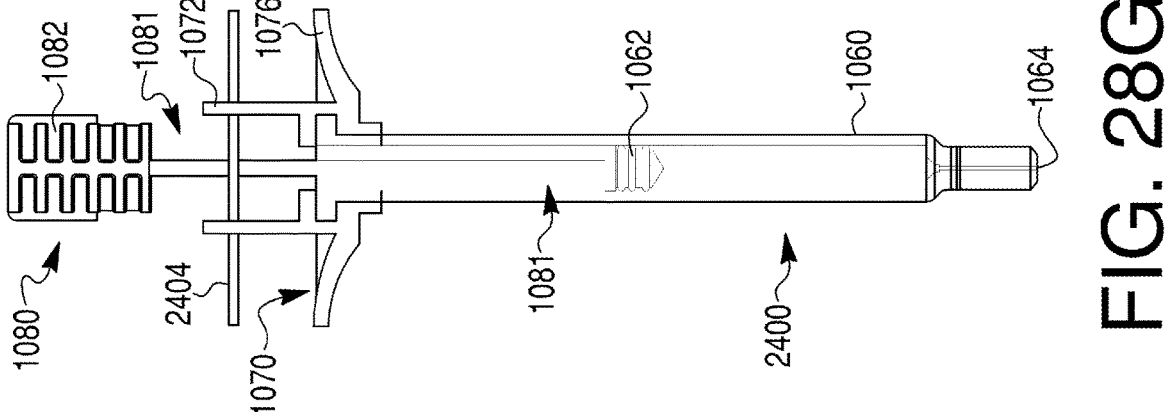

In other embodiments, as seen in FIGS. 28G-28I, removable clip 2402 may be omitted entirely such that delivery device 2400 may include a single obstruction and/or blocking component, i.e., rod 2404. In this instance, flange piece 1070 may be fixed relative to body 1060. With actuation portion 1082 positioned proximally of rod 2404, delivery device 2400 may be primed in response to plunger rod 1080 translating distally toward flange piece 1070 until encountering rod 2402. It should be appreciated that flange piece 1070 and/or rod 2404 may be configured to inhibit distal translation of plunger rod 1080 relative thereto absent an application of a distally-directed force thereto. In other examples, delivery device 2400 may include a blocking component positioned between actuation portion 1082 and rod 2404 (e.g., removable clip 2404) to inhibit distal movement of plunger rod 1080.

Accordingly, a priming distance of delivery device 2400 may be defined by a distance between the distal end of actuation portion 1082 and rod 2404 when delivery device 2400 is in an assembled, pre-primed state (FIG. 28G). With actuation portion 1082 engaged against rod 2402, as seen in FIG. 28H, delivery device 2400 may be in a primed state. Rod 2402 may be removed from collar 1072 to thereby allow further translation of plunger rod 1080 distally relative to flange piece 1070. As shown in FIG. 28I, a dose may be delivered from delivery device 2400 in response to collar 1072 receiving actuation portion 1082. It should be appreciated that a longitudinal offset of a distal end of actuation portion 1082 and an inner surface of collar 1072 may be determinative to a dosage delivery distance. Accordingly, an extent (e.g., the dosage delivery distance) that plunger rod 1080 translates relative to flange piece 1070 may define a volume of dosage delivered by delivery device 2400.

Figure 28L:
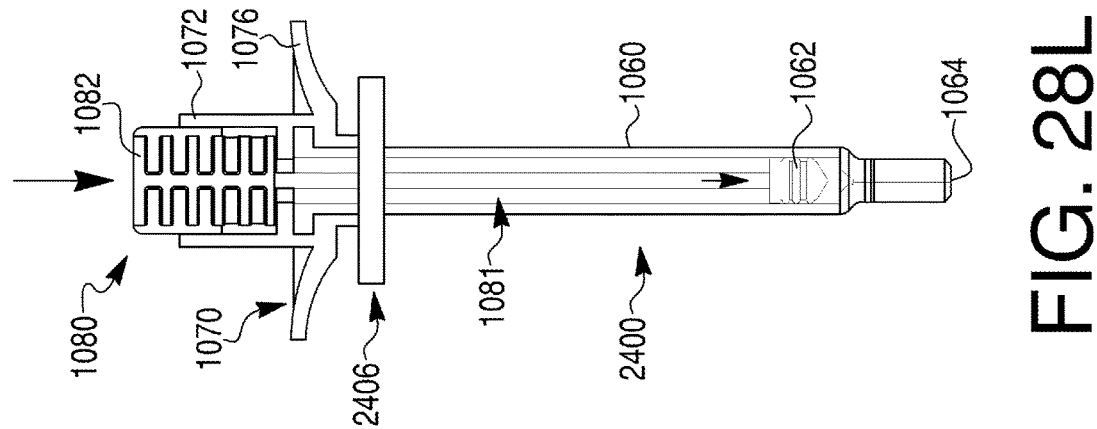
Figure 28K:
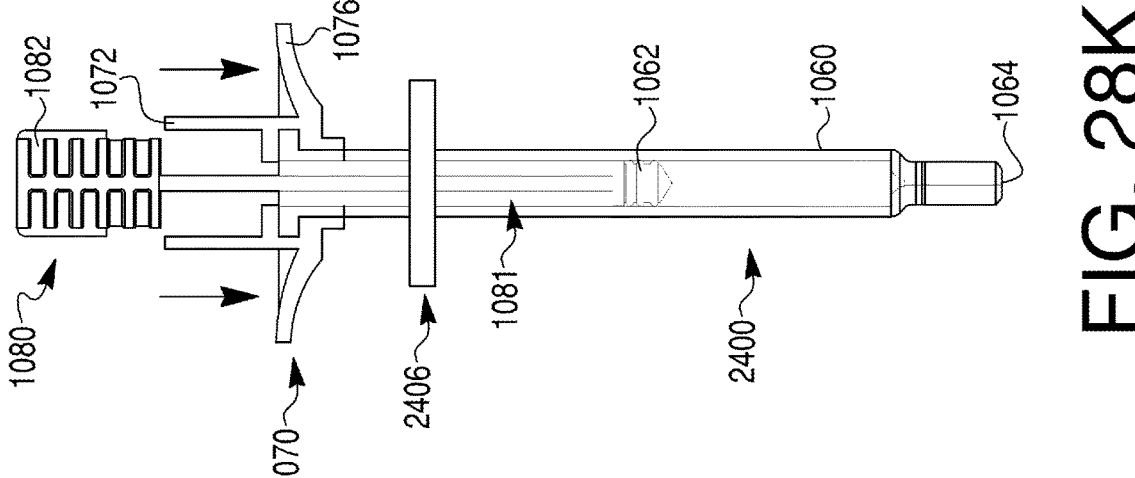
Figure 28J:
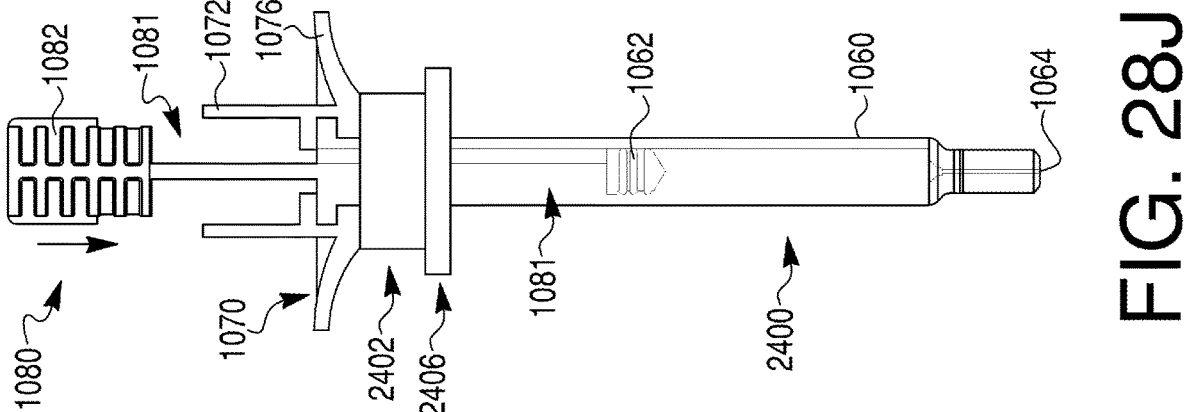

In further embodiments, as shown in FIGS. 28J-28L, delivery device 2400 may include a fixed clip 2406 attached to body 1060 at a location relatively distal of removable clip 2402. Fixed clip 2406 may be an obstruction and/or blocking component positioned in contact with removable clip 2402 such that fixed clip 2406 may be configured to inhibit movement of removable clip 2402 along body 1060. With flange piece 1070 positioned proximally of removable clip 2402, fixed clip 2406 may be further configured to inhibit movement of flange piece 1070 when removable clip 2402 is positioned therebetween.

Referring now to FIG. 28K, flange piece 1070 may be configured to translate distally along body 1060 to prime delivery device 2400 upon removing removable clip 2402 from body 1060. In this instance, plunger rod 1080 may remain stationary relative to flange piece 1070 as the assembly of plunger rod 1080 and flange piece 1070 moves toward fixed clip 2406. With flange piece 1070 translated from a proximal position (FIG. 28J) to a distal position (FIG. 28K) engaged against fixed clip 2406, delivery device 2400 may be in a primed position. It should be appreciated that body 1060 may be configured to limit movement by flange piece 1070 to a defined distance, which may correspond to a priming distance of delivery device 2400.

As seen in FIG. 28L, plunger rod 1080 may be translated distally relative to body 1060 in response to applying a distally-directed force onto actuation portion 1082. Stem 1081 may move relative to flange piece 1070, causing stopper 1062 to move within body 1060 to deliver a dose. It should be appreciated that an extent that plunger rod 1080 translates relative to flange piece 1070 may define a dosage delivery distance of delivery device 2400. The dosage delivery distance may be controlled based on a position of fixed clip 2406 along body 1060.

Figure 28O:
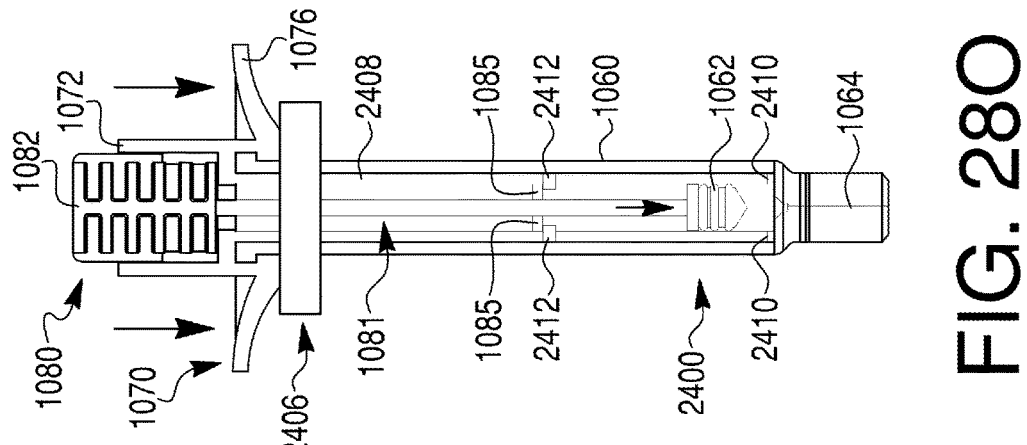
Figure 28N:
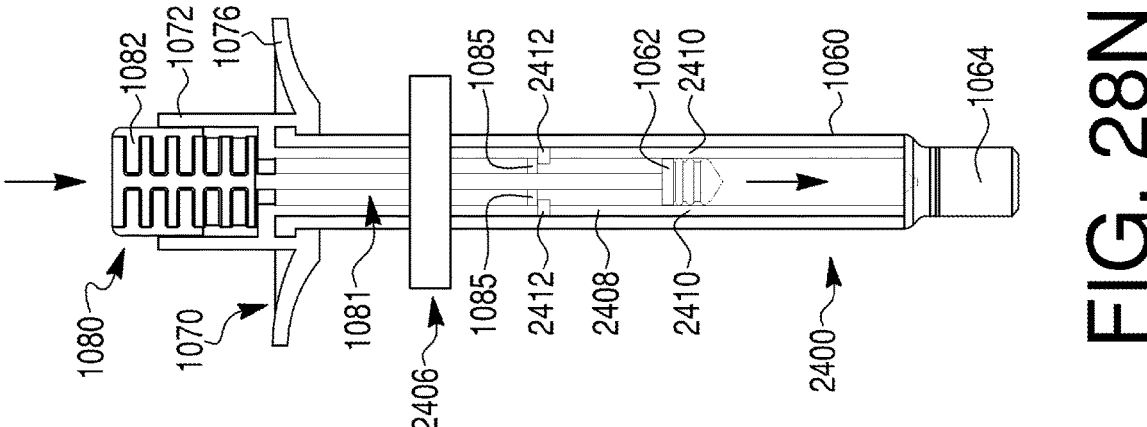
Figure 28M:
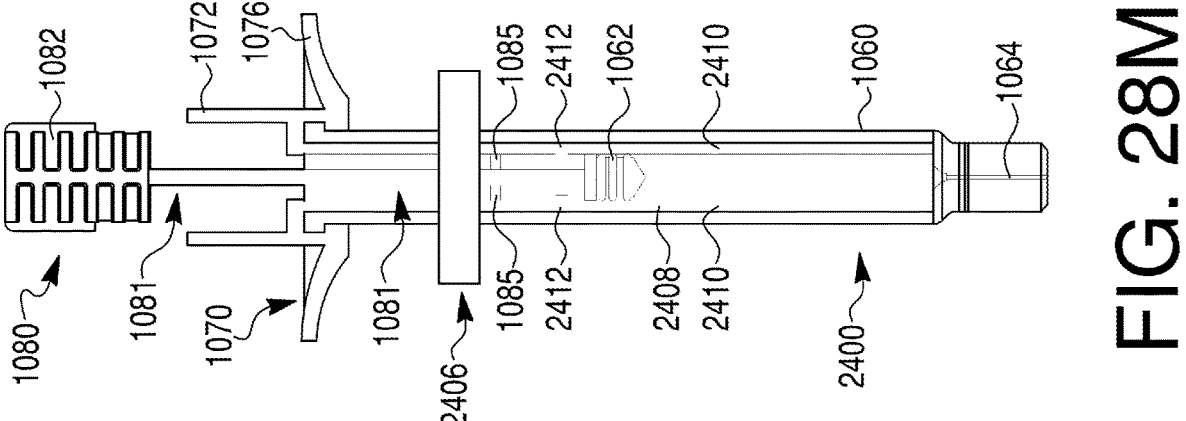

In further embodiments, delivery device 2400 may include a sleeve 2408 extending distally from flange piece 1070, as shown in FIG. 28M. Sleeve 2408 may be attached to a distal end of flange piece 1070 and/or be integral with flange piece 1070, thereby forming a unitary structure. Sleeve 2408 may be disposed within body 1060 and include a distal end 2410. Sleeve 2408 may define a lumen that is sized and shaped to receive stem 1081 when plunger rod 1080 is coupled to flange piece 1070. As described in further detail herein, sleeve 2408 may be configured to move within a lumen of body 1060 in response to flange piece 1070 translating along an exterior of body 1060.

Sleeve 2408 may further include a locking component, such as, for example, a second protrusion 2412 formed along an interior surface of sleeve 2408 such that second protrusion 2412 extends at least partially into the lumen defined by sleeve 2408. In the embodiment, second protrusion 2412 is positioned relatively proximal of distal end 2410. In other embodiments, sleeve 2408 may include various other suitable locking components in lieu of second protrusion 2412, such as, for example, an opening sized, shaped, and configured to receive protrusion 1085.

Referring specifically to FIG. 28M, protrusion 1085 may extend radially outward from stem 1081 and positioned proximally relative to second protrusion 2412 when plunger rod 1080 is received through flange piece 1070 and sleeve 2408. To prime delivery device 2400, plunger rod 1080 may be translated distally relative to flange piece 1070 and sleeve 2408 until protrusion 1085 contacts second protrusion 2412. It should be appreciated that an extent that plunger rod 1080 translates relative to sleeve 2408 may define a priming distance of delivery device 2400. The priming distance may be controlled based on a position of protrusion 1085 and second protrusion 2412 relative to one another.

With protrusion 1085 engaged against second protrusion 2412 and a distal end of actuation portion 1082 received against an inner surface of collar 1072, plunger rod 1080 may be coupled to sleeve 2408 and delivery device 2400 may be in a primed state, as shown in FIG. 28N. Actuation portion 1082 may be fully received within collar 1072 and stem 1081 may be locked onto sleeve 2408. Accordingly, further translation of plunger rod 1080 may provide translation of flange piece 1070 and sleeve 2408 relative to body 1060. For example, as seen in FIG. 28O, plunger rod 1080 and flange piece 1070 may be translated distally relative to body 1060 in response to applying a distally-directed force onto actuation portion 1082. Stem 1081 may move relative to body 1060, causing stopper 1062 to move within body 1060 to deliver a dose.

Distal end 2410 may translate toward expulsion end 1064 as plunger rod 1080 and flange piece 1070 move distally until encountering fixed clip 2406. It should be appreciated that an extent that plunger rod 1080 and flange piece 1070 translate may define a dosage delivery distance of delivery device 2400. The dosage delivery distance may be controlled based on a position of fixed clip 2406 along body 1060.

In other embodiments, as seen in FIGS. 28P-28Q, delivery device 2400 may include an obstruction and/or blocking component in the form of a pull tab 2420. Pull tab 2420 may include a body 2422 having a circular-cross section defining a center opening 2424. Body 2422 may be formed of various flexible materials, including, for example, plastic, rubber, and the like. As described in further detail herein, pull tab 2420 may be frangible and/or deformable in response to an application of force onto body 2422. Pull tab 2420 may further include a graspable feature 2426 extending outwardly from body 2422 and configured to facilitate manual actuation of pull tab 2420. As seen in FIG. 28P, graspable feature 2426 may be integrally formed with body 2422 such that applying a radially-outward force (e.g., a pulling force) onto graspable feature 2426 may cause body 2422 to deform (e.g., tear, break, etc.), as shown in FIG. 28Q.

Referring now to FIG. 28R, pull tab 2420 may be secured to flange piece 1070 along a proximal end of collar 1072. Pull tab 2420 may be disposed over collar 1072 such that flange piece 1070 is separated from actuation portion 1082 by pull tab 2420 positioned therebetween. Stem 1081 may be received through center opening 2424 and into collar 1072 when body 2422 is attached to collar 1072. Pull tab 2420 may be configured to inhibit translation of actuation portion 1082 into collar 1072. A thickness and/or width of body 2422 may be sized such that a diameter of center opening 2424 is smaller than a diameter of actuation portion 1082 to block actuation portion 1082 from passing through pull tab 2420.

Figure 28T:
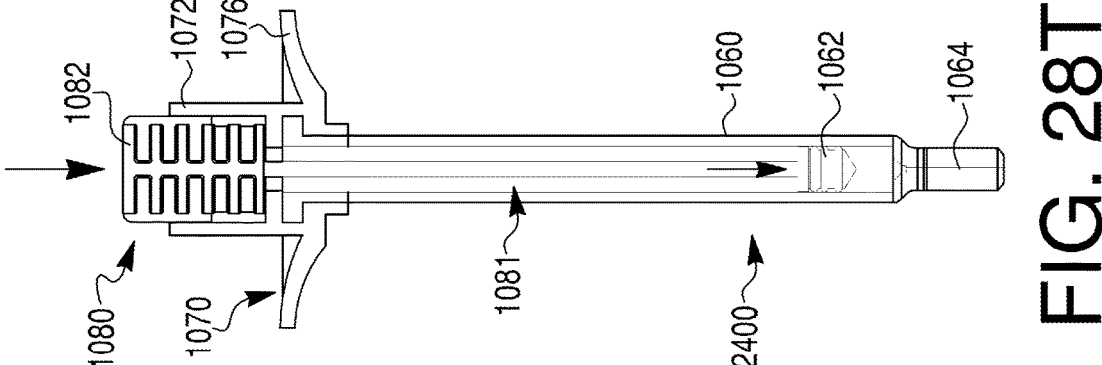
Figure 28S:
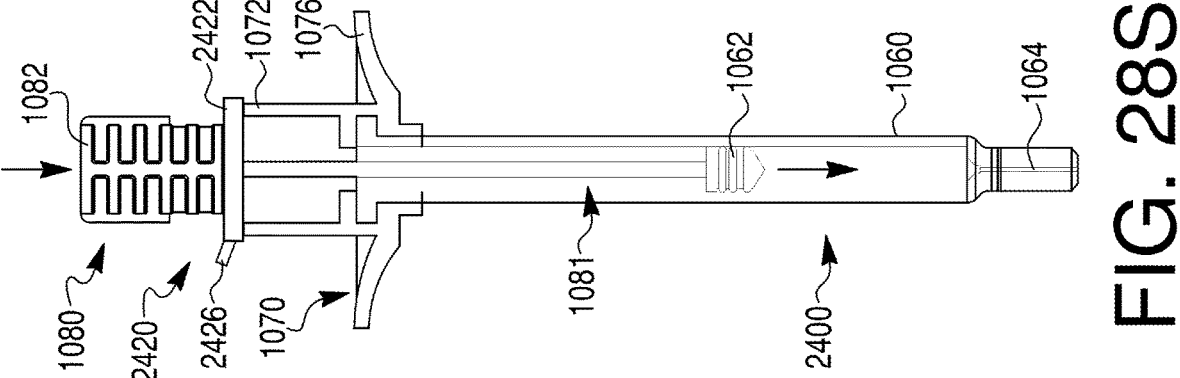

Delivery device 2400 may be primed in response to translating plunger rod 1080 distally relative to flange piece 1070 until encountering body 2422, as seen in FIG. 28S. It should be appreciated that an extent plunger rod 1080 translates relative to flange piece 1070 may correspond to a priming distance of delivery device 2400. The priming distance may be controlled based on a thickness of body 2422, thereby varying a relative distance between actuation portion 1082 and collar 1072. With actuation portion 1082 engaged against body 2422, graspable feature 2426 may be actuated to remove (e.g., break, tear, pull, etc.) pull tab 2420 from collar 1072. In this instance, body 2422 may be deformed (see FIG. 28Q) and disengaged from flange piece 1070, thereby permitting further translation of plunger rod 1080 distally relative to flange piece 1070.

As seen in FIG. 28T, actuation portion 1082 may be received within collar 1072 in response to applying a distally-directed force onto actuation portion 1082. Stem 1081 may move relative to body 1060, causing stopper 1062 to move within body 1060 to deliver a dose. It should be appreciated that an extent that plunger rod 1080 translates relative to collar 1072 may correspond to a dosage delivery distance of delivery device 2400. The dosage delivery distance may be controlled based on a thickness of pull tab 2420, thereby varying a relative distance between actuation portion 1082 and a distal (e.g., bottom) end of collar 1072.

In further embodiments, as shown in FIGS. 28U-28X, delivery device 2400 may include a removable cap 2430 coupled to plunger rod 1080. Removable cap 2430 may include a body 2432 defining a cavity 2434 that is sized and shaped to receive at least a portion of plunger rod 1080 therein (e.g., actuation portion 1082). Removable cap 2430 may include an opening along a bottom (e.g., distal) wall of body 2342 for receiving stem 1081. In some embodiments, removable cap 2430 may be attached to actuation portion 1082, while in other embodiments body 2342 may be directly coupled to stem 1081. Removable cap 2340 may be an obstruction and/or blocking component configured to increase a cross-sectional profile of actuation portion 1082 to inhibit movement of plunger rod 1080 relative to flange piece 1070, and more specifically to prevent translation of actuation portion 1082 into collar 1072.

Figures 28U, 28V, 28X:
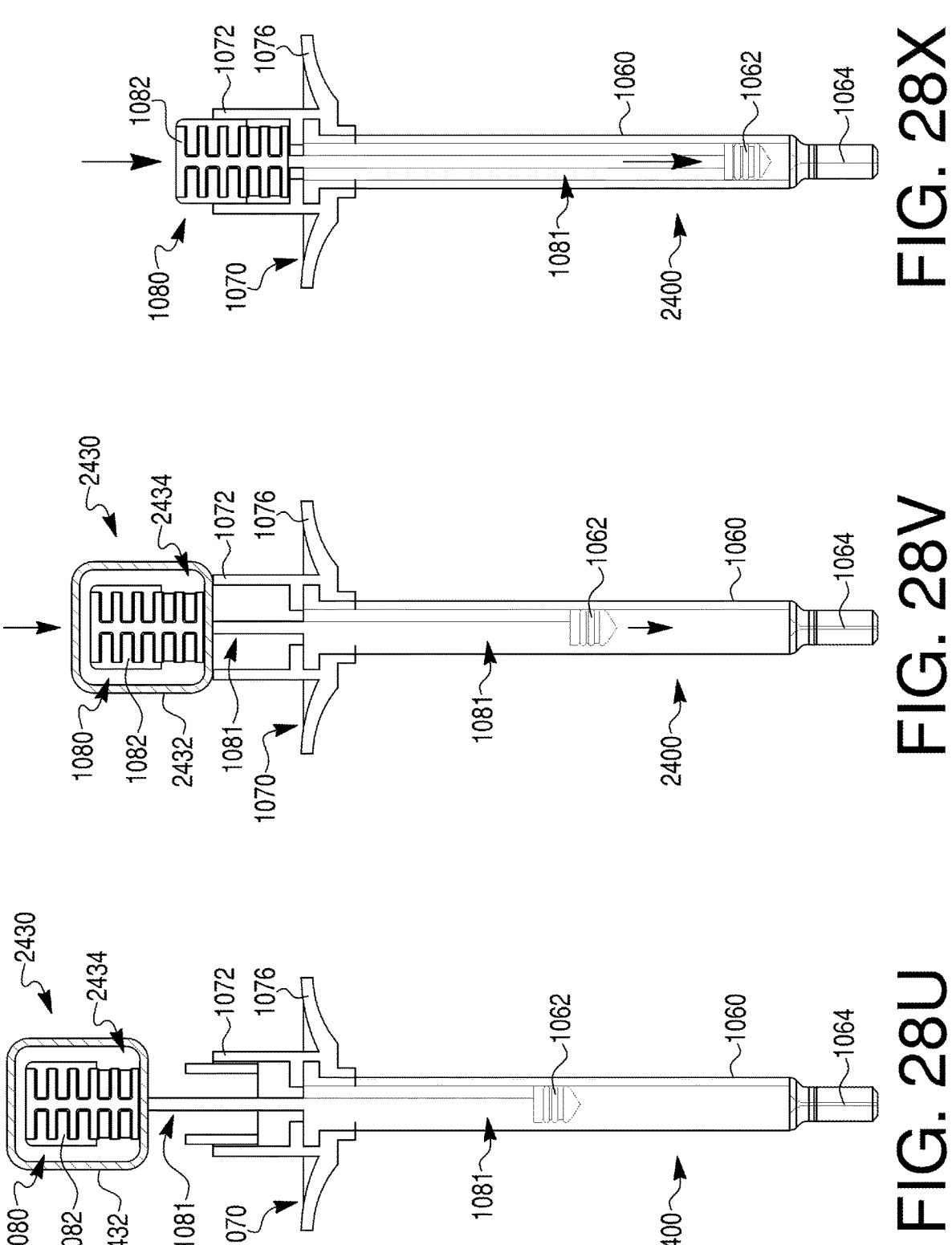

Referring now to FIG. 28V, plunger rod 1080 may be configured to translate distally relative to flange piece 1070 to prime delivery device 2400 until a bottom wall of body 2432 encounters a proximal end of collar 1072. Removable cap 2430 may inhibit actuation portion 1082 from being received within collar 1072 due to at least a portion of body 2342 being disposed between actuation portion 1082 and collar 1072. With plunger rod 1080 translated from a proximal position (FIG. 28U) to a distal position (FIG. 28V) with body 2432 engaged against collar 1072, delivery device 2400 may be in a primed position. It should be appreciated that an extent that plunger rod 1080 translates relative to flange piece 1070 may correspond to a priming distance of delivery device 2400. The priming distance may be controlled based on a size of removable cap 2430 and/or a position of removable cap 2430 relative to plunger rod 1080. For example, in other embodiments, a bottom wall of body 2432 may be secured to a proximal portion of stem 1081 positioned relatively distal of actuation portion 1082. In this instance, a priming distance of delivery device 2400 may be reduced relative to that shown and described herein as body 2432 may be positioned in closer proximity to collar 1072. Accordingly, plunger rod 1080 may be required to move a smaller distance for removable cap 2430 to encounter collar 1072.

As seen in FIG. 28X, removable cap 2430 may be detached from plunger rod 1080 such that actuation portion 1082 may be exposed from body 2432. Plunger rod 1080 may be translated distally relative to body 1060 and received within collar 1072 in response to applying a distally-directed force onto actuation portion 1082. Stem 1081 may move relative to flange piece 1070, causing stopper 1062 to move within body 1060 to deliver a dose. It should be appreciated that an extent that plunger rod 1080 translates relative to flange piece 1070 may correspond to a dosage delivery distance of delivery device 2400. The dosage delivery distance may be controlled based on an attachment of removable cap 2430 relative to actuation portion 1082 and/or stem 1081 as described above. Further, a depth of collar 1072 may be determinative of the dosage delivery distance such that a size of collar 1072 may be adjusted accordingly to form various suitable dosage delivery distances.

For example, attaching removable cap 2430 such that a distal wall of removable cap 2430 is positioned flush against a distal end of actuation portion 1082 may increase a relative priming distance of delivery device 2400 by providing a longer separation between removable cap 2430 and collar 1072. Accordingly, the attachment position of removable cap 2430 may correspond to a smaller dosage delivery distance upon translating actuation portion 1082 into collar 1072 after removal of removable cap 2420. Alternatively, attaching removable cap 2430 such that the distal wall of removable cap 2430 is positioned distally from the distal end of actuation portion 1082 may decrease a relative priming distance, thereby providing a greater dosage delivery distance as actuation portion 1082 may require further longitudinal translation to be fully received within collar 1072. It should be appreciated that a size and/or shape of removable cap 2430 may vary to accommodate the various attachment positions described above.

Figure 28Z:
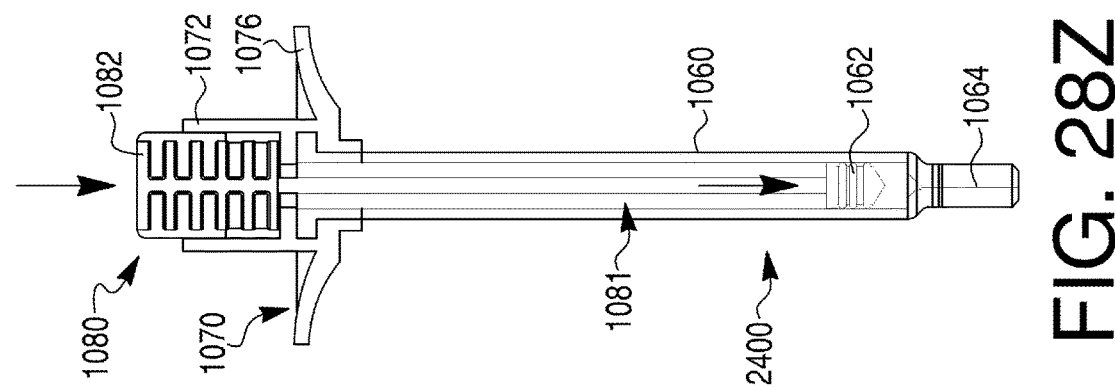

In some embodiments, as shown in FIGS. 28W-28Z, delivery device 2400 may include one or more tabs 2440 secured to plunger rod 1080, such as, for example, along actuation portion 1082, stem 1081, and/or various other portions of plunger rod 1080. In the example, delivery device 2400 includes a pair of tabs 2440 extending radially outward from a distal end of actuation portion 1082. Tabs 2440 may be an obstruction and/or blocking component configured to increase a cross-sectional profile of actuation portion 1082 to inhibit movement of plunger rod 1080 relative to flange piece 1070, and more specifically to inhibit translation of actuation portion 1082 into collar 1072. In some embodiments, tabs 2440 may be selectively removable from actuation portion 1082 upon an application of force thereto. In other embodiments, tabs 2440 may be compressible and configured to be pushed into actuation portion 1082 in response to an application of force thereto. In either instance, tabs 2440 may be configured to transition actuation portion 1082 from an expanded profile (FIGS. 28W-28Y) to a compressed profile (FIG. 28Z).

Figure 28Y:
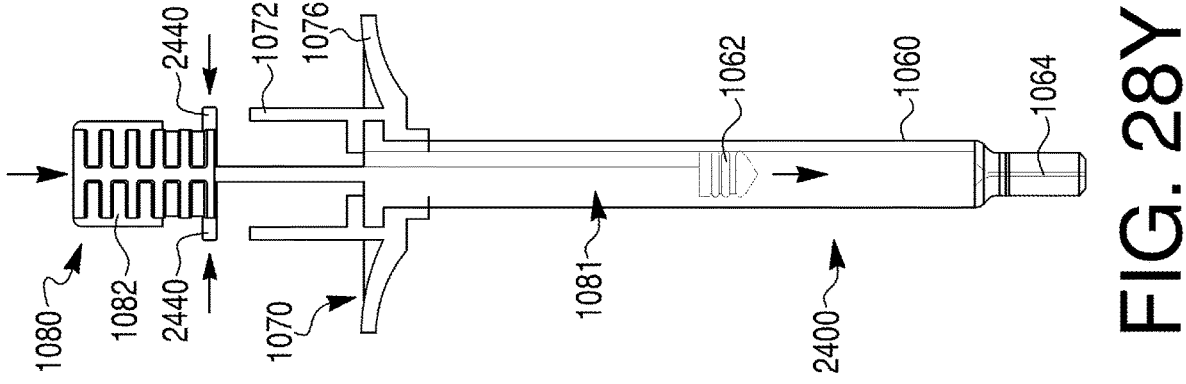
Figure 28W:
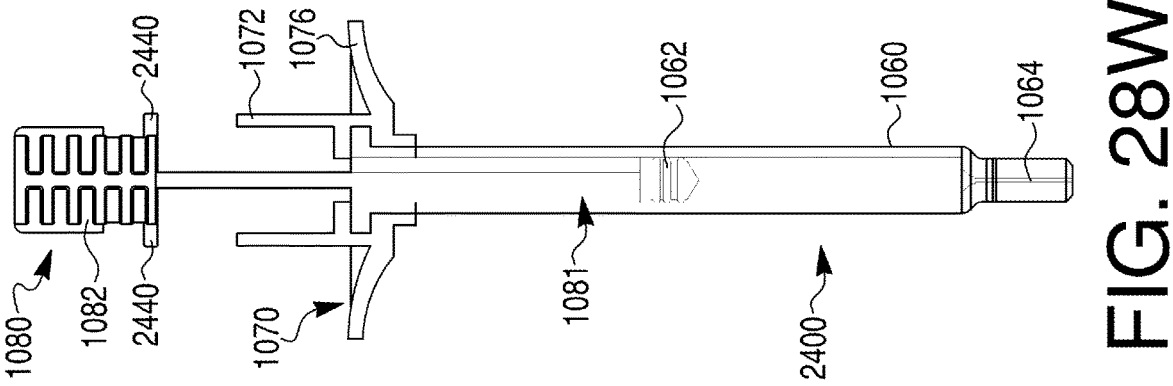

Referring now to FIG. 28Y, plunger rod 1080 may be configured to translate distally relative to flange piece 1070 to prime delivery device 2400 until tabs 2440 encounter a proximal end of collar 1072. Tabs 2440 may inhibit collar 1072 receiving actuation portion 1082 therein. With plunger rod 1080 translated from a proximal position (FIG. 28W) to a distal position (FIG. 28Y) with tabs 2440 engaged against collar 1072, delivery device 2400 may be in a primed position. It should be appreciated that an extent that plunger rod 1080 translates relative to flange piece 1070 may correspond to a priming distance of delivery device 2400.

The priming distance may be controlled based on a size (e.g., thickness, width, height, etc.) of tabs 2440 and/or a position of tabs 2440 relative to plunger rod 1080. For example, in other embodiments, the pair of tabs 2440 may be secured to an intermediate and/or proximal portion of actuation portion 1082, or alternatively along stem 1081. In this instance, a priming distance of delivery device 2400 may be increased and/or decreased, respectively, relative to that shown and described herein.

As seen in FIG. 28Z, tabs 2440 may be compressed into actuation portion 1082 by collar 1072 applying an inward, pushing force thereto (or alternatively decoupled from actuation portion 1082 by applying an outward, pulling force, a rotating snapping force, or the like) such that actuation portion 1082 may form a smaller cross-sectional profile. Plunger rod 1080 may be translated distally relative to body 1060 and received within collar 1072 in response to applying a distally-directed force onto actuation portion 1082. Stem 1081 may move relative to flange piece 1070, causing stopper 1062 to move within body 1060 to deliver a dose. It should be appreciated that an extent that plunger rod 1080 translates relative to flange piece 1070 may correspond to a dosage delivery distance of delivery device 2400. As described above, the dosage delivery distance may be controlled based on a position of tabs 2440 relative to actuation portion 1082, a size (e.g., longitudinal depth) of collar 1072, and the like. For example, a relative position of tabs 2440 that increases a priming distance of delivery device 2400 may correspond to a smaller dosage delivery distance, and a position of tabs 2440 that corresponds to a reduced priming distance may provide a greater dosage delivery distance. In other examples, plunger rod 1080 may include a second set of tabs (not shown) along actuation portion 1082 which may define a dosage delivery distance based on a relative position of the tabs relative to tabs 2440.

Figures 29A, 29B, 29C:
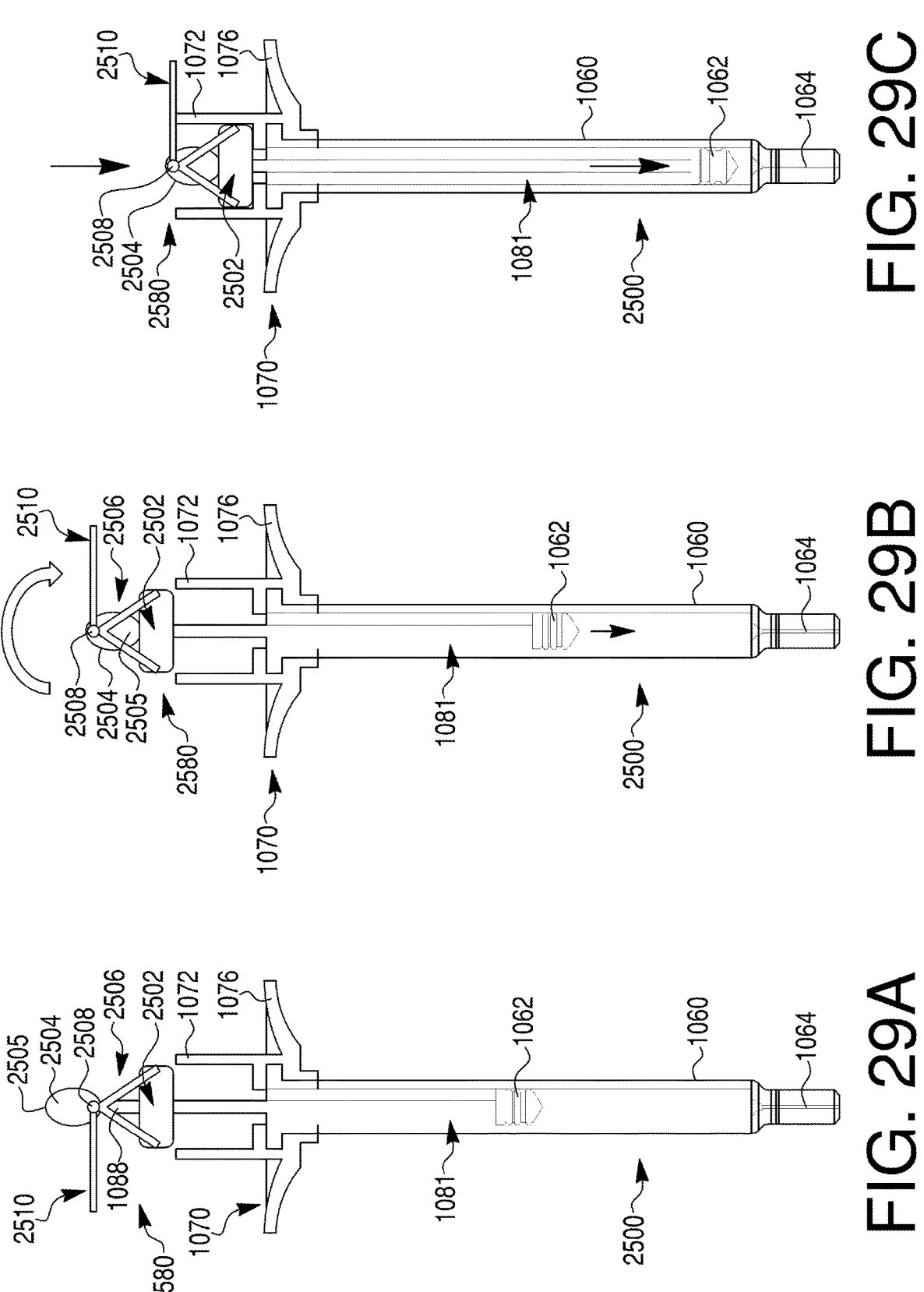
FIGS. 29A-29C depict a further exemplary delivery device and method of using said delivery device, according to aspects of the present disclosure.

FIGS. 29A-29C depict an exemplary delivery device 2500 and method of using delivery device 2500. Delivery device 2500 may include substantially similar features as those shown and described above such that like reference numerals are used to identify like components. As shown in FIG. 29A, delivery device 2500 may include a plunger rod 2580 comprising a first actuation portion 2502, a second actuation portion 2504, and a cam lever 2510. First actuation portion 2502 may be coupled to second actuation portion 2504 by one or more arms 2506. In the example, a pair of arms 2506 may be fixed to first actuation portion 2502 along a first end of arms 2506, and arms 2506 may be further coupled to second actuation portion 2504 at a second end of arms 2506 that is opposite of the first end. Second actuation portion 2504 may be a rotatable element including a proximal end 2505 and an opposing distal end having a joint 2508. The pair of arms 2506 may be coupled to the distal end of second actuation portion 2504 at joint 2508.

It should be understood that, when in a ready position as seen in FIG. 29A, second actuation portion 2504 may be oriented such that joint 2508 is positioned proximate to first actuation portion 2502 relative to proximal end 2505. A proximal end 1088 of stem 1081 may be positioned adjacent to joint 2508 at a distal end of second actuation portion 2504. For example, proximal end 1088 may be in contact with and/or abut against the distal end of second actuation portion 2504. In some embodiments, stem 1081 may extend through a center of first actuation portion 2502 and/or be positioned alongside first actuation portion 2502. Second actuation portion 2504 may be configured to move relative to first actuation portion 2502 and about joint 2508. Cam lever 2510 may be coupled to second actuation portion 2504 at joint 2508 and configured to move (e.g., rotate, pivot, translate, etc.) second actuation portion 2504 relative to first actuation portion 2502. Accordingly, it should be appreciated that second actuation portion 2504 may be configured to move stem 1081 relative to body 1060 in response to cam lever 2510 moving second actuation portion 2504 relative to first actuation portion 2502.

For example, referring to FIG. 29A, cam lever 2510 may be actuated by rotating cam lever 2510 about joint 2508, thereby causing second actuation portion 2504 to rotate about joint 2508. Proximal end 2505 may be moved toward first actuation portion 2502 in response to second actuation portion 2504 rotating about joint 2508. In this instance, proximal end 2505 may be moved toward first actuation portion 2502. With proximal end 2505 moved from a proximal position (FIG. 29A) to a distal position (FIG. 29B), proximal end 1088 may be pushed distally, thereby translating stem 1081 relative to body 1060 to prime delivery device 2500. Stated differently, rotation of cam lever 2510 and/or second actuation portion 2504 relative to first actuation portion 2502 may prime delivery device 2500 by forcing stem 1081 distally.

It should be appreciated that a travel length of proximal end 2505 toward first actuation portion 2502 may correspond to a priming distance of delivery device 2500. In other words, a priming distance of delivery device 2500 may be controlled by a longitudinal length of second actuation portion 2504 between proximal end 2505 and joint 2508. In some embodiments, first actuation portion 2502, arms 2506, and/or cam lever 2510 may be to inhibit further rotation of second actuation portion 2504 after plunger rod 2580 is moved from the ready position (FIG. 29A) to the primed position (FIG. 29B).

As seen in FIG. 29C, plunger rod 2580 may be translated distally relative to body 1060 in response to applying a distally-directed force onto first actuation portion 2502 and second actuation portion 2504. In this instance, cam lever 2510 may be depressed (e.g., pushed and/or pulled) distally to move first actuation portion 2502 and second actuation portion 2504 toward flange piece 1070 until encountering a proximal end of collar 1072. Stem 1081 may move relative to collar 1072 thereby causing stopper 1062 to move within body 1060 to deliver a dose. It should be appreciated that an extent of translation of plunger rod 2580 relative to flange piece 1070 may correspond to a dosage delivery distance of delivery device 2500. The dosage delivery distance may be controlled based on a gap formed between collar 1072 and cam lever 2510.

Figure 31:
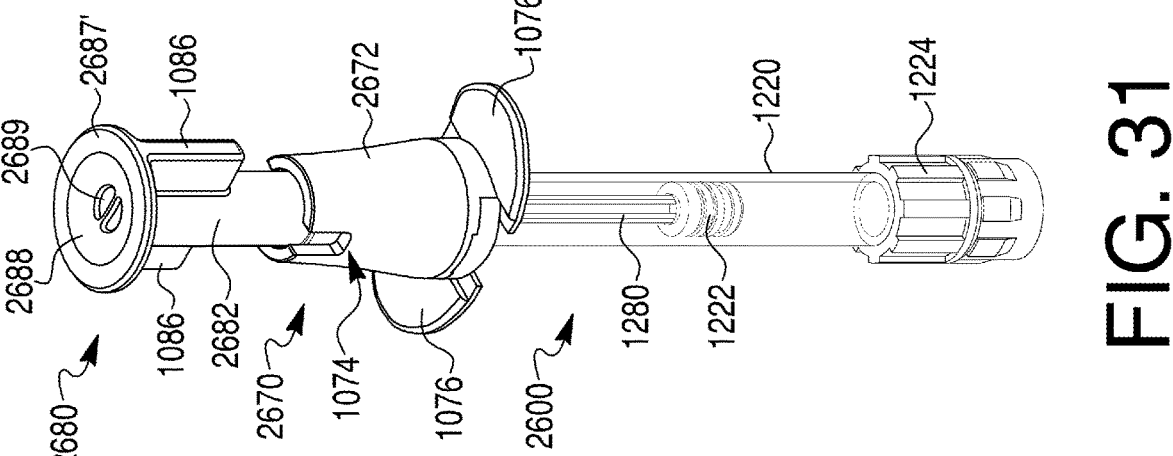
FIGS. 30-31 depict a further exemplary delivery device and method of using said delivery device, according to aspects of the present disclosure.
Figure 30:
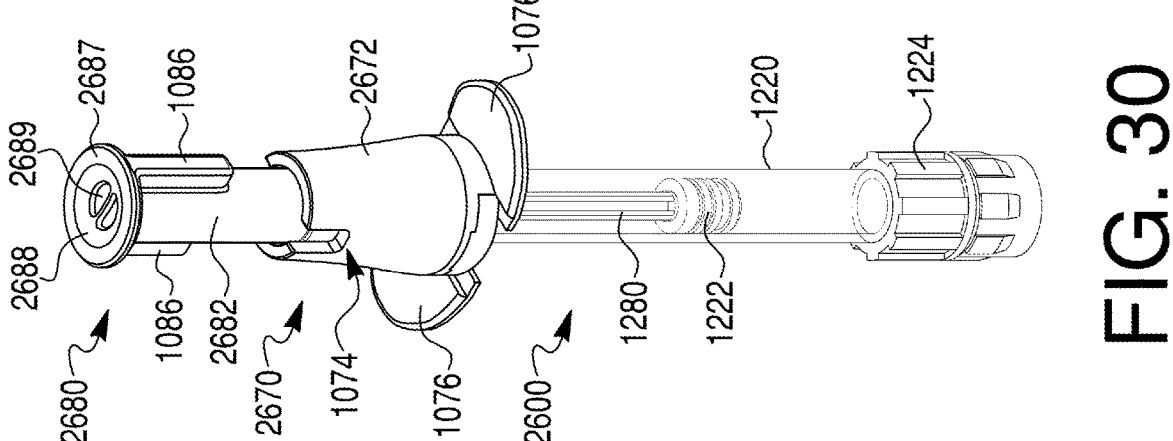

FIGS. 30-31 depict an exemplary delivery device 2600 that may include substantially similar features as those shown and described above such that like reference numerals are used to identify like components. Delivery device 2600 may include a flange piece 2670, a plunger rod 2680, and body 1220. Flange piece 2670 may include a tapered collar 2672 having a varying size and/or shape between a distal end and a proximal end. In the example, tapered collar 2672 may have a greater cross-sectional profile (e.g., diameter) along a distal end adjacent to flanges 1076 than at a proximal end adjacent to slots 1074. Tapered collar 2672 may be configured to minimize an overall profile and/or weight of delivery device 2600 by minimizing a configuration of flange piece 2670. In some embodiments, flanges 1076 may have a reduced length to facilitate enhanced control and maneuverability of flange piece 2670.

Plunger rod 2680 may include an actuation portion 2682 having a cross-sectional profile (e.g., diameter) that is relatively smaller than tapered collar 2672 to facilitate receipt of actuation portion 2682 therethrough. Accordingly, actuation portion 2682 may be similarly configured to minimize an overall profile and/or weight of delivery device 2600 by minimizing a configuration of actuation portion 2682. Further, plunger rod 2680 may omit inclusion of a textured and/or ribbed surface along actuation portion 2682 to simplify an exterior appearance of plunger rod 2680.

Referring specifically to FIG. 30, actuation portion 2682 may further include a proximal end having an outer ring 2687, an inner surface 2688, and one or more openings 2689 formed through inner surface 2688. In the example, inner surface 2688 may be disposed within outer ring 2687 and may have an angled profile that is sloped radially-inward toward the one or more openings 2689. Inner surface 2688 may be configured to define an interface for actuating plunger rod 2680 (e.g., applying a distally-directed force onto actuation portion 2682 by a finger of a user). Although plunger rod 2680 is shown as including a pair of openings 2689, it should be appreciated that in other embodiments additional and/or fewer openings 2689 may be included on inner surface 2688.

In some embodiments, as seen in FIG. 31, plunger rod 2680 may include an outer ring 2687' having a width that defines an outer surface disposed about inner surface 2688. For example, an outer surface of outer ring 2687' may be angled inwardly toward inner surface 2688 and openings 2689 and/or be transverse relative to inner surface 2688. In the present example, outer ring 2687' defines a planar outer surface that is substantially perpendicular to a longitudinal length of actuation portion 2682. The enhanced width of outer ring 2687' may provide additional surface area for a user of device 1050 to contact when actuating plunger rod 2680. It should be appreciated that a width of outer ring 2687' may be greater and/or less than that shown and described herein without departing from a scope of this disclosure.

Figure 33:
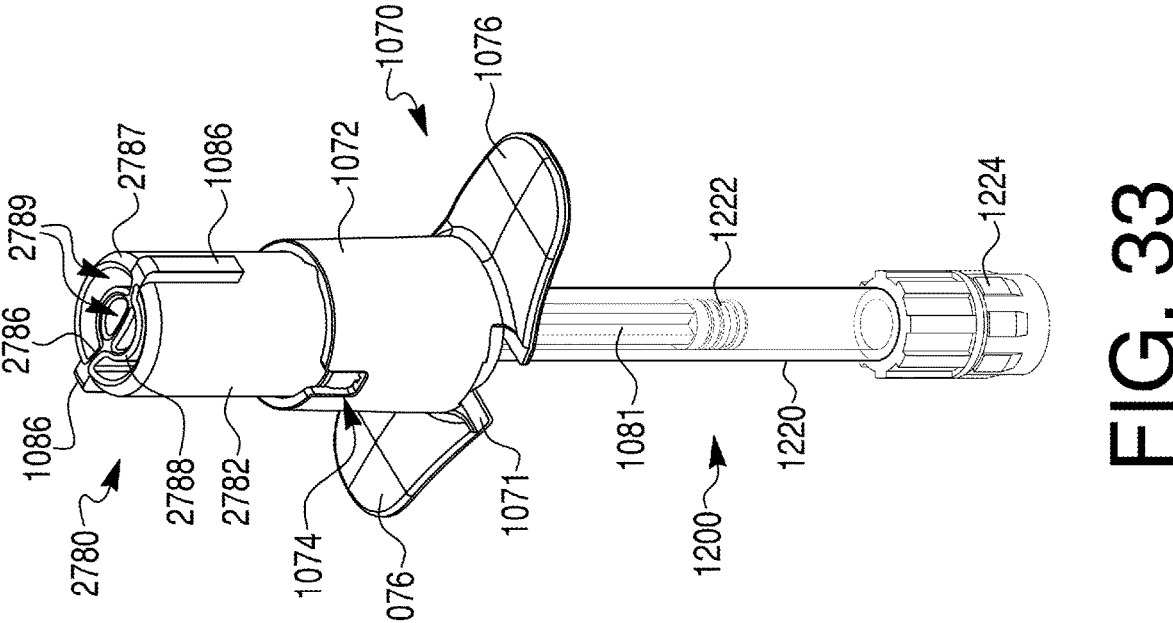
FIGS. 32-33 depict a further exemplary delivery device and method of using said delivery device, according to aspects of the present disclosure.
Figure 32:
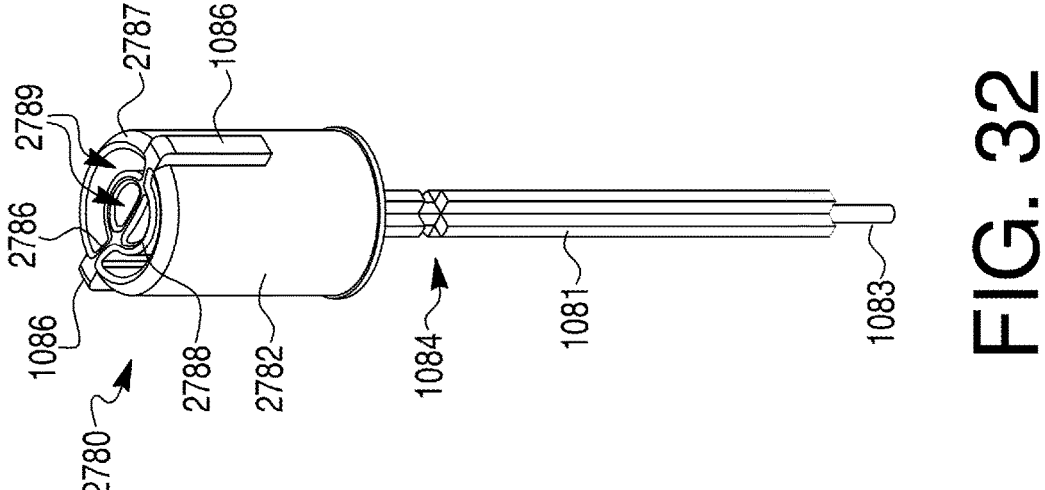

FIGS. 32-33 depict an exemplary plunger rod 2780 that may include substantially similar features as plunger rod 1080 shown and described above such that like reference numerals are used to identify like components. Plunger rod 2780 may include an actuation portion 2782 having a proximal end defined by an outer ring 2787, an inner ring 2788, and one or more openings 2789. In the example, inner ring 2788 may be disposed within outer ring 2787 and may define at least one opening 2789. Outer ring 2787 may further define at least one opening 2789 positioned radially outward of inner ring 2788. One or more of openings 2789 may minimize an overall weight of plunger rod 2780, enhance a molding manufacturing ability of plunger rod 2780 by providing nominal wall thicknesses for actuation portion 2782, and more. Additionally, actuation portion 2782 may include a lateral ledge 2786 extending across a width of the distal end and aligned with protrusions 1086. Lateral edge 2786 may bifurcate the one or more openings 2789 defined by outer ring 2787 and inner ring 2788. Lateral edge 2786 may be collinear with protrusions 1086 to provide visual alignment and/or identification of protrusions 1086 to a user of plunger rod 2780.

As seen in FIG. 33, with plunger rod 2780 received within flange piece 1070 and body 1220, lateral edge 2786 may be configured to enhance an identification of movement by plunger rod 2780 relative to flange piece 1070 from a perspective proximal of device 1200. For example, lateral ledge 2786 may facilitate identifying a relative position of protrusions 1086 to slots 1074 from a perspective proximal to actuation portion 2782 during use of device 1200. In some embodiments, plunger rod 2780 may omit a textured and/or ribbed surface along actuation portion 2782 to simplify an exterior appearance of plunger rod 2780.

Figures 34, 35:
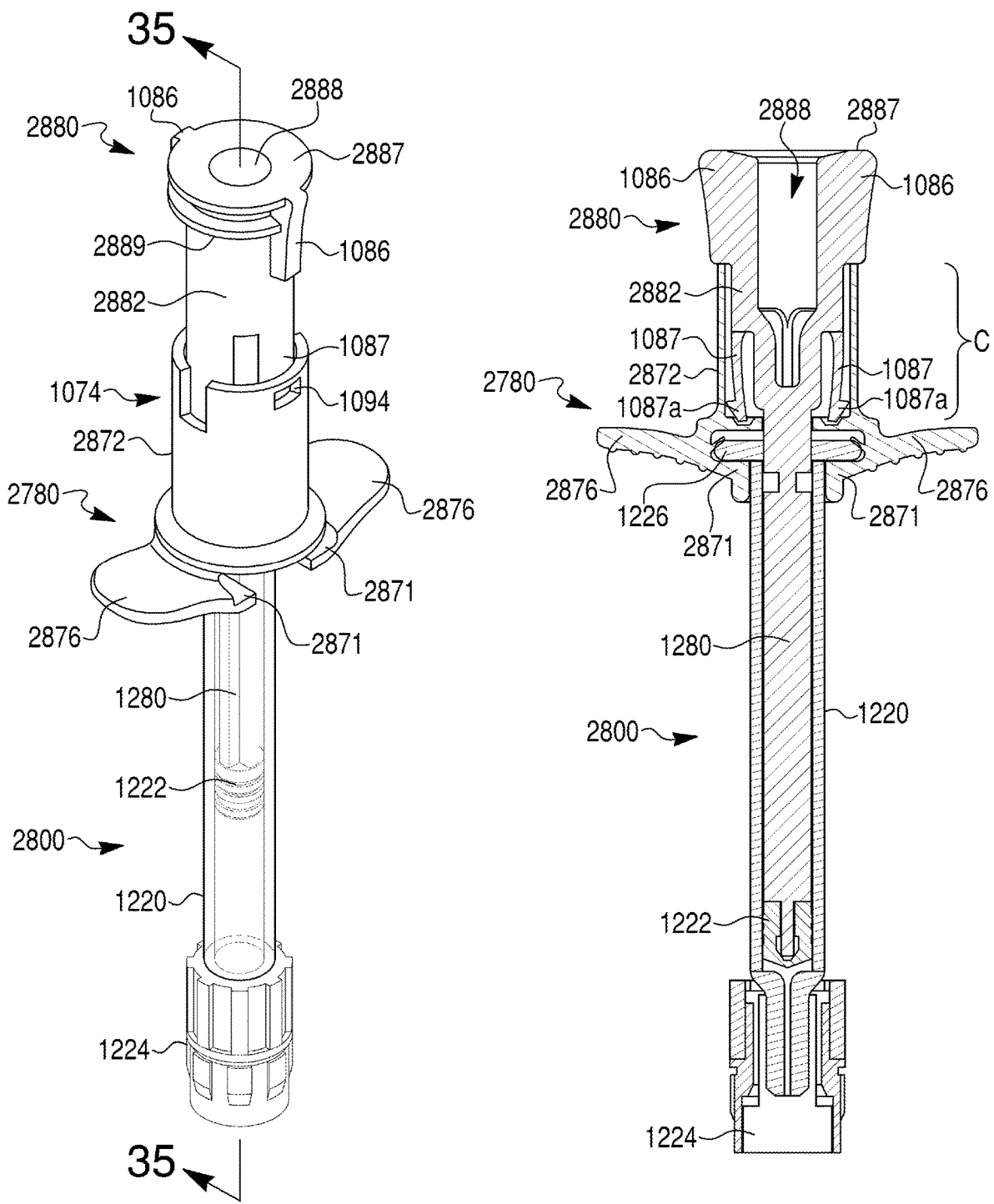

FIG. 34 depicts another exemplary delivery device 2800 in accordance with an example of this disclosure. Delivery device 2800 may include substantially similar features as delivery device 1050 and delivery device 1200 shown and described above such that like reference numerals are used to identify like components. Delivery device 2800 may include a flange piece 2870, a plunger rod 2880, and body 1220. Flange piece 2870 may have a collar 2872 and a pair of flanges 2876 extending laterally outward from collar 2872. Collar 2872 may have a narrowed profile, such as, for example, relative to collar 1072. Additionally, flanges 2876 may have a shortened length relative to flanges 1076. Accordingly, flange piece 2870 of the present example may generally have a narrowed profile. Flange piece 2870 may further include a lip 2871 that may slide under or otherwise receive body flange 1226 (FIG. 35). Lip 2871 may be configured to hold flange piece 2870 in place by slidably coupling flange piece 2870 to body 1220. As described in further detail below, lip 2871 may be made of a flexible or semi-flexible material capable of forming a snap-fit connection with body flange 1226.

Plunger rod 2880 may include an actuation portion 2882 having one or more protrusions 1086 along a proximal end and one or more extensions 1087 along a distal end. Actuation portion 2882 may have a diameter that is generally smaller than actuation portion 1082 shown and described above. Accordingly, it should be appreciated that plunger rod 2880 and flange piece 2870 may collectively form a narrowed profile relative to an assembly of plunger rod 1080 and flange piece 1070. By providing a reduced profile, delivery device 2800 may be configured to provide a user enhanced control and maneuverability of plunger rod 2880 and flange piece 2870 during use of delivery device 2800.

In the embodiment, protrusions 1086 may have a curvature configured to enhance a grip, comfort, and/or ergonomics of plunger rod 2880 for a user of delivery device 2800. A curvature of protrusions 1086 may have a concave exterior configuration that taper inwardly along a distal portion of protrusions. A proximal end of actuation portion 2882 may further include a first ring 2887, an opening 2888, and a second ring 2889 positioned distally relative to first ring 2887. First ring 2887 may define a proximal interface of actuation portion 2882 and opening 2888 may be positioned at a center of first ring 2887. The proximal interface defined by first ring 2887 may be angled toward opening 2888 such that a proximal end of actuation portion 2882 may be sloped radially inward. In some embodiments, first ring 2887 may be sized, shaped, and configured to facilitate actuation of plunger rod 2880 by defining a finger pad for receiving a finger of a user. Opening 2888 may be configured to maintain a nominal wall thickness of actuation portion 2882 to facilitate molding of plunger rod 2880 during a manufacturing process of delivery device 2800. Openings 2888 may further minimize an overall weight of plunger rod 2880.

Still referring to FIG. 34, second ring 2889 may extend radially outward from an exterior surface of actuation portion 2882 and is positioned adjacent to first ring 2887. Second ring 2889 may be configured to form a graspable feature along actuation portion 2882 to enhance control of plunger rod 2880, such as, for example, when rotating plunger rod 2880. First ring 2887 may have a greater diameter than actuation portion 2882 such that the finger pad formed by first ring 2887 may have a greater cross-sectional profile than actuation portion 2882. In some embodiments, second ring 2889 may include a diameter greater than actuation portion 2882 and substantially similar to first ring 2887. Plunger rod 2880 may omit inclusion of a textured and/or ribbed surface along actuation portion 2882 to simplify an appearance of plunger rod 2880.

As seen in FIG. 35, actuation portion 2882 may be sized to have a predetermined length C between a distal end of protrusion 1086 and hook or clip shaped part 1087a of extensions 1087. In some embodiments, predetermined length C may be sized in accordance with a type and/or size of a syringe cap used with delivery device 2800 (e.g., Ompi Alba ITC, Ompi Alba OVS, Gerresheimer TELC, silicone-free syringes, etc.). For example, predetermined length C may be decreased and/or increased according to a lower and/or higher fill volume requirement, respectively, determined based on the syringe cap. Further, predetermined length C may be sized to provide a complete stroke of plunger rod 2880 into flange piece 2870 to ensure a complete dosage is delivered by delivery device 2800. The predetermined length C may be further adjusted to provide one of a plurality of suitable dosage delivery distances for delivery device 2800. Flange piece 2870 may include additional features and/or components configured to allow for a complete stroke of plunger rod 2880.

Figure 36:
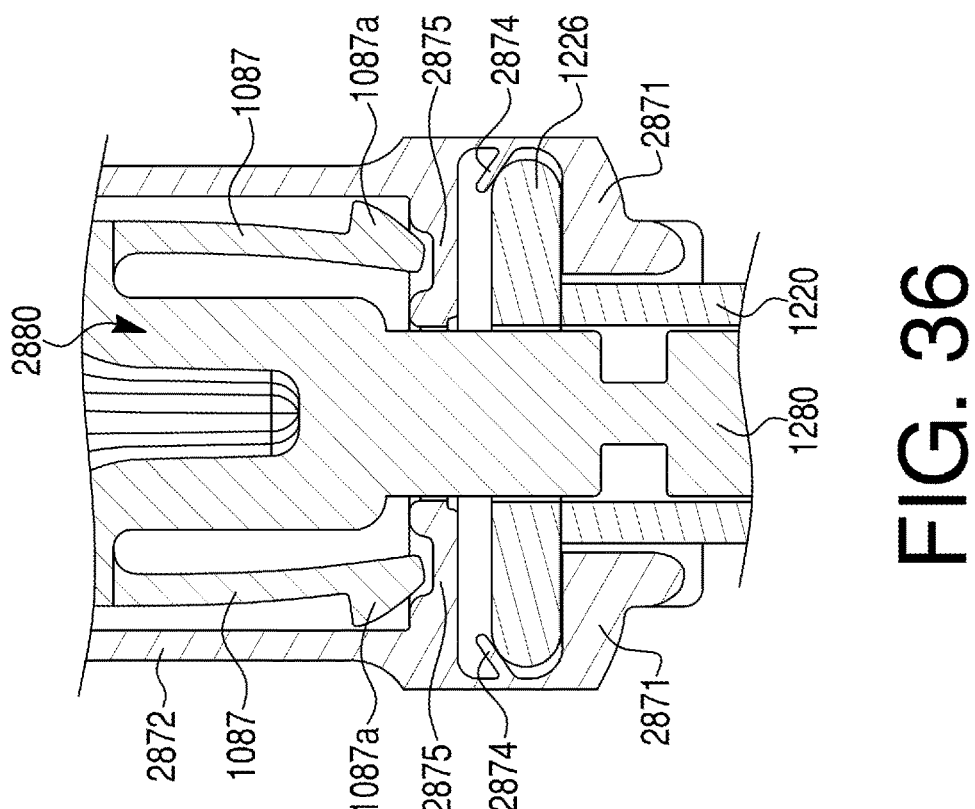

For example, referring now to FIG. 36, flange piece 2870 may include one or more indents 2875 formed along a proximally-facing and distally-located (bottom) surface of collar 2872. Indent 2875 may be sized and/or shaped to form a recessed surface into the bottom surface of collar 2872. Indent 2875 may be configured to facilitate receipt of plunger rod 2880 into flange piece 2870 to allow for a complete stroke. Stated differently, indent 2875 may provide an increased space and/or clearance within collar 2872 to receive one or more components of plunger rod 2880, such as, for example, hook or clip shaped part 1087a of extensions 1087.

In the present example, delivery device 2800 may be configured to deliver a complete dose upon the pair of protrusions 1086 contacting a distal end (the bottom) of slots 1074. The pair of extensions 1087 may be positioned adjacent to (but not in contact with) a bottom surface of collar 2872 when protrusions 1086 contact the distal end of slots 1074. That is, in some embodiments, extensions 1087 may positioned proximal to the bottom surface of collar 2872 such that extensions 1087 do not contact the bottom surface when plunger rod 2880 has bottomed out and/or when a complete dose has been delivered from delivery device 2800. By forming a depression along the bottom surface of collar 2872, indent 2875 may allow actuation portion 2882 to translate distally relative to collar 2872 to complete a full stroke of plunger rod 2880 without extensions 1087 engaging or contacting the bottom surface of collar 2872. In some embodiments, extensions 1087 may bend inwardly toward indent 2875 upon hook or clip shaped parts 1087a encountering the bottom surface of collar 2872, thereby guiding hook or clip shaped parts 1087a into indent 2875. It should be appreciated that an increased space formed by indent 2875 may ensure extensions 1087 are not prevented from contacting the bottom surface of collar 2872 to complete the full stroke of plunger rod 2880 and/or to deliver a complete dose.

Still referring to FIG. 36, flange piece 2870 may further include one or more ribs 2874 configured to engage body flange 1226 when body 1220 is coupled to flange piece 2870. The one or more ribs 2874 may be positioned adjacent to lip 2871, such as, for example, distally of the bottom surface of collar 2872 and proximally of lip 2871. In some embodiments, ribs 2874 may extend radially inward from an inner sidewall of flange piece 2870, while in other embodiments ribs 2874 may extend outwardly from an inner top wall of flange piece 2870. In the present example, ribs 2874 may extend radially inward at an angle relative to the inner sidewall of flange piece 2870. It should be appreciated that ribs 2874 may be positioned and/or extend from various other suitable locations, and at various other suitable angles, within flange piece 2870 for engaging body flange 1226.

In the embodiment, ribs 2876 may be formed of a flexible and/or semi-flexible material (e.g., plastic, rubber, etc.) and configured to interact with body flange 1226 upon receipt of body 1220 within flange piece 2870. By way of illustrative example, ribs 2874 may be configured to flex and/or bend proximally toward a bottom surface of collar 2872 in response to lip 2871 receiving body flange 1226. Ribs 2874 may be operable to secure body flange 1226 to flange piece 2870 by applying a distally-directed force thereto. Accordingly, ribs 2874 may secure a position (e.g., longitudinal, rotational, etc.) of body 1220 relative to flange piece 2870 by engaging a top/proximal surface of body flange 1226 as lip 2871 engages a bottom surface of body flange 1226. In other embodiments, additional and/or fewer ribs 2874 may be included for inhibiting movement of body flange 1226 and/or body 1220 relative to flange piece 2870.

Figure 37:
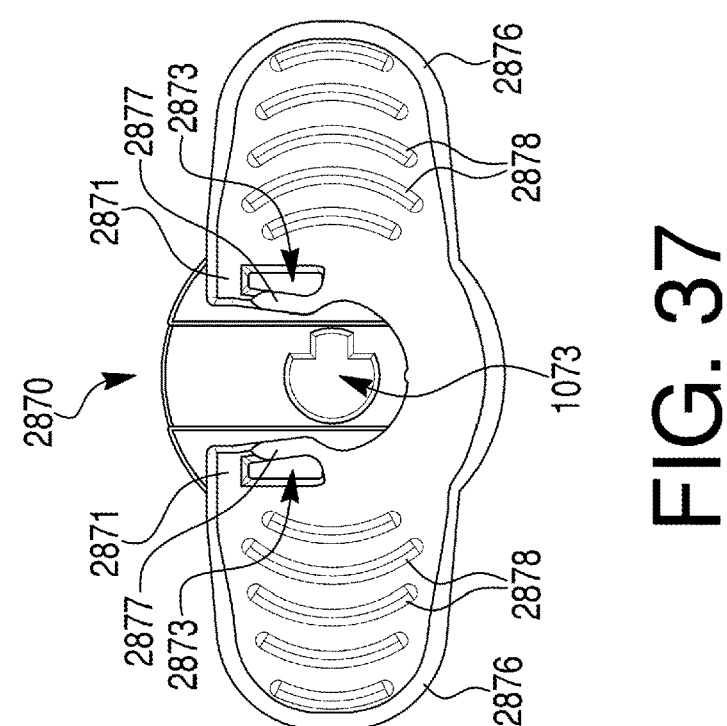

Referring now to FIG. 37, flange piece 2870 may include a textured and/or patterned interface 2878 along a bottom, distally-facing surface of flanges 2876. Textured interface 2878 may include one or more protrusions, depressions, and/or various other features forming at least one of a plurality of patterns to enhance a grip, control, and/or ergonomics of flange piece 2870. In the example, textured interface 2878 includes a plurality of semi-circular protrusions of varying sizes. As shown in FIG. 37, each interface 2878 may be concave when viewed from a radial center of flange 2876. However, in alternate embodiments, one or more interface 2878 may be convex when viewed from the radial center of flange 2876. As described in further detail below, textured interface 2878 may include various other designs, features, and/or patterns along the bottom surface (see FIGS. 41A-41D) of flanges 2876. Flange piece 2870 may further include a pair of movable tabs 2877 positioned adjacent to lip 2871 and along opposing sides of opening 1073. Movable tabs 2877 may be formed of a flexible and/or semi-flexible material and may be configured to move relative to collar 2872 and/or flanges 2876 in response to a force being applied thereto (e.g., by body 1220).

Each movable tab 2877 may define an opening 2873 disposed between movable tab 2877 and flange 2876. Accordingly, movable tabs 2877 may be separated from flanges 2876 by opening 2873 formed therebetween. Openings 2873 may provide a gap and/or clearance space to accommodate lateral movement of movable tabs 2877 upon receiving a radially-outward directed force. For example, movable tabs 2877 may be deflected radially outward toward flanges 2876 in response to flange piece 2870 receiving body 1220 through opening 1073, thereby changing a size and/or shape of openings 2873. In this instance, movable tabs 2877 may bend outwardly away from opening 1073 until body flange 1226 is received by lip 2871. Movable tabs 2877 may be configured to bend inwardly toward body 1220 to return to an original configuration upon lip 2871 fully receiving body flange 1226 therein. In some embodiments, movable tabs 2877 may bend toward body 1220 to a substantially originally configuration such that movable tabs 2877 may remain at least partially compressed against body 1220 to inhibit movement of body 1220 relative to flange piece 2870 to allow pressure to be continually applied onto body 1220 to prevent slippage.

Still referring to FIG. 37, movable tabs 2877 may be configured to apply a radially-inward directed force onto body 1220 (e.g., with a radially-inward directed material bias), thereby forming a snap-fit connection between flange piece 2870 and body 1220. Additionally, movable tabs 2877 may maintain body 1220 in a stabilized and fixed position relative to flange piece 2870, thereby coupling flange piece 2870 to body 1220. It should be appreciated that openings 2873 may be included between movable tabs 2877 and flanges 2876 to decrease a required force to couple body 1200 to flange piece 2870. For example, openings 2873 may be operable to reduce a force necessary to snap body 1200 into flange piece 2870 by a minimum force ranging from about 15 Newton to about 25 Newton, compared to a design omitting openings 2873.

Figure 38B:
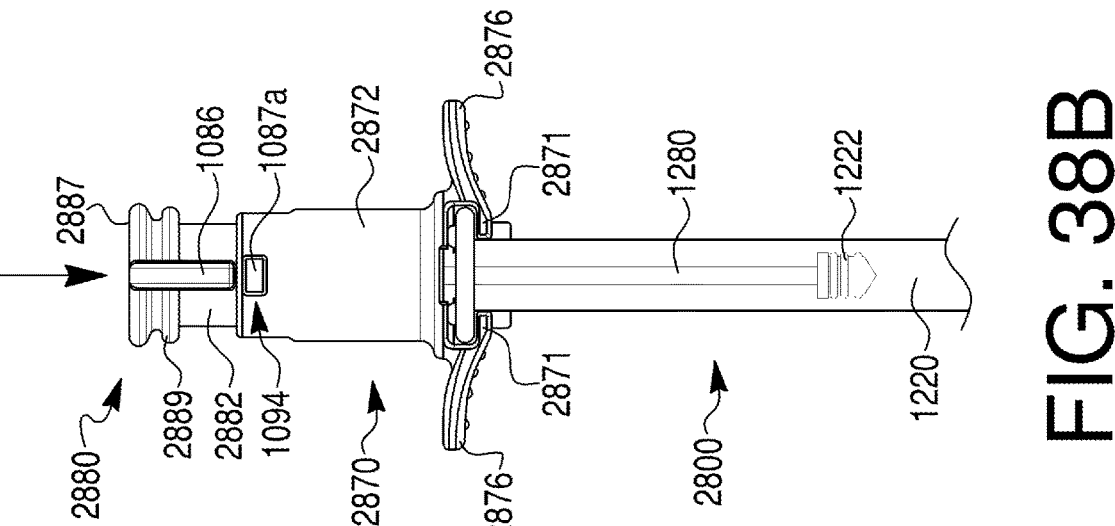
Figure 38A:
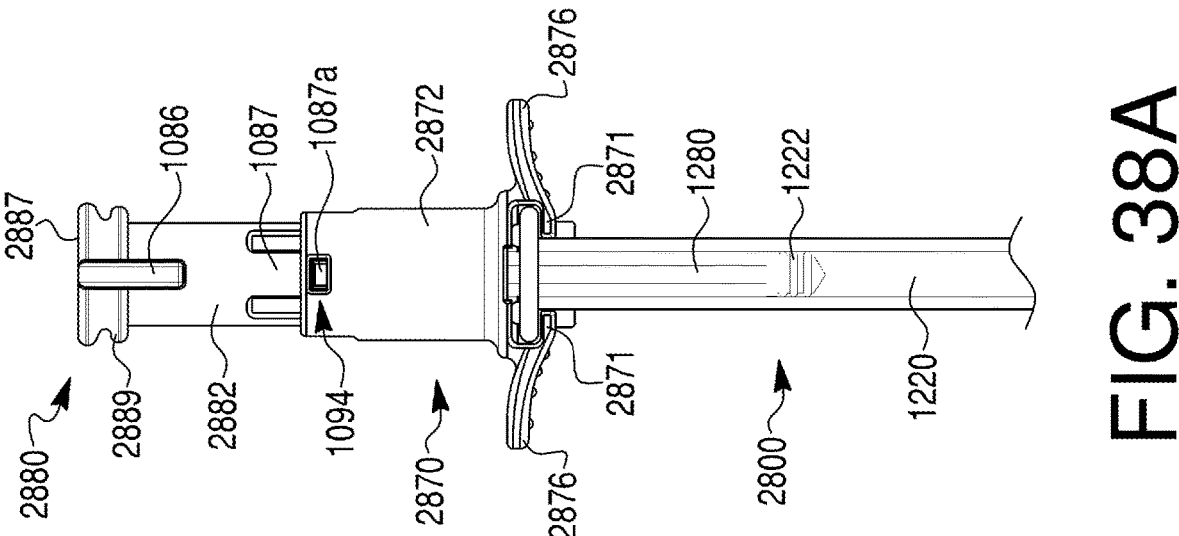

FIGS. 38A-40C show an illustrative method of using delivery device 2800. As seen in FIG. 38A, delivery device 2800 may be preassembled with a distal portion of actuation portion 2882 received within collar 2872 and extensions 1087 received within and coupled to openings 1094. With extensions 1087 coupled to collar 2872 via openings 1094, it should be appreciated that flange piece 2870 may inhibit proximal retraction of actuation portion 2882. Accordingly, disassembly of plunger rod 2880 from flange piece 2870 may be prevented. In this instance, delivery device 2800 may be primed by distally translating plunger rod 2880 into flange piece 2870.

As seen in FIG. 38B, actuation portion 2882 may be translated distally relative to flange piece 2870 until protrusions 1086 encounter a proximal end of collar 2872. Plunger rod 2880 may complete a priming process of delivery device 2800 upon protrusions engaging and/or abutting collar 2872. It should be appreciated that an extent that plunger rod 2880 translates distally relative to flange piece 2870 may correspond to a priming distance of delivery device 2800. The priming distance may be controlled based on a longitudinal length of protrusions 1086 and/or extensions 1087, thereby varying a relative distance between the proximal end of collar 2872 and a distal end of protrusions 1086.

Figure 38D:
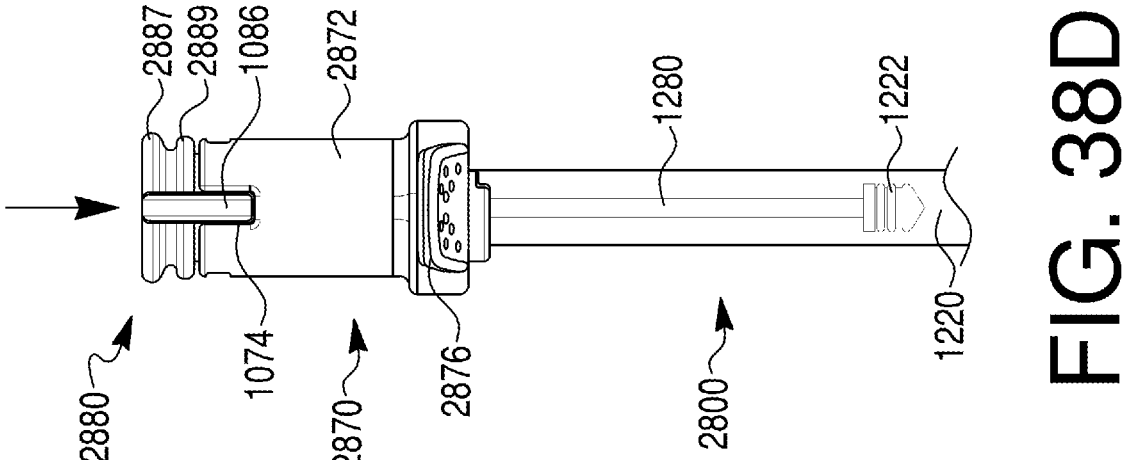
Figure 38C:
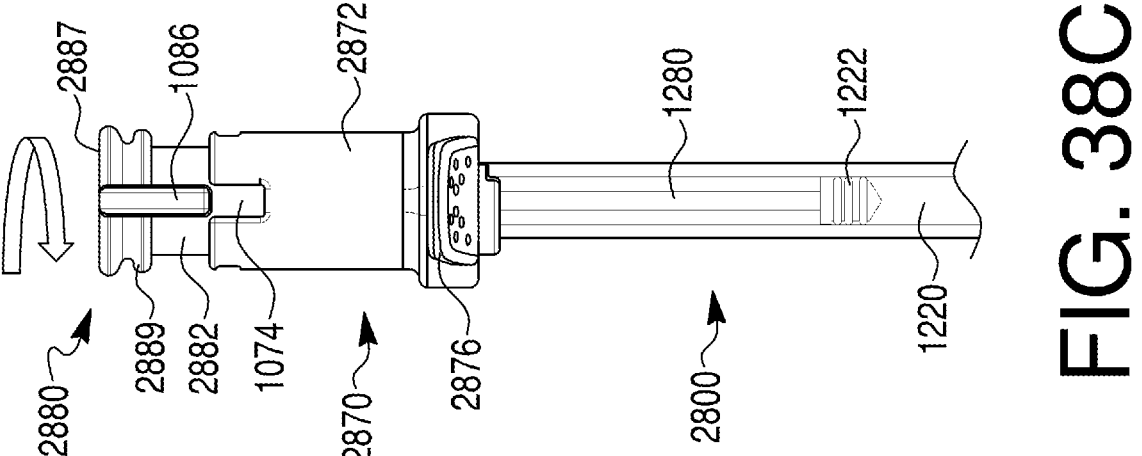
Figure 39A:
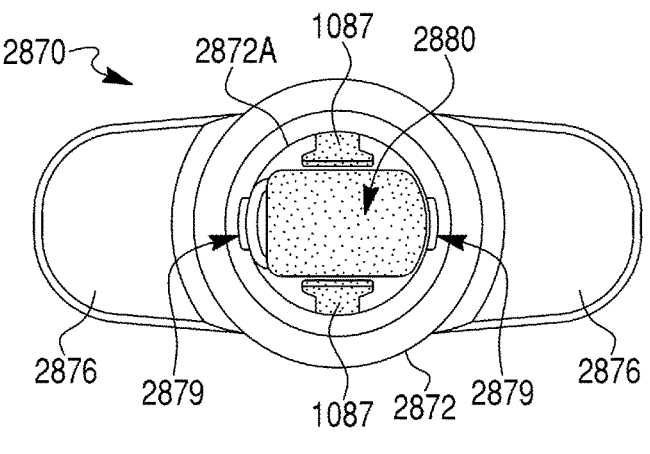
Figure 39B:
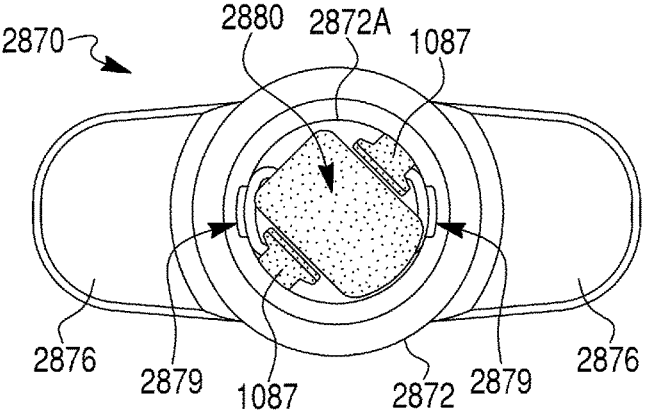
Figure 39C:
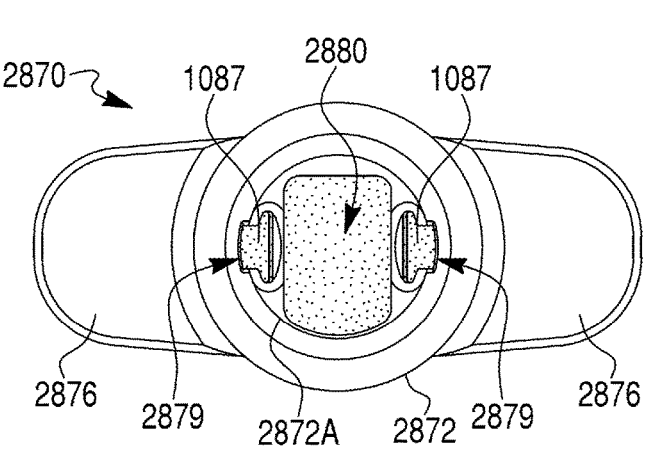
Figure 39D:
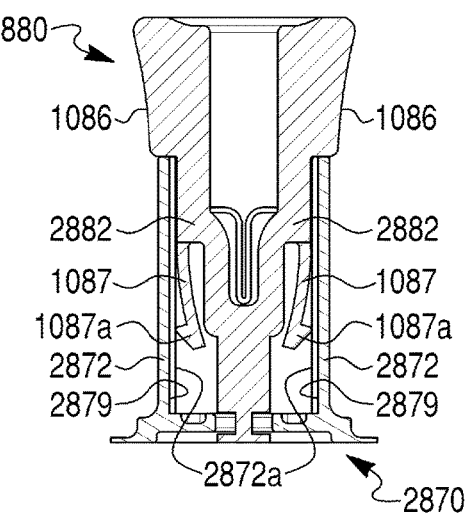
Figure 39E:
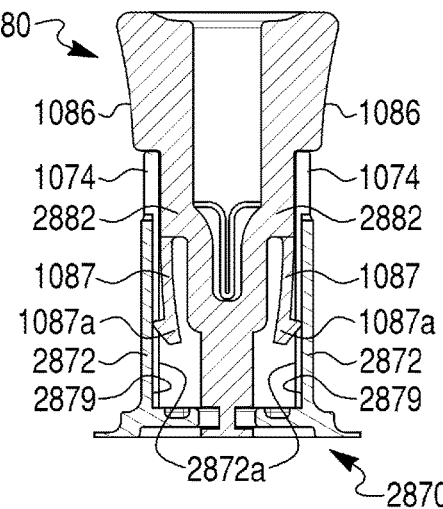

As shown in FIG. 38C, flange piece 2870 may be rotated relative to plunger rod 2880, or vice versa, to move protrusions 1086 relative to collar 2872 until arriving into radial and longitudinal alignment with slots 1074. Referring to FIGS. 39A-39B, extensions 1087 may contact an interior surface 2872A of collar 2872 as plunger rod 2880 rotates relative to flange piece 2870. As seen in FIG. 39D, with hook or clip shaped part 1087a engaged against interior surface 2872A, extensions 1087 may be deflected radially-inward by collar 2872 until plunger rod 2880 is rotated to align extensions 1087 with internal grooves 2879 of flange piece 2870. Internal grooves 2879 may define recesses formed along interior surface 2872A. As seen in FIG. 39C and FIG. 39E, internal grooves 2879 may be sized and shaped to receive extensions 1087 therein. It should be appreciated that collar 2872 may have a greater diameter at internal grooves 2879 than along interior surface 2872A such that extensions 1087 are configured to expand radially-outward from a compressed configuration (FIGS. 39A-39B and FIG. 39D) to an expanded configuration (FIG. 39C and FIG. 39E) when extensions 1087 are moved into radial alignment with internal grooves 2879.

Stated differently, extensions 1087 may be transitioned to a relaxed state when received within internal grooves 2879 due to the additional space provided by internal grooves 2879, as seen in FIG. 39E. In some instances, a feedback (e.g., tactile, auditory, etc.) may be generated in response to extensions 1087 being received within internal grooves 2879. Delivery device 2800 may be positioned in a dosage delivery state such that further actuation of plunger rod 2880 may provide a dose delivery. In some embodiments, flange piece 2870 may be operable to generate a user feedback (e.g., tactile, audible, etc.) upon rotating plunger rod 2880 relative to flange piece 2870 to prime delivery device 2800.

As described in detail above and as seen in FIGS. 40A-40C, opening 1073 may have a semi-circular shape with one or more edges 2873 extending into opening 1073. With plunger rod 2880 coupled to flange piece 2870, stem 1280 may be received through opening 1073. Stem 1280 may include a rounded sidewall 2884 that is configured to interact with the one or more edges 2873 as plunger rod 2880 rotates relative to collar 2872. For example, rounded sidewall 2884 may define a semi-circular end along stem 1280 that may contact edges 2873 when plunger rod 2880 is moved from the primed position (FIG. 38B) to the dosage delivery position (FIG. 38C). As described in detail above (FIGS. 4K-4X), it should be appreciated that stem 1280 may have various suitable shapes and/or configurations for facilitating movement (e.g., rotation) of plunger rod 2880 relative to flange piece 2870.

Referring now to FIG. 38D, with protrusions 1086 aligned with slots 1074, actuation portion 2880 may be translated distally relative to collar 2872 to complete a full stroke of plunger rod 2880 in response to applying a distally-directed force onto actuation portion 2882. In this instance, stem 1280 may move relative to flange piece 2870, thereby causing stopper 1222 to move within body 1220 to deliver a dosage. In this instance, protrusions 1086 may be received within slots 1074 and second ring 2889 may be positioned proximate to a proximal end of collar 2872. In other words, in some embodiments, second ring 2889 does not contact the proximal end of collar 2872. Further, as described in greater detail above, indents 2875 may receive extensions 1087 (FIG. 36) therein when completing a full stroke of plunger rod 2880. It should be appreciated that an extent that plunger rod 2880 translates relative to flange piece 2870 may define a dosage delivery distance of delivery device 2800. The dosage delivery distance may be controlled based on a longitudinal length of protrusions 1086 relative to actuation portion 2882 and/or a depth of slots 1074 relative to collar 2872.

As seen in FIGS. 41A-41D, delivery device 2800 may include various other flange pieces 2870 having at least one of a plurality of textured interfaces on flanges 2876. As merely an illustrative example, as seen in FIG. 41A, an alternative exemplary flange piece 2870A may include a textured interface 2878A on flanges 2876 comprising a plurality of circular protrusions and/or depressions arranged in an annular array relative to one another. As seen in FIG. 41B, another exemplary flange piece 2870B may include a textured interface 2878B comprising an ornamental design, such as a snowflake, on each flange 2876. FIG. 41C shows an exemplary flange piece 2870C including a textured interface 2878C on flanges 2876 comprising a plurality of circular protrusions and/or depressions arranged in an irregular pattern relative to one another.

By way of further example, referring now to FIG. 41D, a flange piece 2870D may include a textured interface 2878D comprising a plurality of diamond-shaped protrusions and/or apertures positioned in a grid-like arrangement along flanges 2876. It should be understood that the various textured interfaces shown and described herein may be configured to enhance a grip, control, aesthetic, and/or ergonomics of the flange piece. It should further be appreciated that the textured interfaces shown and described herein are merely illustrative such that various other suitable patterns, textures, and/or features may be included on the flange pieces without departing from a scope of this disclosure.

Components of the devices described herein may be designed and/or suited for manufacture in one or more ways. In some embodiments, for example, components of the devices described herein (e.g., device 1050, device 1200, device 1300, device 1400, device 2400, device 2500, device 2600, device 2800, etc.) may be suitable for manufacture via, e.g., injection molding, 3-dimensional printing, or machining. In one embodiment, for example, components of device 1050 may be particularly suited for manufacture via injection molding. For example, in some existing devices, molding is not suitable for high volume production, resulting in the use of 3-dimensional printing. In some embodiments, while manufacturing tolerances may be tighter with molding techniques than with 3-dimensional printing techniques, devices formed by 3-dimensional printing do not have the same level of precision as devices formed by molding. Precision may be particularly important for devices of the present disclosure, for example, those devices used for vitreous injections at volumes of 100 µL or less.

Accordingly, it should be appreciated that devices of the present disclosure described herein may be designed to store predefined volumes of therapeutic agent that may be suitable for vitreous (IVT) injections, such as, for example, 100 µL or less. In some embodiments, the devices described herein may be designed for injection of certain volumes of a medicament based on an intended use of the device in a particular procedure. For example, devices of the present disclosure may be configured to store a volume of a medicament of about 65 µL to about 75 µL for high dose aflibercept procedures; about 95 µL to about 105 µL for Mini Trap procedures; and/or about 5 µL to about 15 µL for Retinopathy of Prematurity (ROP). In some embodiments, the devices described herein may be designed for injection of certain concentrations of a medicament based on an intended use of the device in a particular procedure. For example, devices of the present disclosure may be configured to store and inject concentrations of a medicament for high dose aflibercept procedures wherein: about 8 mg is delivered in less than about 80 μL, less than about 75 μL, less than about 70 μL, less than about 65 μL, less than about 60 μL; about 7 mg is delivered in less than about 80 μL, less than about 75 μL, less than about 70 μL, less than about 65 μL, less than about 60 μL; about 6 mg is delivered in less than about 80 μL, less than about 75 μL, less than about 70 μL, less than about 65 μL, less than about 60 μL; about 5 mg is delivered in less than about 80 μL, less than about 75 μL, less than about 70 μL, less than about 65 μL, less than about 60 μL; about 4 mg is delivered in less than about 80 μL, less than about 75 μL, less than about 70 μL, less than about 65 μL, less than about 60 μL; about 3 mg is delivered in less than about 80 μL, less than about 75 μL, less than about 70 μL, less than about 65 μL, less than about 60 μL; about 2 mg is delivered in less than about 80 μL, less than about 75 μL, less than about 70 μL, less than about 65 μL, less than about 60 μL; and about 1 mg is delivered in less than about 80 μL, less than about 75 μL, less than about 70 μL, less than about 65 μL, less than about 60 μL.

Devices of the present disclosure may be further configured to store relatively greater volumes of a medicament for injection based on a degree of myopia, such as about 3 milliliters, 4 milliliters, and greater. Additionally, the devices described herein may be designed for injection of larger volumes of a medicament based on an intended procedure, such as, about 3 ml to about 6 ml of silicone or gas for tamponade post vitrectomy. It should be appreciated that the devices of the present disclosure may be designed to inject various other volumes of a medicament relative to other procedures, such as, Diabetic Eye Disease, post-injection noninfectious Endophthalmitis, Neovascular (Wet) Age-related Macular Degeneration (AMD), Macular Edema following Retinal Vein Occlusion (RVO), Diabetic Macular Edema (DME), and Diabetic Retinopathy (DR).

Devices of the present disclosure are operable to provide accurate measurements in delivering large volumes of a medicament with high precision by minimizing instances of user error in improperly setting a dose line. As described in detail above, the various designs and configurations of the one or more components of the devices described herein (e.g., a plunger rod, a flange piece, etc.) may provide dosage precision by controlling a priming distance and a dosage delivery distance of the device, thereby removing user determination in setting the device at each respective configuration.

As alluded to above, embodiments of the present disclosure may be suitably sterilized prior to use. In some embodiments, a pre-filled syringe may be sterilized by the systems and methods for the application of vaporized chemicals as described in more detail below. For example, delivery devices of embodiments of the present disclosure may be sterilized by the exemplary systems and methods for the terminal sterilization of medical products using vaporized hydrogen peroxide (VHP) described herein. More particularly, the following description of method and systems for sterilization relate to, e.g., systems and methods for the terminal sterilization of medical products, such as pre-filled syringes (PFS).

It is generally desired that exposure to sterilization cycles have no adverse impact and minimized risk of damage or alteration to products being sterilized. Medical products that undergo terminal sterilization, such as PFS, may thus require sterilization equipment, machinery, controls, cycle, and methods to conform to certain constraints and requirements in order to achieve appropriate sterilization and/or avoid damage to the medical products and/or devices, formulated drug substances, drug products, or other products. Such constraints and requirements may include, e.g.:

The medical products and/or surrounding packaging may be sensitive to deep vacuum pressures during the sterilization cycle. For example, PFS may include pre-positioned plungers susceptible to becoming dislodged when exposed to deep vacuum environments. Additionally, medical products may include fragile materials, such as glass, which may be affected by deep vacuum environments.

The medical products, compositions contained in medical products, and/or surrounding environment may be adversely affected by extreme temperatures during sterilization cycle. For example, products containing liquid formulations (e.g., liquid medicaments in PFS) may not be stable when heated to the higher temperatures to which they may be exposed during typical sterilization cycles. For example, medicaments in such liquid formulations may become denatured, deactivated, or otherwise altered when exposed to and/or heated to high temperatures.

Medical products may be densely packed; e.g., bulk packaged medical products may contain a large sum of fully assembled, packaged, and labeled medical products. In the case of terminal sterilization, sterilizing agents may need to traverse several layers of packaging materials, container materials, and/or labels.

In the case of some types of sterilization, such as terminal sterilization, sterilizing agents may need to traverse a semi-permeable membrane, either by heat or by mass, to sterilize the exterior of each medical product as well as the interior of packaging elements.

Packaging for medical products may resist penetration of sterilization materials, and/or may be sensitive to temperature and pressure changes caused by sterilization. For example, a syringe may be packaged in a plastic 'blister' configured to house the syringe and restrict it from movement. Such a blister may be only somewhat permeable to sterilization materials, and/or may be sensitive to changes in pressure.

Medical products may be sealed using temperature- or pressure-sensitive elements. For example, PFS may be sealed using a semi-permeable gas membrane 'lidding.'

Chemical sterilization, including moist chemical sterilization, may provide advantages addressing some of the above-described characteristics of medical product sterilization. For example, sterilization using a combination of VHP and vaporized water may advantageously be performed at relatively low temperatures, negating the need to expose medical products to disruptive high temperatures. However, there is limited evidence demonstrating successful application of VHP sterilization technology for terminal sterilization (e.g., for terminal sterilization of PFS), due to, e.g., sterilization cycles achieving incomplete sterilization, sterilization cycles unable to operate within allowable temperature and/or pressure ranges for medical products, difficulties in removing toxic residual VHP from sterilized articles, and/or long sterilization times. Ethylene oxide ("EtO") is a viable alternative to VHP, and is known to be an effective agent for sterilization of items sensitive to high temperatures and pressures. However, EtO is more toxic to humans than VHP, and as such presents health and safety issues during and after its use in a sterilization system.

For at least the above reasons, it may be desirable to more successfully apply VHP in terminal sterilization of medical products. It may also be desirable to do so while achieving relative sterilization "cycle efficiency" (e.g., (1) a decrease in overall sterilization cycle time, and/or (2) a decrease in extremity of the temperature at which a sterilization cycle operates). There is potentially significant value associated with successful application of VHP in terminal sterilization (e.g., of PFS), as well as improving cycle efficiency while applying VHP in terminal sterilization of PFS. The potential value may be derived by minimizing risk to product, and to business, by allowing more overall throughput of medical products (e.g., PFS) per unit of time.

Several aspects of VHP sterilization may (positively or negatively) affect the safety, efficacy, efficiency, and other aspects of sterilization processes for medical products. For example:

Vaporized sterilizing chemicals, such as VHP, may be stored as aqueous liquid mixtures, may be vaporized in the presence of water, and/or may otherwise exist in environments with water vapor. Under some sterilization conditions, vaporized sterilizing chemicals may not behave as a dry and/or ideal gas. VHP, for example, may not fully dissociate from water vapor in a sterilization chamber; the VHP may instead behave as a binary mixture of VHP and water vapor.

During some or all of a sterilization cycle, chemical sterilant vapors and water vapors in a sterilization chamber may adsorb to and/or condense on surfaces having cooler temperatures than the environmental temperature in the sterilization chamber. For example, during vapor sterilization of PFS loads, "cold spots" created by aqueous, high heat capacity, liquid product in each PFS, may serve to attract vapor adsorption and promote surface condensation. Upon proximity to a surface, chemical sterilant vapors and water vapors may adsorb to the surfaces due to the chemical properties of the vapors themselves, the operating conditions inside the chamber during sterilization, and the cooler temperatures on the surfaces of the PFS load as compared to the rest of the chamber environment.

During some or all of a sterilization cycle, VHP may preferentially adsorb onto surfaces as compared to water vapor, due to the fact that hydrogen peroxide is more dense and less volatile than water. In some instances, VHP and water vapor may be adsorbing and condensing on surfaces at the same time, with VHP adsorbing and condensing in greater quantities and percentages as compared to the water vapor, and in closer proximity to the surfaces of the sterilization load than the water vapor.

During some or all of a sterilization cycle, multiple layers of adsorption may form on the surfaces of PFS loads. In some instances, each layer of adsorption and/or condensation further away from the surface may contain less VHP and more water vapor, such that a gradient of VHP to water is formed on the surface. VHP may preferentially adsorb and condense closer to the surfaces of the load because of the thermodynamic behavior of binary mixtures of VHP and water vapor close to or at saturation (vapor/liquid equilibrium). Vapor/liquid equilibrium may be analogous to gas/adsorbate equilibrium for binary mixtures of VHP and water vapor in sterilization applications.

During or after a VHP sterilization cycle, condensed/adsorbed hydrogen peroxide may be difficult to remove from surfaces that it has sterilized, due in part to the condensation of water vapor over, and adsorption of water around, the condensed hydrogen peroxide, which may trap the hydrogen peroxide in place on the sterilized surfaces.

Systems and methods disclosed herein may advantageously be used in successfully sterilizing medical products, while decreasing the impact and/or risk of the sterilization process on the products undergoing sterilization. For example, systems and methods disclosed herein may provide for full (e.g., 100%) sterilization of medical products using VHP, followed by full (e.g., 100%) removal of VHP from sterilized products. Systems and methods disclosed herein may, e.g., increase efficiency, safety, and efficacy of sterilization, and/or decrease sterilization cycle time. Additionally, while aspects of the present disclosure may be described with respect to the use of VHP in terminal sterilization of PFS, sterilization of other medical products is contemplated by the present disclosure as well.

The present disclosure also contemplates performance of "moist chemical sterilization," by which chemical sterilization may be achieved in the presence of water vapor. Comparison of "moist chemical sterilization" to "chemical sterilization" may be analogous, in some cases, to comparison of "moist heat sterilization" to "heat sterilization." In some instances, moist chemical sterilization may be a more effective and efficient means of achieving sterilization than chemical sterilization technology that currently exists, in the same way that "moist heat sterilization" is considered to be, in some cases, more effective and efficient than only "heat sterilization."

"Moist chemical sterilization" may take place when environmental conditions of relatively high chemical concentration, high water vapor concentration, and high pressure (e.g., above 400 mbar) act in concert to force the chemical and water vapor to behave as a binary mixture. In order to achieve the desired relatively high chemical concentration, high water vapor concentration, and high pressure, the sterilization chamber (e.g., sterilization chamber 3102) may be saturated with a combination of water vapor and sterilizing chemical (e.g., VHP), forcing vapor to condense on surfaces of the "load" or item or items to be sterilized (e.g., products 3105). Most commercially available hydrogen peroxide is available and sold as aqueous liquid mixtures in varying concentrations (e.g., 3%, 15%, 35%, 59%), and thus, vaporizing hydrogen peroxide will generally simultaneously include vaporizing water. When VHP is used, because VHP has a higher density than water vapor, VHP may preferentially condense on the surfaces of the item or items to be sterilized over water vapor.

It is recognized herein that a portion of a sterilization load having a lower temperature than the surrounding sterilization environment (e.g., the ambient temperature of sterilization chamber 3102), may act as a "cold spot" that attracts vapor to condense on the surface area of the load. If specific "cold spots" within the load are located inside packages which require vapor to travel through a semi-permeable membrane, these "cold spots" can advantageously attract condensation of vaporized VHP to the surface area surrounding the "cold spots," thus creating a higher density of condensed VHP in areas of the load and promoting diffusion of the sterilizing chemical through semi-permeable membranes that it contacts. On the other hand, it is recognized that if "cold spots" are too cold, that is, if there is too much of a temperature difference (delta) between the load or portions of the load and the surrounding sterilization environment (e.g., the temperature of sterilization chamber 102), the presence of the "cold spots" may prevent distribution and penetration of VHP over the entire load. Thus, it is recognized that a balanced temperature differential between the temperature of the sterilization environment (e.g., sterilization chamber 3102) and the temperature of "cold spots" on items to be sterilized (e.g., products 3105) is required, such that VHP is drawn to condense at "cold spots," but not to the detriment of diffusion over the load as a while.

Figure 42:
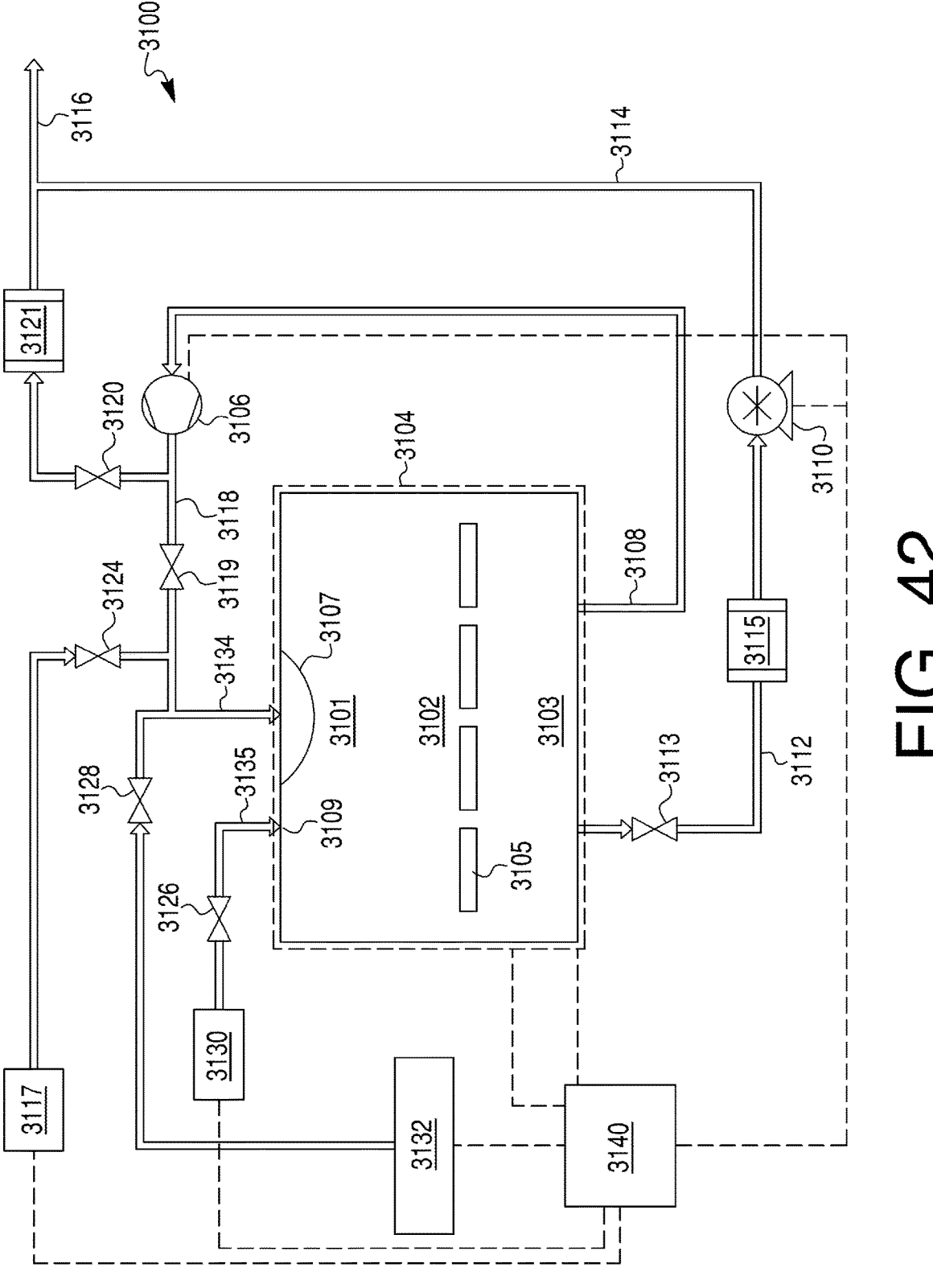
FIG. 42 is a schematic drawing of an exemplary sterilization system that may be used for sterilizing the delivery devices of the present disclosure, according to aspects of the present disclosure.

Referring now to FIG. 42, an exemplary sterilization system 3100 is schematically depicted. Sterilization system 3100 includes a sterilization chamber 3102, surrounded by a temperature control jacket 3104. Sterilization chamber 3102 has an interior cavity, including an upper interior 3101 and a lower interior 3103. Sterilization chamber 3102 is configured to house one or more products 3105 for sterilization. An inlet conduit 3134, fluidly connected to sterilization chamber 3102, is configured to allow various fluids to enter sterilization chamber 3102 via a distribution manifold 3107 in sterilization chamber 3102. A second inlet conduit 3135 is also fluidly connected to sterilization chamber 3102, also to allow fluids to enter sterilization chamber 3102 via an inlet 3109. A blower 3106 is fluidly connected to sterilization chamber 3102 via a blower exit conduit 3108. A blower circulation conduit 3118 fluidly connects blower 3106 to move fluids from blower exit conduit 3108 either towards an exhaust 3116, or back towards sterilization chamber 3102 via inlet conduit 3134. An exhaust valve 3120 is located between blower circulation conduit 3118 and exhaust 3116, and selectively closes or opens a connection between blower circulation conduit 3118 and exhaust 3116. A recirculation valve 3119 is located between blower circulation conduit and inlet conduit 3134, and selectively closes or opens a connection between blower circulation conduit 3118 and inlet conduit 3134. A vacuum pump 3110 is also fluidly connected to sterilization chamber 3102, via a vacuum conduit 3112 and a catalytic converter 3115. A vacuum valve 3113 is located on vacuum conduit 3112, and selectively allows, partially allows, or blocks flow from sterilization chamber 3102 through catalytic converter 3115 and vacuum pump 3110. A vacuum exhaust conduit 3114 fluidly connects vacuum pump 3110 to exhaust 3116.

Several fluid supplies are also fluidly connected to sterilization chamber 3102 via inlet conduit 3134 or inlet conduit 3135. An air supply 3117 is configured to supply air to sterilization chamber 3102 via inlet conduit 3134. An air valve 3124 is coupled to the fluid connection between air supply 3117 and inlet conduit 3134, and selectively allows, partially allows, or blocks flow of air from air supply 3117 to sterilization chamber 3102 via inlet conduit 3134. Further, a VHP injector 3132, fluidly connected to inlet conduit 3134, is configured to inject VHP to sterilization chamber 3102 via inlet conduit 3134. A VHP injector valve 3128 is coupled to the fluid connection between VHP injector 3132 and inlet conduit 3134, and selectively allows, partially allows, or blocks flow of VHP from VHP injector 3132 to sterilization chamber 3102 via inlet conduit 3134. Additionally, a dry air supply 3130 fluidly connected to inlet conduit 3135 is configured to supply dry air to sterilization chamber 3102 via inlet conduit 3135. A dry air supply valve 3126 is coupled to the fluid connection between dry air supply 3130 and inlet conduit 3135, and is configured to selectively allow, partially allow, or block flow of dry air from dry air supply 3130 to sterilization chamber 3102 via inlet conduit 3134. A controller 3140 is connected to one or more other components of sterilization system 3100, such as sterilization chamber 3102, temperature control jacket 3104, blower 3106, VHP injector 3132, air supply 3117, dry air supply 3130, and/or any other components of sterilization system 3100.

Sterilization system 3100 may be configured to run sterilization cycles within sterilization chamber 3102 at a variety of temperatures and pressures, and for a variety of time durations and/or time intervals. In some embodiments, the temperature(s), pressure(s), and time interval(s) at which sterilization system 3100 may run sterilization cycles may be selectively and individually modified and customized. Sterilization system 3100 may be configured to control the environment in the interior of sterilization chamber 3102, including temperature, pressure, humidity, atmosphere, intake of fluids via, e.g., inlet conduit 3134, exit of fluids via one or more of temperature or pressure controls, and/or via e.g., blower exit conduit 3108 and/or vacuum conduit 3112. Further, sterilization system 3100 may include any suitable number and location of sensors configured to sense, e.g., temperature, pressure, flow, chemical concentration, or other parameters throughout sterilization system 3100, including in sterilization chamber 3102, temperature control jacket 3104, blower 3106, vacuum pump 3110, and/or any of conduits 3108, 3112, 3114, 3118, and 3134. Such sensors may be configured to transmit sensed data to, e.g., controller 3140 and/or a human-machine interface.

Sterilization chamber 3102 may be a sealable chamber defining an interior, including upper interior 3101 and lower interior 3103. Sterilization chamber 3102 may be openable into an open configuration, such that one or more items, e.g., products 3105, may be placed inside as a part of a load for sterilization, and may be removed subsequent to sterilization. In some embodiments, sterilization chamber 3102 may have an operating orientation, e.g., such that upper interior 3101 is located above lower interior 3103, and such that matter may fall (e.g., under the forces of gravity) from the vicinity of upper interior 3101 towards lower interior 3103. Sterilization chamber 3102 may have one or more delivery apparatus to which one or more of inlet conduit 3134 and inlet conduit 3135 may be connected. As depicted in FIG. 42, for example, distribution manifold 3107 is one such delivery apparatus. Distribution manifold 3107 may be configured to disperse gas, vapor, or liquid into sterilization chamber 3102 in a given configuration, such as a stream or an even spray across upper interior 3101 of sterilization chamber 3102. Inlet 3109 is another such delivery apparatus. Inlet 3109 may also be configured to disperse gas, vapor, or liquid into sterilization chamber 3102 in a given configuration, such as a stream, or an even spray across upper interior 3101. In some embodiments, distribution manifold 3107 may be configured to disperse gas, vapor, or liquid into sterilization chamber 3102 in one configuration, such as an even spray, and inlet 3109 may be configured to disperse gas or vapor into sterilization chamber 3102 in a different configuration, such as in a stream. In some embodiments, there may be no inlet 3109, and both inlet conduits 3134 and 3135 may be connected to distribution manifold 3107.

Temperature control jacket 3104 may be any material surrounding sterilization chamber 3102, that is configured or effective to afford temperature control to the environment inside sterilization chamber 3102. In some embodiments, for example, temperature control jacket 3104 may be a water jacket surrounding sterilization chamber 3102. In such embodiments, a temperature and/or a flow of water or other liquid through temperature control jacket 3104 may be controlled by, e.g. controller 3140.

Products 3105 may be any item or items suitable for sterilization using sterilization system 3100. In some embodiments, products 3105 may be medical products in primary packaging, secondary packaging, or both. In some embodiments, products 3105 may be medical products having moving parts or parts otherwise sensitive to deep vacuum environments, such as environments having pressure of less than about 100 millibars. Products 3105, therefore, may be, e.g., containers filled with a volume of formulated drug substance, such as, e.g., vials or PFS. In further embodiments, products 3105 may be or include medical products sensitive to high temperatures, e.g., above 30° C. Such medical products may include, for example, formulated drug substances or other compositions that may be sensitive to high temperatures, such as proteins (e.g., antibodies or enzymes), nucleic acids, blood, blood components, vaccines, allergenics, gene therapy medicaments, tissues, other biologics, etc. For example, products 3105 may be packaged PFS containing a formulated drug substance that includes an antibody.

Blower 3106 may be, for example, a blower having the capacity to forcibly draw vapor and gas from lower interior 3103 of sterilization chamber 3102 through blower exit conduit 3108, and to reintroduce said vapor and gas back to upper interior 3101 of sterilization chamber 3102 via inlet conduit 3134 (or, alternatively, to draw such vapor and gas through exhaust valve 3120 and catalytic converter 3121, to exhaust 3116). Blower 3106 may be any device or mechanism configured or effective to perform this function. For example, blower 3106 may have an impeller and rotating blades, or rotating vanes configured to draw vapor and gas from lower interior 3103 out of blower exit conduit 3108, through blower circulation conduit 3118, and back to upper interior 3101 of sterilization chamber 3102 via inlet conduit 3134. In some embodiments, blower 3106 may be external to sterilization chamber 3102, as shown in FIG. 42. In other embodiments, blower 3106 may be disposed within sterilization chamber 3102. In some embodiments, blower 3106 may be configured to draw vapor and gas from lower interior 3103 of sterilization chamber 3102 and reintroduce said vapor and gas back to upper interior 3101 with sufficient force to create a flow of vapor and gas from upper interior 3101 to lower interior 3103 of sterilization chamber 3102. This flow may be termed a "turbulent flow." In some embodiments, the force with which blower 3106 may operate may be adjustable (via, for example, controller 3140), such that a more turbulent (e.g., more forceful), or less turbulent, flow of vapor and gas within sterilization chamber 3102 may be generated. In some embodiments, blower 3106 may be configured to generate a stronger force to draw vapor and gas than, e.g., vacuum pump 3110.

Vacuum pump 3110 may be a vacuum pump having the capacity to draw gas from the interior (e.g., lower interior 3103) of sterilization chamber 3102, via vacuum conduit 3112 and catalytic converter 3115, and towards exhaust 3116, thereby creating a vacuum within sterilization chamber 3102 and/or a closed system containing sterilization chamber 3102 and, e.g., blower 3106. In some embodiments, vacuum pump 3110 may have an impeller, rotating blades, or vanes configured to draw vapor and gas towards exhaust 3116. Vacuum pump 3110 may be fluidly connected to exhaust 3116 via, e.g., vacuum exhaust conduit 3114. In some embodiments, exhausts from vacuum pump 3110 and blower 3106 may be separated instead of being combined into one.

In some embodiments, vacuum-type functions may also or alternately be performed by, e.g., blower 3106, which may selectively circulate vapor and gas out of and into sterilization chamber 3102 or out of sterilization chamber 3102, through exhaust valve 3120, and towards exhaust 3116. Exhaust valve 3120 may be selectively opened or closed so as to permit or prevent flow of gas or vapor from blower circulation conduit 3118 towards exhaust 3116 or towards inlet conduit 3134 for reintroduction into sterilization chamber 3102. Exhaust valve 3120 may be manually controlled, or may be controlled by, e.g., controller 3140.

Sterilization system 3100 may include several supplies of air and/or vapor from which fluid may be introduced into sterilization chamber 3102 via inlet conduit 3134 or inlet conduit 3135. Air supply 3117, for example, may be any supply of air (e.g., room air, or compressed dry air) or other fluid external from the rest of sterilization system 3100. In some embodiments, air supply 3117 may be a supply of "room air" surrounding sterilization system 3100, which may have gone through an indoor filtration system. In some embodiments, air supply 3117 may include more water vapor than "room air." In some embodiments, air supply 3117 may be a supply of filtered outdoor air. Air valve 3124, coupled to the fluid connection between air supply 3117 and inlet conduit 3134, may be configured to selectively allow, partially allow, or block flow of air from air supply 3117 to sterilization chamber 3102 via inlet conduit 3134, thus controlling the intake of air into closed portions of sterilization system 3100. Air valve 3124 may be manually controllable and/or controllable by, e.g., controller 3140.

Dry air supply 3130 may be a supply of air having a relatively low humidity, such that it may be used to dry the interior of, e.g., sterilization chamber 3102 and/or one or more of conduits 3108, 3112, 3114, 3118, and 3134. In some embodiments, for example, air in dry air supply 3130 may include a dew point of, e.g., −10 degrees Celsius or less, −40 degrees Celsius or less, or anywhere between −10 degrees Celsius and −40 degrees Celsius. In some embodiments, dry air supply 3130 may be a supply of hygienic dry air, such as air that has been sterilized or otherwise filtered to at least 0.2 microns. In some embodiments, dry air supply 3130 may be a sealed supply of air. In some embodiments, dry air supply 3130 may be a supply of compressed air. Dry air supply valve 3126, coupled to the fluid connection between dry air supply 3130 and inlet conduit 3135, may be configured to selectively allow, partially allow, or block flow of dry air from dry air supply 3130 to sterilization chamber 3102 via inlet conduit 3135. Dry air supply valve 3126 may be manually controllable and/or may be controllable by, e.g., controller 3140. In some embodiments, dry air supply 3130 may be connected to inlet conduit 3134 instead of inlet conduit 3135. In further embodiments, air supply 3117 may supply any of the types of air that dry air supply 3130 includes.

VHP injector 3132 may include a supply of VHP, or VHP and vaporized water, and may be configured to inject VHP or a combination of VHP and vaporized water into sterilization chamber 3102 via, e.g., inlet conduit 3134. VHP injector 3132 may be configured to inject vapor into sterilization chamber 3102 at an adjustable concentration. VHP injector valve 3128 may be coupled to the fluid connection between VHP injector 3132 and inlet conduit 3134, and may be configured to selectively allow or block flow of VHP from VHP injector 3132 to sterilization chamber 3102 via inlet conduit 3134. VHP injector valve 3128 may be manually controllable and/or may be controllable by, e.g., controller 3140. Dry air supply valve 3126 and VHP injector valve 3128 may also be used in concert to allow a desired combination of dry air and vaporized VHP/water into sterilization chamber 3102, via inlet conduit 3134.

Catalytic converter 3115 and catalytic converter 3121 may be, for example, any catalytic converters known in the art suitable for converting toxic gaseous or vaporized fluids circulated within sterilization system 3100, e.g., during a sterilization cycle, to less toxic gases or vapors. For example, catalytic converters 3115, 3121 may be configured to convert VHP injected into sterilization system 3100 by VHP injector 3132 into water vapor, oxygen, or other non-toxic fluids.

Some or all aspects of sterilization system 3100 may be controllable by, e.g., controller 3140. Controller 3140 may be, for example, an analog or digital controller configured to alter aspects of the environment of sterilization chamber 3102 such as an internal temperature or pressure of sterilization chamber 3102 and/or one or more of blower 3106, vacuum pump 3110, air supply 3117, dry air supply 3130, VHP injector 3132, exhaust 3116, one or more of valves 3113, 3119, 3120, 3124, 3126, and 3128, one or more of catalytic converters 3115, 3121, one or more of conduits 3108, 3112, 3114, 3116, 3118, and 3134, and any and/or other aspects of sterilization system 3100. In some embodiments, sterilization system 3100 may be controllable by multiple controllers 3140. In other embodiments, sterilization system may only have one controller 3140. In some embodiments, controller 3140 may be a digital controller, such as a programmable logic controller.

In some embodiments, controller 3140 may be pre-programmed to execute one or more sterilization cycles using sterilization system 3100. In some embodiments, sterilization system 3100 may be controllable by a controller having one or more human machine interface ("HMI") elements, which may be configured to allow a user to input or alter desired parameters for a sterilization cycle, which may be executable by a controller on or operably coupled to sterilization system 3100. Thus, in some embodiments, HMI elements may be used to program a customized sterilization cycle for execution by sterilization system 3100. For example, in some embodiments, sterilization system 3100 may be controllable by a controller connected to, e.g., a computer, tablet, or handheld device having a display. Such a display may include, for example, options to select or alter a desired temperature, pressure, time, amount of VHP intake, etc., for one or more steps of a sterilization cycle.

FIGS. 43 and 44A-44C depict flow diagrams of phases and steps in methods for sterilization according to the present disclosure. As will be recognized by one of ordinary skill in the art, some phases and/or steps in FIGS. 43 and 44A-44C may be omitted, combined, and/or performed out of order while remaining consistent with the present disclosure. In some embodiments, the phases and steps in FIGS. 43 and 44A-44C may be performed using, e.g., sterilization system 3100 or a variation of sterilization system 3100. It will be recognized that the customizable and controllable aspects of sterilization system 3100 may be used in order to carry out phases and steps depicted in FIGS. 43 and 44A-44C. For example, in some embodiments, controller 3140 may be employed to direct, adjust, or modify a series of sterilization steps, setpoints, and phases performable by sterilization system 3100. Additionally, although the phases and steps described in FIGS. 43 and 44A-44C are recited in relation to sterilization system 3100, one of ordinary skill in the art will understand that these phases and steps may be performed by another sterilization system, or another system having the capacity to carry out the steps.

Figure 43:
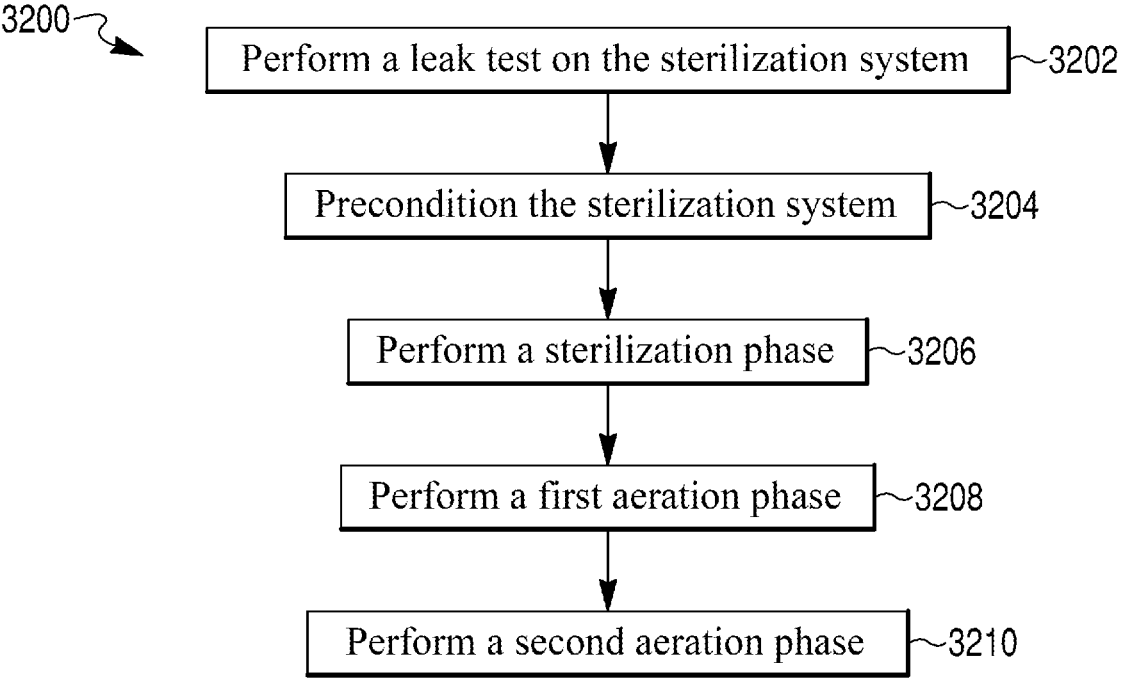
FIG. 43 is a flow diagram of steps in an exemplary method of sterilizing the delivery devices using vaporized chemicals, according to aspects of the present disclosure.

FIG. 43 depicts a flow diagram of a series of steps in a method 3200 for sterilization according to the present disclosure in a sterilization system, such as sterilization system 3100. According to step 3202, a leak test may be performed on sterilization system 3100. According to step 3204, sterilization system 3100 may be preconditioned. According to step 3206, a sterilization phase may be performed. According to step 3208, a first aeration phase may be performed. According to step 3208, a second aeration phase may be performed.

Prior to performance of the steps of method 3200, a sterilization load, such as products 3105, may be placed within a sterilization chamber, such as sterilization chamber 3102, of a sterilization system, such as sterilization system 3100. The closed-system sterilization environment—including sterilization chamber 3102, blower exit conduit 3108, blower 3106, blower circulation conduit 3118, inlet conduit 3134, and any elements connecting these components—may then be sealed.

According to step 3202, a leak test may be performed on the closed-system sterilization environment. The leak test may include, for example, creating a vacuum through the closed system. The vacuum may be created by, e.g., expelling gas and vapor from the closed system using vacuum pump 3110. During the leak test, blower 3106 may be in operation, so as to circulate any remaining air through the closed system and create a homogenous environment. The leak test may be performed in this manner in part to verify that a suitable vacuum may be held within the closed system. Additionally, inclusion of, and circulation of air through, the entirety of the closed system in the leak test may assist in increasing the heat transfer coefficient between the environment within the closed system and the load to be sterilized, which may assist in equalizing the temperature between the environment within the closed system and the load to be sterilized prior to sterilization.

According to step 3204, the sterilization system (e.g., sterilization system 3100) may be preconditioned. Preconditioning may include, for example, increasing the temperature of the closed system to temperatures intended to be maintained during a sterilization phase (e.g., between about 25° C. and about 50° C.). In some embodiments, preconditioning may be performed for longer than is performed in standard chemical sterilization procedures, which may allow more time for any temperature difference between the environment in the closed system (including, e.g., the environment of sterilization chamber 3102) and the load to be sterilized to decrease. In some embodiments, preconditioning may be performed for between about 15 minutes and about two hours, such as between about 20 minutes and about 1.5 hours, between about 25 minutes and about 1 hour, between about 30 minutes and about 1 hour, between about 30 minutes and about 45 minutes, between about 45 minutes and about 1 hour, such as about 30 minutes, about 40 minutes, about 45 minutes, or about 1 hour. Preconditioning according to step 3204 also may include operating at pressures which are at or near atmospheric pressure, e.g., between about 400 millibars and about 700 millibars, between about 500 millibars and about 700 millibars, between about 500 millibars and about 600 millibars, between about 800 millibars and about 1000 millibars, or between about 900 millibars and about 1100 millibars. Operation of the preconditioning step at or near atmospheric pressure may promote convective heat transfer from the chamber environment to the load, assisting in minimizing the difference in temperature between the chamber environment and the load. Additionally, blower 3106 may be operated during preconditioning according to step 3204, which may contribute to a higher heat transfer coefficient, and thus potentially faster equalization of temperature between the closed system, including the environment of sterilization chamber 3102, and the load to be sterilized. Equalization of temperature between the closed system and the load to be sterilized may allow for warming of "cold spots," or locations on or in the load having a cooler temperature than the majority of the load and/or the surrounding environment. For example, liquid contents of PFS may absorb heat more slowly than their non-liquid packaging, thus acting as "cold spots" within a load containing the PFS. Reduction of such cold spots by equalizing the temperature throughout the closed system and the load to be sterilized may advantageously allow for even diffusion of a vaporized sterilizing chemical (e.g., VHP) through sterilization chamber 3102, across the load to be sterilized, and/or diffusion through permeable membranes and barriers in the load to be sterilized. Maintaining some temperature difference between the closed system and the "cold spots" may be desirable, however, to promote preferential surface adsorption and condensation of VHP and water vapor onto the load to be sterilized.

As is discussed elsewhere herein, it is also contemplated that, in some embodiments, maintaining "cold spots" via keeping a temperature differential between the load to be sterilized and the surrounding closed system may also have advantages; for example, controlled condensation of vaporized sterilizing chemical (e.g., VHP) on "cold spots" of a load to be sterilized may concentrate the sterilizing chemical on the load and lead to more efficient diffusion of the chemical into the load, thus decreasing the overall amount of sterilizing chemical needed in the sterilization chamber 3102 to achieve effective sterilization. In such embodiments, preconditioning according to step 3204 may be performed for a shorter amount of time and/or in a shallow vacuum created by, e.g., vacuum pump 3110, in order to allow for or maintain "cold spots" within the load to be sterilized.

According to step 3206, a sterilization phase may be performed. The sterilization phase may include, for example, initiating circulation of fluid through the sterilization system, achieving a vacuum level, injecting vaporized chemical into the sterilization chamber, maintaining a post-injection hold, injecting gas into the sterilization chamber to transition to a shallower vacuum, and maintaining a post-transition hold. The sterilization phase according to step 3206 may be repeated multiple times. A sterilization phase according to step 3206 is depicted in further detail in FIG. 44A.

According to step 3208, a first aeration phase may be performed. The first aeration phase may include, for example, achieving a vacuum level, holding the vacuum level, breaking the vacuum level, and aerating and exhausting the system. The first aeration phase may be performed multiple times. A first aeration phase according to step 3208 is depicted in further detail in FIG. 44B.

According to step 3210, a second aeration phase may be performed. The second aeration phase may include, for example, achieving a vacuum level, holding the vacuum level, and breaking the vacuum level. The second aeration phase may be performed multiple times. A second aeration phase according to step 3210 is depicted in further detail in FIG. 44C.

Both steps 3208 and 3210 may be performed multiple times. Additionally, while in some embodiments, step 3208 may be performed before step 3210, in alternative embodiments, step 3210 may be performed before step 3208.

Figure 44A:
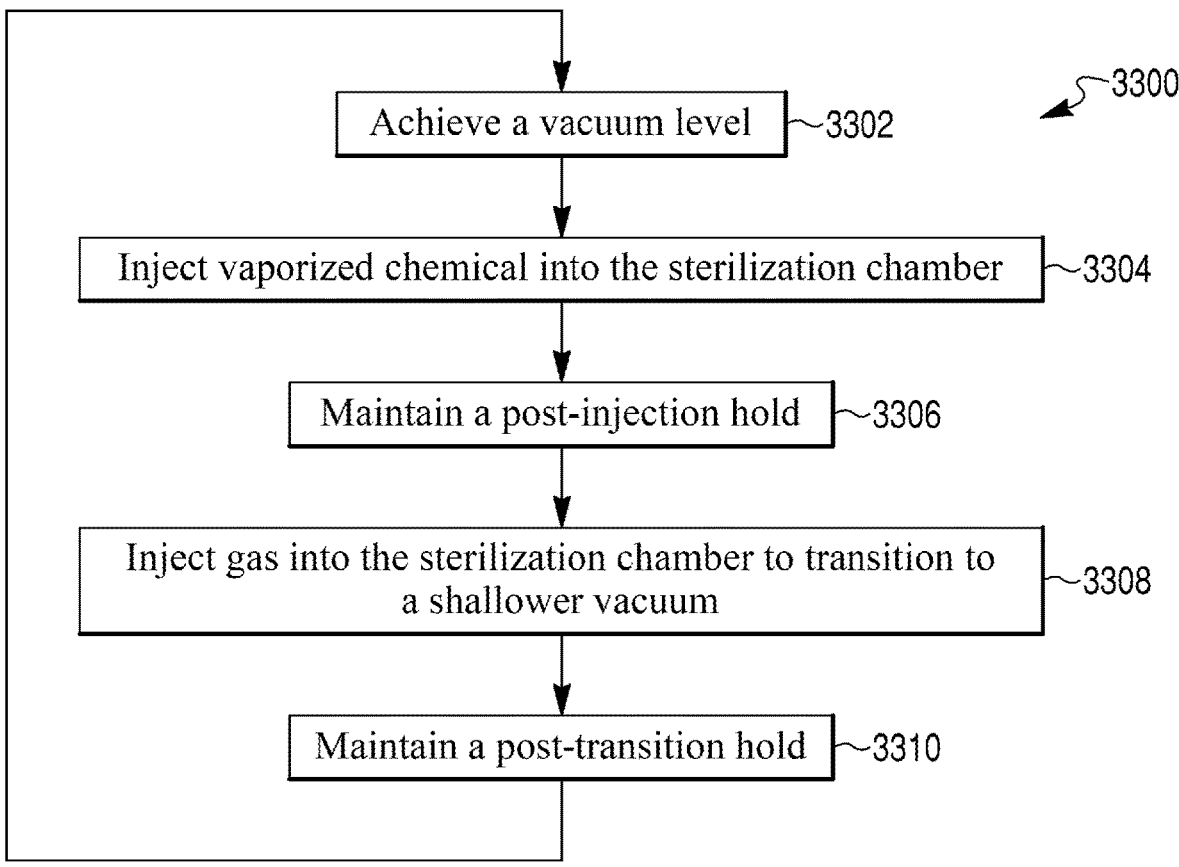
FIGS. 44A-44C are additional flow diagrams of steps in an exemplary method of sterilizing the delivery devices using vaporized chemicals, according to aspects of the present disclosure.

FIG. 44A is a flow diagram of a sterilization phase 3300 that may be performed as step 3206 of sterilization method 3200. Prior to sterilization phase 3300, a sterilization load (e.g., products 3105) may be introduced into sterilization chamber 3102. According to step 3302, a vacuum level may be achieved. According to step 3304, vaporized chemical may be injected into the sterilization chamber. According to step 3306, a post-injection hold may be maintained. According to step 3308, gas may be injected into the sterilization chamber to transition to a shallower vacuum. According to step 3310, a post-injection hold may be maintained.

As a part of sterilization phase 3300, a turbulent flow may be initiated and maintained in sterilization system 3100.

According to step 3302, a vacuum level may be achieved within sterilization chamber 3102 of sterilization system 3100. The vacuum level may be, for example, between about 400 millibars and about 700 millibars, such as between about 450 millibars and about 650 millibars, or between about 450 millibars and about 550 millibars. For example, the vacuum may be about 450 millibars, about 500 millibars, about 550 millibars, or about 600 millibars. This vacuum may promote a higher concentration of sterilizing chemical on the sterilization load, extending the amount of time at which the closed system is kept at a deeper vacuum increases exposure of the sterilization load to the sterilizing chemical.

According to step 3304, vaporized chemical may be injected into the sterilization chamber. In some embodiments, the vaporized chemical may include VHP. In some embodiments, the vaporized sterilization chemical may be a vaporized aqueous hydrogen peroxide solution, having a concentration of, for example, between about 5% and about 75% hydrogen peroxide by weight. In some embodiments, the vaporized chemical may be a vaporized aqueous hydrogen peroxide solution having a concentration of, for example, between about 10% and about 65% hydrogen peroxide by weight, between about 15% and about 60% hydrogen peroxide by weight, between about 30% and about 60% hydrogen peroxide by weight, between about 30% and about 60% hydrogen peroxide by weight, or between about 45% and about 60% hydrogen peroxide by weight. In some embodiments, the vaporized chemical may be a vaporized aqueous hydrogen peroxide having a concentration of about 35% hydrogen peroxide (and 65% water) by weight. In further embodiments, the vaporized chemical may be a vaporized aqueous hydrogen peroxide having a concentration of about 59% hydrogen peroxide (and 41% water) by weight.

In some embodiments, an injected supply of VHP may be, for example, between about 50 g and about 700 g of aqueous VHP. For example, the injected supply of VHP may be between about 50 g and about 600 g, between about 100 g and about 600 g, between about 300 g and about 550 g, or between about 450 g and about 550 g. For example, the injected supply of VHP may be about 100 g, about 200 g, about 300 g, about 400 g, about 450 g, about 475 g, about 500 g, about 525 g, about 550 g, about 600 g, or about 650 g. In some embodiments, an injected supply of VHP may be quantified based on the volume or amount of load to be sterilized inside sterilization chamber 3102. For example, if a number of drug products, such as pre-filled syringes, are to be sterilized in sterilization chamber 3102, an injected supply of VHP may be between about 0.01 and about 0.15 grams of VHP per unit of the drug product inside sterilization chamber 3102, such as between about 0.01 and about 0.10 grams of VHP, such as about 0.015 grams, 0.02 grams, 0.025 grams, 0.03 grams, 0.04 grams, 0.05 grams, 0.06 grams, 0.07 grams, 0.08 grams, 0.09 grams, 0.1 grams, or 0.11 grams per drug product. In other embodiments, an injected supply of VHP may be quantified based on the volume of the sterilization environment, such as the interior of sterilization chamber 3102. For example, an injected supply of VHP may be between about 0.2 and 3.0 grams per cubic foot of volume in a sterilization chamber. For example, an injected supply of VHP may be between about 0.2 and about 2.0 grams per cubic foot, such as about 0.25 grams, about 0.50 grams, about 0.75 grams, about 1.0 gram, about 1.2 grams, about 1.4 grams, about 1.5 grams, about 1.6 grams, about 1.8 grams, or about 2.0 grams per cubic foot.

In some embodiments, step 3210 may also include injecting dry air from, e.g., dry air supply 3130, into the sterilization system, so as to create a desired balance between concentrations of vaporized chemical and water vapor, at different pressures, inside the chamber.

According to step 3306, a post-injection hold may be maintained. During the post-injection hold, turbulent flow is maintained through the closed system including sterilization chamber 3102 and blower 3106. No fluids are added or removed from the closed system in which the turbulent flow is maintained. The time for which a post-injection hold is maintained (or the "post-injection hold time") may be selected so as to allow the vaporized sterilization chemical adequate time to contact the load to be sterilized. In some embodiments, the post-injection hold time may be between about 2 minutes and about 20 minutes. In some embodiments, the post-injection hold time may be at least about 5 minutes, at least about 10 minutes, or at least about 15 minutes. In some embodiments, the post-injection hold time may be between about 5 minutes and about 20 minutes, between about 8 minutes and about 20 minutes, between about 10 minutes and about 20 minutes, or between about 10 minutes and about 15 minutes. In such a manner, the need for adding excess VHP into the system to ensure its contact with the sterilization load may be avoided.

According to step 3308, gas may be injected into the sterilization chamber to transition to a shallower vacuum (i.e., a higher pressure) in the sterilization chamber. The gas may be any suitable gas that can break or lessen the vacuum in sterilization chamber 3102. In some embodiments, the gas may be a dry gas, such as a gas containing nitrogen (e.g., commercially available supplies of only nitrogen or primarily nitrogen), or air having a dew point of, for example, −10° C. or colder. In some embodiments, gas may be injected from dry air supply 3130. The gas may be injected in a volume to achieve a pressure between about 500 millibars and about 1100 millibars, such as between about 550 millibars and about 1000 millibars, between about 600 millibars and about 1000 millibars, between about 700 millibars and about 700 millibars and about 900 millibars, or between about 750 millibars and about 850 millibars. For example, the second post-injection pressure may be about 700 millibars, about 750 millibars, about 800 millibars, about 850 millibars, or about 900 millibars.

According to step 3310, a post-transition hold may be maintained. During the post-transition hold, the pressure achieved during step 3308 may be maintained for, for example, at least about 5 minutes, at least about 10 minutes, or at least about 15 minutes. In some embodiments, the second post-injection pressure may be maintained for between about 5 minutes and about 20 minutes, between about 8 minutes and about 20 minutes, between about 10 minutes and about 20 minutes, or between about 10 minutes and about 15 minutes.

The steps of sterilization phase 3300 may be repeated, for example, between 1 and 10 times, such as 2, 3, 4, 5, 6, 7, 8, 9, or 10 times. This may aid in ensuring full sterilization of the sterilization load within sterilization chamber 3102. In some embodiments, the number of times that sterilization phase 3300 may be repeated may be inversely proportional to the time that the post-injection hold is maintained in each repetition. For example, if the time that the post-injection hold is maintained is short (e.g., 10 minutes), then steps 3210 through 3216 may be repeated a greater number of times. In some embodiments, the post-injection hold is maintained for a longer period of time (e.g., 15-20 minutes), to increase the time during which the sterilization load is exposed to the sterilizing chemical in each repetition of sterilization phase 3300. In further embodiments, the number of times that sterilization phase 3300 may be repeated may depend on a total desired amount of VHP for the sterilization process. In some embodiments, for example, injection of a total amount of at least 200 g of VHP may be desired. For example, in some embodiments, injection of a total amount of at least 250 g may be desired. In some embodiments, injection of a total amount of between about 200 g and about 700 g of VHP may be desired.

Figure 44B:
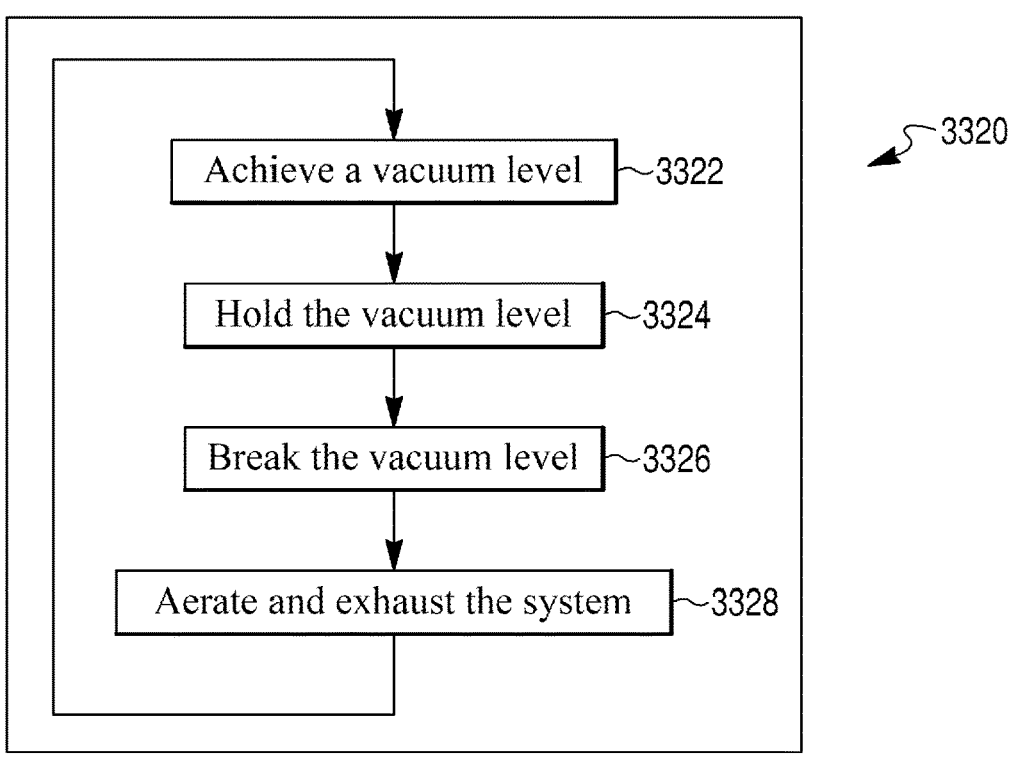

FIG. 44B is a flow diagram of a first aeration phase 3320 that may be performed as step 3208 of sterilization method 3200, after performing one or more repetitions of sterilization phase according to step 3206. According to step 3322, a vacuum level may be achieved. According to step 3324, the vacuum level may be held. According to step 3326, the vacuum level may be broken. According to step 3328, the sterilization system (e.g., sterilization system 3100) may be aerated and exhausted.

According to step 3322, a vacuum level may be achieved in sterilization chamber 3102, while also injecting dry gas into sterilization chamber 3102 near upper interior 3101 of sterilization chamber 3102, such as via distribution manifold 3107 or inlet 3109. The dry gas may include, for example, oxygen and/or nitrogen. The dry gas may have a dew point of, for example, −10° C. or lower. The dry gas may be injected from, e.g., dry air supply 3130. While dry gas is being injected into sterilization chamber 3102, a vacuum may be pulled by, e.g., vacuum pump 3110 via vacuum conduit 3112, catalytic converter 3115, and vacuum exhaust conduit 3114. The vacuum may be pulled at a greater rate than the rate of injection of dry gas, such that a vacuum level is gradually achieved. The vacuum level may be, for example, between about 500 millibars and about 850 millibars, such as between about 500 millibars and about 800 millibars, between about 550 millibars and about 750 millibars, or between about 600 millibars and about 700 millibars. For example, the vacuum level may be 500 millibars, 550 millibars, 600 millibars, 650 millibars, or 700 millibars. Injection of the dry gas near upper interior 3101 of sterilization chamber 3102 while achieving a desired vacuum level reduces condensation of VHP and water vapor at upper interior 3101 of the chamber, and promotes the movement of denser molecules in sterilization chamber towards the lower interior (e.g., lower interior 3103) of sterilization chamber 3102, and to some extent out of sterilization system 3100 through vacuum exhaust conduit 3114.

According to step 3324, injection of dry gas may be stopped and the vacuum level may be held for, e.g., between about 1 minute and about 20 minutes, such as between about 2 min and about 20 min, between about 5 min and about 20 min, between about 5 min and about 15 min, or between about 5 min and about 10 min. For example, the vacuum level may be maintained for about 2, 5, 8, 10, or 15 minutes. Holding the vacuum level may continue to promote settling of denser molecules (e.g., sterilization chemical molecules) down towards the lower interior 3103 of sterilization chamber 3102, and away from the sterilization load.

According to step 3326, the vacuum level may be broken by the addition of more dry gas near upper interior 3101 of sterilization chamber 3102, via, for example, distribution manifold 3107 or inlet 3109. A volume of dry gas sufficient to achieve a higher pressure may be added. The higher pressure may be, for example, between 50 and 200 millibars higher than the vacuum level achieved in step 3322. The vacuum level may be, for example, between about 550 millibars and about 1000 millibars, such as between about 550 millibars and about 850 millibars, between about 600 millibars and about 700 millibars, or between about 650 millibars and about 750 millibars. For example, the vacuum level may be about 550 millibars, 600 millibars, 650 millibars, 700 millibars, 750 millibars, or 800 millibars. The addition of more dry gas may continue to force sterilization chemicals to settle to the lower interior 3101 of sterilization chamber 3102, thus moving them away from the sterilization load and positioning them for removal via vacuum conduit 3112 or blower exit conduit 3108.

According to step 3328, the sterilization system (e.g., sterilization system 3100) may be aerated and exhausted. During this step, blower 3106 may be turned on while recirculation valve 3119 is closed and exhaust valve 3120 is opened, such that blower 3106 pulls fluid from within sterilization chamber 3102 and expels it through exhaust 3116 via catalytic converter 3121. Because blower exit conduit 3108 is connected to sterilization chamber 3102 at lower interior 3103 of sterilization chamber 3102, denser fluids that have settled to lower interior 3103 (such as sterilizing chemicals) may be removed by this step. Air (e.g., from air supply 3117) may be concurrently allowed to vent into sterilization chamber 3102, such that the pressure in sterilization chamber 3102 returns to, or near, atmospheric pressure.

First aeration phase 3320 may be repeated, for example, between 1 and 35 times, such as 2, 5, 10, 15, 17, 19, 22, 25, 27, 29, 30, 32, or 35 times. Repetition of first aeration phase 3320 may ensure that the majority of sterilization chemical (e.g., VHP) is removed from sterilization system 3100.

Figure 44C:
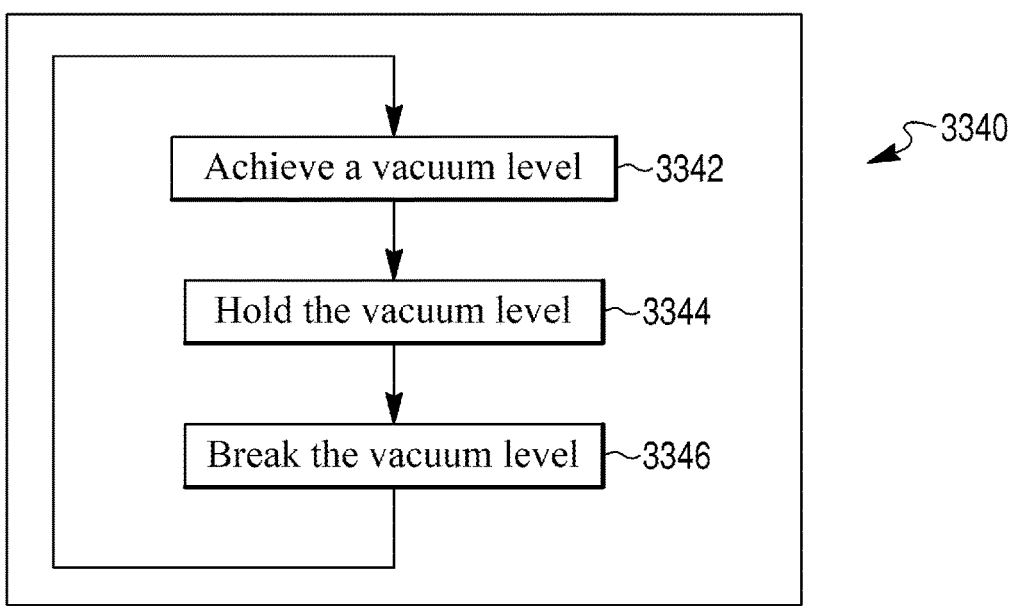

FIG. 44C is a flow diagram of a second aeration phase 3340 that may be performed as step 3210 of sterilization method 3200. According to step 3342, a vacuum level may be achieved. According to step 3344, a vacuum level may be held. According to step 3346, the vacuum level may be broken.

According to step 3342, a vacuum level may be achieved in sterilization chamber 3102. Like with the first aeration phase, the vacuum level achieved in this phase may be, for example, between about 500 millibars and about 850 millibars, such as between about 500 millibars and about 800 millibars, between about 550 millibars and about 750 millibars, or between about 600 millibars and about 700 millibars. For example, the vacuum level may be 500 millibars, 550 millibars, 600 millibars, 650 millibars, or 700 millibars. Achieving a vacuum level may promote removing of moisture from sterilization chamber 3102 and thus the sterilization load. Thus, the sterilization load may be dried.

According to step 3344, the vacuum level may be held for, e.g., between about 1 minute and about 20 minutes, such as between about 2 min and about 20 min, between about 5 min and about 20 min, between about 5 min and about 15 min, or between about 5 min and about 10 min. For example, the vacuum level may be maintained for about 2, 5, 8, 10, or 15 minutes. Holding the vacuum level may continue to promote removal of moisture from sterilization chamber 3102, and thus the sterilization load. Thus, the sterilization load may be further dried. In some embodiments, step 3344 may be omitted.

According to step 3346, the vacuum level in sterilization chamber 3102 may be broken, or raised to a higher pressure, by the addition of dry gas from, e.g., dry air supply 3130.

Second aeration phase 3340 may be repeated, for example, between 1 and 50 times, such as 2, 5, 10, 15, 20, 25, 30, 35, 38, 40, 42, 45, 47, 49, or 50 times. Repetition of second aeration phase 3340 may ensure drying of sterilization chamber 3102 and the sterilization load.

As has been previously described, second aeration phase 3340 may be performed either before or after first aeration phase 3320. First aeration phase 3320 may ensure, for example, that the concentration of sterilizing chemical (e.g., VHP) in sterilization chamber 3102 is relatively low, and second aeration phase 3340 may ensure that the sterilization load is dried, and may also remove residual sterilizing chemical remaining in sterilization chamber 3102 after first aeration phase 3320. In cases where second aeration phase 3340 is performed after first aeration phase 3320, first aeration phase may ensure that the concentration of sterilization chemical (e.g., VHP) in sterilization chamber 3102 is relatively low so that when sterilization chamber 3102 and the sterilization load are dried in second aeration phase 3340, there is little remaining need to remove residual sterilization chemical from the sterilization system 3100.

Figure 45A:
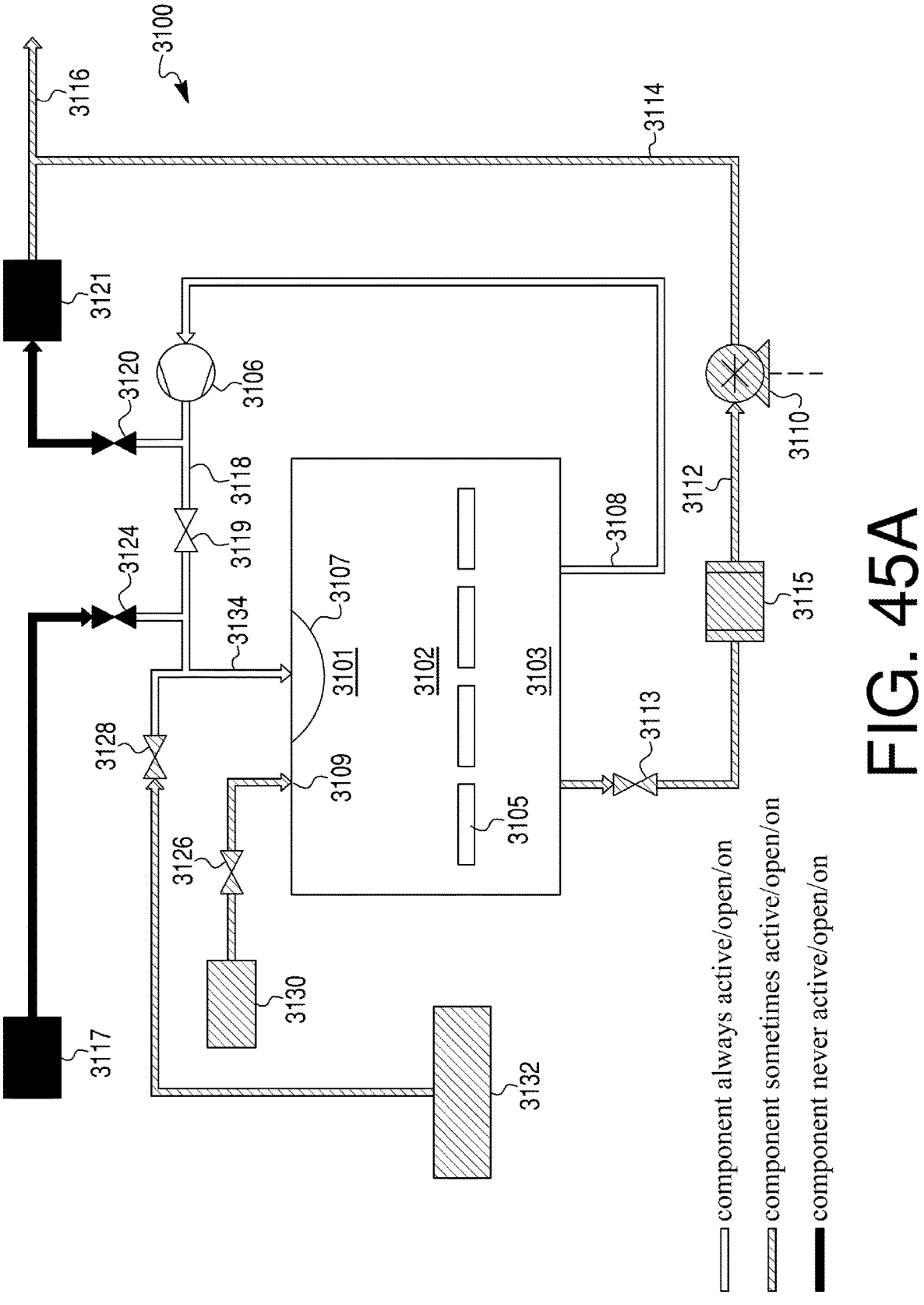
FIGS. 45A-45C are schematic drawings of an exemplary sterilization system at various stages in an exemplary method of sterilizing the delivery devices using vaporized chemicals, according to aspects of the present disclosure.
Figure 45B:
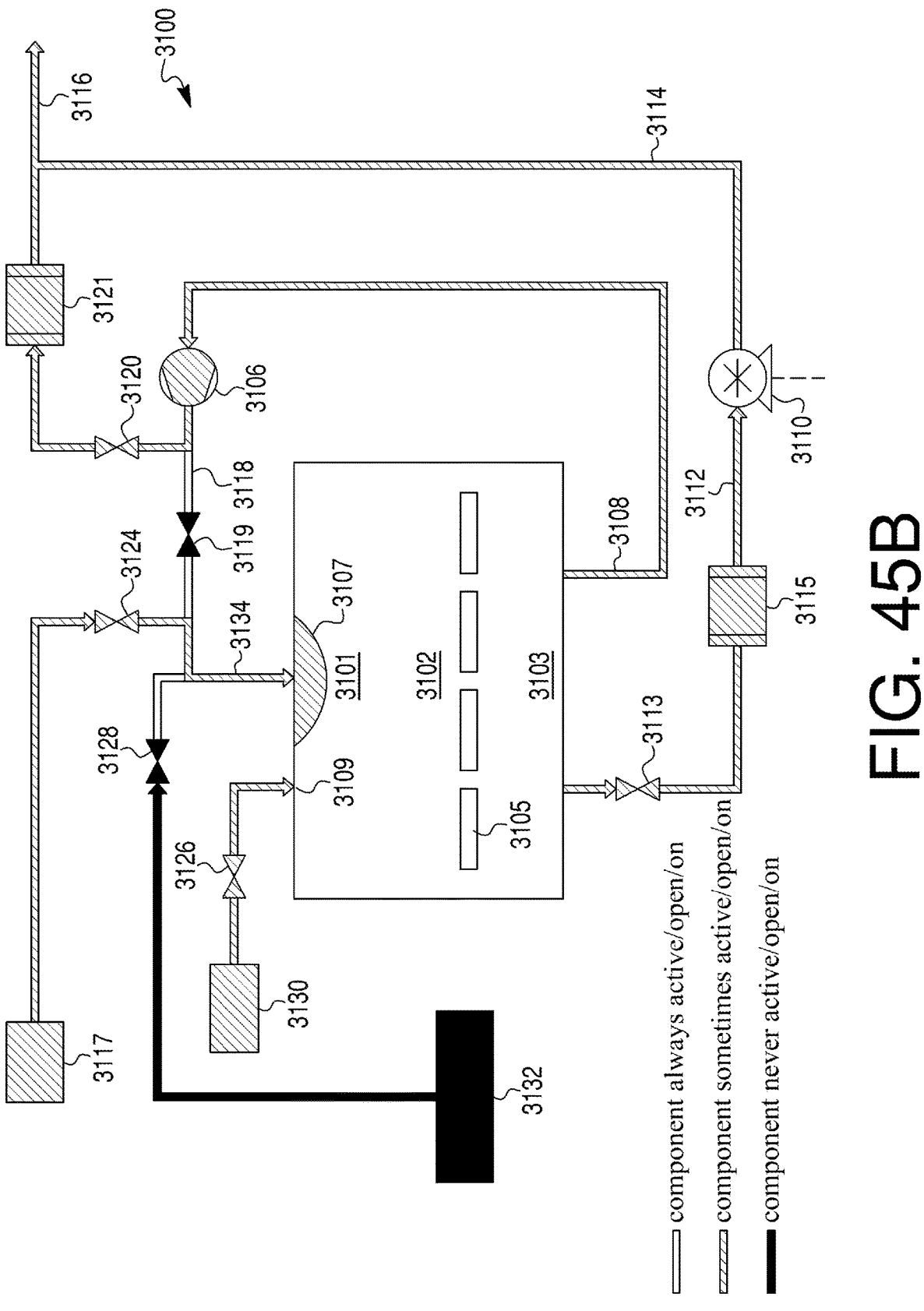
Figure 45C:
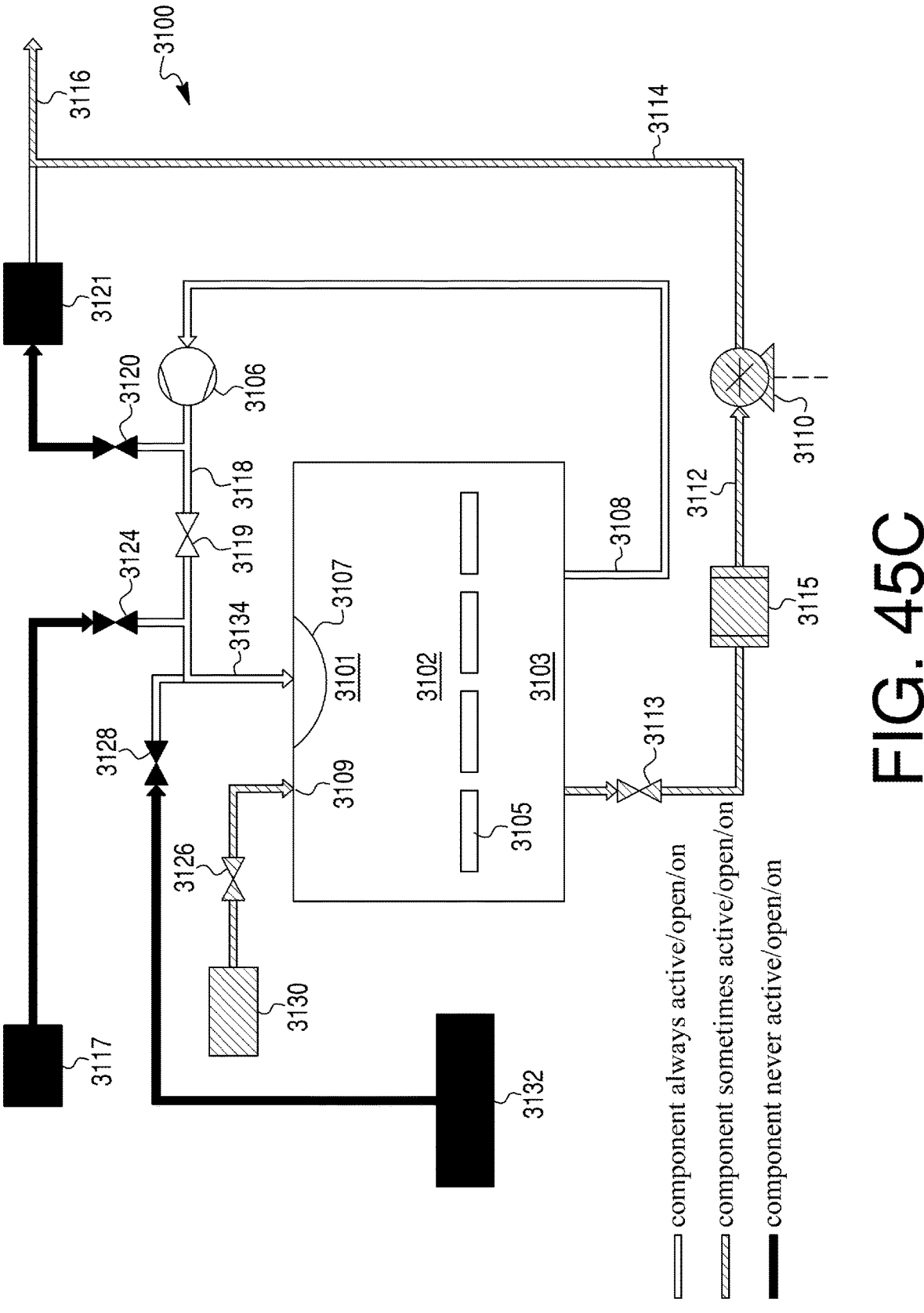

FIGS. 45A-45C depict, in schematic form, sterilization system 3100, and in particular, which parts of sterilization system 3100 may be active, open, or on (as opposed to inactive, closed, or off) during phases 3300, 3320, and 3340. For clarity, controller 3140 and thermal jacket 3104 are not pictured.

FIG. 45A depicts, in schematic form, the various parts of sterilization system 3100 in various stages of activity or inactivity during sterilization phase 3300. As is shown, during sterilization phase 3300, blower exit conduit 3108, blower circulation conduit 3118, blower 3106, and recirculation valve 3119 remain open, on, or active throughout sterilization phase 3300. Air supply 3117, air supply valve 3124, exhaust valve 3120, and catalytic converter 3121 remain closed, off, or inactive throughout sterilization phase 3300. The remaining components are sometimes open, on, or active during sterilization phase 3300. The following table indicates when these components are open, on or active:

TABLE 1

| Components | Vacuum valve 3113; vacuum conduit 3112; catalytic converter 3115; vacuum pump 3110; vacuum exhaust conduit 3114; exhaust 3116 | VHP injector 3132; VHP injector valve 3128 | Dry air supply 3130; dry air supply valve 3126; inlet 3109 |
|---|---|---|---|
| Steps | | | |
| Achieving vacuum level (step 3302) | On/open/active | | |

TABLE 1-continued

| Components | Vacuum valve 3113; vacuum conduit 3112; catalytic converter 3115; vacuum pump 3110; vacuum exhaust conduit 3114; exhaust 3116 | VHP injector 3132; VHP injector valve 3128 | Dry air supply 3130; dry air supply valve 3126; inlet 3109 |
|---|---|---|---|
| Injecting vaporized chemical (step 3304) | | On/open/active | |
| Maintaining post-injection hold (step 3306) | | | |
| Transitioning to shallower vacuum (step 3308) | | | On/open/active |
| Maintaining post-transition hold (step 3310) | | | |

FIG. 45B depicts, in schematic form, the various parts of sterilization system 3100 during first aeration phase 3320. As is shown, during first aeration phase 3320, VHP injector 3132, VHP injector valve 3128, and recirculation valve 3119 remain off or closed. The remaining components are sometimes open, on, or active during first aeration phase 3320, as indicated in the following table:

TABLE 2

| | Components | air supply 3117; air valve 3124; inlet conduit 3134; distribution manifold 3107; blower 3106; blower exit conduit 3108; exhaust valve 3120; catalytic converter 3121 | Vacuum conduit 3112; vacuum valve 3113; catalytic converter 3115; vacuum pump 3110; vacuum exhaust conduit 3114 | Dry air supply 3130; dry air supply valve 3126; inlet 3109 | Exhaust 3116 |
|---|---|---|---|---|---|
| Steps | Achieving vacuum level (step 3322) | | On/open/active | On/open/active | On/open/active |
| | Holding the vacuum level (step 3324) | | | | |
| | Breaking the vacuum level (step 3326) | | | On/open/active | |
| | Aerating and exhausting the system (step 3328) | On/open/active | | | On/open/active |

FIG. 45C depicts, in schematic form, the various parts of sterilization system 3100 during second aeration phase 3340. As is shown, during second aeration phase 3340, air supply 3117, air supply valve 3124, VHP injector, VHP injector valve 3128, exhaust valve 3120, and catalytic converter 3121 remain closed. Blower exit conduit 3108, blower 3108, blower circulation conduit 3118, recirculation valve 3119, inlet conduit 3134, and distribution manifold 3107 remain open during aeration phase 3340. The remaining components are sometimes open, on, or active during aeration phase 3340. The following table indicates when these components are open, on or active:

TABLE 3

| | Components | Vacuum conduit 3112; vacuum valve 3113; catalytic converter 3115; vacuum pump 3110; vacuum exhaust conduit 3114; exhaust 3116 | Dry air supply 3130; dry air supply valve 3126; inlet 3109 |
|---|---|---|---|
| Steps | Achieving vacuum level (step 3342) | On/open/active | On/open/active |
| | Holding the vacuum level (step 3344) | | |
| | Breaking the vacuum level (step 3346) | | On/open/active |

In some embodiments, any or all of the above-described steps and phases may be executed automatically by sterilization system 3100 as directed by, e.g., controller 3140, which may be programmed or otherwise configured in advance by e.g., a user. The methods of sterilization disclosed herein may be qualified as "limited overkill" sterilization methods, in that they may ensure sterilization of a load of, e.g., PFS while minimizing impact of the sterilization method on the product.

Embodiments of the present disclosure further relate to methods for treating a patient with a drug delivery device that reduces occurrence of undesired side effects (e.g., intraocular inflammation or other infections) endured by the patient, such as with the exemplary delivery devices (e.g., PFS) of the present disclosure described in detail above. The exemplary methods for treating a patient may further reduce the rate of undesired side effects to the patient by sterilizing the delivery devices of the present disclosure, such as via one or more of the sterilization systems and/or methods of described above. For example, embodiments of the present disclosure may relate to systems and methods for treating angiogenic eye disorders using pre-filled syringes that have undergone terminal sterilization with vaporized chemicals (e.g. vaporized hydrogen peroxide according to the description herein) to decrease a likelihood of the patient developing adverse events associated with intraocular inflammation (IOI) the eye, e.g., anterior chamber cell, anterior chamber flare, anterior chamber inflammation, anterior chamber fibrin, aqueous fibrin, autoimmune uveitis, chorioretinitis, choroiditis, cyclitis, endophthalmitis, eye infection intraocular, eye inflammation, hypopyon, infectious iridocyclitis, infective iritis, infective uveitis, iridocyclitis, iritis, noninfectious endophthalmitis, noninfective chorioretinitis, pseudoendophthalmitis, uveitis, vitreal cells, vitreous fibrin, vitritis, candida endophthalmitis, mycotic endophthalmitis, and serpiginous choroiditis.

In the exemplary method, any of the drug delivery devices (e.g., pre-filled syringes) described herein (FIGS. 1-41C) may be sterilized with one or more of the sterilization methods and/or systems (FIGS. 42-45) of the present disclosure for use in delivering an injection to a patient for treating an eye disorder. The exemplary method may provide a corresponding reduction in the rate of likelihood of the patient developing IOI as a result of the injection, relative to patients receiving injections from other delivery devices (e.g., non-prefilled syringes or syringes that are filled from a vial just immediately prior to administering the medicament to a patient) sterilized using different processes and/or not sterilized.

Figure 46A:
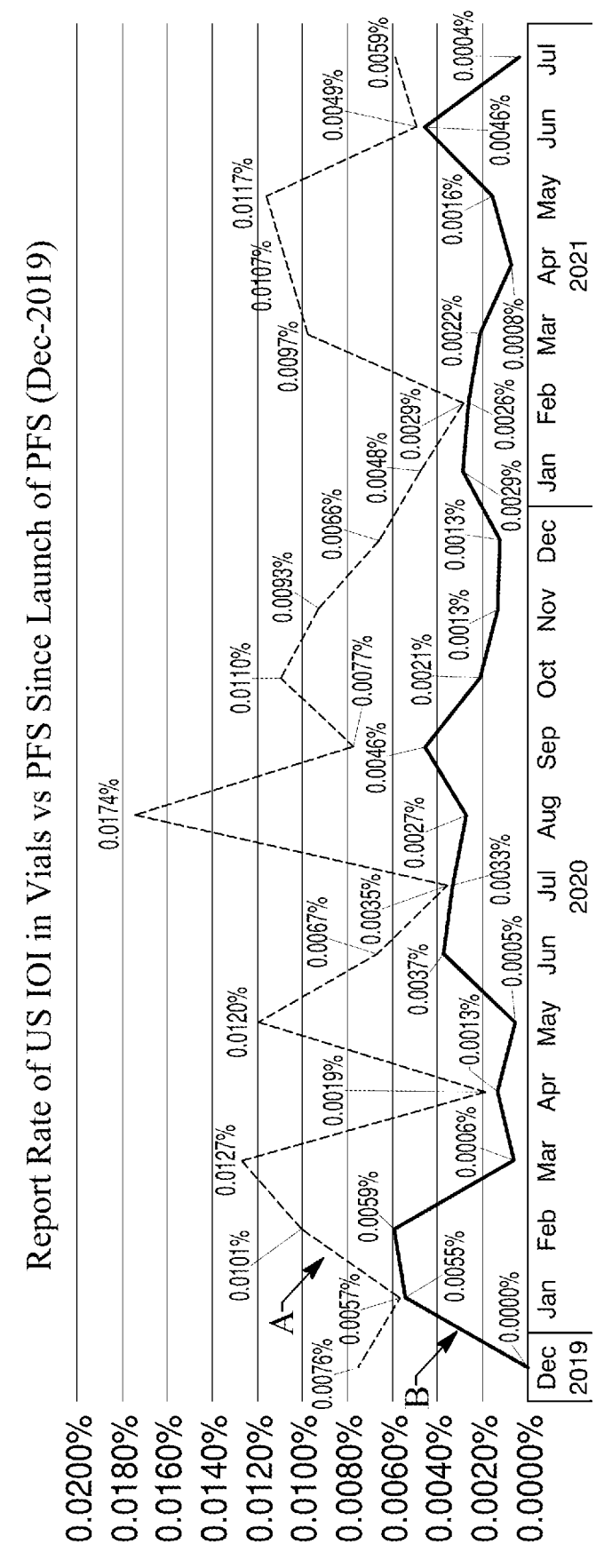
FIG. 46A depicts a graph illustrating a comparison of report rates of intraocular inflammation (IOI) in the United States from injections delivered by non-prefilled syringes and pre-filled syringes, such as the delivery devices of FIGS. 1-41C that are sterilized using the methods of sterilization and sterilization systems of FIGS. 42-45C, over a defined period.

FIG. 46A depicts a graph illustrating a rate of reporting of patients experiencing IOI when receiving an injection from non-prefilled syringes A and pre-filled syringes B. It should be understood that injections from the non-prefilled syringes A generally entail retrieving a medicament from a vial storing said medicament, e.g., prior to administering the medicament to a patient and/or subsequently to any sterilization procedures. Particularly, FIG. 46A depicts reporting rates of patients over a defined period of December 2019 to July 2021, and for injections in patients located in the geographic location of the United States. As described in further detail herein, it should be appreciated that the correlations shown in FIG. 46A are illustrative such that the reported rates of IOI derived from the graph between non-prefilled syringes A and pre-filled syringes B may extend beyond the defined period and geographic location shown.

In the graph of FIG. 46A, the rates shown for non-prefilled syringes A may correspond to injections by delivery devices that include a vial for storing a medicament and a syringe for extracting the medicament from the vial prior to delivery to the patient. The rates shown for pre-filled syringes B may correspond to injections by delivery devices of the present disclosure, including those terminally sterilized using the exemplary methods and/or systems described above.

As seen in FIG. 46A, the rate of reports of patients experiencing IOI varies based on the source of the injection. Particularly, the rate of patients reporting IOI may be greater when the patient receives an injection from non-prefilled syringes A (e.g. syringes extracting the medicament from a vial) as compared to pre-filled syringes B (e.g. PFS). In each of the measurement sets (e.g. months) within the defined period, the rate of reports of patients experiencing IOI in response to injections from non-prefilled syringes A may be greater than those receiving injections from pre-filled syringes B. Stated differently, the rate of reported cases of IOI among patients receiving injections via non-prefilled syringes A was greater for 20 straight months during the defined period from December 2019 to July 2021, as compared to injections via pre-filled syringes B. In some instances, a single patient may experience multiple IOI events. Therefore, it should be appreciated that the data shown in FIG. 46A may include one or more reports of IOI from each patient.

It should be appreciated that the data shown in FIG. 46A may be indicative of a correlation between patients experiencing IOI (including anterior chamber cell, anterior chamber flare, anterior chamber inflammation, anterior chamber fibrin, aqueous fibrin, autoimmune uveitis, chorioretinitis, choroiditis, cyclitis, endophthalmitis, eye infection intraocular, eye inflammation, hypopyon, infectious iridocyclitis, infective iritis, infective uveitis, iridocyclitis, iritis, noninfectious endophthalmitis, noninfective chorioretinitis, pseudoendophthalmitis, uveitis, vitreal cells, vitreous fibrin, vitritis, candida endophthalmitis, mycotic endophthalmitis, and serpiginous choroiditis) and the source of an injection (e.g. drug delivery device). Therefore, the defined period depicted in the graph of FIG. 46A is merely illustrative such that additional data collected beyond the defined period may continue to demonstrate a causation between patients experiencing an increased likelihood of intraocular inflammation when receiving an injection via non-prefilled syringes relative to patients receiving an injection from pre-filled syringes. The geographic location within the United States from which the data in FIG. 46A derives is also illustrative such that data collected in other geographic locations may continue to indicate the increased reporting rate of IOI from patients receiving an injection from non-prefilled syringes than patients receiving injections from pre-filled syringes.

Further, it should be understood that the data of FIG. 46A may at least partially rely upon the completeness and accuracy of reporting of such events (e.g., patients experiencing IOI) by users of non-prefilled and pre-filled syringes. Accordingly, the data of FIG. 46A may include a representative sample of reporting of patients experiencing IOI from each source of injection, such that it may be possible that a complete and accurate assessment of patients experiencing IOI may include additional and/or fewer reports than those shown in FIG. 46A. Furthermore, to the extent that the data presented in FIG. 46A contains any inaccuracies, it is not believed that the underlying trends illustrated in FIG. 46A are affected by these inaccuracies.

The increase in likelihood of patients experiencing IOI when receiving an injection from a non-prefilled syringe may be due to various causes. For example, the necessity to perform additional steps to administer the injection to the patient when using non-prefilled syringes may cause an increased likelihood of causing undesirable effects (e.g. IOI) to the patient. Utilizing non-prefilled syringes may generally require additional time for preparing the delivery device, extracting the medicament from a vial prior to delivering the medicament, and administering the injection to the patient. Accordingly, the introduction of additional steps for preparing the medicament for delivery may prolong the procedure time, thereby providing a greater likelihood for human error and/or contamination of the delivery device.

For instance, contaminants (e.g., bacteria, viruses, fungi or undesirable inorganic matter (dust)) that may be present in the surrounding environment may have an increased probability of coming into contact with the patient, the non-prefilled syringe, and/or the administrator of the injection when extracting the medicament from a vial. Steps such as removing a cap on the non-prefilled syringe to expose an underlying needle, opening a packaging and/or container storing the vial to obtain access to a stopper, and/or manual handling of the syringe and vial to facilitate transfer of the medicament from one device to the other, may each increase the likelihood of contaminating the medicament or the drug delivery device, including, e.g., the needle of the non-prefilled syringe.

Contaminants located on the non-prefilled syringe, such as on the needle, may cause health complications for the patient when delivering the medicament. For example, contaminants present on the needle may be transferred to the patient when delivering the medicament, thereby causing harmful injury or undesirable side effects to the patient (e.g., IOI). Contaminants located on the vial storing the medicament, such as on the stopper that is to be pierced by the needle of the non-prefilled syringe, may further cause an increased likelihood for the patient to experience health complications from the injection. Moreover, piercing the stopper of a vial with a needle may also introduce the likelihood of a portion of the stopper material becoming lodged within the needle (e.g., via coring as the needle passes through the stopper). Such lodged material may be then inadvertently delivered in the patient's eye, further increasing the likelihood of undesirable side effects in the patient.

For example, contaminants present on the stopper may be transferred to the patient when the needle of the non-prefilled syringe extracts the medicament from the vial. Contaminants on the stopper may be received along an exterior surface of the needle and/or mixed into the medicament within the vial when the needle punctures the stopper during a procedure for extracting the medicament, thereby contaminating the dose. In either instance, the use of non-prefilled syringes may increase a rate of patients developing IOI or otherwise undesirable symptoms, relative to patients receiving injections from delivery devices of the present disclosure (e.g., PFS), at least partly due to the additional steps required for delivering a medicament stored in a vial.

By way of further example, the sterilization of the non-prefilled syringe by a method and/or system that varies from the exemplary terminal VHP sterilization processes and systems of the present disclosure, or lack thereof, may provide a greater likelihood for contamination of the delivery device. Other sterilization processes or systems may be ineffective or unsuccessful in substantially removing all biological agents from the delivery device prior to use relative to the exemplary sterilization methods of the present disclosure. Accordingly, the use of other sterilization systems and/or methods may increase a report rate of patients developing IOI, relative to patients receiving injections from pre-filled syringes sterilized with vaporized chemicals in accordance with methods of the present disclosure.

FIG. 46B shows data corresponding to the graph depicted in FIG. 46A, and particularly the reported case rates of patients experiencing IOI during the defined period (e.g. December 2019 to July 2021) from non-prefilled syringes A and pre-filled syringes B. As seen in FIG. 46B, the rate of reported IOI events among patients is significantly greater (e.g., about four to five times) when the injection is administered via a non-prefilled syringe (with a vial) as compared to pre-filled syringes (PFS). As previously mentioned above, to the extent that the data presented in FIG. 46B contains any inaccuracies, it is not believed that the underlying trends illustrated in FIG. 46B are affected by these inaccuracies.

For example, among the approximately 1,396,103 units distributed that were using non-prefilled syringes with a vial, 111 cases of patients experiencing IOI were reported. In other words, use of non-prefilled syringes where the medicament is stored in a vial and extracted by the non-prefilled syringe results in a reporting rate of IOI of about 0.0080%. In contrast, only 95 cases of IOI were reported from approximately 4,060,038 units distributed using pre-filled syringes, e.g., terminally sterilized according to the methods described above. Therefore, use of pre-filled syringes results in a reporting rate of IOI of about 0.0023%. As such, the reported rates of patients experiencing IOI during the defined period (e.g. December 2019 to July 2021) is substantially greater for patients receiving the injection from non-prefilled syringes than pre-filled syringes.

The table below outlines findings that are consistent with the data described and illustrated in FIGS. 46A and 46B above with respect to the injection of a formulated drug substance via different administration techniques, i.e., via non-prefilled syringes with a vial and pre-filled syringes.

TABLE 4

Report Rates of Expected Endophthalmitis
Following Intravitreal Injection

| | Non-prefilled syringe with vial | Prefilled Syringe |
|---|---|---|
| Study One | 0.021% | 0.013% |
| Study Two | 0.026% | 0.015% |
| Study Three | 0.038% | 0.014% |
| Study Four | 0.026% | 0.022% |

With reference to Table 4, four independent studies were conducted between 2009 and 2019 that identified, inter alia, the difference between the expected report rates of endophthalmitis following injection of an anti-VEGF agent (e.g., ranibizumab) between non-prefilled syringes with a vial and prefilled syringes. The relationship represented by the data in Table 4 supports a finding that rates of IOI from intravitreal injection delivered by prefilled syringes may be lower than the rates of IOI from intravitreal injection delivered by non-prefilled syringes.

Figure 47:
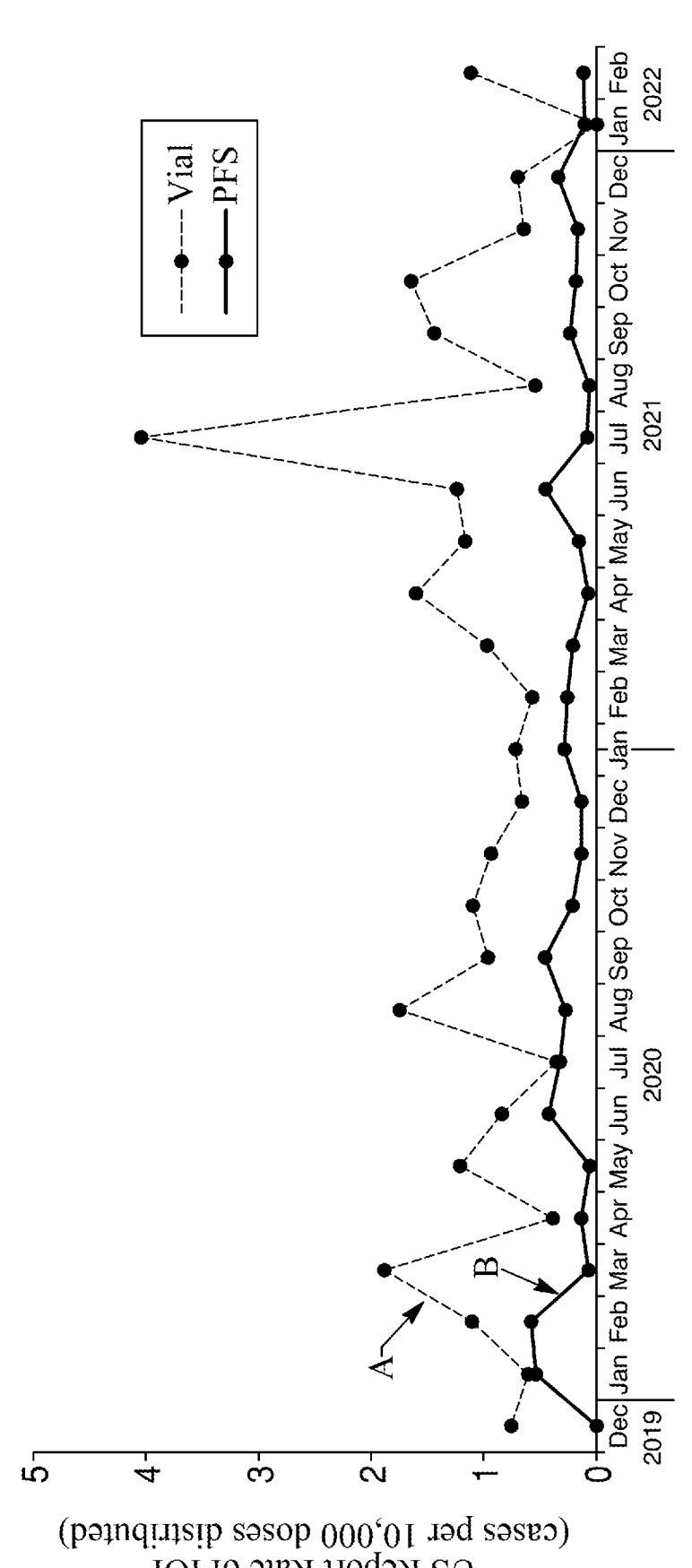
FIG. 47 depicts a graph illustrating a comparison of report rates of IOI in the United States following intravitreal injection of aflibercept delivered by non-prefilled syringes and prefilled syringes over a defined period.

FIG. 47 depicts a graph illustrating monthly report rates of IOI following intravitreal injection of an anti-VEGF agent, such as aflibercept, between non-prefilled syringes with vials A and prefilled syringes B. For the data illustrated in the graph of FIG. 47, the rate of reported cases of IOI was calculated based on the reported cases of IOI per 10,000 doses (non-prefilled syringes or prefilled syringes) distributed in the geographic location of the United States. In the example, approximately 1.6 million non-prefilled syringes (with vials) and approximately 6.0 million prefilled syringes were distributed since the introduction of a prefilled syringe containing aflibercept in December 2019. The Cochcran-Mantel-Haenszel (CMH) test was used to determine an Odds Ratio (95% Confidence Interval).

It should be appreciated that the correlations shown in FIG. 47 are illustrative such that the reported rates of IOI derived from the graph between non-prefilled syringes A and pre-filled syringes B may extend beyond the defined period and geographic location shown. It should further be appreciated that the data illustrated in the graph of FIG. 47, as well as that described in the tables below, are illustrative, such that an actual quantity of intravitreal aflibercept injections and rates of IOI may vary, as the reported rates shown and described herein may be voluntarily and/or spontaneously provided.

The following tables provided herein, i.e., Tables 5-8, support the data illustrated in FIG. 47 and the conclusions described in detail above. In this regard, each of the tables below provide additional illustrative data with respect to the administration of an anti-VEGF agent (e.g., aflibercept) by non-prefilled syringes with a vial and prefilled syringes.

TABLE 5

Yearly Report Rates of IOI Following
Intravitreal Aflibercept Injections

| | Reported IOI Rate (cases/10,000 doses) | | | Odds Ratio (95% Confidence Interval) |
|---|---|---|---|---|
| | 2020 | 2021 | Overall | |
| Vial | 0.93 | 1.27 | 0.98 | — |
| PFS | 0.25 | 0.21 | 0.22 | 0.22 (0.18, 0.28) |

Table 5 above provides a comparison between the reported rates of IOI between non-prefilled syringes (with a vial) and prefilled syringes. For each year shown, e.g., 2020 and 2021, the reported IOI rate for vials was significantly more than PFS (i.e., about 4× more in 2020; about 6× more in 2021). The overall reported IOI rate between the two administration techniques maintained this relationship (i.e., the reported overall IOI rate for vial was about 5× more than PFS). As further deduced from the data of Table 5, the overall relative risk for PFS was about 0.22. It is important to note that the value for the relative risk and the odds ratio were the same. The difference between the two groups is statistically significant with a P-Value measurement of less than about 0.0001.

TABLE 6

Yearly Report Rates of Individual IOI Events
Following Intravitreal Aflibercept Injections

| | Reported IOI cases | | | | |
|---|---|---|---|---|---|
| | December 2019 | 2020 | 2021 | January-February 2022 | Overall |
| Vial | 12 | 55 | 19 | 2 | 88 |
| PFS | 0 | 55 | 69 | 5 | 129 |
| Unknown | 5 | 26 | 32 | 1 | 64 |

TABLE 7

Yearly Report Rates of Reported IOI Rate Following Intravitreal
Aflibercept Injections (Including Unknown Cases)

| | Reported IOI cases (cases/10,000 doses) | | | | | Odds Ratio (95% Confidence Interval) |
|---|---|---|---|---|---|---|
| | December 2019 | 2020 | 2021 | January-February 2022 | Overall | |
| Vial | 0.50 | 0.62 | 0.45 | 0.34 | 0.55 | — |
| PFS | 2.97 | 0.37 | 0.31 | 0.11 | 0.32 | 0.58 (0.45, 0.75) |
| Unknown | | | | | | |

TABLE 8

Yearly Report Rates of IOI Following
Intravitreal Aflibercept Injections

| | Reported IOI cases (cases/10,000 doses) | | | | | Odds Ratio (95% Confidence Interval) |
|---|---|---|---|---|---|---|
| | December 2019 | 2020 | 2021 | January-February 2022 | Overall | |
| Vial | 0.50 | 0.62 | 0.45 | 0.34 | 0.55 | — |
| PFS | 0 | 0.25 | 0.21 | 0.09 | 0.21 | 0.39 (0.30, 0.51) |

Referring to Table 6, illustrative reported cases of IOI resulting from the administration of aflibercept with non-prefilled syringes (with a vial) and prefilled syringes between December 2019 to February 2022 are shown. Additionally provided are the reported cases of IOI resulting from the administration of aflibercept from an "unknown" kit type (i.e., those cases in which the kit type, vial or PFS, was not specified in the report). It can be seen from Table 6 that, outside of December 2019, the reported cases of IOI associated with the administration of aflibercept via prefilled syringes was greater than or equal to the reported cases of IOI associated with the administration of aflibercept via non-prefilled syringes with a vial. However, it is important to note that nearly 4× as many prefilled syringes were distributed during this illustrative timeframe than non-prefilled syringe injections (i.e., approximately 6 million injections via prefilled syringes to approximately 1.6 million injections via non-prefilled syringes with a vial).

Turning now to Table 7, the corresponding reported rates of IOI are shown for the data in Table 6. It is important to note that for the purpose of this example the "unknown" cases (in which the kit type was not specified as either from a vial of PFS) were considered as an injection delivered from a PFS. Despite this conservative characterization of the data shown, the reported rates of IOI during this time period is consistent with the findings shown and described above, i.e., the rates of IOI events are generally lower when administering a dose via a PFS relative to administering a dose via a non-prefilled syringe with a vial. This finding is supported by the odds ratio of 0.58 (0.45, 0.75) (95% confidence interval), with a P-value less than 0.0001.

Referring now to Table 8, illustrates the same reported IOI rates for vials (based on the data shown in Table 6) as shown in Table 7, and updated reported 101 rates for PFS with only the known cases in which IOI was reported from the administration of aflibercept with a prefilled syringe. Accordingly, the reported IOI rates and odds ratio shown in Table 8 exclude those cases in which the kit type were "unknown," thereby illustrating another characterization of the data. As seen in Table 8, the odds ratio for PFS is relatively lower than that shown in Table 7, further supporting the finding described above.

Figure 48:
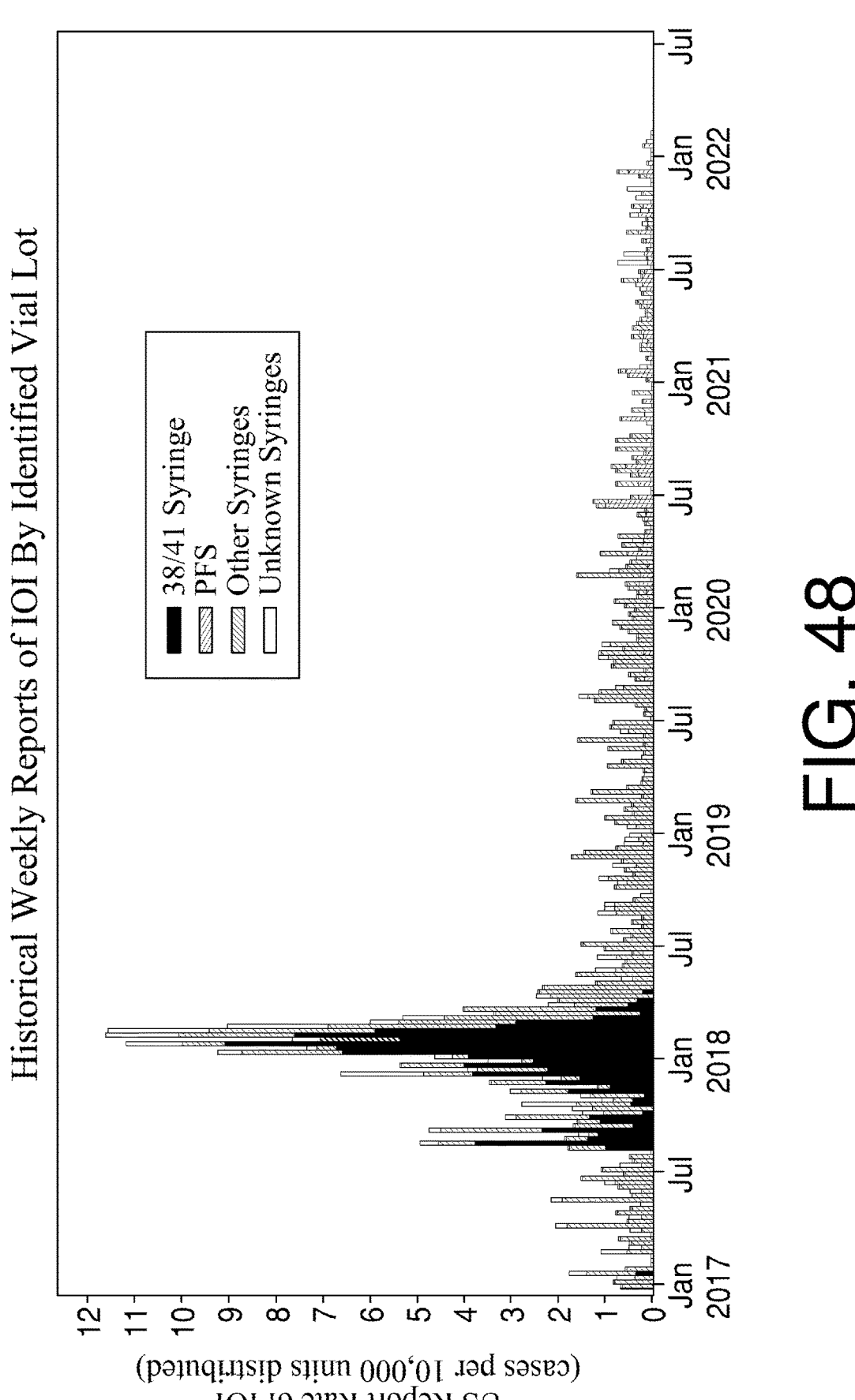
FIG. 48 depicts a graph illustrating a comparison of report rates of IOI in the United States following intravitreal injection of aflibercept between syringe types over a defined period.

FIG. 48 depicts a graph illustrating a historical weekly report rate of IOI following intravitreal injection of an anti-VEGF agent, such as aflibercept, by identified vial lot in the United States from January 2017 to Feb. 3, 2022. The data in the graph provides indications of the type of syringes (e.g., 38/41-type syringes, prefilled syringes, other syringes, and unknown syringes) utilized in the administration of the intravitreal injection that resulted in a reported occurrence of IOI. The relationships between the syringe-based data points in the graph support a finding that rates of IOI from intravitreal injection delivered by prefilled syringes may be lower than rates of IOI from intravitreal injection delivered by non-prefilled syringes.

As described in detail above, a rate of probability for the occurrence of IOI in response to an injection may be at least partly due to a quantity of microbial contamination on the delivery device administering the injection. As such, an exemplary method of treating an eye disorder may include decreasing a microbial content on a drug delivery device by utilizing a terminally sterilized pre-filled syringe in lieu of a non-prefilled syringe. The exemplary methods of treating the eye disorder may further include sterilizing the pre-filled syringe via vaporized chemicals (e.g., VHP) in accordance with methods of the present disclosure.

The exemplary methods of treating the eye disorder may further include decreasing a rate of likelihood for inflammation to an outer, middle, or inner layer in the patient's eye. The exemplary method of treating the eye disorder may further include decreasing a rate of likelihood for intraocular inflammation of tissue within an eye of the patient caused by an infection from microbes contacting the tissue (e.g., endophthalmitis, uveitis, etc.). The exemplary method of treating the eye disorder may further include decreasing a rate of likelihood for causing redness of an eye, pain in the eye, blurred vision, and/or sensitivity to light for the patient. In some embodiments, the exemplary method may include treating an angiogenic eye disorder.

In other embodiments, an exemplary method for treating a patient may include administering a medicament (e.g., an anti-VEGF antagonist) via at least one of the delivery devices of the present disclosure (e.g., a terminally sterilized PFS) to provide for a lower relative likelihood of the patient experiencing intraocular inflammation than by injections from non-prefilled syringes. The exemplary method for treating a patient may further provide lower rates of IOI to patients by administering a medicament from delivery devices that are sterilized with one or more of the sterilization methods and/or systems of the present disclosure (e.g., using VHP), as compared to syringes sterilized by other processes (or not sterilized).

In delivering a medicament with one or more of the delivery devices of the present disclosure, a method of treating a patient may include reducing microbial infections to the patient, reducing an introduction of any microbial content in the medicament, and reducing colonization of contaminants on the delivery device. An exemplary method of reducing intraocular inflammation in a patient may include administering a medicament (e.g., anti-VEGF antagonist) with any combination of the delivery devices of the present disclosure (FIGS. 1-41C) and the sterilization methods and/or systems described in detail above (FIGS. 42-45C).

Features enumerated above have been described within the context of particular embodiments. However, as one of ordinary skill in the art would understand, features and aspects of each embodiment may be combined, added to other embodiments, subtracted from an embodiment, etc. in any manner suitable to assist with controlled preparation and/or delivery of a drug.

Aspects of the embodiments disclosed herein are described with respect to priming drug delivery devices and removing excess air bubbles from within drug delivery devices, and some embodiments disclosed herein are described as being particular types of drug delivery devices (e.g., pre-filled syringes). Aspects of the present disclosure may also be employed and/or found in other types of drug delivery devices (e.g., fillable syringes, pipettes, and the like). For example, devices having features according to the present disclosure may provide more precise means for transferring a volume of a drug substance or other fluid from one container to another, such as from a vial to a syringe. The precision in fluid transfer afforded by embodiments disclosed herein may reduce or minimize unwanted overfilling and/or decrease wastage of a drug substance. Aspects of the embodiments disclosed herein further describe processes and systems for sterilizing drug delivery devices, and reducing eye injuries (e.g., IOI or side effects thereof) in patients receiving injections through use of the exemplary drug delivery devices described herein (e.g., PFS) and/or the sterilization processes and systems of the present disclosure (e.g., use of VHP).

While a number of embodiments are presented herein, multiple variations on such embodiments, and combinations of elements from one or more embodiments, are possible and are contemplated to be within the scope of the present disclosure. Moreover, those skilled in the art will appreciate that the conception upon which this disclosure is based may readily be used as a basis for designing other devices, methods, and systems for carrying out the several purposes of the present disclosure.

Embodiments of the present disclosure may include the following features:

Item 1. A method of treating an eye disorder in a patient, the method comprising: administering a medicament to the patient with a prefilled syringe, wherein the administration of the medicament with the prefilled syringe is configured to treat the eye disorder and decrease a rate of likelihood of an ocular infection to the patient's eye.

Item 2. The method of Item 1, wherein the medicament includes an anti-VEGF agent.

Item 3. The method of Item 1, wherein the eye disorder in the patient includes an angiogenic eye disorder.

Item 4. The method of Item 1, wherein the ocular infection includes intraocular inflammation (IOI) or endophthalmitis.

Item 5. The method of Item 1, wherein the administration of the medicament with the prefilled syringe reduces a bacterial content on at least one portion of the pre-filled syringe relative to bacterial content on a non-prefilled syringe.

Item 6. The method of Item 1, wherein prior to administering the medicament to the patient with the prefilled syringe, the method comprises: sterilizing the pre-filled syringe with vaporized chemicals to remove contaminants and other biological agents present on the pre-filled syringe.

Item 7. The method of Item 6, wherein the vaporized chemicals include vaporized hydrogen peroxide (VHP).

Item 8. The method of Item 1, wherein the administration of the medicament with the prefilled syringe is configured to decrease the rate of likelihood of the ocular infection to the patient's eye relative to the administration of the medicament with a non-prefilled syringe with the medicament stored in a vial.

Item 9. The method of Item 1, wherein the administration of the medicament with the prefilled syringe decreases a rate of likelihood for inflammation to at least one of a conjunctiva, a cornea, a sclera, an iris, a ciliary body, a lens, a retina, a choroid, or aqueous and vitreous humor in the patient's eye.

Item 10. The method of Item 1, wherein the administration of the medicament with the prefilled syringe decreases a rate of likelihood for intraocular inflammation of tissue with the patient's eye caused by an infection from bacteria contacting the tissue.

Item 11. The method of Item 1, wherein the administration of the medicament with the prefilled syringe is configured to decrease a rate of likelihood for causing redness, pain, blurred vision, and/or sensitivity to light to the patient's eye.

Item 12. A method of reducing a probability of an occurrence of an ocular infection in a patient being treated for an eye disorder with a medicament, the method comprising: administering the medicament to the patient's eye via a pre-filled syringe Item 13. The method of Item 12, wherein the medicament includes an anti-VEGF antagonist, the eye disorder in the patient includes an angiogenic eye disorder, and the ocular infection includes intraocular inflammation (IOI) or endophthalmitis.

Item 14. The method of item 12, wherein prior to administering the medicament to the patient's eye via the prefilled syringe, the method comprises: sterilizing the pre-filled syringe with vaporized chemicals to remove contaminants and other biological agents present on the pre-filled syringe.

Item 15 The method of Item 14, wherein the vaporized chemicals include vaporized hydrogen peroxide (VHP).

Item 16. The method of Item 12, wherein prior to administering the medicament to the patient's eye via the pre-filled syringe, the method comprises: reducing a degree of bacterial content on a portion of the pre-filled syringe by subjecting the pre-filled syringe to a terminal sterilization process.

Item 17. The method of Item 16, wherein the portion of the pre-filled syringe is a needle.

Item 18. The method of Item 12, wherein administering the medicament via the prefilled syringe decreases a rate of likelihood for inflammation to at least one of a conjunctiva, a cornea, a sclera, an iris, a ciliary body, a lens, a retina, a choroid, or aqueous and vitreous humor in the patient's eye.

Item 19. The method of Item 12, wherein administering the medicament via the prefilled syringe decreases a rate of likelihood for intraocular inflammation of tissue occurring in the patient's eye caused by an infection from bacteria contacting the tissue.

Item 20. The method of Item 12, wherein administering the medicament with the prefilled syringe decreases a rate of likelihood for causing redness, pain, blurred vision, and/or sensitivity to light to the patient's eye.

Item 21. A method of reducing intraocular inflammation in a patient receiving an injection, the method comprising: administering the injection to the patient via a prefilled syringe including a medicament configured to treat an eye disorder, wherein the administration reduces a rate of likelihood of the patient developing an intraocular infection in response to the injection from the pre-filled syringe as compared to patients receiving the injection from non-prefilled syringes.

Item 22. The method of Item 21, wherein the medicament includes an anti-VEGF agent, and the eye disorder includes an angiogenic eye disorder.

Item 23. The method of Item 22, wherein the anti-VEGF agent is aflibercept.

Item 24. The method of Item 23, wherein administering the injection comprises administering a volume of less than 75 µl of aflibercept to an eye of the patient.

Item 25. The method of Item 24, wherein the injection of aflibercept has a concentration of at least 8 mg.

Item 26. The method of Item 21, wherein the rate of likelihood of the patient developing the intraocular infection is decreased by at least 3× in response to the injection from the pre-filled syringe as compared to the injection from the non-prefilled syringes.

Item 27. The method of Item 21, wherein prior to administering the injection to the patient via the prefilled syringe, the method comprises: sterilizing the pre-filled syringe via a terminal VHP sterilization process.

Item 28. The method of Item 21, wherein prior to administering the injection to the patient via the prefilled syringe, the method comprises: sterilizing the pre-filled syringe via a moist chemical sterilization process.

Item 29. The method of Item 21, wherein prior to administering the injection to the patient via the prefilled syringe, the method comprises: positioning the pre-filled syringe within a sterilization chamber configured to run sterilization cycles at a predefined temperatures and pressures for one or more time durations at user-defined intervals; and supplying vaporized hydrogen peroxide into the sterilization chamber during the sterilization cycles and at adjustable concentrations.

Item 30. The method for Item 21, wherein administering the injection to the patient via the prefilled syringe decreases a rate of likelihood for inflammation to at least one of a conjunctiva, a cornea, a sclera, an iris, a ciliary body, a lens, a retina, a choroid, or aqueous and vitreous humor in the patient's eye.

Item 31. The method of Item 21, wherein administering the injection to the patient via the prefilled syringe decreases a rate of likelihood for intraocular inflammation of tissue within the patient's eye caused by a presence of bacteria contacting the tissue.

Item 32. The method of Item 21, wherein administering the injection to the patient via the prefilled syringe decreases a rate of likelihood for causing redness, pain, blurred vision, and/or sensitivity to light to the patient's eye.

What is claimed is:

1. A method of treating an eye disorder in a patient, the method comprising:

administering a medicament to the patient with a prefilled syringe, wherein the administration of the medicament with the prefilled syringe is configured to treat the eye disorder and decrease a rate of likelihood of an ocular infection to the patient's eye;

wherein the prefilled syringe includes:

a body configured to store the medicament;

a flange coupled to the body and including a first side opening and a second side opening, wherein the first side opening is a hole and the second side opening is a slot;

a plunger rod coupled to the flange and including a proximal end portion and a distal end portion disposed partially inside the body;

a protrusion extending from the proximal end portion of the plunger rod; and an extension, longitudinally aligned with the protrusion, protruding distally from the proximal end portion of the plunger rod;

wherein a portion of the extension is configured to be received by the first side opening to restrict proximal movement of the plunger rod relative to the flange prior to the administering step and removed from the first side opening during the administering step; and wherein the protrusion is configured to be positioned outside of the second side opening prior to the administering step and received in the second side opening to restrict distal movement of the plunger rod relative to the flange during the administering step.

2. The method of claim 1, wherein the medicament includes an anti-VEGF agent.

3. The method of claim 1, wherein the eye disorder in the patient includes an angiogenic eye disorder.

4. The method of claim 1, wherein the ocular infection includes intraocular inflammation (IOI) or endophthalmitis.

5. The method of claim 1, wherein the administration of the medicament with the prefilled syringe reduces a bacterial content on at least one portion of the pre-filled syringe relative to bacterial content on a non-prefilled syringe.

6. The method of claim 1, wherein prior to administering the medicament to the patient with the prefilled syringe, the method comprises:

sterilizing the pre-filled syringe with vaporized chemicals to remove contaminants and other biological agents present on the pre-filled syringe.

7. The method of claim 6, wherein the vaporized chemicals include vaporized hydrogen peroxide (VHP).

8. The method of claim 1, wherein the administration of the medicament with the prefilled syringe is configured to decrease the rate of likelihood of the ocular infection to the patient's eye relative to the administration of the medicament with a non-prefilled syringe with the medicament stored in a vial.

9. The method of claim 1, wherein the administration of the medicament with the prefilled syringe decreases a rate of likelihood for inflammation to at least one of a conjunctiva, a cornea, a sclera, an iris, a ciliary body, a lens, a retina, a choroid, or aqueous and vitreous humor in the patient's eye.

10. The method of claim 1, wherein the administration of the medicament with the prefilled syringe decreases a rate of likelihood for intraocular inflammation of tissue with the patient's eye caused by an infection from bacteria contacting the tissue.

11. The method of claim 1, wherein the administration of the medicament with the prefilled syringe is configured to decrease a rate of likelihood for causing redness, pain, blurred vision, and/or sensitivity to light to the patient's eye.

12. A method of reducing a probability of an occurrence of an ocular infection in a patient being treated for an eye disorder with a medicament, the method comprising:

administering the medicament to the patient's eye via a pre-filled syringe;

wherein the pre-filled syringe includes:

a body;

a plunger rod disposed partially inside the body and including an actuation portion;

a blocking component coupled to a proximal end portion of the body;

a protrusion extending laterally from the actuation portion;

wherein the plunger rod further includes an extension, longitudinally aligned with the protrusion, protruding distally from the actuation portion, and the blocking component includes a first side opening and a second side opening, wherein the first side opening is a hole and the second side opening is a slot;

wherein a portion of the extension is configured to be received by the first side opening to restrict proximal movement of the plunger rod relative to the blocking component prior to the administering step, and removed from the first side opening during the administering step; and wherein the protrusion is configured to be positioned outside of the second side opening prior to the administering step and received by the second side opening to restrict distal movement of the plunger rod relative to the blocking component during the administering step.

13. The method of claim 12, wherein the medicament includes an anti-VEGF antagonist, the eye disorder in the patient includes an angiogenic eye disorder, and the ocular infection includes intraocular inflammation (IOI) or endophthalmitis.

14. The method of claim 12, wherein prior to administering the medicament to the patient's eye via the prefilled syringe, the method comprises:

sterilizing the pre-filled syringe with vaporized chemicals to remove contaminants and other biological agents present on the pre-filled syringe.

15. The method of claim 14, wherein the vaporized chemicals include vaporized hydrogen peroxide (VHP).

16. The method of claim 12, wherein prior to administering the medicament to the patient's eye via the pre-filled syringe, the method comprises:

reducing a degree of bacterial content on a portion of the pre-filled syringe by subjecting the pre-filled syringe to a terminal sterilization process.

17. The method of claim 16, wherein the portion of the pre-filled syringe is a needle.

18. The method of claim 12, wherein administering the medicament via the prefilled syringe decreases a rate of likelihood for inflammation to at least one of a conjunctiva, a cornea, a sclera, an iris, a ciliary body, a lens, a retina, a choroid, or aqueous and vitreous humor in the patient's eye.

19. The method of claim 12, wherein administering the medicament via the prefilled syringe decreases a rate of likelihood for intraocular inflammation of tissue occurring in the patient's eye caused by an infection from bacteria contacting the tissue.

20. The method of claim 12, wherein administering the medicament with the prefilled syringe decreases a rate of likelihood for causing redness, pain, blurred vision, and/or sensitivity to light to the patient's eye.

21. A method of reducing intraocular inflammation in a patient receiving an injection, the method comprising:

administering the injection to the patient via a prefilled syringe including a medicament configured to treat an eye disorder, wherein the administration reduces a rate of likelihood of the patient developing an intraocular infection in response to the injection from the pre-filled syringe as compared to patients receiving the injection from non-prefilled syringes;

wherein the prefilled syringe includes:

a body;

a plunger rod including a proximal end portion and a distal end portion disposed partially inside the body; and a flange piece;

wherein the plunger rod includes a protrusion extending from the proximal end portion and an extension, longitudinally aligned with the protrusion, protruding distally from the proximal end portion, and wherein the flange piece includes a first side opening and a second side opening, wherein the first side opening is a hole and the second side opening is a slot;

wherein, when a portion of the extension is received by the first side opening, proximal movement of the plunger rod relative to the flange piece is prevented, and the portion of the extension is configured to exit the first side opening during administration of the injection;

wherein, when the protrusion is received by the second side opening, distal movement of the plunger rod relative to the flange piece is prevented, and the protrusion is configured to move from outside of the flange piece into the second side opening during administration of the injection.

22. The method of claim 21, wherein the medicament includes an anti-VEGF agent, and the eye disorder includes an angiogenic eye disorder.

23. The method of claim 22, wherein the anti-VEGF agent is aflibercept.

24. The method of claim 23, wherein administering the injection comprises administering a volume of less than 75 μl of aflibercept to an eye of the patient.

25. The method of claim 24, wherein the injection of aflibercept has a concentration corresponding to at least 8 mg in the volume of less than 75 μl.

26. The method of claim 21, wherein the rate of likelihood of the patient developing the intraocular infection is decreased by at least 3× in response to the injection from the pre-filled syringe as compared to the injection from the non-prefilled syringes.

27. The method of claim 21, wherein prior to administering the injection to the patient via the prefilled syringe, the method comprises:

sterilizing the pre-filled syringe via a terminal VHP sterilization process.

28. The method of claim 21, wherein prior to administering the injection to the patient via the prefilled syringe, the method comprises:

sterilizing the pre-filled syringe via a moist chemical sterilization process.

29. The method of claim 21, wherein prior to administering the injection to the patient via the prefilled syringe, the method comprises:

positioning the pre-filled syringe within a sterilization chamber configured to run sterilization cycles at a predefined temperatures and pressures for one or more time durations at user-defined intervals; and supplying vaporized hydrogen peroxide into the sterilization chamber during the sterilization cycles and at adjustable concentrations.

30. The method of claim 21, wherein administering the injection to the patient via the prefilled syringe decreases a rate of likelihood for inflammation to at least one of a conjunctiva, a cornea, a sclera, an iris, a ciliary body, a lens, a retina, a choroid, or aqueous and vitreous humor in the patient's eye.

31. The method of claim 21, wherein administering the injection to the patient via the prefilled syringe decreases a rate of likelihood for intraocular inflammation of tissue within the patient's eye caused by a presence of bacteria contacting the tissue.

32. The method of claim 21, wherein administering the injection to the patient via the prefilled syringe decreases a rate of likelihood for causing redness, pain, blurred vision, and/or sensitivity to light to the patient's eye.

* * * * *